(12) United States Patent
Brown et al.

(10) Patent No.: US 12,146,004 B2
(45) Date of Patent: Nov. 19, 2024

(54) POLYMYXIN COMPOUNDS AND USES THEREOF

(71) Applicant: New Pharma Licence Holdings Limited, Valletta (MT)

(72) Inventors: Pamela Brown, Reading (GB); Michael Dawson, Reading (GB); Mona Simonovic, Reading (GB); Steven Boakes, Reading (GB); Esther Duperchy, Reading (GB); Steven James Stanway, Ongar (GB); Antoinette Wilson, Ongar (GB); Stephen Frederick Moss, Ongar (GB)

(73) Assignee: SPERO THERAPEUTICS, INC., Cambridge, MA (US)

( * ) Notice: Subject to any disclaimer, the term of this patent is extended or adjusted under 35 U.S.C. 154(b) by 0 days.

(21) Appl. No.: 15/529,786

(22) PCT Filed: Nov. 26, 2015

(86) PCT No.: PCT/EP2015/077821
§ 371 (c)(1),
(2) Date: May 25, 2017

(87) PCT Pub. No.: WO2016/083531
PCT Pub. Date: Jun. 2, 2016

(65) Prior Publication Data
US 2018/0030092 A1 Feb. 1, 2018

(30) Foreign Application Priority Data

Nov. 26, 2014 (GB) ..................... 1421020
Sep. 10, 2015 (GB) ..................... 1516059

(51) Int. Cl.
| | | |
|---|---|---|
| A61K 38/00 | (2006.01) | |
| A61K 38/12 | (2006.01) | |
| C07K 5/00 | (2006.01) | |
| C07K 7/00 | (2006.01) | |
| C07K 7/62 | (2006.01) | |

(52) U.S. Cl.
CPC .............. *C07K 7/62* (2013.01); *A61K 38/12* (2013.01); *A61K 38/00* (2013.01); *Y02A 50/30* (2018.01)

(58) Field of Classification Search
None
See application file for complete search history.

(56) References Cited

U.S. PATENT DOCUMENTS

| | | |
|---|---|---|
| 4,510,132 A | 4/1985 | Vaara |
| 5,565,423 A | 10/1996 | Sandow et al. |

(Continued)

FOREIGN PATENT DOCUMENTS

| | | |
|---|---|---|
| CN | 101851270 A | 10/2010 |
| EP | 0571921 A2 | 12/1993 |

(Continued)

OTHER PUBLICATIONS

Cleveland Clinic, Polymyxin B injection, available online at: https://my.clevelandclinic.org/health/drugs/20275-polymyxin-b-injection, accessed Feb. 2, 2020. (Year: 2020).*

(Continued)

*Primary Examiner* — Thea D' Ambrosio
(74) *Attorney, Agent, or Firm* — CANTOR COLBURN LLP

(57) ABSTRACT

The present invention provides a compound of formula (I), and its use in methods of treatment, including the treatment of bacterial infections. Methods for the preparation of the compound of formula (I) are also provided. The compound of formula (I) has the structure shown below, where —$R^6$ and —$R^7$ are each together with the carbonyl group and nitrogen alpha to the carbon to which it is attached an amino acid residue, except that R6 together with the carbonyl group and nitrogen alpha to the carbon to which it is attached is not a phenylalanine, leucine or valine residue and/or —$R^7$ together with the carbonyl group and nitrogen alpha to the carbon to which it is attached is not a leucine, iso-leucine, phenylalanine, threonine, valine or nor-valine residue, and -T, -$A^1$, -$A^2$, -$A^3$ and —$R^{10}$ are as discussed in the application:

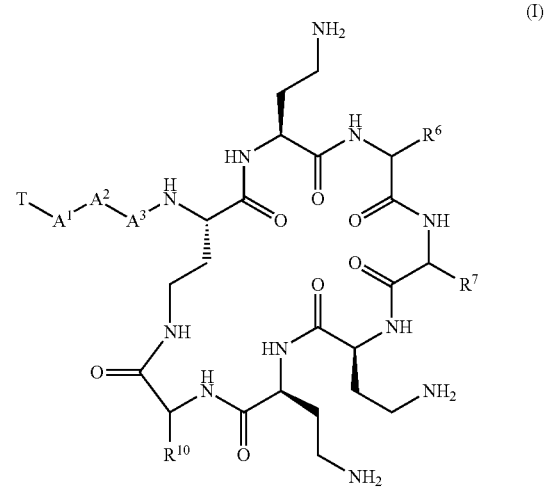

26 Claims, No Drawings

(56) References Cited

U.S. PATENT DOCUMENTS

| | | | |
|---|---|---|---|
| 5,767,068 A | 6/1998 | Vandevanter et al. | |
| 8,329,645 B2 * | 12/2012 | Vaara | C07K 7/62 514/2.4 |
| 8,343,912 B2 | 1/2013 | Leese | |
| 8,415,307 B1 | 4/2013 | Curran et al. | |
| 9,234,006 B2 | 1/2016 | Saadi et al. | |
| 10,407,467 B2 | 9/2019 | Brown et al. | |
| 2001/0021697 A1 | 9/2001 | Lowenstein et al. | |
| 2008/0207874 A1 | 8/2008 | Leese et al. | |
| 2008/0279820 A1 | 11/2008 | Hicks et al. | |
| 2008/0287345 A1 * | 11/2008 | Vaara | C12Q 1/18 514/1.1 |
| 2009/0215677 A1 | 8/2009 | Vaara et al. | |
| 2009/0239792 A1 | 9/2009 | Vaara et al. | |
| 2010/0160215 A1 | 6/2010 | Leese | |
| 2012/0316105 A1 * | 12/2012 | Magee | C07K 7/62 514/2.8 |
| 2016/0222061 A1 | 8/2016 | Brown et al. | |
| 2017/0073373 A1 | 3/2017 | Brown et al. | |
| 2021/0221848 A1 | 7/2021 | Brown et al. | |
| 2021/0246169 A1 | 8/2021 | Brown et al. | |
| 2023/0012121 A1 * | 1/2023 | Brown | C07K 7/62 |

FOREIGN PATENT DOCUMENTS

| | | | |
|---|---|---|---|
| GB | 2128617 A | 5/1984 | |
| WO | 8800950 | 2/1988 | |
| WO | 2008017734 A1 | 2/2008 | |
| WO | 2009098357 A1 | 8/2009 | |
| WO | 2010075416 A1 | 1/2010 | |
| WO | 2010029196 A1 | 3/2010 | |
| WO | WO-2010130007 A1 * | 11/2010 | A61P 31/04 |
| WO | 2012051663 A1 | 4/2012 | |
| WO | 2012168820 A1 | 12/2012 | |
| WO | 2013072695 A1 | 5/2013 | |
| WO | 2014188178 A1 | 11/2014 | |
| WO | 2015135976 A1 | 9/2015 | |
| WO | 2015149131 A1 | 10/2015 | |
| WO | 2016166103 A1 | 10/2016 | |
| WO | 2017054047 A1 | 4/2017 | |

OTHER PUBLICATIONS

Ashenhurst, Huckel's Rule: What Does 4n+2 Mean?—Master Organic Chemistry, available online at https://www.masterorganicchemistry.com/2012/06/29/huckels-rule-what-does-4n2-mean, accessed on Aug. 30, 2020. (Year: 2012).*

Merriam-Webster dictionary, Halo-Definition of Halo by Merriam-Webster, available online at https://www.merriam-webster.com/dictionary/halo, accessed on Aug. 30, 2020. (Year: 2020).*

Christe, et al., "Halogen". Encyclopedia Britannica, Oct. 23, 2020, https://www.britannica.com/science/halogen. Accessed Feb. 25, 2021 (Year: 2020).*

The New World Encyclopedia, "Threonine," available online at https://www.newworldencyclopedia.org/entry/Threonine, 3 pages ( first available 2008) (Year: 2008).*

U.S. Appl. No. 18/139,030 filed Apr. 2023, Brown; Pamela.*

United States Patent and Trademark Office, Restriction Requirement for U.S. Appl. No. 14/356,868, dated Nov. 14, 2014, 8 pages.

Vaara, M., et al., "A Novel Polymyxin Derivate That Lacks the Fatty Acid Tail and Carries Only Three Positive Charges Has Strong Synergism with Agents Excluded by the Intact Outer Membrane" Antimicrobial Agents and Chemotherapy, 2010, p. 3341-3346.

Vaara, M., et al., "Novel Polymyxin Derivatives Carrying Only Three Positive Charges Are Effective Antibacterial Agents" Antimicrobial Agents and Chemotherapy, 2008, vol. 52, No. 9, pp. 3229-3236.

Vaara, M., et al., "Susceptibility of carbapenemase-producing strains of Klebsiella pneumoniae and Escherichia coli to the direct antibacterial activity of NAB739 and to the synergistic activity of NAB7061 with rifampicin and clarithromycin" J. Antimicrob Chemother 2010, 65, pp. 942-945.

Varra, M. "Agents that Increase the Permability of the Outer Membrane" Microbiological Reviews (1992) vol. 56, No. 3 pp. 395-411.

Velkov, T., et al., "Structure-Activity Relationships of Polymyxin Antibiotics" J. Med. Chem. (2010) vol. 53, No. 5, pp. 1898-1916.

Velkov, T., et al., "Teaching 'Old' Polymyxins New Tricks: New-Generation Lipopeptides Targeting Gram-Negative 'Superbugs'" ACS Chemical Biology (2014) pp. 1172-1177.

Voitenko, G. V., et al., "Relationship between structure and histamine releasing action of polymyxin B and its analogues" Agents and Actions, vol. 30. 1:2 (1990) 4 pages.

Weinstein, J., et al., "Selective Chemical Modifications of Polymyxin B" Bioorganic & Medicinal Chemistry Letters 8 (1998) pp. 3391-3396.

Written Opinion of the International Searching Authority of PCT/EP2015/077821, filed Nov. 26, 2015, dated Apr. 19, 2016, 7 pages.

Yamada, K., et al., "Facile synthesis of Nα-protected-l-α,γ-diaminobutyric acids mediated by polymer-supported hypervalent iodine reagent in water" J. Peptide Res., 2004, 64, pp. 43-50.

Yousef, M. J., et al., "Melatonin Attenuates Colistin-Induced Nephrotoxicity in Rats" Antimicrobial Agents and Chemotherapy, 2011, p. 4044-4049.

Bergen J. P., et al., "Pharmacokinetics and pharmacodynamics of "old" polymyxins: what is new?" Diagnostic Microbiology and Infectious Disease (2012) vol. 74, pp. 213-223.

Bergen, J. P., et al., "Colistin Methanesulfonate Is an Inactive Prodrug of Colistin against Pseudomonas aerginosa" Antimicrobial Agents and Chemotherapy (2006) p. 1953-1958.

ChemFiles, "Peptide Synthesis" (2007) vol. 7, No. 2, 20 pages.

De Visser, P. C., et al., "Solid-phase synthesis of polymyxin B1 and analogues via a safety-catch approach" J. Peptide Res., 2003, 61, 298-306.

Diaz, L. J., et al., "Fast and Efficient Access to a Family of Multifunctional 1, 3, 5-Trisubstituted Piperidines, Synthetic Communications: An International Journal for Rapid Communication of Synthetic Organic Chemistry" (2008) 38:16 2799-2813.

European Patent Office, Examination Report for Application No. EP 12797961.5, dated Jun. 1, 2015, 6 pages.

Gallardo-Godoy, A., et al., "Activity and Predicted Nephrotoxicity of Synthetic Antibiotics Based on Polymyxin B" Journal of Medicinal Chemistry (2016) vol. 59, pp. 1068-1077.

Gallou, I., et al., "Practical Synthesis of Unsymmetricial Ureas from Isopropenyl Carbamates" J. Org. Chem. 2005, 70, 6960-6963.

International Search Report and the Written Opinion of the International Searching Authority for International Application No. PCT/EP2015/055046, dated Jul. 10, 2015, 12 pages.

International Search Report and the Written Opinion of the International Searching Authority for International Application No. PCT/EP2015/077821, dated Apr. 19, 2016, 13 pages.

International Search Report and the Written Opinion of the INternational Searching Authority for International Application No. PCT/GB2012/052844, dated Feb. 11, 2013, 17 Pages.

International Search Report and the Written Opinion of the International Searching Authority for International Application No. PCT/GB2014/051547, dated Dec. 8, 2014, 12 pages.

International Search Report of PCT/EP2015/077821, filed Nov. 26, 2015, dated Apr. 19, 2016, 6 pages.

Kanazawa, K., et al., "Contribution of Each Amino Acid Residue in Polymyxin B3 to Antimicrobial and Lipopolysaccharide Binding Activity" Chem. Pharm. Bull. (2009) vol. 57, No. 3, pp. 240-244.

Kato, K., et al., "The Structure of Octapeptin D" The Journal of Antibiotics (1980) vol. 33, pp. 186-191.

Katsuma, N., et al., "Antimicrobial Activity of Des-Fatty Acyl-Polymyxin B Decapeptide N-Terminal Analogs" Peptide Science 2004, 2 pages.

Katsuma, N., et al., "Development of Des-Fatty Acyl-Polymyxin B Decapeptide Analogs with Pseudomonas aeruginosa-Specific Antimicrobial Activity" Chem. Pharm. Bull. (2009) 57(4) 332-336.

Kimura, Y., et al., "Polymyxin B Octapeptide and Polymyxin B Heptapeptide are potent outer membrane permeability-increasing agents" The Journal of Antiboitics, May 1992, 8 pages.

(56) References Cited

OTHER PUBLICATIONS

Kline, T., et al., "Synthesis and characterization of the colistin peptide polymyxin E1 and related antimicrobial peptides" Journal of Peptide Res. (2001) vol. 57, pp. 175-187.
Li, J., et al., "Use of High-Performance Liquid Chromatography to Study the Pharmacokinetics of Colistin Sulfate in Rats following Intravenous Administration" Antimicrobial Agents and Chemotherapy, May 2003, vol. 47, No. 5, pp. 1766-1770.
Machine Translation of CN101851270A, dated Jun. 3, 2014.
Machine Translation of WO 8800950, dated Jun. 3, 2014, 8 pages.
Magee, V. T., et al., "Discovery of Dap-3 Polymyxin Analogs for the Treatment of Multidrug-Resistant Gram-negative Nosocomial Infections" Journal of Medicinal Chemistry, 2013, 57 pages.
O'Dowd, H., et al., "Preparation of tetra-Boc-protected polymyxin B nonapeptide" Tetrahedron Letters 48 (2007) pp. 2003-2005.
Okimura, K., et al., "Antimicrobial Activity of Various Aminocyclohexylcarbonyl-polymyxin B (2-10) Derivatives" Peptide Science 2008, pp. 243-244.
Okimura, K., et al., "Chemical Conversion of Natural Polymyxin B and Colistin to Their N-Terminal Derivatives" Bull. Chem. Soc. Jpn. vol. 80, No. 3, 543-552 (2007) pp. 543-552.
Petrosillo, N., "Colistin monotherapy vs. combination therapy: evidence from microbiological, animal and clinical studies" European Society of Clinical Microbiology and Infectious Diseases, 2008, pp. 816-827.
Quale, J., et al., "Activity of Polymyxin B and the Novel Polymyxin Analogue CB-182,804 Against Contemporary Gram-Negative Pathogens in New York City" Microbial Drug Resistance, 2012, 5 pages.
Sato, Y., et al., "Des-Fatty Acyl-Polymyxin B Decapeptide Analogs with Antimicrobial Activity Specifically against Pseudomonas aeruginosa" Peptide Society 2007, 2 pages.
Sato, Y., et al., "Novel Des-Fatty Acyl-Polymyxin B Derivatives with Pseudomonas aeruginosa-Specific Antimicrobial Activity" Chem. Pharm. Bull. 59(5), 2011, pp. 597-602.
Search Report of Application No. GB1421019.9, dated Aug. 21, 2015, 4 pages.
Search Reporton Application No. GB1309248.1, dated Nov. 11, 2013, 5 pages.
Search Report on Application No. GB1404301.2, dated Dec. 8, 2014, 5 pages.
Search Report on Application No. GB1421020.7, dated Aug. 24, 2015, 5 pages.
Shecter, Y., et al., "N-[(2-Sulfo)-9-fluorenylmethoxycarbonyl]3-gentamicin C1 Is a Long-Acting Prodrug Derivative" Journal of Medicincal Chemistry, 2002, vol. 45. No. 19, pp. 4264-4270.
Shoji, J., et al., "The Structure of Polymyxin T1" The Journal of Antibiotics, (1977) pp. 1042-1048.
State Intellectual Property Office of China, First Office Action for Application No. 201280055987.6, dated Nov. 24, 2015, 6 pages.
Taiwan Intellectual Property Office, First Office Action for Application No. 101142961, dated May 12, 2016, 5 pages.
The Eurasian Patent Organization, First Office Action for Application No. 201490634, dated Jun. 3, 2015, 4 pages.
The Eurasian Patent Organization, Second Office Action for Application No. 201490634, dated Oct. 12, 2015, 2 pages.
Tsubery, H., et al., "Modulation of the Hydrophobic Domain of Polymyxin B Nonapeptide: Effect on Outer-Membrane Permeabilization and Lipopolysaccharide Neutralization" Molecular Pharmacology (2002) vol. 62, No. 5, pp. 1036-1042.
Tsubery, H., et al., "N-terminal modifications of Polymyxin B nonapeptide and their effect on antibacterial activity" Peptides (2001) vol. 22, pp. 1675-1681.
United Kingdom Intellectual Property Office, CAS Search Results, tilted "Short fatty acid tail polymyxin derivatives and uses thereof" 68 Pages.
United States Patent and Trademark Office, Non-Final Office Action for U.S. Appl. No. 14/356,868, dated Mar. 13, 2015, 30 pages.
International Preliminary Report on Patentability of International Application No. PCT/EP2015/077821, international filing date—Nov. 26, 2015; dated May 30, 2017, 7 pages.
Kurtzhals et al., "Albumin Binding of Insulins Acylated With Fatty Acids: Characterization of the Ligand—Protein Interaction and Correlation Between Binding Affinity and Timing of the Insulin Effect in Vivo," Biochem J. (1995), vol. 312, pp. 725-731.
Magee, V. T., et al., "Discovery of Dap-3 Polymyxin Analogs for the Treatment of Multidrug-Resistant Gram-Negative Nosocomial Infections" Journal of Medicinal Chemistry, 2013, pp. 5079-5093.
Seebach et al., "The World of Beta and Gamma Peptides Comprised of Homologated Proteinogenic Amino Acids and Other Components," Chemistry & Biodiversity (2004), vol. 1, 1111-1239.
VAARA "Novel Derivatives of Polymyxins," Journal of Antimicrobial Chemotherapy, (2013), vol. 68, 1213-1219.
VAARA "Polymyxins and Their Novel Derivatives," Current Opinion in Microbiology, (2010), vol. 13, 574-581.

\* cited by examiner

POLYMYXIN COMPOUNDS AND USES THEREOF

CROSS-REFERENCE TO RELATED APPLICATIONS

This Application is a U.S. National Stage Application of PCT/EP2015/077821 filed Nov. 26, 2015, which claims priority to GB Application 1516059.1 filed Sep. 10, 2015, which claims priority to GB Application 1421020.7 filed Nov. 26, 2014 all of which are incorporated by reference in their entirety.

FIELD OF THE INVENTION

The present invention relates to novel polymyxin compounds, combinations of compounds, pharmaceutical compositions comprising the compounds and the use of the compounds, pharmaceutical compositions and combinations for treatment, for example treatment of microbial infections, particularly by Gram-negative bacteria.

BACKGROUND

In susceptible individuals, certain Gram-negative bacteria such as *Escherichia coli*, *Klebsiella pneumoniae*, *Pseudomonas aeruginosa* and *Acinetobacter baumanii* can cause serious infections, such as pneumonia, urinary tract infections, skin and skin structure infections such as wound infections, ear infections, eye infections, intra-abdominal infections, bacterial overgrowth in the gastrointestinal tract and bacteraemia/sepsis. The treatment of serious bacterial infections in clinical practice can be complicated by antibiotic resistance. Recent years have seen a rise in infections by Gram-negative bacteria which are resistant to many types of antimicrobials including broad spectrum antibiotics such as aminoglycosides, cephalosporins and even carbapenems. There is therefore a need to identify new antimicrobials that are effective against Gram-negative bacteria, in particular against multidrug resistant Gram-negative bacteria.

Polymyxins are a class of antibiotics produced by the Gram-positive bacterium *Bacillus polymyxa*. First identified in the late 1940s, polymyxins, particularly polymyxin B and polymyxin E (colistin, usually as its prodrug colistin methane sulphonate) were used in the treatment of Gram-negative infections. However, these antibiotics exhibited side effects such as neurotoxicity and nephrotoxicity. Nevertheless the polymyxins now play an important role in the therapy of MDR Gram-negative infections due to the lack of viable alternatives. However, their use in therapy is limited to treatment of last resort.

WO 2008/017734 tries to address this toxicity problem by providing polymyxin derivatives carrying at least two but no more than three positive charges. These compounds are said to be effective antibacterial agents with reduced renal toxicity. It is hypothesised in the disclosure that the reduced number of positive charges decreases the affinity of the compound for isolated rat kidney tissue which in turn may lead to a reduction in nephrotoxicity.

Certain des-fatty acyl polymyxin derivatives have also been disclosed with reduced acute toxicity in mice whilst retaining good activity against pseudomonads (Katsuma et al. Chem. Pharm. Bull. 2009; 57, 332-336; Sato et al. Chem. Pharm. Bull. 2011; 59, 597-602). The compounds were significantly less active than polymyxin B against *E. coli* and *K. pneumoniae*.

WO 2010/075416 provides urea linked aryl polymyxin decapeptides including CB182,804, which is reported to have similar activity but reduced renal toxicity compared with polymyxin B. Phenyl cyclopropane polymyxin derivatives are also described in U.S. Pat. No. 8,415,307. These compounds are shown to have similar or reduced activity compared with polymyxin B.

WO 2012/168820 provides a further series of polymyxin derivatives reported to have reduced toxicity, and sometimes enhanced activity compared with polymyxin B, in which the diaminobutyrate group at position 3 in the tripeptide side chain is replaced by a diaminopropionate moiety.

WO 2015/149131 and Velkov et al. describe modified polymyxin compounds. Typically these compounds retain a fatty acyl group at the N terminal of a polymyxin decapeptide, including, for example, an octanoyl or a nonanoyl group.

There remains a need for less toxic polymyxin derivatives which offer therapeutic preparations with consistently potent activity across the target pathogens and acceptable toxicity.

The present inventors have previously described in WO 2013/072695, TW 101142961 and GCC 2012/22819, the contents of each of which are hereby incorporated in their entirety, polymyxin compounds for use in the treatment of microbial infections.

The present inventors have also described in WO 2014/188178 and WO 2015/135976, the contents of both of which are hereby incorporated in their entirety, alternative polymyxin compounds for use in the treatment of microbial infections. In particular, WO 2014/188178 describes modifications to the N terminal of polymyxin decapeptides and nonapeptides. WO 2015/135976 describes modifications to the N terminal of polymyxin nonapeptides.

Surprisingly, the present inventors have found certain polymyxin derivatives which have reduced toxicity compared to polymyxin or colistin and are particularly active against Gram-negative bacteria, including bacterial strains with decreased susceptibility to polymyxin B and/or and polymyxin E. These agents thus offer therapeutic options of consistently potent activity, but lower toxicity than currently available therapies.

SUMMARY OF THE INVENTION

In a general aspect the present invention provides a polymyxin compound of formula (I) or formula (II), as described herein, and its use in a method of treatment or prophylaxis, and optionally in combination with a second agent (which may be referred to as an active agent). The compounds of formula (I) of formula (II) may be used to treat a microbial infection, such as a Gram-negative bacterial infection.

In a first aspect of the invention, there is provided a compound of formula (I), and pharmaceutically acceptable salts and solvates thereof. The compound of formula (I) is represented thus:

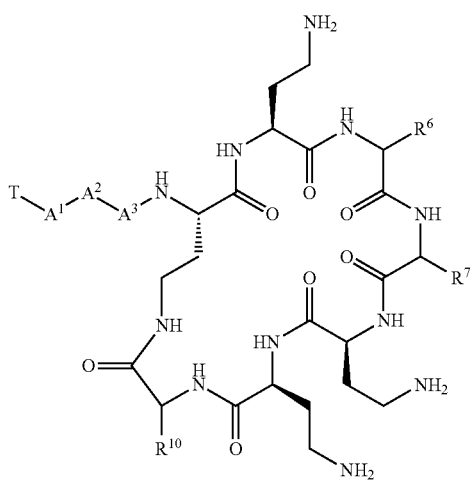

wherein:
-T is $R^T$—X—;
-$A^1$- is absent or is an amino acid residue;
-$A^2$- is an amino acid residue selected from threonine and serine, such as L-threonine and L-serine;
-$A^3$- is an amino acid residue represented by:

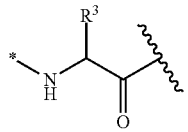

where the asterisk is the point of attachment to -$A^2$-, and —$R^3$ is $C_{1-6}$ alkyl, such as $C_{1-4}$, having one amino or one hydroxyl substituent;

—X— is —C(O)—, —NHC(O)—, —OC(O)—, —$CH_2$— or —$SO_2$—;

—$R^T$ is a terminal group containing hydroxyl and/or amino functionality, and where -$A^1$- is absent, $R^T$—X— is not an α-amino acid residue having a free α-amino group (—$NH_2$), for example where the amino acid is selected from the group consisting of Ala, Ser, Thr, Val, Leu, Ile, Pro, Phe, Tyr, Trp, His, Lys, Arg, α,γ-diaminobutyric acid (Dab) and α,β-diaminopropionic acid (Dap);

—$R^6$ together with the carbonyl group and nitrogen alpha to the carbon to which it is attached is an amino acid residue;

—$R^7$ together with the carbonyl group and nitrogen alpha to the carbon to which it is attached is an amino acid residue;

and —$R^6$ together with the carbonyl group and nitrogen alpha to the carbon to which it is attached is not a phenylalanine, leucine or valine residue and/or —$R^7$ together with the carbonyl group and nitrogen alpha to the carbon to which it is attached is not a leucine, iso-leucine, phenylalanine, threonine, valine or nor-valine residue;

$R^{10}$ together with the carbonyl group and nitrogen alpha to the carbon to which it is attached, is a threonine or leucine residue;

and salts, solvates, protected forms and/or prodrug forms thereof.

In one embodiment, the amino acid at position 6 is substituted with another amino acid.

In one embodiment, the amino acid at position 7 is substituted with another amino acid.

In one embodiment, where -$A^1$- is absent, $R^T$—X— is not an α-amino acid residue, and in particular an α-amino acid residue having a free α-amino group (—$NH_2$).

In one embodiment, where -$A^1$- is absent, $R^T$—X— is not an α-amino acid residue selected from the group consisting of Ala, Ser, Thr, Val, Leu, Ile, Pro, Phe, Tyr, Trp, His, Lys, Arg, α,γ-diaminobutyric acid (Dab) and α,β-diaminopropionic acid (Dap), where the α-amino acid has a free α-amino group (—$NH_2$).

In a second aspect of the invention, there is provided a compound of formula (II), and pharmaceutically acceptable salts and solvates thereof. The compound of formula (II) is represented thus:

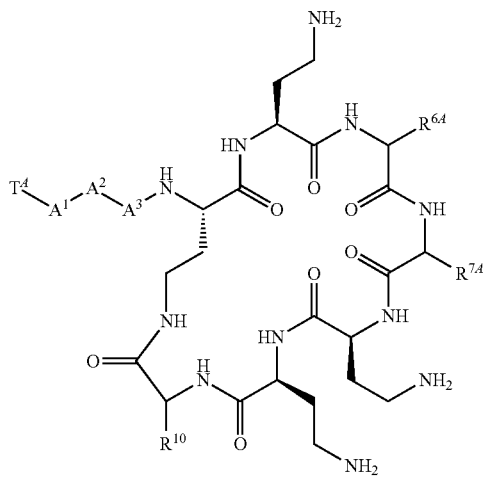

wherein:
-$T^A$ is hydrogen, $C_{1-4}$ alkyl or $R^N$—X—;
-$A^1$- is absent or is an amino acid residue;
-$A^2$- is absent or is an amino acid residue;
-$A^3$- is absent or is an amino acid residue;

—X— is —C(O)—, —NHC(O)—, —OC(O)—, —$CH_2$— or —$SO_2$—;

—$R^N$ is a terminal group, such as a group —$R^T$ as described herein;

—$R^{6A}$ is $C_{1-12}$ alkyl, $C_{0-12}$ alkyl($C_{3-10}$ cycloalkyl), $C_{0-12}$ alkyl($C_{3-10}$ heterocyclyl) or $C_{0-12}$ alkyl($C_{5-10}$ aryl), where the $C_{1-12}$ alkyl, $C_{3-10}$ cycloalkyl group $C_{3-10}$ heterocyclyl group, and the $C_{5-10}$ aryl group are optionally substituted, and the optional substituents are as described herein, and with the proviso that —$R^{6A}$ is not benzyl, iso-butyl, iso-propyl, and optionally —$R^{6A}$ is not methyl, phenyl, 4-hydroxyphenyl, (1H-indol-3-yl) methyl, 4-phenylphen-1-yl methyl, —$(CH_2)_7CH_3$, 4-(OBn)-phen-1-yl methyl or —$CH_2S(CH_2)_5CH_3$ —$R^{7A}$ together with the carbonyl group and nitrogen alpha to the carbon to which it is attached is an amino acid residue;

$R^{10}$ together with the carbonyl group and nitrogen alpha to the carbon to which it is attached, is a threonine or leucine residue;

and salts, solvates, protected forms and/or prodrug forms thereof.

In a third aspect the invention provides a pharmaceutical composition comprising a compound of formula (I) or formula (II) and a biologically acceptable excipient, optionally together with a second active agent.

In a fourth aspect there is provided a compound of formula (I) or formula (II) or a pharmaceutical composition comprising the compound of formula (I) or formula (II) for use in a method of treatment.

The invention additionally provides a compound of formula (I) or formula (II) or a pharmaceutical composition comprising the compound of formula (I) or formula (II) for use in a method of treating a microbial infection, such as a Gram-negative bacterial infection.

The present invention also provides a method of identifying useful combinations for therapy, the method comprising testing a combination of a compound of formula (I) or formula (II) with a biologically active compound and determining the biological efficacy of the combination, for example with comparison to the biologically active compound alone and/or the compound of formula (I) or formula (II).

In an alternative aspect, the compounds of formula (I) or formula (II) are suitable for use in the treatment of fungal infections, for example in combination together with an antifungal agent.

In a further aspect of the invention there is provided a polymyxin compound of formula (I) or formula (II) for use in a method of treatment or prophylaxis, in combination with an active agent.

Also provided are methods for preparing compounds of formula (I) and formula (II).

In one aspect of the invention there is provided a compound of formula (IV):

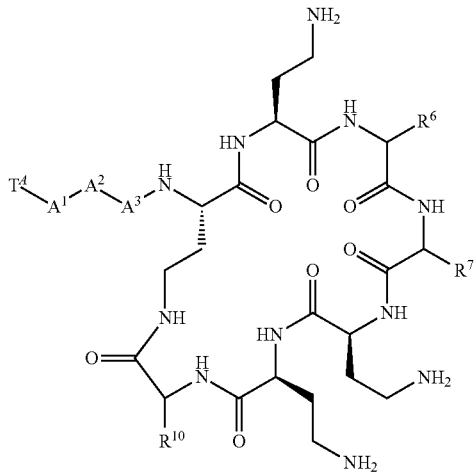

wherein:
-$T^4$ is hydrogen, $C_{1-4}$ alkyl or $R^N$—X—;
-$A^1$- is absent or is an amino acid residue;
-$A^2$- is absent or is an amino acid residue;
-$A^3$- is absent or is an amino acid residue;
—X— is —C(O)—, —NHC(O)—, —OC(O)—, —CH$_2$— or —SO$_2$—;
—$R^N$ is a terminal group, such as a group —$R^T$ as described herein;
—$R^6$ together with the carbonyl group and nitrogen alpha to the carbon to which it is attached is an amino acid residue;
—$R^7$ together with the carbonyl group and nitrogen alpha to the carbon to which it is attached is an amino acid residue; and one of —$R^6$ and —$R^7$ comprises a haloaryl group, such as a halophenyl group, such as a bromophenyl group;

$R^{10}$ together with the carbonyl group and nitrogen alpha to the carbon to which it is attached, is a threonine or leucine residue;
and salts, solvates, and/or protected forms thereof.

In one embodiment, one of one of —$R^6$ and —$R^7$ comprises a benzyl group, where the phenyl is substituted with halo, such as monosubstituted.

In one embodiment, one of —$R^6$ and —$R^7$ comprises a haloaryl group.

In one embodiment, one of —$R^6$ and —$R^7$, comprises a bromoaryl group.

Other aspects of the invention are discussed in detail herein.

DETAILED DESCRIPTION OF THE INVENTION

The present invention provides compounds of formula (I) and formula (II) for use in medical treatment, particularly in combination with a second agent.

Broadly, the compounds of formula (I) and formula (II) are polymyxin compounds carrying an amino acid substitution within the polypeptide core. The N terminal of the polymyxin compound is optionally modified.

In the compounds of formula (I) the amino acid at position 6 and/or the amino acid at position 7 is substituted with another amino acid. Thus, the amino acid residue at position 6 and/or position 7 is not an amino acid residue present in Polymyxin B or Colistin.

In the compounds of formula (II) the amino acid at position 6 is substituted with another amino acid, and optionally the amino acid at position 7 is also substituted. Thus, the amino acid residue at position 6 and optionally position 7 is not an amino acid residue present in Polymyxin B or Colistin.

In both compounds (I) and (II) the amino acids at one or more of positions 1, 2, 3, and 10 are optionally substituted with another amino acid. Thus, the amino acid residues at positions 1, 2, 3, and 10 may not be amino acid residues that are present in Polymyxin B or Colistin. The amino acids at positions 1, 2, and 3 may be optionally deleted.

The compound of formula (I) is a polymyxin compound having a modified N terminal. For example, the compound has an N terminal group that contains one, two or three hydroxyl groups and/or one, two or three amino groups. In addition to, or as an alternative to, the N terminal group has a nitrogen-containing heterocyclyl (or heterocyclylene) group and/or a nitrogen-containing heteroalkylene group. The N terminal group may be a substituted alkyl group or may be or include an optionally substituted aryl, cycloalkyl or heterocyclyl group. The presence of a hydroxyl group or a basic amino group within the terminal group is associated with particular advantages, as discussed below.

The compound of formula (II) is a compound where the N terminal is optionally modified. Where the N terminal is modified, the terminal groups may include those fatty acid groups that are found within the known polymyxin series of compounds, such as Polymyxin B and Colistin, and other polymyxin compounds reported in the art, such as those polymyxin derivatives described in WO 2012/168820, WO 2013/072695 and WO 2015/135976.

The N terminal group within the compounds of formula (II), where present, may be the same as the N terminal group within the compounds of formula (I).

The compounds of formula (I) and formula (II) may have comparable or improved biological activity compared to Polymyxin B or Colistin against one or more of E. coli, P.

*aeruginosa, K. pneumonia,* or *A. baumannii* bacterial strains. Such compounds are useful alternatives to the polymyxin type compounds previously described in the art.

Furthermore, the present inventors have found that each compound of formula (I) and formula (II) is active against a broad range of bacteria. In contrast the compounds previously described in the art have a varied profile of biological activity.

Some of the polymyxin compounds or polymyxin derivatives in the art are known or suspected to have a poor toxicity profile. For example, the use of compounds having a fatty acyl chain at the N terminal, such as Polymyxin B and Colistin, is associated with nephrotoxicity. The use of alternative N terminal group may therefore reduce toxicity. Thus, the compounds of formula (I) include hydroxyl and/or amino functionality which the inventors have shown is associated with a reduction in toxicity, especially a reduction in nephrotoxicity.

Vaara et al. (Antimicrob. Agents Chemother. 2008, 52, 3229) have suggested that the pharmacological and toxicity properties of a polymyxin compound may be altered with changes to the polymyxin polypeptide sequence. In particular, Vaara et al. have prepared a polymyxin compound having only three positive charges, whereas the polymyxin B nonapeptide carries five positive charges.

In contrast the present inventors have shown that adaptations to the N terminal of a polymyxin compound may reduce nephrotoxicity. As described herein, the N terminal has a substituent containing a hydroxyl group or an amino group (which may be in the form of a nitrogen-containing heterocycle).

Furthermore, the compounds of formula (I) and formula (II) are believed to be capable of increasing the antimicrobial activity of a second antimicrobial agent, such as rifampicin. Such combinations may have comparable or improved biological activity compared to the combination of the second agent with Polymyxin B or Colistin, for example against one or more of *E. coli, P. aeruginosa, K. pneumonia,* or *A. baumannii* strains. For example, compounds of formula (I) and formula (II) may have comparable biological activity compared to Polymyxin B or Colistin against one or more of *E. coli, P. aeruginosa, K. pneumonia,* or *A. baumannii* strains.

Polymyxin Compounds of Formula (I)

The compounds of formula (I) are variants of Polymyxin B and are also N-terminal derivatives of the polymyxin series of compounds. The core of the compound of formula (I) is a variant of a polymyxin compound, such as a variant of the polymyxin B decapeptide, nonapeptide (PMBN, Polymyxin 2-10), octapeptide or heptapeptide, where the amino acid at position 6 and/or position 7 is substituted with another amino acid as described herein, and optionally the amino acid residues at positions 1, 2, 3 and 10 are substituted with another amino acid residue. Optionally the amino acid residue at position 1 (-A$^1$-) may be deleted.

Further, the present inventors have also established that the group attached to the N terminal of a polymyxin nonapeptide is an important determinant of biological activity and compound toxicity. The inventors have identified certain N terminal substituent groups that show enhanced activity and/or exhibit less toxicity compared to Polymyxin B or Colistin, for example as measured against HK-2 cells. The activity is associated with the presence of amino functionality at specific locations within the N terminal group. Further improvements in activity are also found where certain substituents are present in the N terminal group, and the chiral centres in the terminal group have a specific stereochemistry.

The inventors' earlier work relating to N terminal groups is included in the present application for useful support to the present invention. Whilst the present invention is primarily focused on new substitutions at positions 6 and 7 of the polymyxin core, the variant polypeptide core may be used together with the N terminal group modifications described in the inventors' earlier work, such as described in WO 2013/072695, PCT/GB2014/051547 (published as WO 2014/188178) and GB 1404301.2, and most particularly as described in PCT/GB2014/051547 and in GB 1404301.2.

The variant polypeptide core may be used together with the N terminal group modifications described in the inventors' earlier work, such as described in WO 2015/135976, which claims priority to GB 1404301.2. Thus, the group —R$^{15}$ described in WO 2015/135976 may be used as a group —R$^T$ in the present case.

Substitutions and deletions within the polypeptide sequence of the polymyxin compounds are known.

For example, the presence of the Dab amino acid residue at position 1 of Polymyxin B was not believed to be important for activity, and this amino acid is often absent from polymyxin derivatives described in the prior art. See, for example, WO 2008/017734 and WO 2009/098357, where the amino acid residue at position 1 is absent. Similarly, Okimura et al. dispense with the amino acid residue at position 1, providing instead an aminocyclohexylcarbonyl substituent at the N terminal of the amino acid residue at position 2.

The present inventors have also described polymyxin nonapeptide forms where the amino acid residue at position 1 is absent, and the N terminal of the amino acid reside at position 2 is modified. See, for example, WO 2013/072695.

WO 2012/168820 describes the substitution of the (S)-Dab amino acid residue at position 3 of Polymyxin B with (S)-Dap. The authors explain that this substitution provides compounds having reduced cytotoxicity in human renal cells and improved antibacterial activity, for example against *P. aeruginosa, K. pneumonia,* and/or *A. Baumannii.*

WO 2012/168820 suggests that other positions in the polymyxin polypeptide sequence may be modified, such as at positions 6 and 7.

Substitutions and deletions of the amino acids at positions 1, 2 and 3 are also described. The work in WO 2008/017734 and WO 2009/098357 describes the changes in biological activity that are associated with the changes in the amino acid residues at positions 1, 2 and 3.

The present invention provides a compound of formula (I) and the use of this compound in a method of treatment. The compound of formula (I) is represented thus:

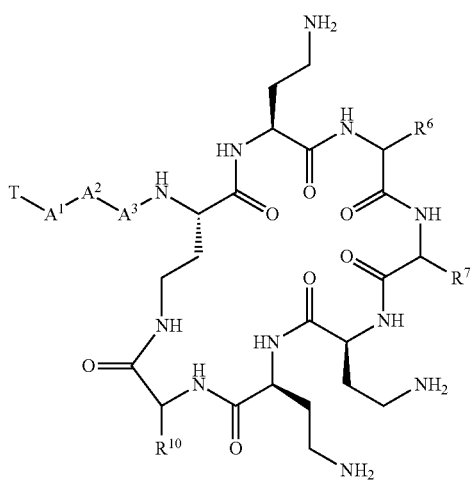

wherein:
-T is $R^T$—X—;
-$A^1$- is absent or is an amino acid residue;
-$A^2$- is an amino acid residue selected from threonine and serine, such as L-threonine and L-serine;
-$A^3$- is an amino acid residue represented by:

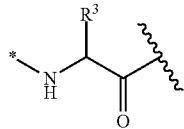

where the asterisk is the point of attachment to -$A^2$-, and —$R^3$ is $C_{1-6}$ alkyl, such as $C_{1-4}$, having one amino or one hydroxyl substituent;

—X— is —C(O)—, —NHC(O)—, —OC(O)—, —$CH_2$— or —$SO_2$—;

—$R^T$ is a terminal group containing hydroxyl and/or amino functionality, and where -$A^1$- is absent, $R^T$—X— is not an α-amino acid residue having a free α-amino group (—$NH_2$), for example where the α-amino acid residue is selected from the group consisting of Ala, Ser, Thr, Val, Leu, Ile, Pro, Phe, Tyr, Trp, His, Lys, Arg, α,γ-diaminobutyric acid (Dab) and α,β-diaminopropionic acid (Dap);

—$R^6$ together with the carbonyl group and nitrogen alpha to the carbon to which it is attached is an amino acid residue;

—$R^7$ together with the carbonyl group and nitrogen alpha to the carbon to which it is attached is an amino acid residue;

and —$R^6$ together with the carbonyl group and nitrogen alpha to the carbon to which it is attached is not a phenylalanine, leucine or valine residue and/or —$R^7$ together with the carbonyl group and nitrogen alpha to the carbon to which it is attached is not a leucine, iso-leucine, phenylalanine, threonine, valine or nor-valine residue;

$R^{10}$ together with the carbonyl group and nitrogen alpha to the carbon to which it is attached, is a threonine or leucine residue;

and salts, solvates, protected forms and/or prodrug forms thereof.

—$R^6$ and —$R^7$

In one embodiment, —$R^6$ together with the carbonyl group and nitrogen alpha to the carbon to which it is attached is a phenylalanine, leucine or valine residue. In this embodiment, the group —$R^7$ together with the carbonyl group and nitrogen alpha to the carbon to which it is attached is not a leucine, iso-leucine, phenylalanine, threonine, valine or nor-valine residue.

In one embodiment, —$R^6$ together with the carbonyl group and nitrogen alpha to the carbon to which it is attached is not a phenylalanine, leucine or valine residue. Additionally or alternatively, —$R^6$ together with the carbonyl group and nitrogen alpha to the carbon to which it is attached is not an alanine, tyrosine, tryptophan or phenylglycine residue.

Thus, the amino acid residue present at the 6-position may be regarded as a replacement to the amino acid residues at that position of the polymyxin core.

In one embodiment, —$R^7$ together with the carbonyl group and nitrogen alpha to the carbon to which it is attached is a leucine, iso-leucine, phenylalanine, threonine, valine or nor-valine residue. In this embodiment, —$R^6$ together with the carbonyl group and nitrogen alpha to the carbon to which it is attached is not a phenylalanine, leucine or valine residue.

In one embodiment, —$R^7$ together with the carbonyl group and nitrogen alpha to the carbon to which it is attached, is an α-amino acid residue, such as a proteinogenic amino acid residue, so long as the amino acid residue is not a leucine, iso-leucine, phenylalanine, threonine, valine or nor-valine residue.

In one embodiment, —$R^6$ together with the carbonyl group and nitrogen alpha to the carbon to which it is attached, is an α-amino acid residue, such as a proteinogenic amino acid residue, so long as the amino acid residue is not a phenylalanine, leucine or valine residue.

In one embodiment, —$R^6$ together with the carbonyl group and nitrogen alpha to the carbon to which it is attached, is an amino acid residue selected from the group consisting of Leu, OctGly, BipAla, Tyr, norvaline, and norleucine, and for example the D-forms thereof.

In one embodiment, —$R^7$ together with the carbonyl group and nitrogen alpha to the carbon to which it is attached in an amino acid residue selected from the group consisting of leucine, OctGly, BipAla, Cys(S-Hex) and Cys(S-Bzl), and for example the L-forms thereof. Additionally or alternatively, —$R^7$ together with the carbonyl group and nitrogen alpha to the carbon to which it is attached in an amino acid residue selected from the group consisting of alanine, threonine, serine, valine, 2-aminobutyric acid (Abu) and 2-aminoisobutyric acid (Aib), and for example the L-forms thereof.

Alternatively, —$R^7$ together with the carbonyl group and nitrogen alpha to the carbon to which it is attached in an amino acid residue selected from the group consisting of alanine, phenylalanine, threonine, serine, valine, 2-aminobutyric acid (Abu) and 2-aminoisobutyric acid (Aib), and for example the L-forms thereof.

In one embodiment, —$R^7$ together with the carbonyl group and nitrogen alpha to the carbon to which it is attached is a leucine residue, such as L-leucine. In this embodiment, the amino acid residue at the 7-position is not substituted with reference to the amino acid residue at the 7-position of Polymyxin B.

In one embodiment, the α-amino acid residue at position 6 or position 7 is not a proteinogenic amino acid residue.

In one embodiment, the α-amino acid residue does not contain hydroxyl (—OH) or amino (—$NH_2$) functionality in its side chain (i.e. the group —$R^6$ does not contain a hydroxyl group or an amino group). Optionally, the α-amino acid residue does not contain thiol (—SH) functionality in its side chain (i.e. the group —$R^6$ does not contain a thiol group).

In one embodiment, the amino acid residue at position 6 is an L- or D-amino acid residue, such as a D-amino acid residue. In one embodiment, the amino acid residue at position 7 is an L- or D-amino acid residue, such as an L-amino acid residue.

Where position 6 has a D-amino acid residue and position 7 has an L-amino acid residue, the structure of the compound of formula (I) is:

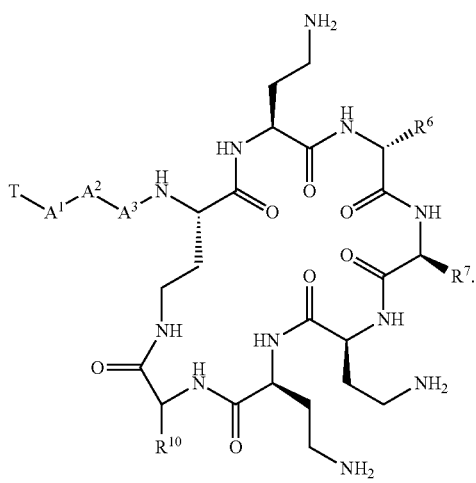

In one embodiment, the compound of formula (I) is the compound as shown above.

In one embodiment, a group —$R^6$ or a group —$R^7$ is a group —$R^{6A}$ as defined below.

For example, in one embodiment, —$R^6$ and/or —$R^7$ is $C_{1-12}$ alkyl, $C_{0-12}$ alkyl($C_{3-10}$ cycloalkyl), $C_{0-12}$ alkyl ($C_{3-10}$ heterocyclyl) or $C_{0-12}$ alkyl($C_{5-10}$ aryl), where the $C_{1-12}$ alkyl, $C_{3-10}$ cycloalkyl group $C_{3-10}$ heterocyclyl group, and the $C_{5-10}$ carboaryl group are optionally substituted.

In one embodiment, the group —$R^6$ is not benzyl, iso-butyl or iso-propyl (the residue at position 6 may not be phenylalanine, leucine or valine).

In one embodiment, the group —$R^6$ is not 4-phenylphen-1-yl methyl or —$CH_2S(CH_2)_5CH_3$.

The $C_{1-12}$ alkyl group, $C_{3-10}$ cycloalkyl group, $C_{3-10}$ heterocyclyl group, and the $C_{5-10}$ aryl group may be substituted with one or more groups —$R^Z$, where each group —$R^Z$ is selected from halo, optionally substituted $C_{1-12}$ alkyl, optionally substituted $C_{2-12}$ alkenyl, optionally substituted $C_{2-12}$ alkynyl, optionally substituted $C_{3-10}$ cycloalkyl, optionally substituted $C_{3-10}$ heterocyclyl, optionally substituted $C_{5-12}$ aryl, —CN, —$NO_2$, —$OR^Q$, —$SR^Q$, —N($R^W$)C(O)$R^Q$, —N($R^Q$)$_2$, and —C(O)N($R^Q$)$_2$, where —$R^W$ is H or $C_{1-4}$ alkyl; and —$R^Q$ is H or —$R^{Q1}$, and —$R^{Q1}$ is selected from optionally substituted $C_{1-12}$ alkyl, $C_{2-12}$ alkenyl, $C_{2-12}$ alkynyl, and $C_{5-12}$ aryl, and in a group —N($R^Q$)$_2$ the groups —$R^Q$ may together with the nitrogen atom to which they are attached form a $C_{5-6}$ heterocycle, where the heterocycle is optionally substituted, with the proviso that $C_{1-12}$ alkyl is not substituted with alkyl, alkenyl or alkynyl.

In one embodiment, —$R^6$ and/or —$R^7$ is optionally substituted $C_{1-12}$ alkyl.

In one embodiment, —$R^6$ and/or —$R^7$ is optionally substituted $C_{1-12}$ alkyl, where the $C_{1-12}$ alkyl is optionally substituted with one or more groups selected from halo, such as fluoro, optionally substituted $C_{3-10}$ cycloalkyl, optionally substituted $C_{3-10}$ heterocyclyl, optionally substituted $C_{5-12}$ aryl, —CN, —$NO_2$, —$OR^Q$, —$SR^Q$, —N($R^W$)C(O)$R^Q$, —N($R^Q$)$_2$, and —C(O)N($R^Q$)$_2$.

An alkyl group is typically a $C_{1-12}$ alkyl group, such as $C_{2-12}$ alkyl, such as $C_{4-12}$ alkyl, such as $C_{5-12}$ alkyl, such as $C_{6-12}$ alkyl, such as $C_{8-12}$ alkyl, for example $C_{2-10}$ alkyl, $C_{4-10}$ alkyl, $C_{5-10}$ alkyl and $C_{6-10}$ alkyl.

Additionally or alternatively, an alkyl group may be $C_{3-12}$ alkyl, such as $C_{3-10}$ alkyl.

The alkyl group may be linear or branched.

Where the alkyl group is substituted, it may be monosubstituted. A substituent may be provided at a terminal of the alkyl group.

In one embodiment, —$R^6$ and/or —$R^7$ is $C_{1-12}$ alkyl substituted with alkylthio or arylalkylthio. Compounds containing an amino acid residue at position 7 with this functionality are described by Velkov et al.

In one embodiment, —$R^6$ and/or —$R^7$ is $C_{1-12}$ alkyl substituted with alkylthio, such as $C_{1-12}$ alkylthio.

In one embodiment, the alkylthio is $C_6$ alkylthio.

In one embodiment, —$R^6$ and/or —$R^7$ is arylalkylthio, such as $C_{5-10}$ aryl-$C_{1-12}$ alkylthio, such as phenyl-$C_{1-12}$ alkylthio, such as phenyl-$C_{1-12}$ alkylthio.

In one embodiment, the arylalkylthio is benzylthio ($PhCH_2S$—).

In one embodiment, —$R^7$ is $C_3$ or $C_4$ alkyl.

In one embodiment, —$R^7$ is n-propyl.

A $C_{0-12}$ alkyl group, such as present in the groups $C_{0-12}$ alkyl($C_{3-10}$ cycloalkyl), $C_{0-12}$ alkyl($C_{3-10}$ heterocyclyl) and $C_{0-12}$ alkyl($C_{5-10}$ aryl), may be a $C_{1-12}$ alkyl group. References to an alkyl group here are understood to refer to an alkylene linker.

A $C_{0-12}$ alkyl group may be $C_{1-12}$ alkyl, such as $C_{1-6}$ alkyl, such as $C_{1-4}$ alkyl, such as $C_{1-2}$ alkyl, such as —$CH_2$— and —$CH_1CH_2$—, such as —$CH_2$—.

A $C_{0-12}$ alkyl group may be $C_{1-12}$ alkyl such as $C_{6-12}$ alkyl, such as $C_{6-10}$ alkyl.

The $C_{0-12}$ alkyl group may be absent i.e. $C_{0-12}$ alkyl group may be $C_0$.

In one embodiment, —$R^6$ and/or —$R^7$ is $C_{0-12}$ alkyl($C_{3-10}$ cycloalkyl), where the $C_{3-10}$ cycloalkyl is optionally substituted.

The $C_{3-10}$ cycloalkyl may be a $C_{5-7}$ cycloalkyl group, such as $C_{5-6}$ cycloalkyl group.

In one embodiment, $C_{3-10}$ cycloalkyl is cyclopentyl or cyclohexyl, such as cyclohexyl.

A cycloalkyl group may be optionally substituted, such as optionally monosubstituted.

Where, the cycloalkyl group is cyclohexyl, the cyclohexyl is optionally substituted at the 2- or 4-position, such as the 4-position.

In one embodiment, —$R^6$ and/or —$R^7$ is $C_1$ alkyl($C_6$ cycloalkyl). Here, the amino acid residue formed from —$R^6$ and/or —$R^7$ together with the carbonyl group and nitrogen alpha to the carbon to which it is attached may be referred to as cyclohexylalanine.

In one embodiment, —$R^7$ is cyclohexyl ($C_6$ cycloalkyl). Here, the amino acid residue formed from —$R^7$ together with the carbonyl group and nitrogen alpha to the carbon to which it is attached may be referred to as cyclohexylglycine.

In one embodiment, —$R^6$ is $C_1$ alkyl($C_6$ cycloalkyl).

In one embodiment, —$R^7$ is $C_1$ alkyl($C_6$ cycloalkyl).

In one embodiment, —$R^6$ and/or —$R^7$ is not —$(CH_2)_4$-cyclohexyl.

In one embodiment, —R⁶ and/or —R⁷ is not —(C₆H₁₀)—Pr, such as where the —Pr group is a linear propyl group.

In one embodiment, —R⁶ and/or —R⁷ is C₀₋₁₂ alkyl(C₅₋₁₀ aryl), where the C₅₋₁₀ aryl is optionally substituted.

It is preferred that an aryl group, where present, is a carboaryl group. The inventors have found that the carboaryl is associated with an increase antimicrobial effect compared with heteroaryl functionality.

In one embodiment, —R⁶ and/or —R⁷ is substituted C₀₋₁₂ alkyl(C₅₋₁₀ aryl).

In one embodiment, —R⁶ and/or —R⁷ is substituted benzyl (—CH₂Ph). The benzyl group may be substituted on the phenyl ring, such as only on the phenyl ring.

In one embodiment, —R⁶ and/or —R⁷ is monosubstituted benzyl.

In one embodiment, —R⁶ and/or —R⁷ is monosubstituted benzyl, where the phenyl group is substituted at the 2-, 3- or 4-position, such as the 2- or 4-position, such as the 4-position.

As noted above, $C_{1-12}$ alkyl group, $C_{3-10}$ cycloalkyl group, $C_{3-10}$ heterocyclyl group, and the $C_{5-10}$ aryl group may be substituted with one or more groups —$R^Z$. Examples of —R⁷ include optionally substituted alkyl, alkenyl, alkynyl, cycloalkyl, aryl and heterocycle groups.

Where a group, such as alkyl, alkenyl, alkynyl, cycloalkyl, aryl and heterocycle, is optionally substituted, the group may have one or more substituent groups selected from halo, haloalkyl, alkyl, alkenyl, alkynyl, and aryl, except that alkyl alkenyl, and alkynyl groups are not substituents to the alkyl alkenyl, and alkynyl groups.

The optional substituents may include groups such as —$OR^Q$, —$SR^Q$, —$N(R^W)C(O)R^Q$, —$N(R^Q)_2$, and —$C(O)N(R^Q)_2$.

In one embodiment, each —$R^Q$ is —$R^{Q1}$. Thus, hydroxyl (—OH) and primary amino functionality (—NH₂) is not present.

An aryl group may be a carboaryl group, such as $C_{6-10}$ carboaryl, or a heteroaryl group, such as $C_{5-10}$ heteroaryl.

In one embodiment, a reference to aryl is a reference to phenyl.

A haloalkyl group is an alkyl group, such as described above, having one or more halo substituents. The haloalkyl group may be a perhaloalkyl group. In one embodiment, a haloalkyl group is —CF₃.

An alkenyl group is typically a $C_{2-12}$ alkenyl, such as $C_{4-12}$ alkenyl, such as $C_{5-12}$ alkenyl, such as $C_{6-12}$ alkenyl, for example $C_{2-10}$ alkenyl, $C_{4-10}$ alkenyl, $C_{6-10}$ alkenyl and $C_{6-10}$ alkenyl.

An alkynyl group is typically a $C_{2-12}$ alkynyl, such as $C_{4-12}$ alkynyl, such as $C_{6-12}$ alkynyl, such as $C_{6-12}$ alkynyl, for example $C_{2-10}$ alkynyl, $C_{4-10}$ alkynyl, $C_{5-10}$ alkynyl and $C_{6-10}$ alkynyl.

An alkyl, alkenyl or alkynyl group may be a linear or branched group.

In one embodiment, the alkyl, alkenyl or alkynyl group is unsubstituted.

A cycloalkyl group is typically $C_{3-10}$ cycloalkyl may be a $C_{5-7}$ cycloalkyl group, such as $C_{5-6}$ cycloalkyl group.

In one embodiment, $C_{3-10}$ cycloalkyl is cyclopentyl or cyclohexyl, such as cyclohexyl.

A group —$R^Z$ may be halo, such as bromo.

A group —$R^Z$ may be alkyl, such as $C_{1-12}$ alkyl, such as $C_{2-12}$ alkyl, such as $C_{4-12}$ alkyl, such as $C_{5-12}$ alkyl, such as $C_{6-12}$ alkyl, for example $C_{2-10}$ alkyl, $C_{4-10}$ alkyl, $C_{5-10}$ alkyl and $C_{6-10}$ alkyl.

The alkyl group may be a linear or branched alkyl group.

A group —$R^Z$ may be aryl, such as carboaryl, such as $C_{6-10}$ carboaryl, or heteroaryl, such as $C_{5-10}$ heteroaryl. A group —$R^Z$ may be phenyl. The aryl group may be substituted with one or more, such as one, substituent groups. In one embodiment, the aryl group is substituted with halo, haloalkyl, alkyl and aryl.

In one embodiment, —R⁶ and/or —R⁷ is benzyl, where the phenyl group is substituted at the 2- or 4-position, such as the 4-position, with phenyl (i.e. forming a biphenyl group).

In one embodiment, —R⁶ and/or —R⁷ is benzyl, where the phenyl group is substituted at the 2- or 4-position, such as the 4-position, with alkyl, such as $C_{1-12}$ alkyl.

In one embodiment, —R⁶ and/or —R⁷ is benzyl, where the phenyl group is substituted at the 2-, 3- or 4-position, such as the 2- or 4-position, such as the 4-position, with halo, such as bromo.

In one embodiment, —R⁶ and/or —R⁷ is benzyl, where the phenyl group is substituted at the 2- or 4-position, such as the 4-position, with cycloalkyl, such as $C_6$ cycloalkyl.

In one embodiment, —R⁶ and/or —R⁷ is not 4-hydroxyphenylmethyl (i.e. —R⁶ together with the carbonyl group and nitrogen alpha to the carbon to which it is attached is not a tyrosine residue).

The comments above refer to compounds where the a amino acid residue at position 6 or position 7 has an α carbon atom that is substituted with —R⁶ and —H, or —R⁷ and —H. The —H may also be a site for substitution, providing di-substituted α amino acid residues at position 6 and/or position 7.

In an alternative embodiment, the α carbon atom within the α amino acid residue at position 6 and/or position 7 is di-substituted, where each substituent is a group —R⁶ or —R⁷ as described herein.

In an alternative embodiment, the a carbon atom within the a amino acid residue at position 6 and/or 7 is di-substituted, where each substituent is a group —R⁶ or —R⁷ as appropriate, where the groups —R⁶ may together with the a carbon atom to which they are attached form a $C_{4-6}$ carbocycle or a $C_{5-6}$ heterocycle, and/or the groups —R⁷ may together with the α carbon atom to which they are attached form a $C_{4-6}$ carbocycle or a $C_{5-6}$ heterocycle, wherein the carbocycle and the heterocycle are optionally substituted with one or more groups —$R^Z$, as described above. The carbocycle is a cycloalkyl group as described herein. The heterocycle is a heterocyclyl group as described herein.

Where a heterocycle is present the heteroatom of the heterocyclyl group is not provided at the β position (i.e. the heteroatom is not connected to the α carbon).

The heterocycle contains a heteroatom selected from N, O and S, and optionally contains further heteroatoms. A reference to N is a reference to a group —NH— within a heterocycle, and a reference to S is —S—, —S(O)— or —S(O)₂—.

In one embodiment, —R⁶ and/or —R⁷ together with the carbonyl group and nitrogen alpha to the carbon to which it is attached is an amino having a piperidine side chain that is a gem di-substituent to the α-carbon. Thus the α-carbon is a ring atom in the piperidine ring. This is a cyclic analogue of Dab.

—R¹⁰

The —R¹⁰ position corresponds to amino acid position 10 in the polymyxin compounds.

In one embodiment —R¹⁰ together with the carbonyl group and nitrogen alpha to the carbon to which it is attached is a threonine residue, such as L-threonine.

-A$^1$-, -A$^2$- and -A$^3$-

In one embodiment, -A$^1$- is absent, and -A$^2$- and -A$^3$- are present. Such a compound may be referred to as a nonapeptide. Nonapeptide forms of Polymyxin B and E are well known in the art.

In one embodiment, -A$^1$-, -A$^2$- and -A$^3$- are present. Such a compound may be referred to as a decapeptide, and are based on, for example, deacylated decapeptide forms of Polymyxin B, E and M. Deacylated forms of Polymyxin B, E and M are well known in the art. Alternative decapeptides may be prepared from a nonapeptide or heptapeptide by appropriate coupling of an amino acid/s to the N terminal of the nonapeptide or heptapeptide. It is noted that the deacylated form Polymyxin M would appear to be identical to that reported for Polymyxin A by Cubist (see WO 2010/075416 and U.S. Pat. No. 8,415,307).

It is noted that the compounds of the invention differ from Polymyxin B, E and M, and their deacylated forms, for at least the reason that the amino acid residue at position 6 and/or position 7 differs from the amino acid residue present in Polymyxin B, E and M.

The compounds of the invention, such as the compounds of formula (I) may also differ from Polymyxin B, E and M in the nature of the N terminal group. Polymyxins B, E and M have an fatty acid (fatty acyl) group at the N terminal. In contrast, the compounds of formula (I) have a terminal group with hydroxyl and/or amino functionality.

The group -A$^1$- may be an α-amino acid.

A reference to an α-amino acid includes proteinogenic ("natural") α-amino acids, optionally together with other α-amino acids.

Examples of α-amino acids that are not proteinogenic are those amino acids generated by post-translational modification, or by other means. Examples include Dab, Dap, Dgp (α,β-diguanidinopropanoyl), ornithine and nor-valine.

Also included are amino having a piperidine side chain that is a gem di-substituent to the α-carbon. Thus the α-carbon is a ring atom in the piperidine ring. This is a cyclic analogue of Dab.

In one embodiment, -A$^1$- is an amino acid residue.
In one embodiment, -A$^1$- is an α-amino acid residue.
In one embodiment, -A$^1$- is an amino acid selected from the group consisting of Lys, Arg, Dap, Ser, Thr, Ile, Tyr, His, Phe, Pro, Trp, Leu, Ala, Dab, Dap, Dgp (α,β-diguanidino-propanoyl), ornithine and nor-valine, including L- and D-forms thereof.

In one embodiment, -A$^1$- is an amino acid selected from the group consisting of Dab, Pro, Dap, Gly, Ser, His, Phe, Arg, Tyr, and Leu, including L- and D-forms thereof.

In one embodiment, -A$^1$- is a D α-amino acid.
In one embodiment, -A$^1$- is an L α-amino acid.
In one embodiment, -A$^1$- is a β-amino acid.

The compounds of the invention where -A$^1$- is an amino acid may be prepared from deacylated forms by appropriate derivatisation of the N terminal.

In one embodiment, -A$^1$- is selected from Lys, Arg, Dap, Ser, Phe, Trp, Leu, Ala, Dab, Dap, ornithine or nor-valine, including L- and D-forms thereof.

In one embodiment, -A$^1$- is selected from Thr, Ser, Lys, Dab or Dap, for example L-Thr, L-Ser, L-Lys, L-Dab or L-Dap.

In one embodiment, -A$^1$- is Dab, such as L-Dab.

In an alternative embodiment, where -A$^1$- is an amino acid it is not Dab, for example it is not L-Dab.

In one embodiment, -A$^2$- is an amino acid residue selected from threonine and serine, such as L-threonine and L-serine.

In one embodiment, -A$^3$- is an amino acid residue represented by:

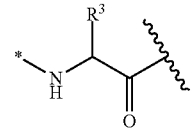

where the asterisk is the point of attachment to -A$^2$-, and —R$^3$ is C$_{1-6}$ alkyl, such as C$_{1-4}$ alkyl, having one amino or one hydroxyl substituent. The amino acid residue may be an L-form.

In one embodiment, —R$^3$ has one amino substituent.
In one embodiment, —R$^3$ has one hydroxyl substituent.
The amino group may be —NH$_2$, —NHMe or —NHEt. In one embodiment, the amino group is —NH$_2$.

In one embodiment, —R$^3$ together with the carbonyl group and nitrogen alpha to the carbon to which it is attached, is α,γ-diaminobutyric acid (Dab), a serine residue, a threonine residue, a lysine residue, an ornithine residue, or α,β-diaminopropionic acid (Dap).

In one embodiment, —R$^3$ together with the carbonyl group and nitrogen alpha to the carbon to which it is attached, is α,γ-diaminobutyric acid (Dab), a serine residue, a lysine residue, or α,β-diaminopropionic acid (Dap).

In one embodiment, —R$^3$ together with the carbonyl group and nitrogen alpha to the carbon to which it is attached, is α,γ-diaminobutyric acid (Dab) or α,β-diaminopropionic acid (Dap), such as L-Dab or L-Dap.

In one embodiment, —R$^3$ together with the carbonyl group and nitrogen alpha to the carbon to which it is attached, is α,γ-diaminobutyric acid (Dab) or α,β-diaminopropionic acid (Dap), such as L-Dab or L-Dap.

In one embodiment, —R$^3$ together with the carbonyl group and nitrogen alpha to the carbon to which it is attached, is a lysine residue, such as L-Lys.

In one embodiment, —R$^3$ together with the carbonyl group and nitrogen alpha to the carbon to which it is attached, is Dab, such as L-Dab.

Compounds of the invention where —R$^3$ is a Dab side chain are obtainable from compounds such as Polymyxin B. Compounds where —R$^3$ is a Dap side chain may be prepared using the methods described in WO 2012/168820. Compounds where —R$^3$ is a serine side chain may be prepared using the methods described by Vaara et al. (see, for example, *Antimicrob. Agents Chemother.* 2008, 52, 3229).

—X—

The group —X— may be selected from —NHC(O)—, —C(O)—, —OC(O)—, —CH$_2$— and —SO$_2$—.

In one embodiment —X— is selected from —C(O)—, —SO$_2$— and —CH$_2$—.

In one embodiment —X— is —C(O)—.
In one embodiment —X— is —SO$_2$—.
In one embodiment —X— is —CH$_2$—.

The right-hand side of the group —X— is the point of attachment to NH, the amino terminal of an amino acid residue, such as -A$^1$-, -A$^2$- or -A$^3$-. The left-hand side of the group —X— is the point of attachment to a group such as —R$^T$ (or —R$^N$ for the compounds of formula (II).

—R$^7$

The group —R$^T$ together with —X— is an N terminal modification of the polymyxin. The group —R$^T$ contains hydroxyl and/or amino functionality.

In one embodiment, $R^T$—X— is not an α-amino acid residue, and specifically $R^T$—X— is not an α-amino acid residue having a free amine N terminal i.e. a group —$NH_2$ that is attached to the α carbon of the amino acid residue. For example, $R^T$—X— is not an α-amino acid residue when -$A^1$- is absent. In one embodiment, $R^T$—X— is not an α-amino acid residue when -$A^1$- is present. The amino acid may be selected from the group consisting of Ala, Ser, Thr, Val, Leu, Ile, Pro, Phe, Tyr, Trp, His, Lys, Arg, α,γ-diaminobutyric acid (Dab) and α,β-diaminopropionic acid (Dap).

The group —$R^T$ may contain one, two or three hydroxyl groups, —OH.

The group —$R^T$ may contain one, two or three amino groups, —$NR^AR^B$, where each —$R^A$ is independently hydrogen or $C_{1-4}$ alkyl, each —$R^B$ is independently hydrogen or $C_{1-4}$ alkyl, or —$NR^AR^B$ is a guanidine group.

The group —$R^T$ may contain one, two or three amino groups, where such amino groups are present within a nitrogen-containing heterocycle, such as azetidine, pyrrolidinyl, piperidinyl, piperazinyl or morpholinyl, or a nitrogen-containing heteroalkyl group.

The group —$R^T$ may contain both hydroxyl and amino functionality.

In one embodiment, —$R^T$ is not amino-substituted cyclohexyl, for example when —X— is —C(O)—.

The compounds of formula (I) do not encompass the deacylated versions of Polymyxin B (Deacylpolymyxin B-DAPB), D, E (Deacylcolistin-DAC) or M, or Circulin A. The compounds of formula (I) do not encompass the nonapeptide versions of Polymyxin B (PMBN), D, E or M, or Circulin A.

In one embodiment, $R^T$—X— is not an α-amino acid residue. An α-amino acid residue is a group where —X— is —C(O)— and —$R^T$ has a group —$NR^AR^B$ (such as —$NH_2$) as a substituent to the carbon atom that is α to the group —X—.

A reference to an α-amino acid may be a reference to a proteinogenic ("natural") α-amino acid, optionally together with other α-amino acids.

Examples of α-amino acids that are not proteinogenic are those amino acids generated by post-translational modification, or by other means. Examples include Dab, Dap, Dgp (α,β-diguanidinopropanoyl), ornithine and nor-valine.

In one embodiment, $R^T$—X— is not Thr, Ser, α,γ-diaminobutyric acid (Dab) or α,β-diaminopropionic acid (Dap) residues.

In one embodiment, for example where the core of the compound of formula (I) is Polymyxin B, $R^T$—X— is not a Lys, Arg, Dap, Ser, Phe, Trp, Leu or Ala residue.

In one embodiment, $R^T$—X— is not a Lys, Arg, Dap, Ser, Phe, Trp, Leu, Ala, Glu, α,γ-diaminobutyric acid (Dab) or α,β-diaminopropionic acid (Dap) residue.

In one embodiment, $R^T$—X— is not an Ala, Ser, Thr, Val, Leu, Ile, Pro, Phe, Tyr, Trp, His, Lys, Glu, or Arg residue.

In one embodiment, $R^T$—X— is not an Ala, Ser, Thr, Val, Leu, Ile, Pro, Phe, Tyr, Trp, His, Lys, Glu, Arg, α,γ-diaminobutyric acid (Dab) or α,β-diaminopropionic acid (Dap) residue.

In one embodiment, $R^T$—X— is not a proteinogenic ("natural") α-amino acid residue or a α,γ-diaminobutyric acid (Dab) or α,β-diaminopropionic acid (Dap) residue.

References to the amino acids above, may be a reference to the L- or D-form, such as the L-form.

In one embodiment, —$R^T$ is not diaminophenyl, such as 3,5-diaminophenyl, for example when —X— is —C(O)—.

Examples of —$R^T$

The present inventors have previously described the modification of the N terminal group of polymyxin nonapeptide compounds, such as N terminal modifications to PMBN.

This work is described in WO 2013/072695, the contents of which are hereby incorporated by reference in their entirety.

The group —$R^T$ may be additionally or alternatively selected from the N terminal groups of PCT/GB2014/051547 and/or GB 1404301.2, the contents of which are hereby incorporated by reference in their entirety.

In one embodiment, —$R^T$ is not a group selected from the terminal groups of WO 2013/072695.

Terminal Groups of WO 2013/072695

The terminal group —$R^T$ in the present case may be a group —$R^5$ as described in WO 2013/072695.

Thus, in one embodiment, and for example where -$A^1$- is absent, —$R^T$ is selected from the group consisting of $C_{0-12}$ alkyl($C_{4-6}$ nitrogen heterocyclyl), or $C_{2-12}$ alkyl or $C_{0-12}$ alkyl($C_{3-8}$ cycloalkyl) wherein the alkyl or cycloalkyl bears (i) one, two or three hydroxyl groups; or (ii) one —$NR^AR^B$ group; or (iii) one —$NR^AR^B$ group and one or two hydroxyl groups. In one embodiment, —$R^T$ is not a group selected from this list, for example where -$A^1$- is absent.

The $C_{0-12}$ alkyl group is an alkylene spacer linking the nitrogen heterocyclyl or cycloalkyl to —X—.

The spacer may be absent (this is $C_0$).

The $C_{0-12}$ alkyl group may be $C_{0-6}$ alkyl or $C_{0-4}$ alkyl, or $C_{1-12}$ alkyl, such as $C_{1-6}$, such as $C_{1-4}$ alkyl. The alkyl group may be linear or branched, such as linear.

In one embodiment, —$R^T$ is $C_{0-12}$ alkyl($C_{4-6}$ nitrogen heterocyclyl).

The $C_{4-6}$ nitrogen heterocyclyl is a saturated carbocyclic ring comprising at least one nitrogen ring atom, for example 1 or 2 nitrogen ring atoms, such as only 1 nitrogen ring atom and optionally containing a further ring heteroatom selected from oxygen and sulfur.

Examples of $C_{4-6}$ heterocyclyl groups include azetidine, pyrrolidinyl, piperidinyl, piperazinyl and morpholinyl, such as azetidine, pyrrolidinyl and piperidinyl.

In one embodiment the heterocyclyl is linked to the remainder of the molecule through nitrogen. In the term "$C_{4-6}$ heterocyclyl", the expression $C_{4-6}$ represents the total number of ring atoms, including carbon and heteroatoms.

In one embodiment, —$R^T$ is $C_{2-12}$ alkyl or $C_{0-12}$ alkyl ($C_{3-8}$ cycloalkyl) wherein the alkyl or cycloalkyl bears (i) one, two or three hydroxyl groups; or (ii) one —$NR^AR^B$ group; or (iii) one —$NR^AR^B$ group and one or two hydroxyl groups.

In one embodiment, —$R^T$ is $C_{2-12}$ alkyl, substituted as described above.

The $C_{2-12}$ alkyl group may be $C_{3-12}$ alkyl, $C_{4-12}$ alkyl, $C_{5-12}$ alkyl or $C_{6-12}$ alkyl.

In one embodiment, —$R^T$ is $C_{0-12}$ alkyl($C_{3-8}$ cycloalkyl) substituted as described above.

The $C_{3-8}$ cycloalkyl group may be $C_{3-6}$ cycloalkyl such as $C_{5-6}$, for example $C_5$ cycloalkyl or $C_6$ cycloalkyl.

In one embodiment —$R^T$ bears one substituent.

In one embodiment —$R^T$ bears two substituents.

In one embodiment —$R^T$ bears three substituents.

In one embodiment —$R^T$ bears one, two or three hydroxyl groups, for example one hydroxyl group.

In one embodiment —$R^T$ bears one amine group, for example a $C_{2-12}$ alkyl bearing one amine, such as $C_{2-4}$ alkyl bearing one amine.

In one embodiment —$R^T$ bears one, two or three hydroxyl groups, such as one hydroxyl.

In one embodiment —$R^T$ bears one amine group and one hydroxyl group.

In one embodiment —$R^T$ bears one amine group and two hydroxyl groups.

In one embodiment wherein —$R^T$ bears one or more hydroxyls then the alkyl chain is $C_{5-12}$.

In one embodiment —$R^T$ does not bear more than one amine group.

In one embodiment wherein —$R^T$ bears more than one substituent, the substituents are not located on the same carbon atom.

In one embodiment at least one —$R^T$ substituent (such as one substituent) is on a terminal carbon of a straight alkyl chain or an alkyl branch, for example a straight alkyl chain. Terminal carbon as employed herein is intended to refer to carbon that would be —$CH_3$ if it bore no substituents.

In one embodiment, the group —$R^T$ is not a group as described above.

—$R^A$ and —$R^B$

In one embodiment, —$R^A$ is hydrogen.

In one embodiment, —$R^A$ is $C_{1-4}$ alkyl, such as methyl, ethyl or propyl, such as methyl.

In one embodiment, —$R^B$ is hydrogen.

In one embodiment, —$R^B$ is $C_{1-4}$ alkyl, such as methyl, ethyl or propyl, such as methyl.

In one embodiment, —$R^A$ is not ethyl when —$R^B$ is hydrogen, methyl or ethyl.

In one embodiment, —$R^A$ is not methyl when —$R^B$ is hydrogen, methyl or ethyl.

In one embodiment, —$R^A$ is hydrogen and —$R^B$ is hydrogen.

In one embodiment, —$NR^AR^B$ is not a guanidine group.

Terminal Groups of PCT/GB2014/051547 (WO 2014/188178)

The inventors have established that additional compounds having modified terminal groups may have biological activity. These additional compounds are described in PCT/GB2014/051547 (now published as WO 2014/188178). There terminal groups are not described in WO 2013/072695.

The terminal group —$R^T$ in the present case may be a group —$R^5$ as described in PCT/GB2014/051547 for the compounds of formula (IIa), (IIb), (IIc), (IId), (IIe), (IIf) and (IIg).

Thus, in one embodiment, —$R^T$ is a group G-$L^2$-$L^1$-, and -G is $C_{5-12}$ aryl,
-$L^1$- is a covalent bond, $C_{1-12}$ alkylene or $C_{2-12}$ heteroalkylene,
-$L^2$- is a covalent bond or $C_{4-10}$ heterocyclylene,
—$R^T$ is substituted with:
(i) one, two or three hydroxyl groups, or
(ii) one, two or three groups —$NR^AR^B$, or
(iii) one or two groups —$NR^AR^B$, and one, two or three hydroxyl groups,
with the proviso that (i), (ii) and (iii) are optional substituents when -$L^1$- is a nitrogen-containing $C_{2-12}$ heteroalkylene and/or -$L^2$- is a nitrogen-containing $C_{4-10}$ heterocyclylene,
and the aryl group is optionally substituted.

In one embodiment, —$R^T$ is a group G-$L^2$-$L^1$-, and -G is $C_{3-10}$ cycloalkyl,
-$L^1$- is a covalent bond, $C_{1-12}$ alkylene or $C_{2-10}$ heteroalkylene,
-$L^2$- is a covalent bond or $C_{4-12}$ heterocyclylene,
with the proviso that -$L^2$- is a covalent bond only when -$L^1$- is $C_{2-10}$ heteroalkylene,
—$R^T$ is substituted with:
(i) one, two or three hydroxyl groups, or
(ii) one, two or three groups —$NR^AR^B$, or
(iii) one or two groups —$NR^AR^B$, and one, two or three hydroxyl groups,
with the proviso that (i), (ii) and (iii) are optional substituents when -$L^1$- is a nitrogen-containing $C_{2-12}$ heteroalkylene and/or -$L^2$- is a nitrogen-containing $C_{4-10}$ heterocyclylene,
and optionally the cycloalkyl group is independently optionally substituted.

In one embodiment, —$R^T$ is G-$L^2$-$L^1$-, where -G is $C_{3-10}$ cycloalkyl or $C_{2-12}$ alkyl,
-$L^1$- is a covalent bond or $C_{1-12}$ alkylene,
-$L^2$- is a covalent bond,
with the proviso that -$L^1$- is not $C_{1-12}$ alkylene when -G is $C_{2-12}$ alkyl,
—$R^T$ is substituted with:
(i) two or three groups —$NR^AR^B$, or
(ii) two groups —$NR^AR^B$, and one, two or three hydroxyl groups;
and the alkyl or cycloalkyl group is independently optionally substituted.

In one embodiment, —$R^T$ is D-$L^1$-, where D-$L^1$- is substituted with:
(i) one, two or three hydroxyl groups, or
(ii) one, two or three groups —$NR^AR^B$, or
(iii) one or two groups —$NR^AR^B$, and one, two or three hydroxyl groups;
-D is $C_{4-10}$ heterocyclyl;
-$L^1$- is a covalent bond, $C_{1-12}$ alkylene or $C_{2-12}$ heteroalkylene,
with the proviso that (i), (ii) and (iii) are optional substituents when -$L^1$- is a nitrogen-containing $C_{2-12}$ heteroalkylene,
and the heterocyclyl group is independently optionally substituted.

In one embodiment, where -$A^1$-, -$A^2$- and -$A^3$- are present, —$R^T$ is —$R^P$.

In one embodiment, where -$A^1$- is absent, and -$A^2$- and -$A^3$- are present, —$R^T$ is —$R^P$, with the proviso —X— and —$R^T$ together are not an L-α-amino acid residue, such as —X— and —$R^T$ together are not L-Lys, L-Arg, L-Dap, L-Ser, L-Dab, L-Dgp (L-α,β-diguanidinopropanoyl) or L-Abu.

The group —$R^P$ is as described below.

Where an aryl group is present in —$R^T$ it is independently optionally substituted one or more substituents selected from —$C_{1-10}$ alkyl, such as —$C_{1-4}$ alkyl, halo, —CN, —$NO_2$, —$CF_3$, —$NR^{10}C(O)R^{10}$, —$OCF_3$, —$CON(R^{10})_2$, —$COOR^9$, —$OCOR^{10}$, —$NR^{10}COOR^{10}$, —$OCON(R^{10})_2$, —$NR^{10}CON(R^{10})_2$, —$OR^9$, —$SR^9$, —$NR^{10}SO_2R^{10}$, —$SO_2N(R^{10})_2$ and —$SO_2R^{10}$ where each —$R^9$ is independently —$C_{1-10}$ alkyl, such as —$C_{1-4}$ alkyl and each —$R^{10}$ is independently —H or —$C_{1-10}$ alkyl, such as —$C_{1-4}$ alkyl.

Where an alkyl, cycloalkyl, or heterocyclyl group is present in —$R^T$ it is independently optionally substituted one or more substituents selected from —$C_{1-10}$ alkyl, such as —$C_{1-4}$ alkyl, halo, —CN, —$NO_2$, —$CF_3$, —$C(O)R^{10}$, —$NR^{10}C(O)R^{10}$, —$OCF_3$, —$CON(R^{10})_2$, —$COOR^9$, —$OCOR^{10}$, —$NR^{10}COOR^{10}$, —$OCON(R^{10})_2$, —$NR^{10}CON(R^{10})_2$, —$OR^9$, —$SR^9$, —$NR^{10}SO_2R^{10}$, —$SO_2N(R^{10})_2$ and —$SO_2R^{10}$ where each —$R^9$ is independently —$C_{1-10}$ alkyl, such as —$C_{1-4}$ alkyl and each —$R^{10}$ is independently —H or —$C_{1-10}$ alkyl, such as —$C_{1-4}$ alkyl, except that alkyl is not substituted with alkyl.

—$R^P$

The group —$R^P$ is G-$L^2$-$L^1$-, where
-G is selected from:
  $C_{2-12}$ alkyl,
  $C_{5-12}$ aryl,
  $C_{3-10}$ cycloalkyl,
-$L^1$- is a covalent bond, $C_{1-12}$ alkylene or $C_{2-12}$ heteroalkylene,
-$L^2$- is a covalent bond or $C_{4-10}$ heterocyclylene,
with the proviso that -$L^1$- is not $C_{1-12}$ alkylene when -G is $C_{2-12}$ alkyl,
and G-$L^2$-$L^1$- is substituted with:
  (i) one, two or three hydroxyl groups, or
  (ii) one, two or three groups —$NR^A R^B$, or
  (iii) one or two groups —$NR^A R^B$, and one, two or three hydroxyl groups,
with the proviso that (i), (ii) and (iii) are optional substituents when -$L^1$- is a nitrogen-containing $C_{2-12}$ heteroalkylene and/or -$L^2$- is a nitrogen-containing $C_{4-10}$ heterocyclylene,
or —$R^P$ is D-$L^1$-, where -D is $C_{4-10}$ heterocyclyl and -$L^1$- is as defined above, and D-$L^1$- is substituted with:
  (i) one, two or three hydroxyl groups, or
  (ii) one, two or three groups —$NR^A R^B$, or
  (iii) one or two groups —$NR^A R^B$, and one, two or three hydroxyl groups,
with the proviso that (i), (ii) and (iii) are optional substituents when -$L^1$- is a nitrogen-containing $C_{2-12}$ heteroalkylene and/or -D is a nitrogen-containing $C_{4-10}$ heterocyclyl.

The optional substituents may be optional substituents as described above.

In one embodiment, —X— and —$R^P$ together are not an L-α-amino acid, such as Lys, Arg, Dap, Ser, Phe, Trp, Leu, Ala, α,γ-diaminobutyric acid (Dab) or α,β-diaminopropionic acid (Dap), optionally together with Dgp and Abu.

Terminal Groups of GB 1404301.2 and WO 2015/135976

In the polymyxins, the amino acid residue at position 1 is a diamino butyric acid (Dab) residue which is acylated at its N-terminal with a fatty acyl chain. Within the compounds described in GB 1404301.2, the N-terminal group of Polymyxin comprising Dab and the fatty acyl chain is replaced by an amine-containing moiety which is linked to a further substituent, but not linked via an amide bond. WO 2015/135976 claims priority to GB 1404301.2.

The N terminal groups described in GB 1404301.2 may be used in the present case. The terminal group —$R^T$ in the present case may be a group —$R^{15}$ as described in GB 1404301.2 for the compounds of formula (III). Additionally or alternatively the N terminal groups described in WO 2015/135976 may be used in the present case. The terminal group —$R^T$ in the present case may be a group —$R^{15}$ as described in WO 2015/135976 for the compounds of formula (III).

GB 1404301.2 and WO 2015/135976 do not explicitly described polymyxin compounds where the amino acids at positions 6 and/or 7 are substituted with another amino acid.

Previously, it has been thought that the presence of the Dab amino acid residue at position 1 of Polymyxin B was not important for activity, and this amino acid could be deleted. Thus, polymyxin nonapeptides are known in the art for use in the treatment of microorganisms.

The inventors believe that, for optimal activity, an amino substituent is required to mimic the Dab side chain in the naturally-occurring polymyxin structure. The inventors have therefore described in GB 1404301.2 (and also in WO 2015/135976) compounds where an amino group —$NR^{16}R^{17}$ or —$N(R^{16})$— is provided at a carbon atom that is β or γ to a group —X— at the N-terminal of a polymyxin nonapeptide. The group —X— may be regarded as equivalent to the carbonyl portion —C(O)— of an amino acid residue at position 1. The inventors have found that compounds where an amino group is provided solely at a carbon atom that is α to the group —X— have inferior biological activity.

Compounds where the amine substituent is provided at a carbon atom that is β or γ to the group —X— at the N-terminal of PMBN have been described in WO 2013/072695. However, these compounds, if substituted, have a substituent on the carbon attached to the amine. The inventors have found that it is important that a further substituent is provided, and furthermore that this substituent is not on the carbon attached to the amine. Accordingly the compounds of GB 1404301.2 have an amino group —$NR^{16}R^{17}$ or —$N(R^{16})$— that is connected to a methylene carbon group (—$CH_2$—).

In some instances, the stereochemistry is an important determinant of activity, for example where an additional substituent is provided at the carbon atom that is α to the group —X—. In these instances, it is preferred that the stereochemistry at this position is the same as that of the L-Dab residue in Polymyxin B.

Provided that the amino group remains β- or γ- to the group —X—, the amine group may be part of a nitrogen-containing heterocycle. WO 2013/072695 describes compounds having a nitrogen-containing heterocycle at the N terminal of a nonapeptide. However such compounds are not substituted. The inventors have found that the addition of a substituent improves activity. The compounds of GB 1404301.2 (and also WO 2015/135976), therefore, where the amine —$N(R^{16})$— is part of a ring structure, have a ring substituent.

The compounds of GB 1404301.2 are characterised over the polymyxin decapeptides for the reason that the compounds of GB 1404301.2 do not possess the amide functionality of a polymyxin that is formed from the amino group at the α carbon of the L-Dab group at position 1 and the fatty acyl chain. In the compounds of the present invention, where an amino group is provided at the α carbon, it is not part of an amide group. The same comments apply to the compounds of WO 2015/135976.

It is known that polymyxin decapeptides derivatives having a short acyl chain (e.g. butanoyl) connected to the L-Dab residue at position 1 via an amide bond have poor antibacterial activity. For instance the pentanoyl and butanoyl derivatives are reported to be 10-20 times less active than Polymyxin B (see de Visser et al. J. Pept. Res. 2003, 61, 298).

As noted above, the presence of an amino group solely at the α carbon is not sufficient to provide good activity. An amino group at a γ or γ carbon is required. Where an amino group, such as —$NR^{16}R^{17}$ or —$N(R^{16})$— is provided at the β or γ carbon, a further substituted amino group may be provided at the α carbon (this amino group is not part of an amide bond). Such compounds have good activity.

The compounds described in GB 1404301.2 (and also WO 2015/135976) are compounds corresponding to those of the present case where -$A^1$- is absent, -$A^2$- is an L-threonine or L-serine residue and -$A^3$- is an amino acid residue represented by:

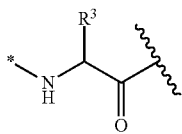

where the asterisk is the point of attachment to -A²- and —R³ is $C_{1-6}$ alkyl, having one amino or one hydroxyl substituent.

Where -A¹-, -A²- and -A³- have these meanings, the group —$R^T$ may an amino-containing group —$R^{15}$.

In one embodiment, —$R^T$ is an amino-containing group:

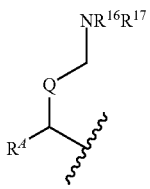

where:
- —$R^A$ is hydrogen or -$L^A$-$R^{AA}$;
- Q- is a covalent bond or —CH($R^B$)—;
- —$R^B$ is hydrogen or -$L^B$-$R^{BB}$;
- or, where -Q- is —CH($R^B$)—, —$R^A$ and —$R^B$ together form a 5- to 10-membered monocyclic or bicyclic carbocycle, or —$R^A$ and —$R^B$ together form a 5- to 10-monocyclic or bicyclic heterocycle;
- and, where -Q- is a covalent bond, —$R^A$ is -$L^A$-$R^{AA}$, and where -Q- is —CH($R^B$)— one or both of —$R^A$ and —$R^B$ is not hydrogen;
- —$R^{16}$ is independently hydrogen or $C_{1-4}$ alkyl;
- —$R^{17}$ is independently hydrogen or $C_{1-4}$ alkyl;
- or —$NR^{16}R^{17}$ is a guanidine group;
- or —$R^{17}$ and —$R^A$ together form a 5- to 10-membered nitrogen-containing monocyclic or bicyclic heterocycle;
- or, where -Q- is —CH($R^B$)—, —$R^{17}$ and —$R^B$ together form a 5- to 10-membered nitrogen-containing monocyclic or bicyclic heterocycle;
- and where —$R^{17}$ and —$R^A$ together form a monocyclic nitrogen-containing heterocycle, each ring carbon atom in —$R^{17}$ and —$R^A$ is optionally mono- or di-substituted with —$R^C$, and the monocyclic heterocycle is substituted with at least one group selected from —$R^C$, —$R^N$, —$R^{NA}$ and -$L^B$-$R^{BB}$ where present,
- and where —$R^{17}$ and —$R^B$ together form a monocyclic nitrogen-containing heterocycle, each ring carbon atom in —$R^{17}$ and —$R^B$ is optionally mono- or di-substituted with —$R^C$, and the monocyclic heterocycle is substituted with at least one group selected from —$R^C$, and —$R^N$, where present, or the monocyclic heterocycle is optionally substituted when —$R^A$ is -$L^A$-$R^{AA}$,
- and a monocyclic nitrogen-containing heterocycle optionally contains one further nitrogen, oxygen or sulfur ring atom, and where a further nitrogen ring atom is present it is optionally substituted with —$R^N$, with the exception of a further nitrogen ring atom that is connected to the carbon that is α to the group —X—, which nitrogen ring atom is optionally substituted with —$R^{NA}$;
- where —$R^{17}$ and —$R^A$ or —$R^{17}$ and —$R^B$ together form a bicyclic nitrogen-containing heterocycle, each ring carbon atom in —$R^{17}$ and —$R^A$ or —$R^{17}$ and —$R^B$ is optionally mono- or di-substituted with —$R^D$;
- and the bicyclic nitrogen-containing heterocycle optionally contains one, two or three further heteroatoms, where each heteroatom is independently selected from the group consisting of nitrogen, oxygen and sulfur, and where further nitrogen ring atoms are present, each further nitrogen ring atom is optionally substituted with —$R^N$, with the exception of a nitrogen ring atom that is connected to the carbon that is α to the group —X—, which nitrogen ring atom is optionally substituted with —$R^{NA}$;
- where —$R^A$ and —$R^B$ together form a 5- to 10-membered monocyclic carbocycle or heterocycle, each ring carbon atom in —$R^A$ and —$R^B$ is optionally mono- or di-substituted with —$R^C$, and a nitrogen ring atom, where present in the monocyclic heterocycle, is optionally substituted with —$R^N$, with the exception of a nitrogen ring atom that is connected to the carbon that is α to the group —X—, which nitrogen ring atom is optionally substituted with —$R^{NA}$;
- where —$R^A$ and —$R^B$ together form a 5- to 10-membered bicyclic carbocycle or heterocycle, each ring carbon atom in —$R^A$ and —$R^B$ is optionally mono- or di-substituted with —$R^D$, and a nitrogen ring atom, where present in the bicyclic heterocycle, is optionally substituted with —$R^N$, with the exception of a nitrogen ring atom that is connected to the carbon that is α to the group —X—, which nitrogen ring atom is optionally substituted with —$R^{NA}$;
- and where $R^{17}$ and —$R^A$ or —$R^{17}$ and —$R^B$ together form a 5- to 10-membered nitrogen-containing monocyclic or bicyclic heterocycle, or where —$R^A$ and —$R^B$ together form a 5- to 10-membered monocyclic or bicyclic carbocycle, or together form a 5- to 10-membered monocyclic or bicyclic heterocycle, a carbon ring atom in —$R^{17}$ and —$R^A$, —$R^{17}$ and —$R^B$, or —$R^A$ and —$R^B$ is optionally alternatively substituted with oxo (=O);
- each —$R^C$ is independently -$L^C$-$R^{CC}$;
- each —$R^C$ is independently selected from —$R^C$, halo, —$NO_2$, —OH, and —$NH_2$,
- each —$R^N$ is independently -$L^N$-$R^{NN}$;
- each —$R^{NA}$ is independently —$R^L$—$R^{NN}$ or —$R^{NN}$.
- —$R^{AA}$; —$R^{BB}$; and each —$R^{CC}$ and —$R^{NN}$ where present, is independently selected from $C_{1-12}$ alkyl, $C_{3-10}$ cycloalkyl, $C_{4-10}$ heterocyclyl, and $C_{5-12}$ aryl;
- each -$L^A$- is independently a covalent bond or a linking group selected from —$R^L$—*, —O-$L^{AA}$-*, —OC(O)-$L^{AA}$-*, —N($R^{11}$)-$L^{AA}$-*, and —C(O)-$L^{AA}$-*, where the asterisk indicates the point of attachment of the group -$L^A$- to —$R^{AA}$;
- each -$L^B$- and -$L^C$- is independently a covalent bond or a linking group selected from —$R^L$—*, —OC(O)-$L^{AA}$-*, —N($R^{11}$)-$L^{AA}$-*, —N($R^{11}$)C(O)-$L^{AA}$-*, —C(O)-$L^{AA}$-*, —C(O)O-$L^{AA}$-*, and —C(O)N($R^{11}$)-$L^{AA}$-*, and optionally further selected from —N($R^{11}$)S(O)-$L^{AA}$-*, —N($R^{11}$)S(O)$_2$-$L^{AA}$-*, —S(O)N($R^{11}$)-$L^{AA}$-*, and —S(O)$_2$N($R^{11}$)-$L^{AA}$-* where the asterisk indicates the point of attachment of the group -$L^B$- to —$R^{BB}$ or the group -$L^C$- to —$R^{CC}$;
- each -$L^N$- is independently a covalent bond or a group selected from —S(O)-$L^{AA}$-*, —S(O)$_2$-$L^{AA}$-*, —C(O)-

L$^{AA}$-* and —C(O)N(R$^{11}$)-L$^{AA}$-*, where the asterisk indicates the point of attachment of the group -L$^N$- to —R$^{NN}$;

and each -L$^{AA}$- is independently a covalent bond or —R$^L$—;

and each —R$^L$— is independently selected from C$_{1-12}$ alkylene, C$_{2-12}$ heteroalkylene, C$_{3-10}$ cycloalkylene and C$_{5-10}$ heterocyclylene, and where -L$^{AA}$- is connected to a group C$_{1-12}$ alkyl, —R$^L$— is not C$_{1-12}$ alkylene;

and each C$_{1-12}$ alkyl, C$_{3-10}$ cycloalkyl, C$_{4-10}$ heterocyclyl, C$_{5-12}$ aryl, C$_{1-12}$ alkylene, C$_{2-12}$ heteroalkylene, C$_{3-10}$ cycloalkylene and C$_{5-10}$ heterocyclylene group is optionally substituted, where —R$^S$ is an optional substituent to carbon and —R$^{12}$ is an optional substituent to nitrogen;

each —R$^S$ is independently selected from —OH, —OR$^{12}$, —OC(O)R$^{12}$, halo, —R$^{12}$, —NHR$^{12}$, —NR$^{12}$R$^{13}$, —NHC(O)R$^{12}$, —N(R$^{12}$)C(O)R$^{12}$, —SH, —SR$^{12}$, —C(O)R$^{12}$, —C(O)OH, —C(O)OR$^{12}$, —C(O)NH$_2$, —C(O)NHR$^{12}$ and C(O)NR$^{12}$R$^{13}$; except that —R$^{12}$ is not a substituent to a C$_{1-12}$ alkyl group; or where a carbon atom is di-substituted with —R$^S$, these groups may together with the carbon to which they are attached form a C$_{3-6}$ carbocycle or a C$_{5-6}$ heterocycle, where the carbocycle and the heterocycle are optionally substituted with one or more groups —R$^{12}$;

each —R$^{12}$ is independently C$_{1-6}$ alkyl, C$_{1-6}$ haloalkyl, phenyl or benzyl;

each —R$^{13}$ is independently C$_{1-6}$ alkyl, C$_{1-6}$ haloalkyl, phenyl or benzyl;

or —R$^{12}$ and —R$^{13}$, where attached to N, may together form a 5- or 6-membered heterocyclic ring, which is optionally substituted with C$_{1-6}$ alkyl, C$_{1-6}$ haloalkyl, phenyl or benzyl;

each —R$^{11}$ is independently hydrogen or C$_{1-4}$ alkyl.

Polymyxin Compounds of Formula (II)

The compounds of formula (II) are variants of Polymyxin B. The core of the compound of formula (II) is a variant of a polymyxin compound, such as a variant of the polymyxin B decapeptide, nonapeptide (PMBN, Polymyxin 2-10), octapeptide or heptapeptide, where the amino acid at position 6 is substituted with another amino acid as described herein, and optionally the amino acid residues at positions 1, 2, 3, 7 and 10 are substituted with another amino acid residue. Optionally one, two or three of the amino acid residues at positions 1, 2, 3 may be deleted.

The N terminal group of the compounds of formula (II), the group -T$^A$, is not particularly limited, but certain preferences are discussed below.

The compounds of formula (II) may have the same N terminal groups as the compounds of formula (I). Where this is the case, the compounds of formula (II) are a selection from the compounds of formula (I). Thus, the group -T$^A$ may be a group R$^T$—X— according to the compounds of formula (I).

The compounds of formula (I) and (II) allow for substitution of the amino acid reside at position 6. The substitutions described for the compounds of formula (II) are a selection of the possible substitutions described for the compounds of formula (I). The amino acid residues at 6-position in the compounds of formula (II) are believed to be newly disclosed herein. Thus, the amino acid residue at position 6 is not believed to be described in Velkov et al., WO 2010/130007 or WO 2012/051663.

Velkov et al. describe substitutions at the 6-position of Polymyxin B and colistin. The authors disclose the replacement of D-phenylalanine or D-leucine at position 6 with three different amino acid residues. Each amino acid differs from phenylalanine and leucine in the nature of the amino acid side group. Thus, the phenyl group of phenylalanine or the butyl group of leucine is replaced with octyl (D-OctGly), diphenylmethyl (D-BipAla) or benzyl-protected 4-hydroxyphenyl (D-Tyr(Bzl). No other modifications to the 6-position are described or suggested.

Velkov et al. also describe the modification of the polymyxin N terminal group along with the 6-position substitution. Thus, the ethyloctanoyl or methylheptanoyl terminal group of Polymyxin B is replaced with octanoyl, biphenyl acyl, or phenacyl.

The supplementary information accompanying Velkov et al. shows that compounds carrying a D-OctGly, D-BipAla or a D-Tyr(Bzl) substitution at the 6-position have activity against *P. aeruginosa*, *A. baumannii* and *K. pneumoniae* strains, with MIC values in the range 2-32 mg/L. The variants are also said to have activity against polymyxin-resistant strains of *P. aeruginosa*, *A. baumannii* and *K. pneumoniae* amongst others.

WO 2010/130007 broadly describes substitutions at the 6- and 7-positions of polymyxin. The worked examples however only demonstrate the preparation of compounds that are substituted at the 7-position. All the worked examples retain D-phenylalanine at position 6. The polymyxin N terminal group is also modified. The worked examples have an octanoyl, nonanoyl or biphenylacyl group at the N terminal.

WO 2012/051663 broadly describes substitutions at the 6- and 7-positions of polymyxin. The worked examples include compounds where the 6-position is substituted. However, the examples are limited. In one example, the amino acid residue at position 6 is D-OctGly and in another example the amino acid residue at position 6 is D-Cys(S-Hex) (i.e. a cysteine amino acid where the thiol group is a hexylthio group). The polymyxin N terminal group is also modified. The worked examples have an octanoyl, decanoyl, biphenylacyl or biphenylmethylacyl group at the N terminal.

The inventors have found that certain alternative substitutions at the 6-position provide compounds having antimicrobial activity, for example against Gram-negative bacteria, such as against *E. coli*, *P. aeruginosa*, *K. pneumonia*, and *A. Baumannii*.

Such substitutions may also enhance antimicrobial activity compared with the parent unmodified compounds. As shown in the present case, the compound of formula (II) is a Polymyxin B variant, where the phenylalanine amino acid residue at position 6 is replaced with a phenylalanine analogue bearing a bromo substituent at the 4-position of the phenyl group. The compound of formula (II) has superior activity to Polymyxin B against many *E. coli*, *P. aeruginosa*, *K. pneumonia*, and *A. baumannii* strains.

The compounds of formula (II) encompass compounds having amino acid residues at position 6 that are structurally non-obvious in the light of earlier work by Velkov et al.

The present invention provides a compound of formula (II) and the use of this compound in a method of treatment. The compound of formula (II) is represented thus:

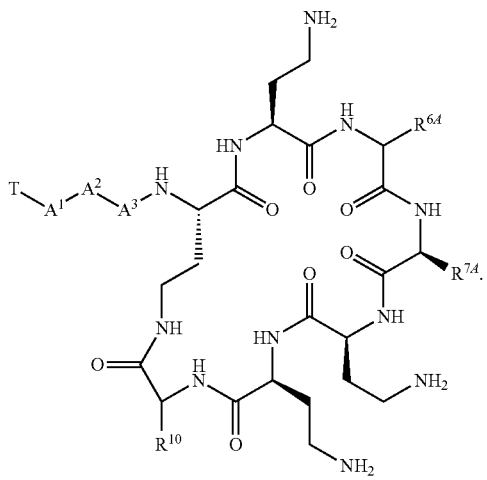

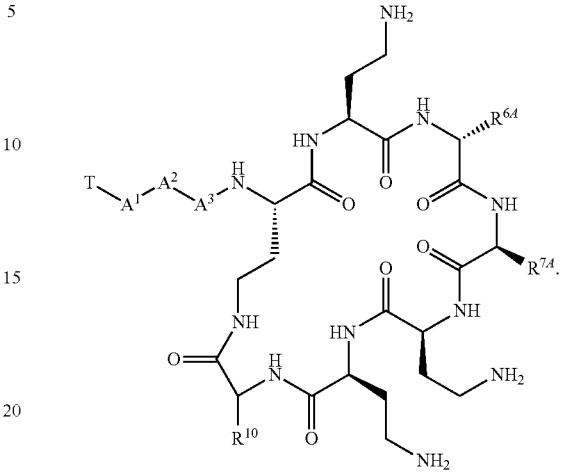

wherein:

-$T^A$ is hydrogen, $C_{1-4}$ alkyl or $R^N$—X—;

-$A^1$- is absent or is an amino acid residue;

-$A^2$- is absent or is an amino acid residue;

-$A^3$- is absent or is an amino acid residue;

—X— is —C(O)—, —NHC(O)—, —OC(O)—, —$CH_2$— or —$SO_2$—;

—$R^N$ is a terminal group, such as a group —$R^T$ as described herein;

—$R^{6A}$ is $C_{1-12}$ alkyl, $C_{0-12}$ alkyl ($C_{3-10}$ cycloalkyl), $C_{0-12}$ alkyl ($C_{3-10}$ heterocyclyl) or $C_{0-12}$ alkyl ($C_{5-10}$ aryl), where the $C_{1-12}$ alkyl, $C_{3-10}$ cycloalkyl group $C_{3-10}$ heterocyclyl group, and the $C_{5-10}$ aryl group are optionally substituted, and the optional substituents are as described herein, and with the proviso that —$R^{6A}$ is not benzyl, iso-butyl, iso-propyl, and optionally —$R^{6A}$ is not methyl, phenyl, 4-hydroxyphenyl, (1H-indol-3-yl) methyl, 4-phenylphen-1-yl methyl, —$(CH_2)_7CH_3$, 4-(OBn)-phen-1-yl methyl or —$CH_2S(CH_2)_5CH_3$, and optionally —$R^{6A}$ is not n-propyl, n-butyl, or tert-butyl;

—$R^{7A}$ together with the carbonyl group and nitrogen alpha to the carbon to which it is attached is an amino acid residue;

$R^{10}$ together with the carbonyl group and nitrogen alpha to the carbon to which it is attached, is a threonine or leucine residue;

and salts, solvates, protected forms and/or prodrug forms thereof.

It is noted that compounds of formula (II) where -$T^A$ is hydrogen (—H) may be used as intermediates for the preparation of compounds of formula (I) and other compounds of formula (II), where -$T^A$ is $C_{1-4}$ alkyl or $R^N$—X—.

In one embodiment, the compound of formula (II) is represented thus:

—$R^{6A}$

In one embodiment, —$R^{6A}$ is $C_{1-12}$ alkyl, $C_{0-12}$ alkyl ($C_{3-10}$ cycloalkyl), $C_{0-12}$ alkyl($C_{3-10}$ heterocyclyl) or $C_{0-12}$ alkyl($C_{5-10}$ aryl), where the $C_{1-12}$ alkyl, $C_{3-10}$ cycloalkyl group $C_{3-10}$ heterocyclyl group, and the $C_{5-10}$ aryl group are optionally substituted.

In one embodiment, —$R^{6A}$ is $C_{0-12}$ alkyl($C_{3-10}$ cycloalkyl), $C_{0-12}$ alkyl($C_{3-10}$ heterocyclyl) or $C_{0-12}$ alkyl($C_{5-10}$ aryl), where the $C_{3-10}$ cycloalkyl group, $C_{3-10}$ heterocyclyl group, and the $C_{5-10}$ aryl group are optionally substituted.

In one embodiment, —$R^{6A}$ is $C_{0-12}$ alkyl($C_{3-10}$ cycloalkyl) or $C_{0-12}$ alkyl($C_{5-10}$ aryl), where the $C_{3-10}$ cycloalkyl group and the $C_{5-10}$ aryl group are optionally substituted.

In one embodiment, the group —$R^{6A}$ is not benzyl, iso-butyl or iso-propyl (the residue at position 6 may not be phenylalanine, leucine or valine, and particularly the D-forms thereof).

Additionally or alternatively, in one embodiment the group —$R^{6A}$ is not methyl, 4-hydroxyphenyl, (1H-indol-3-yl) methyl or phenyl (the residue at position 6 may not be alanine, tyrosine, tryptophan and phenylglycine).

In one embodiment, the group —$R^{6A}$ is not 4-phenylphen-1-yl methyl, —$(CH_2)_7CH_3$, 4-(OBn)-phen-1-yl or —$CH_2S(CH_2)_5CH_3$.

Additionally or alternatively, the residue at position 6 may not be norvaline, norleucine and t-butylglycine, particularly the D-forms thereof. Thus, the group —$R^{6A}$ may not be n-propyl, n-butyl and tert-butyl.

Alternatively, the residue at position 6 may not be phenylalanine, leucine, norvaline, norleucine and t-butylglycine, particularly the D-forms thereof. Thus, the group —$R^{6A}$ may not be benzyl, iso-butyl, n-propyl, n-butyl and tert-butyl.

The $C_{1-12}$ alkyl group, $C_{3-10}$ cycloalkyl group, $C_{3-10}$ heterocyclyl group, and the $C_{5-10}$ aryl group may be substituted, such as optionally substituted with one or more groups —$R^Z$, where each group —$R^Z$ is selected from halo, optionally substituted $C_{1-12}$ alkyl, optionally substituted $C_{2-12}$ alkenyl, optionally substituted $C_{2-12}$ alkynyl, optionally substituted $C_{3-10}$ cycloalkyl, optionally substituted $C_{3-10}$ heterocyclyl, optionally substituted $C_{5-12}$ aryl, —CN, —$NO_2$, —$OR^Q$, —$SR^Q$, —$N(R^W)C(O)R^Q$, —$N(R^Q)_2$, and —C(O)N$(R^Q)_2$, where —$R^W$ is H or $C_{1-4}$ alkyl; and —$R^Q$ is H or —$R^{Q1}$, and —$R^{Q1}$ is selected from optionally substituted $C_{1-12}$ alkyl, $C_{2-12}$ alkenyl, $C_{2-12}$ alkynyl, and $C_{5-12}$ aryl, and in a group —$N(R^Q)_2$ the groups —$R^Q$ may together with the nitrogen atom to which they are attached form a $C_{5-6}$ heterocycle, where the heterocycle is optionally substituted, with the proviso that $C_{1-12}$ alkyl is not substituted with alkyl, alkenyl or alkynyl.

The group —$R^{6A}$ together with the carbonyl group and nitrogen alpha to the carbon to which it is attached is not a leucine, iso-leucine, phenylalanine, threonine, valine or norvaline residue. Additionally or alternatively, —$R^{6A}$ together with the carbonyl group and nitrogen alpha to the carbon to which it is attached is not a tyrosine residue.

As noted above, the $C_{1-12}$ alkyl group, $C_{3-10}$ cycloalkyl group, $C_{3-10}$ heterocyclyl group, and the $C_{5-10}$ aryl group may be substituted with one or more groups —$R^Z$. Examples of —$R^Z$ include optionally substituted alkyl, alkenyl, alkynyl, cycloalkyl, aryl and heterocycle groups.

Where a group, such as alkyl, alkenyl, alkynyl, cycloalkyl, aryl and heterocycle, is optionally substituted, the group may have one or more substituent groups selected from halo, haloalkyl, alkyl, alkenyl, alkynyl, and aryl, except that alkyl alkenyl, and alkynyl groups are not substituents to the alkyl alkenyl, and alkynyl groups. Suitable groups are described in relation to the definition of —$R^P$ for —$R^6$.

In one embodiment, —$R^{6A}$ is $C_{0-12}$ alkyl($C_{5-10}$ aryl), where the $C_{5-10}$ aryl group is optionally substituted, and the $C_{5-10}$ aryl group is substituted with one or more groups —$R^Z$, where each group —$R^Z$ is selected from halo, optionally substituted $C_{1-12}$ alkyl, —CN, and —$NO_2$.

In one embodiment, —$R^{6A}$ is $C_{0-12}$ alkyl($C_{5-10}$ aryl), where the $C_{5-10}$ aryl group is optionally substituted, and the $C_{5-10}$ aryl group is substituted with one or more groups —$R^Z$, where each group —$R^Z$ is selected from halo, optionally substituted $C_{1-12}$ alkyl, optionally substituted $C_{2-12}$ alkenyl, —CN, and —$NO_2$.

In one embodiment, —$R^{6A}$ is $C_{0-12}$ alkyl($C_{3-10}$ cycloalkyl), where the $C_{3-10}$ cycloalkyl group is optionally substituted, and the $C_{3-10}$ cycloalkyl group is substituted with one or more groups —$R^Z$, where each group —$R^Z$ is selected from halo, optionally substituted $C_{1-12}$ alkyl, optionally substituted $C_{2-12}$ alkenyl, optionally substituted $C_{2-12}$ alkynyl, optionally substituted $C_{3-10}$ cycloalkyl, optionally substituted $C_{3-10}$ heterocyclyl, optionally substituted $C_{5-12}$ aryl, —$OR^Q$, —$SR^Q$, —$N(R^W)C(O)R^Q$, —$N(R^Q)_2$, and —$C(O)N(R^Q)_2$.

In one embodiment, —$R^{6A}$ is $C_{0-12}$ alkyl($C_6$ cycloalkyl), such as $C_1$ alkyl($C_6$ cycloalkyl). The worked examples in the present case include numerous compounds where the group —$R^{6A}$ is $C_1$ alkyl($C_6$ cycloalkyl) (—$CH_2(C_6H_{11})$).

In one embodiment, —$R^{6A}$ is optionally substituted $C_{1-12}$ alkyl, where the $C_{1-12}$ alkyl is optionally substituted with one or more groups selected from halo, such as fluoro, optionally substituted $C_{3-10}$ cycloalkyl, optionally substituted $C_{3-10}$ heterocyclyl, optionally substituted $C_{5-12}$ aryl, —CN, —$NO_2$, —$OR^Q$, —$SR^Q$, —$N(R^W)C(O)R^Q$, —$N(R^Q)_2$, and —$C(O)N(R^Q)_2$.

In one embodiment, —$R^{6A}$ is optionally substituted $C_{1-12}$ alkyl.

The alkyl group is typically a $C_{1-12}$ alkyl group, such as $C_{2-12}$ alkyl, such as $C_{5-12}$ alkyl, such as $C_{4-12}$ alkyl, such as $C_{5-12}$ alkyl, such as $C_{6-12}$ alkyl, such as $C_{8-12}$ alkyl, for example $C_{2-10}$ alkyl, $C_{4-10}$ alkyl, $C_{5-10}$ alkyl and $C_{6-10}$ alkyl.

The alkyl group may be a $C_{9-12}$ alkyl group, such as $C_9$, $C_{11}$ and $C_{12}$ alkyl.

The alkyl group may be a $C_{1-5}$ alkyl group.

The alkyl group may be a $C_{5-12}$ alkyl group.

In one embodiment, —$R^{6A}$ is optionally substituted $C_{2-12}$ alkyl.

The alkyl group may be linear or branched.

Where the alkyl group is substituted, it may be monosubstituted. A substituent may be provided at a terminal of the alkyl group.

A $C_{0-12}$ alkyl group may be a $C_{1-12}$ alkyl group, such a $C_{2-12}$ alkyl group, a $C_{1-3}$ alkyl group, and a $C_{5-12}$ alkyl group.

In one embodiment, a $C_{0-12}$ alkyl group is $C_1$ alkyl.

In one embodiment, a $C_{0-12}$ alkyl group is $C_0$ alkyl.

In one embodiment, a $C_{0-12}$ alkyl group is not linear $C_4$ alkyl.

In one embodiment, a $C_{0-12}$ alkyl group is not $C_0$ alkyl and/or $C_1$ alkyl.

In one embodiment, —$R^{6A}$ is not —$CH_2S(CH_2)_5CH_3$, —$CH_2O(CH_2)_5CH_3$, —$CH_2S(CH_2)_5CF_3$, —$CH_2OCH_2Ph$, or —$CH_2SCH_2Ph$.

In one embodiment, —$R^{6A}$ is $C_{0-12}$ alkyl($C_{5-10}$ aryl), such as $C_{1-12}$ alkyl($C_{5-10}$ aryl), where the $C_{5-10}$ aryl group is optionally substituted.

In one embodiment, —$R^{6A}$ is $C_{0-1}$ alkyl($C_{5-10}$ aryl).

In one embodiment, —$R^{6A}$ is $C_{2-12}$ alkyl($C_{5-10}$ aryl).

In one embodiment, —$R^{6A}$ is $C_{0-12}$ alkyl($C_{5-10}$ heteroaryl).

In one embodiment, —$R^{6A}$ is $C_{0-12}$ alkyl($C_{5-10}$ aryl), where the aryl is optionally substituted with halo, optionally substituted $C_{2-12}$ alkenyl, optionally substituted $C_{2-12}$ alkynyl, substituted $C_{3-10}$ cycloalkyl, optionally substituted $C_{3-10}$ heterocyclyl, substituted $C_{5-12}$ aryl, —CN, —$NO_2$, —$SR^Q$, —$N(R^W)C(O)R^Q$, —$N(R^Q)_2$, and —$C(O)N(R^Q)_2$.

In one embodiment, —$R^{6A}$ is $C_{0-12}$ alkyl($C_{5-10}$ aryl), where the aryl is optionally substituted with halo, optionally substituted $C_{2-12}$ alkenyl, optionally substituted $C_{2-12}$ alkynyl, optionally substituted $C_{3-10}$ heterocyclyl, —CN, —$NO_2$, —$SR^Q$, —$N(R^W)C(O)R^Q$, —$N(R^Q)_2$, and —$C(O)N(R^Q)_2$.

The aryl group may be a carboaryl or heteroaryl group.

The carboaryl group may be phenyl. The alkyl group may be linear or branched.

In one embodiment, —$R^{6A}$ is substituted benzyl (—$CH_2Ph$).

In one embodiment, —$R^{6A}$ is monosubstituted benzyl.

In one embodiment, —$R^{6A}$ is monosubstituted benzyl, where the phenyl group is substituted at the 2-, 3- or 4-position, such as the 2- or 4-position.

In one embodiment, —$R^{6A}$ is monosubstituted benzyl, where the phenyl group is substituted at the 2-position with halo, optionally substituted alkyl, optionally substituted alkenyl, optionally substituted cycloalkyl, or optionally substituted aryl.

In one embodiment, —$R^{6A}$ is monosubstituted benzyl, where the phenyl group is substituted at the 2-position with halo, optionally substituted alkyl, optionally substituted cycloalkyl, or optionally substituted aryl.

In one embodiment, —$R^{6A}$ is monosubstituted benzyl, where the phenyl group is substituted at the 2-position with halo, optionally substituted alkyl, or optionally substituted aryl.

In one embodiment, —$R^{6A}$ is monosubstituted benzyl, where the phenyl group is substituted at the 4-position with halo, optionally substituted alkyl, optionally substituted alkenyl, optionally substituted aryl or optionally substituted heteroaryl.

In one embodiment, —$R^{6A}$ is monosubstituted benzyl, where the phenyl group is substituted at the 4-position with halo, optionally substituted alkyl, optionally substituted aryl or optionally substituted heteroaryl.

In one embodiment, —$R^{6A}$ is monosubstituted benzyl, where the phenyl group is substituted at the 4-position with halo, optionally substituted alkyl, substituted aryl or optionally substituted heteroaryl.

In one embodiment, —$R^{6A}$ is monosubstituted benzyl, where the phenyl group is substituted at the 3-position with halo, optionally substituted alkyl, optionally substituted alkenyl, substituted aryl or optionally substituted heteroaryl.

In one embodiment, —$R^{6A}$ is monosubstituted benzyl, where the phenyl group is substituted at the 3-position with halo, optionally substituted alkyl, substituted aryl or optionally substituted heteroaryl.

In one embodiment, —$R^{6A}$ is monosubstituted benzyl, where the phenyl group is substituted at the 2-position with aryl, such as phenyl.

In one embodiment, —$R^{6A}$ is monosubstituted benzyl, where the phenyl group is substituted at the 3-position with aryl, such as $C_{5-10}$ aryl, such as $C_{5-6}$ aryl, such as phenyl or pyridine. The aryl group is optionally substituted, such as substituted.

In one embodiment, —$R^{6A}$ is monosubstituted benzyl, where the phenyl group is substituted at the 4-position with aryl, such as $C_{5-10}$ aryl, such as $C_{5-6}$ aryl, such as phenyl or pyridine. The aryl group is optionally substituted, such as substituted.

In one embodiment, —$R^{6A}$ is monosubstituted benzyl, where the phenyl group is substituted at the 3-position with heteroaryl, such as $C_{5-10}$ heteroaryl, such as $C_{5-6}$ heteroaryl, such as pyridine.

In one embodiment, —$R^{6A}$ is monosubstituted benzyl, where the phenyl group is substituted at the 4-position with heteroaryl, such as $C_{5-10}$ heteroaryl, such as $C_{5-6}$ heteroaryl, such as pyridine.

In one embodiment, —$R^{6A}$ is monosubstituted benzyl, where the phenyl group is substituted at the 3-position with halo, such as bromo.

In one embodiment, —$R^{6A}$ is monosubstituted benzyl, where the phenyl group is substituted at the 4-position with halo, such as bromo.

In one embodiment, —$R^{6A}$ is monosubstituted benzyl, where the phenyl group is substituted at the 3-position with alkyl, such as $C_{1-12}$ alkyl, such as $C_{2-12}$ alkyl, such as $C_{6-12}$ alkyl, such as $C_8$ alkyl. The alkyl group may be linear or branched.

In one embodiment, —$R^{6A}$ is monosubstituted benzyl, where the phenyl group is substituted at the 4-position with alkyl, such as $C_{1-12}$ alkyl, such as $C_{2-12}$ alkyl, such as $C_{6-12}$ alkyl, such as $C_8$ alkyl. The alkyl group may be linear or branched.

In one embodiment, —$R^{6A}$ is $C_{0-12}$ alkyl($C_{3-10}$ cycloalkyl), such as $C_{1-12}$ alkyl($C_{3-10}$ cycloalkyl), where the $C_{3-10}$ cycloalkyl group is optionally substituted.

In one embodiment, —$R^{6A}$ is $C_1$ alkyl($C_{3-10}$ cycloalkyl), such as $C_1$ alkyl(cyclohexyl), where the $C_{3-10}$ cycloalkyl group is optionally substituted.

In one embodiment, —$R^{6A}$ is $C_{1-12}$ alkyl(cyclohexyl). Compounds of this type may be prepared from compounds where —$R^{6A}$ is $C_{1-16}$ alkyl(phenyl) by appropriate reduction of the phenyl group, such as described herein.

In one embodiment, —$R^{6A}$ is $C_{0-12}$ alkyl($C_{3-10}$ cycloalkyl), such as $C_1$ alkyl(cyclohexyl), where the $C_{3-10}$ cycloalkyl group is optionally substituted with one or more groups selected from halo, substituted $C_{1-12}$ alkyl, optionally substituted $C_{2-12}$ alkenyl, optionally substituted $C_{2-12}$ alkynyl, optionally substituted $C_{3-10}$ cycloalkyl, optionally substituted $C_{3-10}$ heterocyclyl, optionally substituted $C_{5-12}$ aryl, —CN, —$NO_2$, —$OR^Q$, —$SR^Q$, —$N(R^W)C(O)R^Q$, —$N(R^Q)_2$, and —$C(O)N(R^Q)_2$.

In one embodiment, —$R^{6A}$ is $C_{0-12}$ alkyl($C_{3-10}$ cycloalkyl), such as $C_1$ alkyl(cyclohexyl), where the $C_{3-10}$ cycloalkyl group is optionally substituted with one or more groups selected from halo, optionally substituted $C_{2-12}$ alkenyl, optionally substituted $C_{2-12}$ alkynyl, optionally substituted $C_{3-10}$ cycloalkyl, optionally substituted $C_{3-10}$ heterocyclyl, optionally substituted $C_{5-12}$ aryl, —CN, —$NO_2$, —$OR^Q$, —$SR^Q$, —$N(R^W)C(O)R^Q$, —$N(R^Q)_2$, and —$C(O)N(R^Q)_2$.

The $C_{3-10}$ cycloalkyl may be a $C_{5-7}$ cycloalkyl group, such as $C_{5-6}$ cycloalkyl group.

In one embodiment, $C_{3-10}$ cycloalkyl is cyclopentyl or cyclohexyl, such as cyclohexyl.

A cycloalkyl group may be optionally substituted, such as optionally monosubstituted.

Where, the cycloalkyl group is cyclohexyl, the cyclohexyl is optionally substituted at the 2-, 3- or 4-position, such as the 2- or 4-position, such as the 4-position.

In one embodiment, —$R^6$ and/or —$R^7$ is not —$(CH_2)_4$-cyclohexyl.

In one embodiment, —$R^6$ and/or —$R^7$ is not —$(C_6H_{10})$—Pr, such as where the —Pr group is a linear propyl group.

In one embodiment, —$R^{6A}$ is $C_{0-12}$ alkyl($C_{3-10}$ heterocyclyl) such as $C_{1-12}$ alkyl($C_{3-10}$ heterocyclyl), where the $C_{3-10}$ heterocyclyl group is optionally substituted.

Where $C_{0-12}$ alkyl is $C_0$, the heteroatom of the heterocyclyl group is not provided at the β position (i.e. the heteroatom is not connected to the a carbon).

The heterocyclyl group contains a heteroatom selected from N, O and S, and optionally contains further heteroatoms. A reference to N is a reference to a group —NH— within a heterocycle, and a reference to S is —S—, —S(O)— or —$S(O)_2$—.

The heterocyclyl may be substituted at a carbon ring atom or a nitrogen ring atom, if such is present. Where a nitrogen ring atom is substituted the substituent may be a group —$R^Z$ selected from optionally substituted $C_{1-12}$ alkyl, optionally substituted $C_{2-12}$ alkenyl, optionally substituted $C_{2-12}$ alkynyl, optionally substituted $C_{3-10}$ cycloalkyl, optionally substituted $C_{3-10}$ heterocyclyl, optionally substituted $C_{5-12}$ aryl, and —$C(O)N(R^Q)_2$. Where a carbon ring atom is substituted the substituent may be a group —$R^Z$ such as described above.

The heterocyclyl may be $C_{5-10}$, such as $C_{5-6}$, such as $C_5$ or $C_6$ heterocyclyl.

The heterocyclyl may be selected from the group consisting of piperidinyl, piperazinyl, morpholinyl and thiomorpholinyl.

Where an alkyl group is optionally substituted with halo, it is preferred that the alkyl group is optionally substituted with fluoro.

In one embodiment, —$R^{6A}$ is not 4-hydroxyphenylmethyl (i.e. —$R^6$ together with the carbonyl group and nitrogen alpha to the carbon to which it is attached is not a tyrosine residue).

The comments above refer to compounds where the a amino acid residue at position 6 has a a carbon atom that is substituted with —R$^{6A}$ and —H. The —H may also be a site for substitution, providing di-substituted a amino acid residues at position 6.

In an alternative embodiment, a carbon atom at within the a amino acid residue at position 6 is di-substituted, where each substituent is a group —R$^{6A}$ as described herein.

In an alternative embodiment, the a carbon atom at within the a amino acid residue at position 6 is di-substituted, where each substituent is a group —R$^{6A}$, where the groups —R$^{6A}$ may together with the α carbon atom to which they are attached form a C$_{4-6}$ carbocycle or a C$_{5-6}$ heterocycle, wherein the carbocycle and the heterocycle are optionally substituted with one or more groups —R$^Z$, as described above. The carbocycle is a cycloalkyl group as described herein. The heterocycle is a heterocyclyl group as described herein.

Where a heterocycle is present the heteroatom of the heterocyclyl group is not provided at the β position (i.e. the heteroatom is not connected to the a carbon).

The heterocycle contains a heteroatom selected from N, O and S, and optionally contains further heteroatoms. A reference to N is a reference to a group —NH— within a heterocycle, and a reference to S is —S—, —S(O)— or —S(O)$_2$—.

The heterocyclyl may be substituted at a carbon ring atom or a nitrogen ring atom, if such is present. Where a nitrogen ring atom is substituted the substituent may be a group —R$^Z$ selected from optionally substituted C$_{1-12}$ alkyl, optionally substituted C$_{2-12}$ alkenyl, optionally substituted C$_{2-12}$ alkynyl, optionally substituted C$_{3-10}$ cycloalkyl, optionally substituted C$_{3-10}$ heterocyclyl, optionally substituted C$_{5-12}$ aryl, and —C(O)N(R$^Q$)$_2$. Where a carbon ring atom is substituted the substituent may be a group —R$^Z$ such as described above.

The heterocycle may be selected from the groups piperidine, piperazine, morpholine and thiomorpholine.

In one embodiment, —R$^{6A}$ together with the carbonyl group and nitrogen alpha to the carbon to which it is attached is an amino having a piperidine side chain that is a gem di-substituted to the α-carbon. Thus the α-carbon is a ring atom in the piperidine ring. This is a cyclic analogue of Dab.

In one embodiment, —R$^Z$ is selected from halo, optionally substituted C$_{1-12}$ alkyl, optionally substituted C$_{2-12}$ alkenyl, optionally substituted C$_{2-12}$ alkynyl, optionally substituted C$_{5-12}$ aryl, —OR$^Q$, —SR$^Q$, —N(R$^W$)C(O)R$^Q$, —N(R$^Q$)$_2$, and —C(O)N(R$^Q$)$_2$.

In one embodiment, —R$^Z$ is selected from halo, optionally substituted C$_{2-12}$ alkenyl, optionally substituted C$_{2-12}$ alkynyl, optionally substituted C$_{3-10}$ cycloalkyl, optionally substituted C$_{5-12}$ aryl, —OR$^Q$, —SR$^Q$, —N(R$^W$)C(O)R$^Q$, —N(R$^Q$)$_2$, and —C(O)N(R$^Q$)$_2$.

In one embodiment, —R$^Z$ is selected from halo, optionally substituted C$_{2-12}$ alkenyl, optionally substituted C$_{2-12}$ alkynyl, optionally substituted C$_{5-12}$ aryl, —OR$^Q$, —SR$^Q$, —N(R$^W$)C(O)R$^Q$, —N(R$^Q$)$_2$, and —C(O)N(R$^Q$)$_2$.

In one embodiment, —R$^Z$ is selected from halo, optionally substituted C$_{1-12}$ alkyl, optionally substituted C$_{2-12}$ alkenyl, optionally substituted C$_{2-12}$ alkynyl, optionally substituted C$_{3-10}$ cycloalkyl, —OR$^Q$, —SR$^Q$, —N(R$^W$)C(O)R$^Q$, —N(R$^Q$)$_2$, and —C(O)N(R$^Q$)$_2$.

In one embodiment, —R$^Z$ is selected from halo, optionally substituted C$_{2-12}$ alkenyl, optionally substituted C$_{2-12}$ alkynyl, —OR$^Q$, —SR$^Q$, —N(R$^W$)C(O)R$^Q$, —N(R$^Q$)$_2$, and —C(O)N(R$^Q$)$_2$.

In one embodiment, the amino acid residue at position 6 is an L- or D-amino acid residue, such as a D-amino acid residue.

—R$^{7A}$

In one embodiment, —R$^{7A}$ together with the carbonyl group and nitrogen alpha to the carbon to which it is attached may be a leucine, iso-leucine, phenylalanine, threonine, valine or nor-valine residue In one embodiment, the group —R$^{7A}$ may be a group —R$^7$ as described above for the compounds of formula (I).

In one embodiment, —R$^{7A}$ together with the carbonyl group and nitrogen alpha to the carbon to which it is attached is an amino acid residue selected from the group consisting of leucine, OctGly, BipAla, and Cys, such as Cys(S-Hex) and Cys(S-Bzl), and for example the L-forms thereof. Additionally or alternatively, —R$^{7A}$ together with the carbonyl group and nitrogen alpha to the carbon to which it is an amino acid residue selected from the group consisting of threonine, serine, valine, 2-aminobutyric acid (Abu) and 2-aminoisobutyric acid (Aib), and for example the L-forms thereof.

In one embodiment, —R$^{7A}$ together with the carbonyl group and nitrogen alpha to the carbon to which it is a leucine residue, such as L-leucine. In this embodiment, the amino acid residue at the 7-position is not substituted with reference to the amino acid residue at the 7-position of Polymyxin B.

In one embodiment, —R$^{7A}$ together with the carbonyl group and nitrogen alpha to the carbon to which it is attached is an amino acid residue selected from the group consisting of leucine, alanine, phenylalanine, OctGly, BipAla, Cys, such as Cys(S-Hex) and Cys(S-Bzl), threonine, serine, valine, 2-aminobutyric acid (Abu) and 2-aminoisobutyric acid (Aib), and for example the L-forms thereof.

In one embodiment, the amino acid residue at position 7 is an L- or D-amino acid residue, such as an L-amino acid residue.

-T$^A$

In one embodiment, -T$^A$ is hydrogen or —X—R$^N$.

In one embodiment, -T$^A$ is hydrogen. Such a compound has a free amino group (primary amine, —NH$_2$) at the N terminal.

In one embodiment, -T$^A$ is C$_{1-4}$ alkyl. Here, the compound has an alkylated amino group at the N terminal. The C$_{1-4}$ alkyl group may be linear or branched. The C$_{1-4}$ alkyl group may be selected from methyl, ethyl, propyl and butyl, such as methyl and ethyl. The C$_{1-4}$ alkyl group may be methyl.

In one embodiment, -T$^A$ is —X—R$^N$. Here, the N terminal group of the compound is modified. Modifications to the N terminal are well known in the art. Indeed, the natural products Polymyxin B and Colistin are also modified at the N terminal.

—X—

The group —X— is as defined from the compounds of formula (I).

—R$^N$

The group —R$^N$ is a terminal group.

The terminal group may be a group that retains biological activity or provides improved biological activity when that group is compared with the terminal group present in Polymyxin B and Colistin.

In one embodiment, the group —R$^N$ is a group —R$^T$ as defined above for the compounds of formula (I). The group —R$^T$ typically possesses hydroxyl and/or amino functionality.

Alternatively, the group —R$^N$ may be a lipophilic group.

In one embodiment, —R$^N$ is benzyl.

In one embodiment, —$R^N$ is M-$L^{11}$-$L^{10}$-, where:
-$L^{10}$- is a covalent bond, $C_{1-12}$ alkylene or $C_{2-12}$ heteroalkylene,
-M is selected from optionally substituted $C_{1-12}$ alkyl, $C_{2-12}$ alkenyl, $C_{3-10}$ cycloalkyl and $C_{5-12}$ aryl,
and with the proviso that -$L^{10}$- is not $C_{1-12}$ alkylene when -M is $C_{1-12}$ alkyl.

The optional substituents may be selected from the group consisting of optionally substituted $C_{1-10}$ alkyl, $C_{2-12}$ alkenyl, $C_{5-12}$ aryl, $C_{3-10}$ cycloalkyl, —OH, —$OR^{19}$, —$NH_2$, —$NHR^{19}$, —$N(R^{19})_2$, —$COOR^{19}$, —$OCOR^{19}$, —$CON(R^{10})_2$, and —$NR^{10}C(O)R^{10}$, where each —$R^{19}$ is independently $C_{1-10}$ alkyl, $C_{2-12}$ alkenyl, $C_{5-12}$ aryl, $C_{3-10}$ cycloalkyl, and the optional substituents are —OH and —$NH_2$.

In one embodiment, —$R^N$ is selected from optionally substituted $C_{1-12}$ alkyl and -$L^{12}$-V, where -$L^{12}$- is absent or $C_{2-4}$ alkenyl, and V— is optionally substituted $C_{5-12}$ aryl, such as $C_{6-10}$ carboaryl and $C_{5-12}$ heteroaryl, where the optional substituent is W-$L^{13}$, and:
-$L^{13}$- is a covalent bond, $C_{1-3}$ alkylene or $C_{2-7}$ heteroalkylene,
—W is $C_{5-12}$ aryl, such as $C_{6-10}$ carboaryl and $C_{5-12}$ heteroaryl.

In one embodiment, —$R^N$ is $C_{1-12}$ alkyl.
A $C_{1-12}$ alkyl group may be a $C_{4-12}$, $C_{6-12}$, $C_{4-10}$ or a $C_{6-10}$ alkyl group.

An alkyl group may be linear or branched.

In one embodiment, the alkyl group is $C_{6-8}$ alkyl. As noted above, an alkyl group may be linear or branched. Where the $C_{6-8}$ alkyl group is branched, the branch point may be located at the penultimate carbon of the longest linear alkyl chain. The branch may be a methyl branch.

In one embodiment, —$R^N$ is 5-methylheptyl, for example where —X— is —C(O)—. Such a group is the N terminal group is present in Polymyxin B1 and Colistin A (i.e. where —X—$R^N$ together are 6-methyloctanoyl).

In one embodiment, —$R^N$ is 5-methylhexyl, for example where —X— is —C(O)—. Such a group is the N terminal group is present in Polymyxin B2 and Colistin B (i.e. where —X—$R^N$ together are 6-methylheptanoyl).

In one embodiment, $R^N$ is heptyl, for example where —X— is —C(O)—. Such a group is the N terminal group is present in Polymyxin B3 (i.e. where —X—$R^N$ together are 6-octanoyl).

In one embodiment, —$R^N$ is hexyl, for example where —X— is —C(O)—. Such a group is the N terminal group is present in Polymyxin B4 (i.e. where —X—$R^N$ together are heptanoyl).

In one embodiment, —$R^N$ is diphenylmethyl, such as 4-phenylphenylmethyl.

In one embodiment, —$R^N$ is optionally substituted $C_{5-10}$ aryl.

In one embodiment, the optionally substituted $C_{5-10}$ aryl is phenyl substituted with phenyl (i.e. biphenyl), for example 4-phenylphenyl or 2-phenylphenyl.

In one embodiment, —$R^N$ is phenyl or benzyl, where the phenyl or benzyl is optionally substituted with one or more halo or nitro groups.

In one embodiment, —$R^N$ is halophenyl, such as chlorophenyl, such as 2-chlorophenyl for example where —X— is —NH(CO)—.

In one embodiment, —$R^N$ together with —X— is not a group $R^1$ as described in WO 2015/149131, for example where -$A^1$- is L-Dap, L-Dab or L-Lys, -$A^2$ is L-Thr, and -$A^3$- is L-Dap, L-Dab or L-Lys.

-$A^1$-, -$A^2$- and -$A^3$-

In one embodiment, -$A^1$- is absent, and -$A^2$- and -$A^3$- are present.

In one embodiment, -$A^1$- and -$A^2$- are absent, and -$A^3$- is present. Such a compound may be referred to as an octapeptide.

In one embodiment, -$A^1$-, -$A^2$- and -$A^3$- are absent. Such a compound may be referred to as a heptapeptide.

Each of -$A^1$-, -$A^2$- and -$A^3$- may be an α-amino acid.

A reference to an α-amino acid includes proteinogenic ("natural") α-amino acids, optionally together with other α-amino acids.

Examples of α-amino acids that are not proteinogenic are those amino acids generated by post-translational modification, or by other means. Examples include Dab, Dap, Dgp (α,β-diguanidinopropanoyl), ornithine and nor-valine Also included are amino having a piperidine side chain that is a gem di-substituent to the α-carbon. Thus the α-carbon is a ring atom in the piperidine ring. This is a cyclic analogue of Dab.

An amino acid, such as an α-amino acid, may be an L- or D-amino acid. In one embodiment, each of -$A^1$-, -$A^2$- and -$A^3$-, where present, is an L-amino acid.

In one embodiment, where one or more of -$A^1$-, -$A^2$- and -$A^3$- is absent, and optionally where all of -$A^1$-, -$A^2$- and -$A^3$- are present, $R^T$—X— may be an α-amino acid residue, such as an α-amino acid residue selected from the group consisting of Ala, Ser, Thr, Val, Leu, Ile, Pro, Phe, Tyr, Trp, His, Lys, Arg, α,γ-diaminobutyric acid (Dab) and α,β-diaminopropionic acid (Dap).

In one embodiment, -$A^3$- is an amino acid residue represented by:

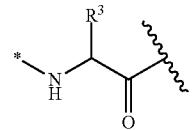

where the asterisk is the point of attachment to -$A^2$-, and —$R^3$ corresponds to the side chain of an amino acid at position 3 in the polymyxin compounds.

In one embodiment, the group —$R^3$ together the carbonyl group and nitrogen alpha to the carbon to which it is attached, is an amino acid residue having an amino- and/or hydroxyl-containing side chain. Thus, the group —$R^3$ has amino and/or hydroxyl functionality.

In one embodiment, for the compounds of formula (II) each of -$A^1$-, -$A^2$- and -$A^3$- has the same meaning as the compounds of formula (I).

Protected Forms

Compounds of the invention, such as compounds of formula (I) and (II), may be provided in a protected form. Here, reactive functionality, such as amino functionality, may be masked in order to prevent its reaction during a synthesis step. A protecting group is provided to mask the reactive functionality, and this protecting groups may be removed at a later stage of the synthesis to reveal the original reactive functionality.

A compound of formula (Ia) is provided, and salts, solvates and hydrates thereof, which is a compound of formula (I) in protected form. For example, amino, hydroxyl, carboxyl and thiol functionality present in compound (I) may be protected with a protecting group, such as described herein. The compound of formula (Ia) may be an intermediate for the preparation of the compound of formula (I). Thus, compound (I) may be prepared from compound (Ia), for example by removal of the protecting groups ("deprotection").

Similarly, a compound of formula (IIa) is provided, and salts, solvates and hydrates thereof, which is a compound of formula (II) in protected form. For example, amino, hydroxyl, carboxyl and thiol functionality present in compound (II) may be protected with a protecting group, such as described herein. The compound of formula (IIa) may be an intermediate for the preparation of the compound of formula (II). Thus, compound (II) may be prepared from compound (IIa), for example by removal of the protecting groups ("deprotection").

In one embodiment, the protected form is a compound where amino, hydroxyl, thiol, and/or carboxyl functionality is protected (masked) by a protecting group. In one embodiment, the protected form is a compound where the side chain functionality of the amino acids residues with the compound are protected.

In the compound of formula (I) and (II), the amino acid residues at positions 5, 8 and 9 are Dab residues, and the side chain of the Dab residue includes amino functionality. The amino acid functionality of each Dab residue may be protected with an amino protecting group, as described herein.

In certain embodiments of the invention, amino acid residue -$A^3$-, where present, is an amino acid residue where the side chain includes amino functionality. Examples of -$A^3$- include Dab, a lysine residue, an ornithine residue, and Dap residues. The amino functionality of these residues may be protected with an amino protecting group, as described herein.

In certain embodiments of the invention, amino acid residue -$A^3$-, where present, is an amino acid residue where the side chain includes hydroxyl functionality. Examples of -$A^3$- include serine and threonine residues. The hydroxyl functionality of these residues may be protected with an hydroxyl protecting group, as described herein.

In certain embodiments of the invention, amino acid residue -$A^2$-, where present, is an amino acid residue where the side chain includes hydroxyl functionality. Examples of -$A^2$- include serine and threonine residues. The hydroxyl functionality of these residues may be protected with an hydroxyl protecting group, as described herein. In certain embodiments of the invention, amino acid residue -$A^2$-, where present, is an amino acid residue where the side chain includes amino functionality. The amino functionality of these residues may be protected with an amino protecting group, as described herein.

In certain embodiments of the invention, amino acid residue -$A^1$-, where present, is an amino acid residue where the side chain includes amino or hydroxyl functionality. Examples include those amino acids mentioned above in relation to -$A^1$-. These functionalities may be protected with hydroxyl or amino protecting groups, as described herein.

An amino acid reside, such as amino acid residue -$A^1$-, where present, may be an amino acid residue where the side chain includes a nitrogen aromatic group, for example an imidazole group, as found in a histidine residue. A nitrogen ring atom may be protected with an amino protecting group as described herein.

An amino acid reside, such as amino acid residue -$A^1$-, where present, may be an amino acid residue where the side chain includes carboxyl functionality. This functionality may be protected with a carboxyl protecting group as described herein.

In certain embodiments of the invention, —$R^{10}$ together with the carbonyl group and nitrogen alpha to the carbon to which it is attached is an amino acid residue where the side chain includes hydroxyl functionality. An example of an amino acid residue including —$R^{10}$ is threonine. The hydroxyl functionality of this residue may be protected with a hydroxyl protecting group, as described herein.

In certain embodiments the —$R^T$ or —$R^N$ contains functionality such as amino, hydroxyl carboxyl or thiol functionality. The amino, hydroxyl carboxyl or thiol functionality may be protected with amino, hydroxyl carboxyl or thiol protecting groups, as described herein.

Protecting groups, such as those for amino acid residues, are well known and well described in the art.

Amino acids having side group protection, optionally together with amino and carboxy protection, are commercially available. Thus, a protected polymyxin compound may be prepared from appropriately protected amino acid starting materials.

Velkov et al. describe the step-wise preparation of polymyxin compounds on the solid-phase using suitably protected amino acid. The use of protected-forms of threonine and Dab is disclosed (see Supplementary Information).

As noted above, however, Velkov et al. do not describe the compounds of formula (II), for at least the reason that the amino acid residues at position 6 are not exemplified in Velkov et al.

Where a protecting group is used is it is removable under conditions that do not substantially disrupt the structure of the polymyxin core, for example conditions that do not alter the stereochemistry of the amino acid residues.

In one embodiment, the protecting groups are acid-labile, base labile, or are removable under reducing conditions.

Example protecting groups for amino functionality include Boc (tert-butoxycabonyl), Bn (benzyl, Bzl), CbZ (Z), 2-CL-Z (2-chloro), Dde (1-[4,4-dimethyl-2,6-dioxocyl-cohex-1-ylidene]-3-methylbutyl), Fmoc (fluorenylmethyl-oxycarbonyl), $HSO_3$-Fmoc (sulfonylated Fmoc, such as 2-sulfo-Fmoc, as described in e.g. Schechter et al, *J. Med Chem* 2002, 45(19) 4264), ivDde (1-[4,4-dimethyl-2,6-di-oxocylcohex-1-ylidene]ethyl), Mmt (4-methoxytrityl), Mtt (4-methyltrityl), Nvoc (6-nitroveratroyloxycarbonyl), and Tfa (trifluroacetyl).

Example protecting groups for aromatic nitrogen functionality includes Boc, Mtt, Trt and Dnp (dinitrophenyl).

In one embodiment, the protecting group for amino functionality is selected from Boc, CbZ, Bn and Fmoc and $HSO_3$-Fmoc.

In one embodiment, the protecting group for amino functionality is Boc, Fmoc or CbZ.

Example protecting groups for hydroxyl functionality include Trt (trityl), Bn (benzyl), tBu (tert-butyl), and 2-acetamido-2-deoxy-3,4,6-tri-Oacetyl-α-galactopyranosyl.

In one embodiment, the protecting group for amino functionality is Trt.

Further example protecting groups include silyl ether protecting groups, such as TMS, TES, TBS, TIPS, TBDMS, and TBDPS. Such protecting groups are removable with TBAF, for example.

Example protecting groups for carboxyl functionality include Bn (benzyl, Bz), tBu (tert-butyl), TMSET (trimethylsilylethyl) and Dmab ({[4,4-dimethyl-2,6-dioxocylcohex-1-ylidene]-3-methylbutyl}amino benzyl).

Example protecting groups for aromatic nitrogen functionality includes Boc, Mtt, Trt and Dnp (dinitrophenyl).

In some embodiments, only some types of functionality are protected. For example, only amino groups may be protected, such as amino groups in the side chain of an amino acid residue.

In one embodiment, amino groups and hydroxyl groups are protected.

Log P

A compound of the invention, such as a compound of formula (I) or (II), may have a partition-coefficient, such as expressed as a Log P value, within certain limits. The partition-coefficient may provide an indication of the lipophilicity of the compound.

A Log P value for a compound may be determined experimentally (for example by partition of the compound between octanol and water), or it may be predicted using standard computational methods. For example, a reference to Log P may be a reference to A Log P, which may be determined using the methods described by Ghose et al. *J. Phys. Chem. A*, 1998, 102, 3762-3772, the contents of which are hereby incorporated by reference in their entirety. Thus, A Log P is the Ghose/Crippen group-contribution estimate for Log P.

In one embodiment, a compound has a Log P value, such as an A Log P value, of at least −3.0, at least −3.5, at least −4.0, at least −6.0, at least −6.3, at least −6.5, at least −6.7, or at least −7.0. In one embodiment, a compound has a Log P value, such as an A Log P, value, of at most −2.0, at most −3.0, at most −3.5, at most −4.0, at most −4.5, at most −5.0, at most −5.2, at most −5.5, or at most −5.7.

In one embodiment, a compound has a Log P value within a range having upper and lower limits appropriately selected from the limits given above, for example within the range −5.0 to −6.3, such as −5.5 to −6.3.

Compounds having Log P values, such as A Log P values, within the limits discussed above are found to have excellent activity against both polymyxin-susceptible and polymyxin-resistant bacterial strains. Such compounds may also have reduced cytotoxicity compared with polymyxin B.

In another embodiment, a compound has a Log P value within a range having upper and lower limits selected from the limits given above, for example within the range −2.0 to −4.0, such as −2.0 to −3.5, such as −2.0 to −3.0.

Compounds having Log P values, such as A Log P values, within the limits discussed above are found to have optimum activity against polymyxin-resistant strains.

The present inventors have found that a compound having suitable Log P values may be obtained by appropriate choice of N terminal group (such as the choice of groups $-R^T$ or $-R^N$) and amino acid residues at position 6 and/or 7 (such as with appropriate selection of $-R^6$ and/or $-R^7$).

Polymyxin B

The deacylated from of the Polymyxin B decapeptide has the structure shown below:

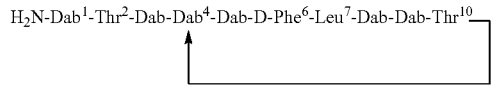

where positions 1, 2, 4, 6, 7 and 10 are indicated (with reference to the standard numbering system used for the Polymyxin B decapeptide), and the amino acid residues are in the L-configuration, unless indicated.

Polymyxin B nonapeptide, octapeptides and heptapeptide forms are also know in the art, and these compounds are truncated versions of the decapeptide shown above The compounds of the invention are variants of the polymyxin B decapeptide, nonapeptide, octapeptides and heptapeptide, where the amino acid at positions 6 and/or positions 7 is substituted with another amino acid, as described herein, and optionally the amino acid residues at positions 2, 3 and 10 are substituted with another amino acid residue.

The compounds of formula (I) are compounds where the N terminal group of the polypeptide (which may be a decapeptide, a nonapeptide or other) is modified.

The compounds of formula (II) are compounds where the N terminal amino group is optionally modified.

For convenience, the compounds of the invention are represented by the formula (I) where the amino acids at positions 1, 2, 3, 6, 7 or 10 are determined by the nature of the groups $-A^1-$, $-A^2-$ and $-A^3-$, $-R^6$, $-R^7$ and $-R^{10}$ respectively. Compounds of the invention, which include the variants described above, are biologically active.

A variant of the compound is a compound in which one or more, for example, from 1 to 5, such as 1, 2, 3 or 4 amino acids are substituted by another amino acid. The amino acid may be at a position selected from position 6 and/or 7 and optionally positions 1, 2, 3, and 10 (referring to the numbering of residues used in polymyxin B). The substitution may be for another amino acid or for a stereoisomer.

Methods of Preparation

Compounds of formula (I) and (II) be prepared by conventional peptide synthesis, using methods known to those skilled in the art. Suitable methods include solution-phase synthesis such as described by Yamada et al, *J. Peptide Res.* 64, 2004, 43-50, or by solid-phase synthesis such as described by Velkov et al., *ACS Chemical Biology*, 9, 2014, 1172 (including Supplementary Information), de Visser et al., *J. Peptide Res*, 61, 2003, 298-306, and Vaara et al., *Antimicrob. Agents and Chemotherapy*, 52, 2008. 3229-3236. These methods include a suitable protection strategy, and methods for the cyclisation step.

As shown herein, it is possible to derivatise the N terminal group of a deacylated polymyxin compound, such as deacylated nonapeptides, without derivatising the amino groups that are present in the side chains of the polymyxin compound. As described herein, the side chains of the polymyxin compound may be selectively protected without protecting the N terminal group. The N terminal group may then be reacted to provide the appropriate N terminal substituent. The side chain protection may subsequently be removed.

The present inventors have also found that an amino acid at position 6 or position 7 of a polymyxin compound may be modified in a method of synthesis, thereby providing a product polymyxin having a product having a modified amino acid.

The inventors have identified halogenated phenylalanine amino acid residues are useful intermediates for the preparation of modified amino acids. The halogen group is a useful reactive functionality, and may be substituted for other groups, for example in a cross-coupling reaction, such as a Suzuki-type cross-coupling reaction with a boronic acid or ester, in the presence of a metal catalyst.

The present invention provides a compound of formula (II) where the amino acid residue at position 6 or position 7 contains a halogenated phenyl group. However, the present invention is not limited to the use of such compounds, and variants of compound of formula (II) are also provided, and are useful in synthesis. For example, the present invention also provides a compound of formula (III), which comprises a halo aryl group.

In one embodiment, the method is the modification of phenylalanine.

In one embodiment of the invention there is provided a method of preparing a halogenated polymyxin compound, the method comprising the step of treating a polymyxin compound with a halogenating agent, thereby to provide the halogenated polymyxin compound. Here, one the amino acid residue at position 6 or position 7 contains an aryl group.

In one aspect there is provided a method of halogenating a polymyxin compound comprising an aryl group, such as an aryl group in an amino acid residue, the method comprising treating the polymyxin compound with a halogenating agent. The product of the reaction is a polymyxin compound containing a haloaryl group, such as a haloaryl group in an amino acid residue. Such a compound may be referred to as a halogenated polymyxin compound.

In one embodiment, the polymyxin compound comprises a phenylalanine, tyrosine or histidine residue.

In one embodiment, the polymyxin compound comprises a phenylalanine residue.

In one embodiment the method is the halogenation of a polymyxin compound having a phenylalanine residue at position 6 or position 7.

The phenyl group of a phenylalanine residue may be halogenated at the 4-position or the 2-position, or the reaction may produce a product having a mixture of the two.

It is possible to separate 2- and 4-halogenated products, for example by HPLC.

In one embodiment, the polymyxin compound comprises an α-amino acid, where the side chain of the amino acid comprises an aromatic group, such as a carboaryl group.

In one embodiment, the polymyxin compound comprises an α-amino acid, where the side chain of the amino acid comprises a phenyl group, which is optionally substituted.

In one embodiment, the polymyxin compound comprises an α-amino acid, where the side chain of the amino acid comprises a benzyl group, which is optionally substituted.

In one embodiment, there is provided a method for the preparation of a polymyxin compound of formula (IV), the method comprising the step of treating an aryl-containing polymyxin compound of formula (III).

In one embodiment, the polymyxin compound of formula (III) and (IV) is represented thus:

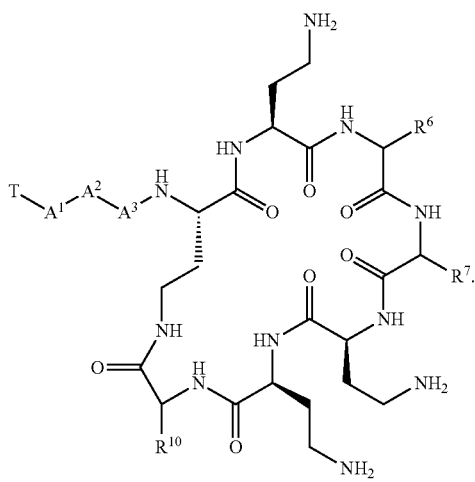

wherein:
-$T^4$ is hydrogen, $C_{1-4}$ alkyl or $R^N$—X—;
-$A^1$- is absent or is an amino acid residue;
-$A^2$- is absent or is an amino acid residue;
-$A^3$- is absent or is an amino acid residue;
—X— is —C(O)—, —NHC(O)—, —OC(O)—, —CH$_2$— or —SO$_2$—;
—$R^N$ is a terminal group, such as a group —$R^T$ as described herein;
—$R^6$ together with the carbonyl group and nitrogen alpha to the carbon to which it is attached is an amino acid residue;
—$R^7$ together with the carbonyl group and nitrogen alpha to the carbon to which it is attached is an amino acid residue;
and for the compounds of formula (IV) one of —$R^6$ and —$R^7$, comprises a haloaryl group; and for the compounds of formula (III) one of —$R^6$ and —$R^7$, comprises an aryl group
$R^{10}$ together with the carbonyl group and nitrogen alpha to the carbon to which it is attached, is a threonine or leucine residue;
and salts, solvates, and/or protected forms thereof.

In one embodiment, —$R^6$ comprises a haloaryl or an aryl group.

In one embodiment, —$R^7$ comprises a haloaryl or an aryl group.

In one embodiment, -$A^1$-, -$A^2$-, -$A^3$- and $R^N$— do not contain an optionally substituted aryl group.

In one embodiment, one of one of —$R^6$ and —$R^7$, comprises a benzyl group, where the phenyl is substituted with halo, such as monosubstituted.

In one embodiment, one of —$R^6$ and —$R^7$, comprises a haloaryl group.

In one embodiment, one of —$R^6$ and —$R^7$, comprises a bromoaryl group.

In one embodiment, the group —$R^N$ is as defined for the compounds of formula (II).

In one embodiment, the polymyxin compound is Polymyxin B. Thus, —X— is —C(O)—, and —$R^N$ is selected from 5-methylheptyl, 5-methylhexyl, heptyl, and hexyl.

In one embodiment, the group —$R^N$ does not contain an aryl group, for example does not contain a carboaryl or heteroaryl group.

In one embodiment, —$R^6$ is benzyl for the compounds of formula (III), and —$R^6$ is benzyl, where the phenyl group is substituted at the 2- or 4- position with halo, such as bromo (for the compounds of formula (IV)).

In one embodiment, the halogenation reaction is performed on a polymyxin compound where the side chain functionality of the amino acid residues and optionally the functionality within —$R^N$ is not protected. The inventors have found that the halogenation reaction may be advantageously performed directly on a polymyxin starting material, without the need to protect the amino acid functionality or protect functionality within —$R^N$. Thus, a halogenated product may be produced from a polymyxin starting material in one step.

A halogenated polymyxin compound, such as compound (IV) may be prepared without the need for protecting groups. After such a compound is prepared ti may be necessary to protect the reactive functionality for future syntheses.

The compound of formula (III) may be reacted with a halogenating reagent to yield the compound of formula (IV).

In one embodiment, the halogenating reagent is a brominating reagent, and the product of the reaction is a brominated product.

In one embodiment, the halogenating reagent is N-halosuccinimide

In one embodiment, the halogenating reagent is selected from NBS (N-bromosuccinimide), NCS (N-chlorosuccinimide), and NIS (N-iodosuccinimide).

In one embodiment, the halogenating reagent is NBS.

In one embodiment, the halogenating reagent is used in at least 1 mole equivalent with respect to the mole amount of aryl-containing compound.

In one embodiment, the halogenating reagent is used in at most 2 moles equivalent with respect to the mole amount of aryl-containing compound.

In one embodiment, the halogenating reagent is used at around 1.5 moles equivalent with respect to the mole amount of aryl-containing compound.

In one embodiment, the halogenating reagent is used together with a Lewis acid.

In one embodiment, the Lewis acid is $BF_3$.

In one embodiment, the Lewis acid is selected from $BF_3 \cdot 2H_2O$ and $BF_3 \cdot 2AcOH$, such as $BF_3 \cdot 2H_2O$.

Additionally or alternatively, $H_2O$, $CH_3CN$, AcOH may be present. Preferably no other solvent is present.

The halogenation reaction may be performed at ambient temperature, or below. Typically the halogenation reaction is performed at greater than 5° C., as the preferred Lewis acids crystallise at temperatures below 5° C.

A halogenated polymyxin compound, such as compound (IV), is suitable for use in methods of medical treatment as described herein. A halogenated polymyxin compound is also suitable for use as an intermediate in the preparation of alternative polymyxin compounds, as described in further detail below.

In one aspect of the invention, there is provided a method of synthesis, the method comprising the step of digesting a halogenated polymyxin compound selected from a halogenated decapeptide, a halogenated nonapeptide and a halogenated octapeptide, thereby to yield a halogenated heptapeptide polymyxin compound. Digesting refers to step of reducing the total number of amino acid residues within a polypeptide.

In one embodiment, a compound of formula (IVa) is digested to yield a compound of formula (IVb).

The compound of formula (IVa) is halogenated decapeptide, a halogenated nonapeptide or a halogenated octapeptide. The compound of formula (IVa) is a compound of formula (IV) where -$A^3$- is an amino acid residue. The compound of formula (IVa) is a compound where —$R^6$ or —$R^7$ comprises a haloaryl group. Following the cleavage reaction, the haloaryl group is retained in the cleaved product.

The compound of formula (IVb) is a halogenated heptapeptide polymyxin compound. The compound of formula (IVb) is a compound of formula (IV) where -$A^1$-, -$A^2$-, and -$A^3$- are absent and -$T^A$ is hydrogen. Where the compound of formula (IVa) is a compound where —$R^6$ or —$R^7$ comprises a haloaryl group, it follows that the compound of formula (IVb) is a compound where —$R^6$ or —$R^7$ comprises a haloaryl group.

In one embodiment a protease is used in the digestion method, such as a serine protease, such as a subtilisin.

In one embodiment, Savinase is used to digest the halogenated polymyxin compound.

The compound of formula (IVb) is a useful intermediate for the preparation of polymyxin compounds. The compound of formula (IVb) has an unmodified N terminal, and this terminal may be functionalised. The compound of formula (IVb) also has a haloaryl group, and the halogen may be substituted with another group to give a substituted aryl group.

Accordingly, in one aspect there is provided a method of synthesis, the method comprising the step of modifying the N terminal of a halogenated heptapeptide polymyxin compound to yield a halogenated polymyxin compound having a halogenated decapeptide, a halogenated nonapeptide and a halogenated octapeptide, wherein the N terminal of the halogenated decapeptide, a halogenated nonapeptide and a halogenated octapeptides is optionally modified, and a halogenated heptapeptide having a modified N terminal.

In one embodiment, the halogenated heptapeptide polymyxin compound is a compound of formula (IVb). The product of the reaction is a polymyxin compound of formula (V):

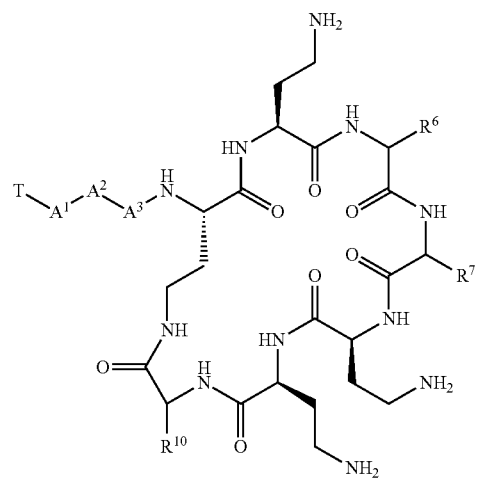

wherein:
-$T^A$ is hydrogen, $C_{1-4}$ alkyl or $R^N$—X—;
-$A^1$- is absent or is an amino acid residue;
-$A^2$- is absent or is an amino acid residue;
-$A^3$- is absent or is an amino acid residue;
and where -$A^1$-, -$A^2$-, and -$A^3$- are absent, -$T^A$ is $C_{1-4}$ alkyl or $R^N$—X—;
—X— is —C(O)—, —NHC(O)—, —OC(O)—, —$CH_2$— or —$SO_2$—;
—$R^N$ is a terminal group, such as a group —$R^T$ as described herein;
—$R^6$ together with the carbonyl group and nitrogen alpha to the carbon to which it is attached is an amino acid residue;
—$R^7$ together with the carbonyl group and nitrogen alpha to the carbon to which it is attached is an amino acid residue;
and one of —$R^6$ and —$R^7$, together with the carbonyl group and nitrogen alpha to the carbon to which —$R^6$ or —$R^7$ is attached, is amino acid residue having a haloaryl group;
$R^{10}$ together with the carbonyl group and nitrogen alpha to the carbon to which it is attached, is a threonine or leucine residue;
and salts, solvates, and/or protected forms thereof.

The compound (V) is typically formed from (IVb) by an amide coupling reaction. Thus, the terminal amino group in the compound of formula (IVb) is reacted with an appropriate carboxylic acid compound or activated carboxylic compound to yield the amide product.

The carboxylic acid compound may be a compound of formula (IVc):

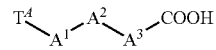

where -A¹-, -A²-, -A³- and -T⁴ have the same meanings as the compounds of formula (V), and activated forms thereof.

In one embodiment, the reaction of a carboxylic acid with an amine may be undertaken in the presence of one or more amide coupling reagents, as are well known in the art. A coupling reagent may optionally be used together with a base, such as an organic base.

Amide coupling reagents suitable for use include carbodiimides (e.g. EDC and DCC), phosphonium salts (e.g. PyBOP), and uronium and guanidinium salts (e.g. HATU and HBTU), such as described in further detail below.

A carbodiimide may include dicyclohexylcarbodiimide (DCC), N-(3-dimethylaminopropyl)-N'-ethylcarbo-diimide (EDC), 1-tert-butyl-3-ethylcarbodiimide, N-cyclohexyl-N'-2-morpholinoethyl)carbodiimide, and diisopropylcarbodiimide.

A phosphonium salt may include benzotriazol-1-yl-oxytripyrrolidinophosphonium hexafluorophosphate (PyBoP), (7-Azabenzotriazol-1-yloxy)tripyrrolidinophosphonium hexafluorophosphate (PyAOP) and chlorotripyrrolidinophosphonium hexafluorophosphate (PyBroP).

Uronium and guanidinium salts include O-(Benzotriazol-1-yl)-N,N,N',N'-tetramethyluronium hexafluorophosphate (HBTU), O-(Benzotriazol-1-yl)-N,N,N',N'-tetramethyluronium tetrafluoroborate (TBTU), O-(7-Azabenzotriazol-1-yl)-N,N,N',N'-tetramethyluronium hexafluorophosphate (HATU), N,N,N',N'-tetramethyl-O—(N-succinimidyl)uronium tetrafluoroborate (T STU) and O-[(ethoxycarbonyl)cyanomethylenamino]-N,N,N',N'-tetramethyluronium tetrafluoroborate (TNTU), amongst others.

Other agents may be used, including other benzotriazole-containing agents such as N-hydroxybenzotriazole (HOBt) and 1-hydroxy-7-azabenzotriazole (HOAt), or reagents such as 1-(mesitylene-2-sulfonyl)-3-nitro-1,2,4-triazole (MSNT) and propylphosphonic anhydride (T3P).

Example coupling reagents are available from commercial sources, for example as described in *ChemFiles* 2007, 4, No. 2, Sigma-Aldrich.

As noted above, the reaction of the acid and the carboxylic acid may be conducted in the presence of a base. Example bases include alkylamine bases such as N,N-diisopropylethylamine (DIPEA) and triethylamine (TEA), 4-dimethylaminopyridine (DMAP), pyridine, and 4-methyl-morpholine (NMM).

The amide-forming reaction may be performed in a solvent or solvent mixture. A solvent for use may include dimethylformamide (DMF) and dichloromethane (DCM), toluene and acetonitrile. Other solvents, such as other alkyl formamides, halogenated hydrocarbons, aromatic hydrocarbons and nitriles may be used as required.

The carboxylic acid compound used in the amide forming reaction may be initially reacted with the amide coupling reagents to pre-form an activated from of the carboxylic acid. The amine compound may then be subsequently added to the reaction mixture. This is not essential, and the reaction components may be mixed in an alternative sequence, such as described in the worked examples herein.

An activated form of the carboxylic acid includes an acyl halide, a haloformate, an anhydride or a carboxylic ester. The carboxylic acid may be reacted to form an acyl halide, haloformate, anhydride or carboxylic ester by methods known in the art.

In one aspect of the invention, there is provided a method of synthesis, the method comprising the step of substituting a halogen within a halogenated polymyxin compound to yield a polymyxin product having a substituted aromatic group. The halogenated polymyxin compound is a compound having a haloaryl group.

In one embodiment, the halogenated heptapeptide polymyxin compound is a compound of formula (IV). The product of the reaction is a polymyxin compound of formula (VI):

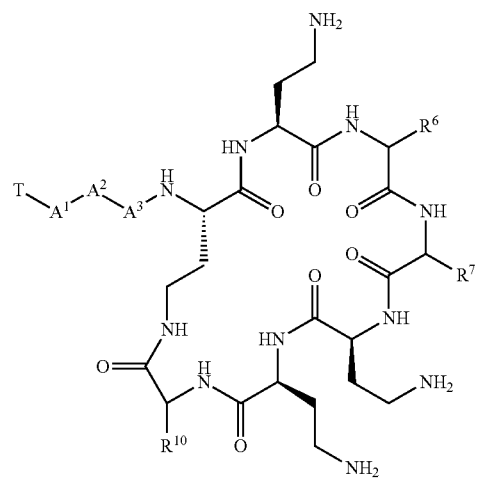

wherein:
-T⁴ is hydrogen, $C_{1-4}$ alkyl or $R^N$—X—;
-A¹- is absent or is an amino acid residue;
-A²- is absent or is an amino acid residue;
-A³- is absent or is an amino acid residue; and where -A¹-, -A²-, and -A³- are absent, -T⁴ is $C_{1-4}$ alkyl or $R^N$—X—;
—X— is —C(O)—, —NHC(O)—, —OC(O)—, —CH₂— or —SO₂—; —$R^N$ is a terminal group, such as a group —$R^T$ as described herein;
—$R^6$ together with the carbonyl group and nitrogen alpha to the carbon to which it is attached is an amino acid residue;
—$R^7$ together with the carbonyl group and nitrogen alpha to the carbon to which it is attached is an amino acid residue; and one of —$R^6$ and —$R^7$, comprises a substituted aryl group;
$R^{10}$ together with the carbonyl group and nitrogen alpha to the carbon to which it is attached, is a threonine or leucine residue;
and salts, solvates, and/or protected forms thereof.

In one embodiment, —$R^6$ comprises a substituted aryl group, such as a benzyl group.

In one embodiment, —$R^7$ comprises a substituted aryl group, such as a benzyl group.

The substitution reaction may be a cross-coupling reaction.

The substitution reaction may be a metal-catalysed substitution reaction.

The substitution reaction may be a Pd-catalysed substitution reaction.

The substitution reaction may be a Suzuki-based coupling (substitution) reaction. Thus, the haloaryl-containing polymyxin compounds is reacted with a boronic acid or ester in the presence of a metal catalyst to yield the substituted product.

In one embodiment, the substituted aryl group is aryl substituted with —$R^F$, where —$R^F$ is selected from optionally substituted $C_{1-12}$ alkyl, optionally substituted $C_{2-12}$ alkenyl, optionally substituted $C_{2-12}$ alkynyl, optionally substituted $C_{3-10}$ cycloalkyl, optionally substituted $C_{3-10}$ heterocyclyl, optionally substituted $C_{5-12}$ aryl, and an optionally substituted group may have one or more substituent groups selected from halo, haloalkyl, alkyl, alkenyl, alkynyl, and aryl, except that alkyl alkenyl, and alkynyl groups are not substituents to the alkyl alkenyl, and alkynyl groups. Suitable groups are described in relation to the definition of —$R^P$ for —$R^6$.

In one embodiment, the substituted aryl group is aryl substituted with optionally substituted $C_{5-12}$ aryl.

Thus, the substitution reaction involves the reaction of a haloaryl groups with a reactive partner containing the group —$R^F$. For example, the reactive partner is a boronic acid or ester comprising the group —$R^F$.

A halogenated polymyxin compound having a modified N terminal may be further reacted to yield a substituted polymyxin compounds having a modified N terminal.

In one aspect of the invention, there is provided a method of synthesis, the method comprising the step of substituting a halogen within a halogenated polymyxin compound having a modified N terminal to yield a polymyxin product having a modified N terminal and a substituted aromatic group. The halogenated polymyxin compound having a modified N terminal is a compound having an amino acid residue with a haloaryl group.

The term "substituted" as used herein with reference to a substitution reaction refers to the formal replacement of the halogen group with another group (which may be a different type of halogen group).

In one embodiment, the method is the replacement of the halogen group with a different halogen group.

The methods of the reaction allow a commercially available starting material or a naturally-produced starting material to be converted to a compound of formula (I) or (II).

In a further aspect of the invention there is provided a method of reducing an aryl-containing polymyxin compound, for example a method or reducing a compound of formula (III) or (VI), such as a protected form of (III) or (VI).

In one embodiment, the method comprises the step of contacting a compound of formula (III) or (VI), or protected forms thereof, with a metal catalyst in the present of hydrogen, thereby to reduce the aryl group. The metal catalyst may be platinum oxide.

Such methods are particularly useful for the preparation of cyclohexyl-containing compounds from phenyl-containing compounds, as exemplified herein.

Active Agent

The compounds of formula (I) or (II) may each be used together with a second agent. The inventors have found that such combinations have greater biological activity than would be expected from the individual activity of both compounds. The compounds of formula (I) or (II) can be used to potentiate the activity of the second agent. In particular, the compounds of formula (I) or (II) may be used together with a second agent to enhance the antimicrobial activity of that agent, for example against Gram-negative bacteria.

Without wishing to be bound by theory it is believed that the compounds of formula (I) or (II) act on the outer membrane of a cell e.g. a Gram-negative bacterial cell, to facilitate the uptake of the second agent into that cell. Thus, agents that are otherwise incapable or poor at crossing the outer membrane may be taken up into a target cell by the action of the compounds of formula (I) or (II).

In one embodiment, the combination of a compound of formula (I) or (II) with the second agent is active against Gram-negative bacteria. Here, it is not essential that individually either of the compound of formula (I) or (II) or the second agent have activity against Gram-negative bacteria.

In one embodiment, the second agent is an agent having a measured MIC value against a particular microorganism, such as a bacterium, that is less than 10, less than 5, or less than 1 micrograms/mL. The microorganism may be a Gram-negative bacteria, such as a Gram-negative bacteria selected from the group consisting of *E. coli, S. enterica, K. pneumoniae, K. oxytoca; E. cloacae, E. aerogenes, E. agglomerans, A. calcoaceticus, A. baumannii; Pseudomonas aeruginosa, Stenotrophomonas maltophila, Providencia stuartii, P. mirabilis*, and *P. vulgaris*.

Examples of second agents that have activity against Gram-negative bacteria include beta-lactams, tetracyclines, aminoglycosides and quinolones.

In one embodiment, the second agent is an agent having a measured MIC value against a particular microorganism, such as a Gram-negative bacterium, that is more than 4, more than 8, more than 16 or more than 32 micrograms/mL. In this embodiment, the second agent may be active against Gram-positive bacteria. For example, the second agent is an agent having a measured MIC value against a particular Gram-positive bacterium that is less than 10, less than 5, or less than 1 micrograms/mL. Here, the compound of formula (I) or (II) acts to facilitate the uptake of the second agent into the Gram-negative bacterial cell. The second agent is therefore able to act on a target within the Gram-negative bacterial cell, which target may be the same as the second agent's target in a Gram-positive bacterial cell.

The Gram-positive bacteria may be selected from the group consisting of *Staphylococcus* and *Streptococcus* bacteria, such as *S. aureus* (including MRSA), *S. epidermis, E. faecalis*, and *E. faecium*.

Examples of second agents that have activity against Gram-positive bacteria (at the MIC values given above, for example), and moderate activity against Gram-negative bacteria, include rifampicin, novobiocin, macrolides, pleuromutilins. In one embodiment, a compound having moderate activity against Gram-negative bacteria may have a measured MIC value against a Gram-negative bacterium that is less than 32, less than 64, or less than 128 micrograms/mL.

Also suitable for use are agents having activity against Gram-positive bacteria and which are essentially inactive against Gram-negative bacteria. Examples include fusidic acid, oxazolidinines (e.g. linezolid), glycopeptides (e.g. vancomycin), daptomycin and lantibiotics.

In one embodiment, a compound having essentially no activity against Gram-negative bacteria may have a measured MIC value against a Gram-negative bacterium that is more than 32, more then 64, more than 128, more than 256 micrograms/mL.

Under normal circumstances such agents are not necessarily suitable for use against Gram-negative bacteria owing to their relatively poor ability to cross the outer membrane of a Gram-negative bacterial cell. As explained above, when used together with a compound of formula (I) or (II), such agents are suitable for use.

In one embodiment, the active agent may be selected from the group consisting of rifampicin (rifampin), rifabutin, rifalazil, rifapentine, rifaximin, aztreonam, oxacillin, novobiocin, fusidic acid, azithromycin, ciprofloxacin, meropenem, tigecycline, erythromycin, clarithromycin and mupirocin, and pharmaceutically acceptable salts, solvates and prodrug forms thereof.

The present inventors have found that the polymyxin compounds of formula (I) or (II) may be used together with certain compounds in the rifamycin family to treat microbial infections. The rifamycin family includes isolates rifamycin A, B, C, D, E, S and SV, and synthetically derivatised versions of these compounds, such as rifampicin (rifampin), rifabutin, rifalazil, rifapentine, and rifaximin, and pharmaceutically acceptable salts and solvates thereof.

In one embodiment, the active agent is rifampicin (rifampin) and pharmaceutically acceptable salts, solvates and prodrug forms thereof.

Salts, Solvates and Other Forms

Examples of salts of compound of formula (I) and (II) include all pharmaceutically acceptable salts, such as, without limitation, acid addition salts of strong mineral acids such as HCl and HBr salts and addition salts of strong organic acids such as a methanesulfonic acid salt. Further examples of salts include sulphates and acetates such as trifluoroacetate or trichloroacetate.

In one embodiment the compounds of the present disclosure are provided as a sulphate salt or a trifluoroacetic acid (TFA) salt. In one embodiment the compounds of the present disclosure are provided as acetate salts.

A compound of formula (I) or (II) can also be formulated as prodrug. Prodrugs can include an antibacterial compound herein described in which one or more amino groups are protected with a group which can be cleaved in vivo, to liberate the biologically active compound. In one embodiment the prodrug is an "amine prodrug". Examples of amine prodrugs include sulphomethyl, as described in e.g., Bergen et al, *Antimicrob. Agents and Chemotherapy,* 2006, 50, 1953 or $HSO_3$-FMOC, as described in e.g. Schechter et al, *J. Med Chem* 2002, 45(19) 4264, and salts thereof. Further examples of amine prodrugs are given by Krise and Oliyai in *Biotechnology: Pharmaceutical Aspects,* 2007, 5(2), 101-131.

In one embodiment a compound of formula (I) or (II) is provided as a prodrug.

A reference to a compound of formula (I) or (II), or any other compound described herein, is also a reference to a solvate of that compound. Examples of solvates include hydrates.

A compound of formula (I) or (II), or any other compound described herein, includes a compound where an atom is replaced by a naturally occurring or non-naturally occurring isotope. In one embodiment the isotope is a stable isotope. Thus a compound described here includes, for example deuterium containing compounds and the like. For example, H may be in any isotopic form, including $^1H$, $^2H$ (D), and $^3H$ (T); C may be in any isotopic form, including $^{12}C$, $^{13}C$, and $^{14}C$; O may be in any isotopic form, including $^{16}O$ and $^{18}O$; and the like.

Certain compounds of formula (I) or (II), or any other compound described herein, may exist in one or more particular geometric, optical, enantiomeric, diasteriomeric, epimeric, atropic, stereoisomeric, tautomeric, conformational, or anomeric forms, including but not limited to, cis- and trans-forms; E- and Z-forms; c-, t-, and r- forms; endo- and exo-forms; R-, S-, and meso-forms; D- and L-forms; d- and l-forms; (+) and (−) forms; keto-, enol-, and enolate-forms; syn- and anti-forms; synclinal- and anticlinal-forms; α- and β-forms; axial and equatorial forms; boat-, chair-, twist-, envelope-, and halfchair-forms; and combinations thereof, hereinafter collectively referred to as "isomers" (or "isomeric forms").

Note that, except as discussed below for tautomeric forms, specifically excluded from the term "isomers," as used herein, are structural (or constitutional) isomers (i.e., isomers which differ in the connections between atoms rather than merely by the position of atoms in space). For example, a reference to a methoxy group, $-OCH_3$, is not to be construed as a reference to its structural isomer, a hydroxymethyl group, $-CH_2OH$. Similarly, a reference to ortho-chlorophenyl is not to be construed as a reference to its structural isomer, meta-chlorophenyl. However, a reference to a class of structures may well include structurally isomeric forms falling within that class (e.g., $C_{1-6}$alkyl includes n-propyl and iso-propyl; butyl includes n-, iso-, sec-, and tert-butyl; methoxyphenyl includes ortho-, meta-, and para-methoxyphenyl).

Unless otherwise specified, a reference to a particular compound includes all such isomeric forms, including mixtures (e.g., racemic mixtures) thereof. Methods for the preparation (e.g., asymmetric synthesis) and separation (e.g., fractional crystallisation and chromatographic means) of such isomeric forms are either known in the art or are readily obtained by adapting the methods taught herein, or known methods, in a known manner.

One aspect of the present invention pertains to compounds in substantially purified form and/or in a form substantially free from contaminants.

In one embodiment, the substantially purified form is at least 50% by weight, e.g., at least 60% by weight, e.g., at least 70% by weight, e.g., at least 80% by weight, e.g., at least 90% by weight, e.g., at least 95% by weight, e.g., at least 97% by weight, e.g., at least 98% by weight, e.g., at least 99% by weight.

Unless specified, the substantially purified form refers to the compound in any stereoisomeric or enantiomeric form. For example, in one embodiment, the substantially purified form refers to a mixture of stereoisomers, i.e., purified with respect to other compounds. In one embodiment, the substantially purified form refers to one stereoisomer, e.g., optically pure stereoisomer. In one embodiment, the substantially purified form refers to a mixture of enantiomers. In one embodiment, the substantially purified form refers to an equimolar mixture of enantiomers (i.e., a racemic mixture, a racemate). In one embodiment, the substantially purified form refers to one enantiomer, e.g., optically pure enantiomer.

In one embodiment, the contaminants represent no more than 50% by weight, e.g., no more than 40% by weight, e.g., no more than 30% by weight, e.g., no more than 20% by weight, e.g., no more than 10% by weight, e.g., no more than 5% by weight, e.g., no more than 3% by weight, e.g., no more than 2% by weight, e.g., no more than 1% by weight.

Unless specified, the contaminants refer to other compounds, that is, other than stereoisomers or enantiomers. In one embodiment, the contaminants refer to other compounds and other stereoisomers. In one embodiment, the contaminants refer to other compounds and the other enantiomer.

In one embodiment, the substantially purified form is at least 60% optically pure (i.e., 60% of the compound, on a molar basis, is the desired stereoisomer or enantiomer, and 40% is the undesired stereoisomer or enantiomer), e.g., at least 70% optically pure, e.g., at least 80% optically pure, e.g., at least 90% optically pure, e.g., at least 95% optically pure, e.g., at least 97% optically pure, e.g., at least 98% optically pure, e.g., at least 99% optically pure.

Methods of Treatment

The compounds of formula (I) or (II), or pharmaceutical formulations containing these compounds, are suitable for use in methods of treatment and prophylaxis. The compounds may be administered to a subject in need thereof. The compounds are suitable for use together with an active agent ("a second active agent"), for example a second active agent that is an antimicrobial agent.

The compounds of formula (I) or (II) are for use in a method of treatment of the human or animal body by therapy. In some aspects of the invention, a compound of formula (I) or (II) may be administered to a mammalian subject, such as a human, in order to treat a microbial infection.

Another aspect of the present invention pertains to use of a compound of formula (I) or (II) in the manufacture of a medicament for use in treatment. In one embodiment, the medicament comprises a compound of formula (I) or (II). In one embodiment, the medicament is for use in the treatment of a microbial infection.

The term "microbial infection" refers to the invasion of the host animal by pathogenic microbes. This includes the excessive growth of microbes that are normally present in or on the body of an animal. More generally, a microbial infection can be any situation in which the presence of a microbial population(s) is damaging to a host animal. Thus, an animal is "suffering" from a microbial infection when excessive numbers of a microbial population are present in or on an animal's body, or when the presence of a microbial population(s) is damaging the cells or other tissue of an animal.

The compounds may be used to treat a subject having a microbial infection, or at risk of infection from a microorganism, such as a bacterium.

The microbial infection may be a bacterial infection such as a Gram-negative bacterial infection.

Examples of Gram-negative bacteria include, but are not limited to, *Escherichia* spp., *Klebsiella* spp., *Enterobacter* spp., *Salmonella* spp., *Shigella* spp., *Citrobacter* spp., *Morganella morganii*, *Yersinia pseudotuberculosis* and other *Enterobacteriaceae*, *Pseudomonas* spp., *Acinetobacter* spp., *Moraxella*, *Helicobacter*, *Stenotrophomonas*, *Bdellovibrio*, acetic acid bacteria, *Legionella* and alpha-proteobacteria such as *Wolbachia* and numerous others.

Medically relevant Gram-negative cocci include three organisms, which cause a sexually transmitted disease (*Neisseria gonorrhoeae*), a meningitis (*Neisseria meningitidis*), and respiratory symptoms (*Moraxella catarrhalis*).

Medically relevant Gram-negative bacilli include a multitude of species. Some of them primarily cause respiratory problems (*Hemophilus influenzae*, *Klebsiella pneumoniae*, *Legionella pneumophila*, *Pseudomonas aeruginosa*), primarily urinary problems (*Escherichia coli*, *Enterobacter cloacae*), and primarily gastrointestinal problems (*Helicobacter pylori*, *Salmonella enterica*).

Gram-negative bacteria associated with nosocomial infections include *Acinetobacter baumannii*, which causes bacteremia, secondary meningitis, and ventilator-associated pneumonia in intensive-care units of hospital establishments.

In one embodiment the Gram-negative bacterial species is selected from the group consisting of *E. coli, S. enterica, K. pneumoniae, K. oxytoca; E. cloacae, E. aerogenes, E. agglomerans, A. calcoaceticus, A. baumannii; Pseudomonas aeruginosa, Stenotrophomonas maltophila, Providencia stuartii, P. mirabilis*, and *P. vulgaris*.

In one embodiment the Gram-negative bacterial species is selected from the group consisting of *E. coli, K. pneumoniae, Pseudomonas aeruginosa*, and *A. baumannii*.

The compounds of formula (I) or (II) or compositions comprising the same are useful for the treatment of skin and soft tissue infections, gastrointestinal infection, urinary tract infection, pneumonia, sepsis, intra-abdominal infection and obstetrical/gynaecological infections. The infections may be Gram-positive or Gram-negative bacterial infections.

The compounds of formula (I) or (II) or compositions comprising the same are useful for the treatment of *Pseudomonas* infections including *P. aeruginosa* infection, for example skin and soft tissue infections, gastrointestinal infection, urinary tract infection, pneumonia and sepsis.

The compounds of formula (I) or (II) or compositions comprising the same are useful for the treatment of *Acinetobacter* infections including *A. baumanii* infection, for pneumonia, urinary tract infection and sepsis.

The compounds of formula (I) or (II) or compositions comprising the same are useful for the treatment of *Klebsiella* infections including *K. pneumoniae* infection, for pneumonia, urinary tract infection, meningitis and sepsis.

The compounds of formula (I) or (II) or compositions comprising the same are useful for the treatment of *E. coli* infection including *E. coli* infections, for bacteremia, cholecystitis, cholangitis, urinary tract infection, neonatal meningitis and pneumonia.

The active agent may be an agent that has activity against the microorganism. The active agent may be active against Gram-negative bacteria. The active agent may be active against a microorganism selected from the list given above.

In one embodiment, the second active agent has an MIC value of 10 micrograms/mL or less against a microorganism such as *E. coli*, in the absence of the compound of formula (I) or (II). The microorganism may be a microorganism selected from the group above.

Specific compounds for use as second active agents are described herein and include:
  rifampicin, rifabutin, rifalazil, rifapentine, and rifaximin;
  oxacillin, methicillin, ampicillin, cloxacillin, carbenicillin, piperacillin, tricarcillin, flucloxacillin, and nafcillin;
  azithromycin, clarithromycin, erythromycin, telithromycin, cethromycin, and solithromycin;
  aztreonam and BAL30072;
  meropenem, doripenem, imipenem, ertapenem, biapenem, tomopenem, and panipenem;
  tigecycline, omadacycline, eravacycline, doxycycline, and minocycline;
  ciprofloxacin, levofloxacin, moxifloxacin, and delafloxacin;
  Fusidic acid;
  Novobiocin;
  teichoplanin, telavancin, dalbavancin, and oritavancin,
  and pharmaceutically acceptable salts and solvates thereof;

In one embodiment, specific compounds for use as second active agents are described herein and include rifampicin (rifampin), rifabutin, rifalazil, rifapentine, rifaximin, aztreonam, oxacillin, novobiocin, fusidic acid, azithromycin, ciprofloxacin, meropenem, tigecycline, erythromycin, clarithromycin and mupirocin, and pharmaceutically acceptable salts and solvates thereof.

In an alternative aspect, the compounds of formula (I) are suitable for use in the treatment of fungal infections, for example in combination together with an antifungal agent. The antifungal agent may be selected from a polyene antifungal, for example amphotericin B, an imidazole, triazole, or thiazole antifungal, for example miconazole, fluconazole or abafungin, an allylamine, an echinocandin, or another agent, for example ciclopirox.

Treatment

The term "treatment," as used herein in the context of treating a condition, pertains generally to treatment and therapy, whether of a human or an animal (e.g., in veterinary applications), in which some desired therapeutic effect is achieved, for example, the inhibition of the progress of the condition, and includes a reduction in the rate of progress, a halt in the rate of progress, alleviation of symptoms of the condition, amelioration of the condition, and cure of the condition. Treatment as a prophylactic measure (i.e., prophylaxis) is also included.

For example, use with patients who have not yet developed the condition, but who are at risk of developing the condition, is encompassed by the term "treatment."

The term "therapeutically-effective amount," as used herein, pertains to that amount of a compound, or a material, composition or dosage form comprising a compound, which is effective for producing some desired therapeutic effect, commensurate with a reasonable benefit/risk ratio, when administered in accordance with a desired treatment regimen.

The term "treatment" includes combination treatments and therapies, as described herein, in which two or more treatments or therapies are combined, for example, sequentially or simultaneously.

Combination Therapy

A compound of formula (I) or (II) may be administered in conjunction with an active agent. Administration may be simultaneous, separate or sequential.

The methods and manner of administration will depend on the pharmacokinetics of the compound of formula (I) or (II) and the second agent.

By "simultaneous" administration, it is meant that a compound of formula (I) or (II) and a second agent are administered to a subject in a single dose by the same route of administration.

By "separate" administration, it is meant that a compound of formula (I) or (II) and a second agent are administered to a subject by two different routes of administration which occur at the same time. This may occur for example where one agent is administered by infusion and the other is given orally during the course of the infusion.

By "sequential" it is meant that the two agents are administered at different points in time, provided that the activity of the first administered agent is present and ongoing in the subject at the time the second agent is administered.

Generally, a sequential dose will occur such that the second of the two agents is administered within 48 hours, preferably within 24 hours, such as within 12, 6, 4, 2 or 1 hour(s) of the first agent. Alternatively, the active agent may be administered first, followed by the compound of formula (I) or (II).

Ultimately, the order and timing of the administration of the compound and second agent in the combination treatment will depend upon the pharmacokinetic properties of each.

The amount of the compound of formula (I) or (II) to be administered to a subject will ultimately depend upon the nature of the subject and the disease to be treated. Likewise, the amount of the active agent to be administered to a subject will ultimately depend upon the nature of the subject and the disease to be treated.

Formulations

In one aspect, the present invention provides a pharmaceutical composition comprising a compound of formula (I) or (II) together with a pharmaceutically acceptable carrier. The pharmaceutical composition may additionally comprise a second active agent. In an alternative embodiment, where a second agent is provided for use in therapy, the second agent may be separately formulated from the compound of formula (I) or (II). The comments below made in relation to the compound of formula (I) or (II) may therefore also apply to the second agent, as separately formulated.

While it is possible for the compound of formula (I) or (II) to be administered alone or together with the second agent, it is preferable to present it as a pharmaceutical formulation (e.g., composition, preparation, medicament) comprising at least one compound of formula (I) or (II), as described herein, together with one or more other pharmaceutically acceptable ingredients well known to those skilled in the art, including, but not limited to, pharmaceutically acceptable carriers, diluents, excipients, adjuvants, fillers, buffers, preservatives, anti-oxidants, lubricants, stabilisers, solubilisers, surfactants (e.g., wetting agents), masking agents, colouring agents, flavouring agents, and sweetening agents. The formulation may further comprise other active agents, for example, other therapeutic or prophylactic agents.

Thus, the present invention further provides pharmaceutical compositions, as defined above, and methods of making a pharmaceutical composition comprising admixing at least one compound of formula (I) or (II), as described herein, together with one or more other pharmaceutically acceptable ingredients well known to those skilled in the art, e.g., carriers, diluents, excipients, etc. If formulated as discrete units (e.g., tablets, etc.), each unit contains a predetermined amount (dosage) of the compound. The composition optionally further comprises the second active agent in a predetermined amount.

The term "pharmaceutically acceptable," as used herein, pertains to compounds, ingredients, materials, compositions, dosage forms, etc., which are, within the scope of sound medical judgment, suitable for use in contact with the tissues of the subject in question (e.g., human) without excessive toxicity, irritation, allergic response, or other problem or complication, commensurate with a reasonable benefit/risk ratio. Each carrier, diluent, excipient, etc. must also be "acceptable" in the sense of being compatible with the other ingredients of the formulation.

Suitable carriers, diluents, excipients, etc. can be found in standard pharmaceutical texts, for example, Remington's Pharmaceutical Sciences, 18th edition, Mack Publishing Company, Easton, Pa., 1990; and Handbook of Pharmaceutical Excipients, 5th edition, 2005.

The formulations may be prepared by any methods well known in the art of pharmacy. Such methods include the step of bringing into association the compound of formula (I) or (II) with a carrier which constitutes one or more accessory ingredients. In general, the formulations are prepared by uniformly and intimately bringing into association the compound with carriers (e.g., liquid carriers, finely divided solid carrier, etc.), and then shaping the product, if necessary.

The formulation may be prepared to provide for rapid or slow release; immediate, delayed, timed, or sustained release; or a combination thereof.

Formulations may suitably be in the form of liquids, solutions (e.g., aqueous, non-aqueous), suspensions (e.g., aqueous, non-aqueous), emulsions (e.g., oil-in-water, water-in-oil), elixirs, syrups, electuaries, mouthwashes, drops, tablets (including, e.g., coated tablets), granules, powders, losenges, pastilles, capsules (including, e.g., hard and soft gelatin capsules), cachets, pills, ampoules, boluses, suppositories, pessaries, tinctures, gels, pastes, ointments, creams, lotions, oils, foams, sprays, mists, or aerosols.

Formulations may suitably be provided as a patch, adhesive plaster, bandage, dressing, or the like which is impregnated with one or more compounds and optionally one or more other pharmaceutically acceptable ingredients, including, for example, penetration, permeation, and absorption enhancers. Formulations may also suitably be provided in the form of a depot or reservoir.

The compound may be dissolved in, suspended in, or admixed with one or more other pharmaceutically acceptable ingredients. The compound may be presented in a liposome or other microparticulate which is designed to target the compound, for example, to blood components or one or more organs. Where a liposome is used, it is noted that the liposome may contain both the compound of formula (I) or (II) and the second agent.

Formulations suitable for oral administration (e.g., by ingestion) include liquids, solutions (e.g., aqueous, non-aqueous), suspensions (e.g., aqueous, non-aqueous), emulsions (e.g., oil-in-water, water-in-oil), elixirs, syrups, electuaries, tablets, granules, powders, capsules, cachets, pills, ampoules, boluses.

Formulations suitable for buccal administration include mouthwashes, losenges, pastilles, as well as patches, adhesive plasters, depots, and reservoirs. Losenges typically comprise the compound in a flavoured basis, usually sucrose and acacia or tragacanth. Pastilles typically comprise the compound in an inert matrix, such as gelatin and glycerin, or sucrose and acacia. Mouthwashes typically comprise the compound in a suitable liquid carrier.

Formulations suitable for sublingual administration include tablets, losenges, pastilles, capsules, and pills.

Formulations suitable for oral transmucosal administration include liquids, solutions (e.g., aqueous, non-aqueous), suspensions (e.g., aqueous, non-aqueous), emulsions (e.g., oil-in-water, water-in-oil), mouthwashes, losenges, pastilles, as well as patches, adhesive plasters, depots, and reservoirs.

Formulations suitable for non-oral transmucosal administration include liquids, solutions (e.g., aqueous, non-aqueous), suspensions (e.g., aqueous, non-aqueous), emulsions (e.g., oil-in-water, water-in-oil), suppositories, pessaries, gels, pastes, ointments, creams, lotions, oils, as well as patches, adhesive plasters, depots, and reservoirs.

Formulations suitable for transdermal administration include gels, pastes, ointments, creams, lotions, and oils, as well as patches, adhesive plasters, bandages, dressings, depots, and reservoirs.

Tablets may be made by conventional means, e.g., compression or moulding, optionally with one or more accessory ingredients. Compressed tablets may be prepared by compressing in a suitable machine the compound in a free-flowing form such as a powder or granules, optionally mixed with one or more binders (e.g., povidone, gelatin, acacia, sorbitol, tragacanth, hydroxypropylmethyl cellulose); fillers or diluents (e.g., lactose, microcrystalline cellulose, calcium hydrogen phosphate); lubricants (e.g., magnesium stearate, talc, silica); disintegrants (e.g., sodium starch glycolate, cross-linked povidone, cross-linked sodium carboxymethyl cellulose); surface-active or dispersing or wetting agents (e.g., sodium lauryl sulfate); preservatives (e.g., methyl p-hydroxybenzoate, propyl p-hydroxybenzoate, sorbic acid); flavours, flavour enhancing agents, and sweeteners. Moulded tablets may be made by moulding in a suitable machine a mixture of the powdered compound moistened with an inert liquid diluent. The tablets may optionally be coated or scored and may be formulated so as to provide slow or controlled release of the compound therein using, for example, hydroxypropylmethyl cellulose in varying proportions to provide the desired release profile. Tablets may optionally be provided with a coating, for example, to affect release, for example an enteric coating, to provide release in parts of the gut other than the stomach.

Ointments are typically prepared from the compound and a paraffinic or a water-miscible ointment base.

Creams are typically prepared from the compound and an oil-in-water cream base. If desired, the aqueous phase of the cream base may include, for example, at least about 30% w/w of a polyhydric alcohol, i.e., an alcohol having two or more hydroxyl groups such as propylene glycol, butane-1, 3-diol, mannitol, sorbitol, glycerol and polyethylene glycol and mixtures thereof. The topical formulations may desirably include a compound which enhances absorption or penetration of the compound through the skin or other affected areas. Examples of such dermal penetration enhancers include dimethylsulfoxide and related analogues.

Emulsions are typically prepared from the compound and an oily phase, which may optionally comprise merely an emulsifier (otherwise known as an emulgent), or it may comprises a mixture of at least one emulsifier with a fat or an oil or with both a fat and an oil. Preferably, a hydrophilic emulsifier is included together with a lipophilic emulsifier which acts as a stabiliser. It is also preferred to include both an oil and a fat. Together, the emulsifier(s) with or without stabiliser(s) make up the so-called emulsifying wax, and the wax together with the oil and/or fat make up the so-called emulsifying ointment base which forms the oily dispersed phase of the cream formulations.

Suitable emulgents and emulsion stabilisers include Tween 60, Span 80, cetostearyl alcohol, myristyl alcohol, glyceryl monostearate and sodium lauryl sulfate. The choice of suitable oils or fats for the formulation is based on achieving the desired cosmetic properties, since the solubility of the compound in most oils likely to be used in pharmaceutical emulsion formulations may be very low. Thus the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils can be used.

Formulations suitable for intranasal administration, where the carrier is a liquid, include, for example, nasal spray, nasal drops, or by aerosol administration by nebuliser, include aqueous or oily solutions of the compound. As an alternative method of administration, a dry powder delivery may be used as an alternative to nebulised aerosols.

Formulations suitable for intranasal administration, where the carrier is a solid, include, for example, those presented as a coarse powder having a particle size, for example, in the range of about 20 to about 500 microns which is administered in the manner in which snuff is taken, i.e., by rapid inhalation through the nasal passage from a container of the powder held close up to the nose.

Formulations suitable for pulmonary administration (e.g., by inhalation or insufflation therapy) include those presented as an aerosol spray from a pressurised pack, with the use of a suitable propellant, such as dichlorodifluoromethane, trichlorofluoromethane, dichloro-tetrafluoroethane, carbon dioxide, or other suitable gases. Additionally or alternatively, a formulation for pulmonary administration may be formulated for administration from a nebuliser or a dry powder inhaler. For example, the formulation may be provided with carriers or liposomes to provide a suitable particle size to reach the appropriate parts of the lung, to aid delivery of an appropriate does to enhance retention in the lung tissue.

Formulations suitable for ocular administration include eye drops wherein the compound is dissolved or suspended in a suitable carrier, especially an aqueous solvent for the compound.

Formulations suitable for rectal administration may be presented as a suppository with a suitable base comprising, for example, natural or hardened oils, waxes, fats, semi-liquid or liquid polyols, for example, cocoa butter or a salicylate; or as a solution or suspension for treatment by enema.

Formulations suitable for vaginal administration may be presented as pessaries, tampons, creams, gels, pastes, foams or spray formulations containing in addition to the compound, such carriers as are known in the art to be appropriate.

Formulations suitable for parenteral administration (e.g., by injection), include aqueous or non-aqueous, isotonic, pyrogen-free, sterile liquids (e.g., solutions, suspensions), in which the compound is dissolved, suspended, or otherwise provided (e.g., in a liposome or other microparticulate). Such liquids may additional contain other pharmaceutically acceptable ingredients, such as anti-oxidants, buffers, preservatives, stabilisers, bacteriostats, suspending agents, thickening agents, and solutes which render the formulation isotonic with the blood (or other relevant bodily fluid) of the intended recipient. Examples of excipients include, for example, water, alcohols, polyols, glycerol, vegetable oils, and the like. Examples of suitable isotonic carriers for use in such formulations include Sodium Chloride Injection, Ringer's Solution, or Lactated Ringer's Injection. Typically, the concentration of the compound in the liquid is from about 1 ng/mL to about 100 µg/mL, for example from about 10 ng/mL to about 10 µg/mL, for example from about 10 ng/mL to about 1 µg/mL. The formulations may be presented in unit-dose or multi-dose sealed containers, for example, ampoules and vials, and may be stored in a freeze-dried (lyophilised) condition requiring only the addition of the sterile liquid carrier, for example water for injections, immediately prior to use.

Extemporaneous injection solutions and suspensions may be prepared from sterile powders, granules, and tablets.

Dosage

Generally, the methods of the invention may comprise administering to a subject an effective amount of a compound of formula (I) or (II) so as to provide an antimicrobial effect. The compound of formula (I) or (II) may be administered at an amount sufficient to potentiate the activity of a second active agent. The second active agent is administered to a subject at an effective amount so as to provide an antimicrobial effect.

It will be appreciated by one of skill in the art that appropriate dosages of the compound of formula (I) or (II) or the active agent, and compositions comprising the compound of formula (I) or (II) or the active agent, can vary from patient to patient. Determining the optimal dosage will generally involve the balancing of the level of therapeutic benefit against any risk or deleterious side effects. The selected dosage level will depend on a variety of factors including, but not limited to, the activity of the particular compound of formula (I) or (II) or the active agent, the route of administration, the time of administration, the rate of excretion of the compound, the duration of the treatment, other drugs, compounds, and/or materials used in combination, the severity of the condition, and the species, sex, age, weight, condition, general health, and prior medical history of the patient. The amount of compound of formula (I) or (II) or the active agent and route of administration will ultimately be at the discretion of the physician, veterinarian, or clinician, although generally the dosage will be selected to achieve local concentrations at the site of action which achieve the desired effect without causing substantial harmful or deleterious side-effects.

Administration can be effected in one dose, continuously or intermittently (e.g., in divided doses at appropriate intervals) throughout the course of treatment. Methods of determining the most effective means and dosage of administration are well known to those of skill in the art and will vary with the formulation used for therapy, the purpose of the therapy, the target cell(s) being treated, and the subject being treated. Single or multiple administrations can be carried out with the dose level and pattern being selected by the treating physician, veterinarian, or clinician.

In general, a suitable dose of a compound of formula (I) or (II) or the active agent is in the range of about 10 µg to about 250 mg (more typically about 100 µg to about 25 mg) per kilogram body weight of the subject per day. Where the compound of formula (I) or (II) or the active agent is a salt, an ester, an amide, a prodrug, or the like, the amount administered is calculated on the basis of the parent compound and so the actual weight to be used is increased proportionately.

Kits

One aspect of the invention pertains to a kit comprising (a) a compound of formula (I) or (II), or a composition comprising a compound as defined in any one of formula (I) or (II), e.g., preferably provided in a suitable container and/or with suitable packaging; and (b) instructions for use, e.g., written instructions on how to administer the compound or composition.

The written instructions may also include a list of indications for which the compound of formula (I) or (II) is a suitable treatment.

In one embodiment, the kit further comprises (c) a second active agent, or a composition comprising the second active agent. Here, the written instructions may also include a list of indications for which the second active agent, together with the compound of formula (I) or (II), is suitable for treatment.

Routes of Administration

A compound of formula (I) or (II), a second agent, or a pharmaceutical composition comprising the compound of formula (I) or (II), or the second agent may be administered to a subject by any convenient route of administration, whether systemically/peripherally or topically (i.e., at the site of desired action).

Routes of administration include, but are not limited to, oral (e.g., by ingestion); buccal; sublingual; transdermal (including, e.g., by a patch, plaster, etc.); transmucosal (including, e.g., by a patch, plaster, etc.); intranasal (e.g., by nasal spray); ocular (e.g., by eyedrops); pulmonary (e.g., by inhalation or insufflation therapy using, e.g., via an aerosol, e.g., through the mouth or nose); rectal (e.g., by suppository or enema); vaginal (e.g., by pessary); parenteral, for example, by injection, including subcutaneous, intradermal, intramuscular, intravenous, intraarterial, intracardiac, intrathecal, intraspinal, intracapsular, subcapsular, intraorbital, intraperitoneal, intratracheal, subcuticular, intraarticular, subarachnoid, and intrasternal; by implant of a depot or reservoir, for example, subcutaneously or intramuscularly.

The Subject/Patient

The subject/patient may be a chordate, a vertebrate, a mammal, a placental mammal, a marsupial (e.g., kangaroo, wombat), a rodent (e.g., a guinea pig, a hamster, a rat, a mouse), murine (e.g., a mouse), a lagomorph (e.g., a rabbit), avian (e.g., a bird), canine (e.g., a dog), feline (e.g., a cat), equine (e.g., a horse), porcine (e.g., a pig), ovine (e.g., a sheep), bovine (e.g., a cow), a primate, simian (e.g., a monkey or ape), a monkey (e.g., marmoset, baboon), an ape (e.g., gorilla, chimpanzee, orang-utan, gibbon), or a human. Furthermore, the subject/patient may be any of its forms of development, for example, a foetus.

In one preferred embodiment, the subject/patient is a human.

It is also envisaged that the invention may be practised on a non-human animal having a microbial infection. A non-human mammal may be a rodent. Rodents include rats, mice, guinea pigs, chinchillas and other similarly-sized small rodents used in laboratory research.

Other Preferences

Each and every compatible combination of the embodiments described above is explicitly disclosed herein, as if each and every combination was individually and explicitly recited.

Various further aspects and embodiments of the present invention will be apparent to those skilled in the art in view of the present disclosure.

"and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

Unless context dictates otherwise, the descriptions and definitions of the features set out above are not limited to any particular aspect or embodiment of the invention and apply equally to all aspects and embodiments which are described. Where technically appropriate embodiments may be combined and thus the disclosure extends to all permutations and combinations of the embodiments provided herein.

Certain aspects and embodiments of the invention will now be illustrated by way of example and with reference to the figures described above.

EXAMPLES

The following examples are provided solely to illustrate the present invention and are not intended to limit the scope of the invention, as described herein.

Nomenclature—Compounds are named based on the natural polymyxin core from which they are synthetically derived.

| Abbreviation | Meaning |
|---|---|
| PMBN | Polymyxin B nonapeptide |
| PMB | Polymyxin B |
| Thr | Threonine |
| Ser | Serine |
| DSer | D-serine |

-continued

| Abbreviation | Meaning |
|---|---|
| Leu | Leucine |
| Ile | Isoleucine |
| Phe | Phenylalanine |
| Dphe | D-phenylalanine |
| Val | Valine |
| Dab | α,γ-Diaminobutyric acid |
| DIPEA | N,N-diisopropylethylamine |
| HATU | 2-(7-aza-1H-benzotriazol-1-yl)-1,1-3,3-tetramethyluronium hexafluorophosphate |
| DCM | Dichloromethane |
| TFA | Trifluoroacetic acid |
| ND | Not determined |
| N/A | Not applicable |
| DMF | N,N-Dimethylformamide |
| PMBH | Polymyxin B heptapeptide (3-10) |
| PMBD | Polymyxin B decapepide |
| Pro | Proline |
| Dap | α,β-Diaminopropionic acid |
| Gly | Glycine |
| His | Histidine |
| Phe | Phenylalanine |
| DCHA | Dicyclohexylamine |
| X phos | 2-Dicyclohexylphosphino-2',4',6'-triisopropylbiphenyl |
| NorLeu | Norleucine |
| NorVal | Norvaline |
| OctGly | Octyl glycine |

Synthesis Examples

Comparator compounds C1 to C3 were prepared.

Polymyxin B has a D-phenylalanine residue at position 6. The N terminal group is a 6-methyloctanoyl group. Polymyxin B is readily available.

Compounds C1 and C2 have previously been prepared by the present inventors. These compounds are polymyxin B nonapeptide derivatives. The compounds have a D-phenylalanine residue at position 6. The N terminal of the amino acid reside at position 2 is modified, as shown. The preparation of these compounds is described herein and is described in GB 1404301.2.

Compound C3 is a Polymyxin B variant differing from Polymyxin B in the substitution of the phenylalanine residue at position 6 with a D-(biphenyl)alanine residue (a D-(4-phenylphenyl)alanine residue). Compound C3 is structurally related close to the variants described by Velkov et al. C3 shares the same N terminal group as Polymyxin B (specifically Polymyxin B1), whilst Velkov et al. describes modified N terminal group. Compound $C_3$ may be prepared by the methods described in Velkov et al. with appropriate replacement of the fatty acid in the terminal coupling step (see the Supporting Information for this paper).

In each of the worked examples 1-26, the amino acid at position 6 is replaced with another amino acid. In some examples the amino acid residue at position 1 is deleted, and the N terminal of the amino acid residue at position 2 is modified, as shown.

Additional example compounds 27-79 are also provided, where the amino acid at position 6 is replaced with another amino acid. In some examples the amino acid residue at position 1 is deleted, and the N terminal of the amino acid residue at position 2 is modified, as shown.

Additionally comparator compounds C4 to C7 were prepared.

The compounds for use in the present case are prepared as described below. Each of the compounds has a polymyxin heptapeptide core (save for the amino acid at position 6 or position 7). The compounds possess an L-Thr residue at the position corresponding to position 2 in polymyxin and an L-Dab or an L-Dap residue at the position corresponding to position 3 in polymyxin (where L-Thr and L-Dab are the natural amino acid residues present at these positions within Polymyxin B).

The compounds of the invention may be prepared by adaptation of the detailed methods described below, and may also be prepared by adaptation of the methods described in WO 2015/135976, the contents of which are hereby incorporated by reference in their entirety. The methods used in the present case also include those of WO 2013/072695 and WO 2014/188178, the contents of which are hereby incorporated by reference in their entirety.

The compounds of the present invention differ from the compounds of WO 2015/135976 in the nature of the amino acid residues at positions 6 and/or 7 (i.e. in the nature of the groups —$R^6$, —$R^{6a}$, —$R^7$, and —$R^{7a}$). However, the N terminal groups of the compounds of WO 2015/135976 are suitable for use in the compounds of the invention. Thus a group —$R^T$ or a group —$R^N$ in the compounds of formula (I) or (II) of the present case may be a group —$R^{15}$ as described in WO 2015/135976.

Therefore the description and exemplification of N terminal modifications in WO 2015/135976 is relevant to the work in the present case. WO 2015/135976 shows that certain N terminal groups provide enhanced antibacterial activity and/or reduced cytotoxicity compared with wild type Polymyxin B (for example). Such N terminal groups may be used together with the amino acid substitutions at positions 6 and/or 7, as described by the inventors in the present case.

In particular, the present case incorporates by reference the detailed synthesis examples of WO 2015/135976 from page 65 to page 90 (which examples are also present in GB 1421020.7 and GB 1516059.1, to which the present case claims priority).

Intermediate 5-Tri-(Boc) Polymyxin B Heptapeptide

PMB sulphate (2 g) was dissolved in water (20 mL) followed by addition of 1,4-dioxane (40 mL) and left to stir for 10 minutes at room temperature. To the reaction mixture was added Boc anhydride (4.42 g) was added as solid and the reaction was stirred at room temperature and was monitored by HPLC. The reaction mixture was then adjusted to pH 6 using 1 M HCl, the precipitate which formed was filtered and washed with water (50 mL) and heptane (50 mL), to leave $Boc_5PMB$ as a white solid (2.4 g, 85%). This material (1 g) was dissolved in 1,4-butanediol (112.5 mL) and the mixture was stirred at 40° C. overnight. To the solution potassium phosphate (75 mL, 0.12 5M pH 8.0) was added over one minute, causing the formation of a white suspension. The reaction was diluted by adding 112.5 mL butanediol and 75 mL potassium phosphate (0.125 M pH 8.0), but the white emulsion persisted. The temperature of the reaction was reduced to 37° C. and then Savinase 16L (250 µL) was added and the reaction was stirred at room temperature overnight. As the reaction progressed the white emulsion cleared to form a transparent solution due to the formation of the more soluble PMBH-$Boc_3$. The reaction mixture was diluted with water (50 ml) and was then extracted with DCM (100 mL) The DCM layer was collected and evaporated in vacuo to afford a colourless oil. The resulting oil was diluted in 50% methanol (aq.) and was loaded onto four preconditioned 10 g Varian Bond Elut SCX cartridges and the flow through was collected. The cartridges were washed with two column volumes of 50% methanol (aq.) and then PMBH-$Boc_3$ was eluted from the column using two column volumes of 20% ammonia in methanol. The resulting eluent was evaporated to dryness in vacuo to afford purified PMBH-$Boc_3$ (610 mg). m/z 1062.6 $[M+H]^+$.

Intermediate 7- Thr(O-$^t$Bu) Tetra-(N-Boc) Polymyxin B nonapeptide

Step 1—(S)-2-((S)-2-Benzyloxycarbonylamino-3-tert-butoxy-butyrylamino)-4-tert-butoxycarbonylamino-butyric acid methyl ester To a stirred suspension of (S)-2-Benzyloxycarbonylamino-3-tert-butoxy-butyric acid DHCA salt (3.65 g, 7.4 mmol) and (S)-2-Amino-4-tert-butoxycarbonylamino-butyric acid methyl ester HCl salt (2.0 g, 7.4 mmol) in a mixture of DCM (60 mL) and DMF (120 mL) was added N,N-diisopropylethylamine (3.85 mL, 22.1 mmol). To this stirred mixture was added 1-hydroxy-7-azabenzotriazole (1.0 g, 7.3 mmol) followed by N-(3-dimethylaminopropyl)-N'-ethylcarbodiimide HCl salt (1.42 g, 7.4 mmol). The mixture was stirred for 17 h at ambient temperature then filtered under suction to remove the insoluble by-product, which was discarded. The filtrate was concentrated to a yellow oil which was partitioned between a solvent mixture of EtOAc/$Et_2O$ (1:1) (250 mL) and 0.5 M hydrochloric acid (200 mL). The aqueous phase was re-extracted with fresh solvent mixture (100 mL) and the combined organic extracts were successively washed with water (150 mL) and sat. $NaHCO_3$ solution (150 mL), dried ($Na_2SO_4$) and concentrated to a colourless oil (3.72 g). This oil was purified by silica gel chromatography on a 100 g SepPak cartridge, eluting with a solvent gradient of EtOAc/i-hexane (0-70%). Fractions containing the product ($R_f$ 0.26 in EtOAc/i-hexane 3:7, visualized with $KMnO_4$ spray) were pooled and concentrated to give the title compound as a colourless foam (3.58 g, 6.8 mmol, 92% yield). m/z 524 ($MH^+$, 100%).

Step 2—(S)-2-((S)-2-Benzyloxycarbonylamino-3-tert-butoxy-butyrylamino)-4-tert-butoxycarbonylamino-butyric Acid A solution of lithium hydroxide monohydrate (0.861 g, 20.5 mmol) in water (16 mL) was added to a stirred solution of (S)-2-((S)-2-Benzyloxycarbonylamino-3-tert-butoxy-butyrylamino)-4-tert-butoxycarbonylamino-butyric acid methyl ester (3.58 g, 6.8 mmol) in methanol (64 mL) at ambient temperature and stirred for 19 h. To this solution was added 1M HCl (24 mL) resulting in a milky mixture (pH 1) which was quickly extracted with DCM (3×135 mL). The combined organic extract was dried ($Na_2SO_4$) and concentrated to give the title compound as a colourless foam (3.27 g, 6.4 mmol, 94% yield). M/z 532[MNa]+, 1041 [2M+Na]+.

Step 3—CbzHNPMBN(OBu)(Boc)$_4$ (S)-2-((S)-2-Benzyloxycarbonylamino-3-tert-butoxy-butyrylamino)-4-tert-butoxycarbonylamino-butyric acid (1.73 g, 3.39 mmol) and Tri-(N-Boc) *Polymyxin B heptapeptide* (prepared according to WO 2012/168820, 3.0 g, 2.8 mmol) were charged to a flask to which dry DCM (85 ml) and dry DMF (17 mL) were added with stirring. To the stirred solution was added N,N-diisopropylethylamine (1.46 ml, 8.4 mmol) and after stirring for 5 min., O-(7-azabenzotriazol-1-yl)-N,N,N'N'-tetramethyluronium hexafluorophosphate (1.29 g, 3.39 mmol) was added in a single portion. The mixture was sonicated for 2 minutes then left to stir at ambient temperature for 18 h. The reaction mixture was then evaporated and the residue re-evaporated from toluene (3×100 mL). The residue was dried under vacuum for 3 h to ensure removal of toluene. Water (50 ml) was added to this material and the mixture was rapidly stirred for 3 h with occasional sonication. The title compound was collected by suction filtration as a fine, white solid and washed with water (2×25 mL) then dried under vacuum for 15 h (4.6 g, 3.0 mmol, 100% yield). m/z 1554[MH+].

Step 4-Title Compound

The product from step 3 (5.41 g, 3.48 mmol), ammonium formate (6.6 g, 104.4 mmol) and 10% Pd—C (2.0 g) were charged to a flask under $N_2$. MeOH (270 mL) was added and the mixture was stirred under $N_2$ for 4.5 h. LCMS showed MH+ for product and loss of starting material. The mixture was filtered under suction through a pad of celite and washed through with MeOH (50 mL). The filtrate and washings were evaporated to a colourless oil which was partitioned between a solvent mixture of EtOAc/MeOH (4:1)(250 mL) and water (250 mL). The aqueous phase was further extracted with the same, fresh solvent mixture (2×100 mL). The combined organic extracts were dried ($Na_2SO_4$) and evaporated to a colourless oil (~6 g). This material was purified by chromatography on silica gel (100 g SepPak column) eluting with a gradient of MeOH/EtOAc (0-4%). Fractions containing the product (Rf 0.30 in EtOAc/MeOH/ $NH_4OH_{880}$ 95:5:1, visualized with $KMnO_4$ spray) were pooled and evaporated to give the title compound as a crispy foam (4.0 g, 2.8 mmol, 81% yield). m/z 1420 [MH+].

Intermediate 11-Tetra- (N-Boc)-L-Thr(O-$^t$Bu)-L-Dap-Polymyxin B Heptapeptide

The title compound was prepared from (S)-2-((S)-2-Benzyloxycarbonylamino-3-tert-butoxy-butyrylamino)-3-tert-butoxycarbonylamino-propionic acid and Intermediate 5 according to the method for Intermediate 7 steps 3 and 4. m/z 1405, [MH]+

Intermediate 16 (BOC)$_3$ D-[(4-Bromo)Phe]-6-Polymyxin Heptapeptide and

Intermediate 17 (BOC)$_3$ D-[(2-Bromo)Phe]-6-Polymyxin Heptapeptide

Step 1-D-[(4-Bromo)Phe]-6-Polymyxin and D-[(2-Bromo)Phe]-6-Polymyxin

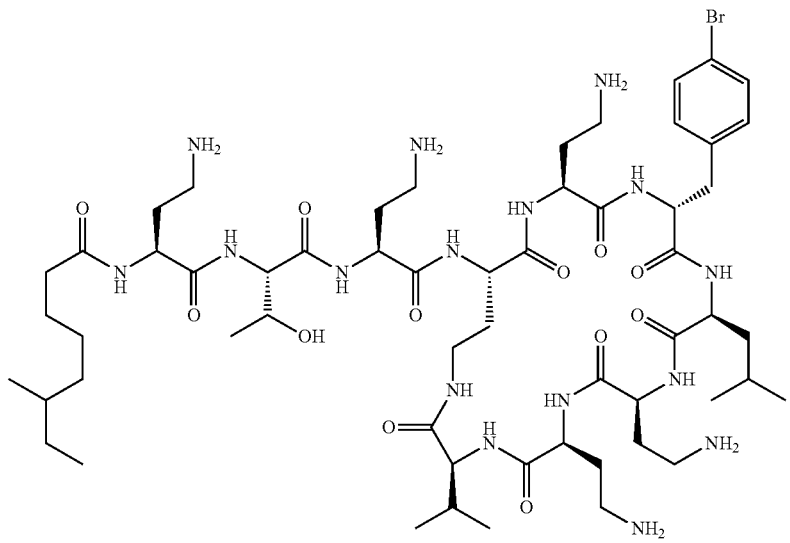 [SMILES: CCC(C)CCCCC(=O)N[C@@H](CCN)C(=O)N[C@H](C(=O)N[C@@H](CCN)C(=O)N[C@H]1CCNC(=O)[C@H](C(C)C)NC(=O)[C@H](CCN)NC(=O)[C@H](CCN)NC(=O)[C@H](CC(C)C)NC(=O)[C@@H](Cc2ccc(Br)cc2)NC(=O)[C@H](CCN)NC1=O)C(C)O]

Polymyxin B sulphate (source: Biotika) (20.0 g, 15.4 mmol) and N-bromosuccinimide (4.2 g, 23.6 mmol) were charged to a 1 L 3-neck round-bottomed flask, fitted with an efficient overhead paddle stirrer and a $N_2$ inlet. To the flask under $N_2$ was added boron trifluoride dihydrate (200 mL) and the mixture was vigorously stirred at ambient temperature for 1 h during which time all solids dissolved to give a frothy, orange solution. The solution was then poured over 5 minutes into a stirred mixture of ammonia 880 solution (400 mL) and ice (900 g) to give a white suspension. To the suspension (pH 9) was added water (300 mL) and the mixture was stirred at ambient temperature for 2 h then filtered under suction through a large (20 cm diameter, porosity 2) glass sinter funnel. The solid was washed with water (200 mL) and sucked free of excessive moisture. The material was then suspended in methanol (1.5 L) and re-evaporated to a residue. This was repeated with more methanol (1.5 L) to afford a foam which was dried at ambient temperature in vacuo for 3 h (22.4 g) and identified as the title compound m/z=1282/4 (MH$^+$), 643 (M+2H)$^{2+}$. The crude material was used without purification in the next stage.

An aliquot was purified by preparative HPLC using the conditions of General method 1, to afford Example Compound 2 (data in Table)

Step 2—(Boc)$_5$ D-[(4-Bromo)Phe]-6-Polymyxin

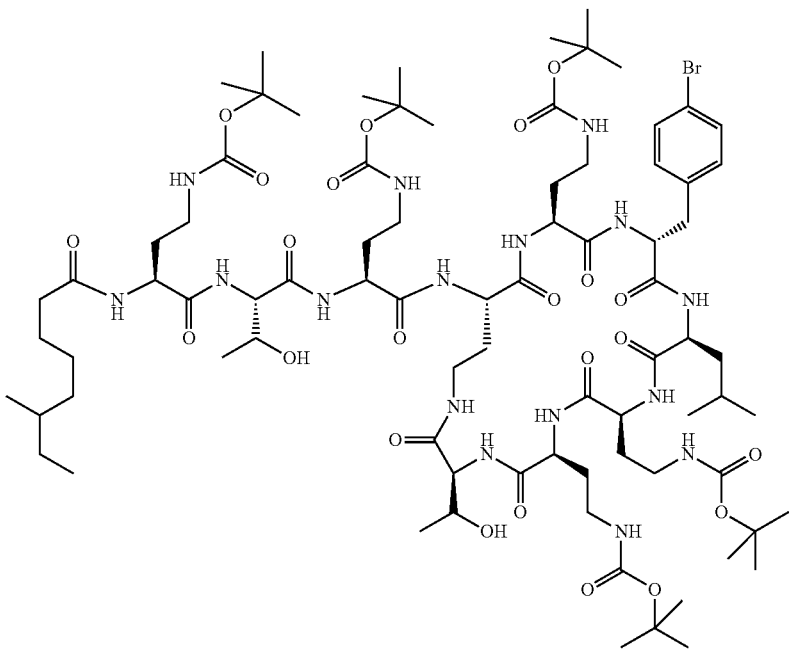 [SMILES: CCC(C)CCCCC(=O)N[C@@H](CCNC(=O)OC(C)(C)C)C(=O)N[C@H](C(=O)N[C@@H](CCNC(=O)OC(C)(C)C)C(=O)N[C@H]1CCNC(=O)[C@H](C(C)O)NC(=O)[C@H](CCNC(=O)OC(C)(C)C)NC(=O)[C@H](CCNC(=O)OC(C)(C)C)NC(=O)[C@H](CC(C)C)NC(=O)[C@@H](Cc2ccc(Br)cc2)NC(=O)[C@H](CCNC(=O)OC(C)(C)C)NC1=O)C(C)O]

Crude D-[(4-Bromo)Phe]-6-Polymyxin (15.4 mmol nominal amount, based on Polymyxin B sulphate used) was charged to a flask and acetonitrile (400 mL) and water (200 mL) were added. To the stirred solution was added triethylamine (15 mL, 108 mmol), followed by a solution of di-tert-butyl-dicarbonate (23.5 g, 108 mmol) in acetonitrile (200 mL). The cloudy mixture was stirred at ambient temperature for 20 h. The reaction mixture was then concentrated in vacuo and the residue re-evaporated from methanol (1 L) and dried. The dry residue was stirred with a mixture of diethyl ether (75 mL) and iso-hexane (75 mL) for 0.5 h and the insoluble solid was filtered off under vacuum. The solid was partitioned between dichloromethane/methanol (9:1) (400 mL) and 10% brine (300 mL). To the organic extract was added methanol (40 mL) and the solution was washed with 10% brine (100 mL), dried ($Na_2SO_4$) and concentrated in vacuo to a foam residue. This material was suspended in dichloromethane/methanol (95:5) (140 mL) and left to stand for 0.5 h. The mixture was filtered under suction to remove unwanted gelatinous solid and the filtrate was purified by column chromatography over silica gel, eluting with a gradient of dichloromethane/methanol to afford the title compound as a colourless foam (5.1 g) m/z 1782/4 ($MH^+$). This partly purified material was used directly in the next stage.

Step 3—$(BOC)_3$ D-[(4-Bromo)Phe]-6-Polymyxin Heptapeptide and $(BOC)_3$ D-[(2-Bromo)Phe]-6-Polymyxin Heptapeptide

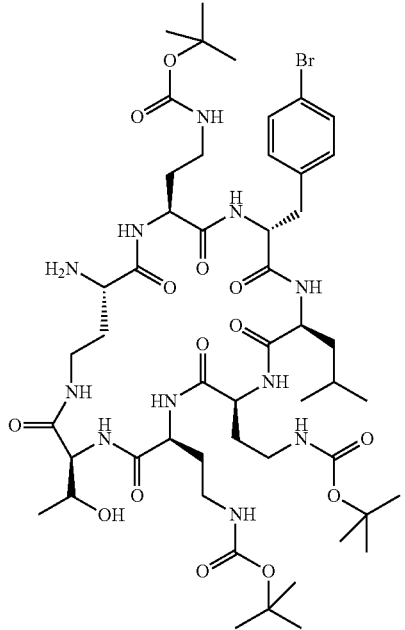 [SMILES: CC(C)C[C@@H]1NC(=O)[C@@H](Cc2ccc(Br)cc2)NC(=O)[C@H](CCNC(=O)OC(C)(C)C)NC(=O)[C@@H](N)CCNC(=O)[C@H](C(C)O)NC(=O)[C@H](CCNC(=O)OC(C)(C)C)NC(=O)[C@H](CCNC(=O)OC(C)(C)C)NC1=O]

A suspension of crude $(Boc)_5$ D-[(4-Bromo)Phe]-6-Polymyxin (2.65 g, 1.49 mmol) in 1,4-butanediol (76 mL) was stirred at 50° C. for 1 h until a thick solution was formed. Phosphate buffer solution (pH 8) (19 mL) was added and the stirred solution was cooled to 37° C. Savinase solution (Protease from *Bacillus* sp. Liquid >16 U/g, from Sigma Aldrich) (3 ml) was added and the viscous solution was stirred at 37° C. for 4 days. The solution was poured into a mixture of ethyl acetate (150 mL) and water (100 mL) and the whole was shaken vigorous.

The aqueous layer was re-extracted with ethyl acetate (50 mL) and the combined organic extracts were re-washed with water (2×75 mL), dried ($Na_2SO_4$) and evaporated in vacuo to afford an oil (1.94 g). This material was dissolved in ethyl acetate/methanol (4:1) (10 mL) and the solution purified by column chromatography over silica gel eluting with a gradient of Solvent A/ethyl acetate (0-60%) where Solvent A=methanol/ammonia 880 solution (9:1). Relevant fractions were pooled and evaporated to a colourless foam (970 mg) identified as the title compound m/z 1140/2 ($MH^+$).

Further purification by preparative HPLC (see Table A, General Method 1) afforded the pure title compound Intermediate 16, $(BOC)_3$ D-[(4-Bromo)Phe]-6-Polymyxin heptapeptide and Intermediate 17, D-[(2-Bromo)Phe]-6-Polymyxin heptapeptide. m/z 1140/2 ($MH^+$).

Intermediate 18—$(Cbz)(BOC)_4 Thr(O^tBu)$-D-[(4-Bromo)Phe]-6-PMB Nonapeptide

Prepared from Intermediate 16 and (S)-2-((S)-2-Benzyloxycarbonylamino-3-tert-butoxy-butyrylamino)-4-tert-butoxycarbonylamino-butyric acid using the method of Intermediate 7 step 3, to afford the title compound m/z 1633 ($MH^+$).

Intermediate 19—$(BOC)_4$ Thr(OtBu)-L-Dap-(D-Cha-6)-PMB Heptapeptide

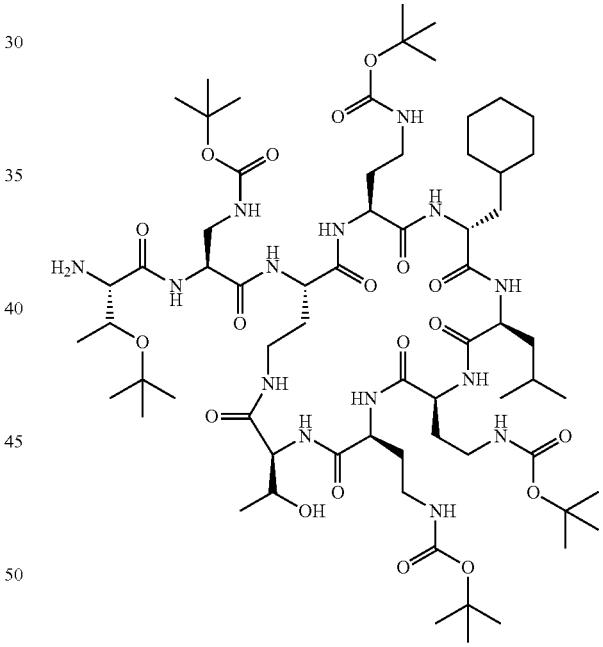

Platinum oxide (200 mg) was added to a solution of tetra-(N-Boc)-L-Thr(O-$^t$Bu)-L-Dap-Polymyxin B heptapeptide (Intermediate 11) (1.8 g, 1.28 mmol) in acetic acid (80 mL). Hydrogen gas was introduced and the reaction was stirred for 24 hours. Platinum oxide (400 mg) was added and the reaction stirred under hydrogen for a further 48 hours. The solvent was evaporated and the crude material was azeotroped with toluene (2×). The crude oil was dissolved in EtOAc and then treated with Ambersep 900 (OH) resin. The resin was filtered off, washed with further EtOAc (2×) and the combined organics were evaporated to afford the title compound as an off-white solid (1.76 g). $MH^+$=1412.0, $C_{66}H_{118}N_{14}O_{19}$ requires 1411.7.

Intermediate 20-(BOC)₄ Thr(OʹBu)-(D-Cha-6)-PMB Nonapeptide

Prepared from Intermediate 7 (Thr(O-ʹBu) Tetra-(N-Boc) Polymyxin B nonapeptide) using the conditions described above for the preparation of Intermediate 19, to afford the title compound, $MH^+$=1425.6, $C_{67}H_{120}N_{14}O_{19}$ requires 1425.8.

General Method 1: Preparation of Nonapeptide Amides

Step 1—The protected polymyxin nonapeptide (0.07 mmol) was dissolved in dichloromethane (4 mL), and treated with the corresponding carboxylic acid (1.5 equiv. with respect to the polymyxin substrate), N,N-Diisopropylethylamine (3.0 equiv.), followed by HATU (2.0 equivalent). After 16 h the completion of the reaction was confirmed by LC-MS and the reaction mixture was evaporated to dryness. Water (~10 mL) was added and the mixture triturated then stirred vigorously for 1 h. The resultant precipitate was collected by filtration and dried in vacuo overnight.

Step 2—The Boc-protected derivative from Step 1 was dissolved in dichloromethane (3 mL) and treated with TFA (1 mL). The reaction mixture was stirred at room temperature until LCMS confirmed complete deprotection. The solvent was evaporated and the residue chromatographed by preparative HPLC using the conditions in Table A:

TABLE A

| Prep HPLC conditions | |
|---|---|
| Column: | Sunfire C18 OBD 5 μm × 30 mm × 150 mm |
| Mobile Phase A: | Acetonitrile + 0.15% TFA |
| Mobile Phase B: | water + 0.15% TFA |
| Flow rate: | 25 mL/min |
| Gradient: | Time 0 min    3% A   97% B |
|  | Time 2 min    3% A   97% B |
|  | Time 25 min   40% A  60% B |
|  | Time 30 min   97% A   3% B |
|  | Time 32 min   97% A   3% B |
| Detection: | 210 nm |

Product-containing fractions were combined, evaporated to low volume, and lyophilised to afford the product as the TFA salt. Compound purity was assessed by HPLC using the conditions outlined in Table B.

TABLE B

| Analytical HPLC conditions | |
|---|---|
| Column: | Zorbax 5 μ C18 (2) 150 × 4.6 mm |
| Mobile Phase A: | 10% Acetonitrile in 90% Water, 0.15% TFA |
| Mobile Phase B: | 90% Acetonitrile in 10% Water, 0.15% TFA |
| Flow rate: | 1 mL/min |
| Gradient: | Time 0 min    100% A   0% B |
|  | Time 10 min    0% A  100% B |
|  | Time 11 min    0% A  100% B |
|  | Time 11.2 min 100% A   0% B |
| Cycle time 15 min | |
| Injection volume: | 20 μL |
| Detection: | 210 nm |

General Method 2: General Method for the Preparation of Dipeptide Amide Derivatives of Polymyxin B Heptapeptide In an alternative method, the carboxylic acid was coupled to a suitably protected amino acid methyl ester using HATU coupling conditions of Intermediate 1 step 3. The methyl ester was hydrolysed as in Intermediate 1 step 2, then coupled to a suitably protected amino acid methyl ester using HATU coupling conditions of Intermediate 7 step 1. After ester hydrolysis (Intermediate 7 step 2), the acyl dipeptide was coupled to the required polymyxin heptapeptide intermediate followed by deprotection, as described in General Method 1, to afford the example compounds.

General Method 3: Suzuki Coupling Method

Exemplified by the synthesis of (Cbz)(BOC)₄ Thr(OʹBu)-D-[(4-phenylphenyl)alanine]-6-PMB nonapeptide To a solution of intermediate 18 (Cbz)(BOC)₄ Thr(OʹBu)-D-[(4-Bromo)Phe]-6-PMB nonapeptide, 605 mg, 0.371 mmol) was added benzene boronic acid (68 mg, 0.556 mmol), palladium (II) acetate (8.3 mg, 0.0371 mmol), XPhos (35 mg, 0.0741 mmol) and potassium phosphate tribasic (157 mg, 0.741 mmol) in toluene (10 mL) and the stirred mixture was degassed with nitrogen for 2 minutes. The reaction was sealed and heated to 100° C. for 18 hours. After cooling the mixture was diluted with EtOAc and water. The phases were separated and the aqueous layer was further extracted with 10% IPA in EtOAc. The combined organics were dried (MgSO₄) and the solvent evaporated to afford a crude oil. This was purified by chromatography: 40 g column, using a gradient of 0 to 10% MeOH in EtOAc to afford the desired compound as a colourless glass m/z 1630 ($MH^+$).

General Method 4: Hydrogenation with Platinum Oxide

Exemplified by the synthesis of D-[Cyclohexyl]alanine-6-Polymyxin

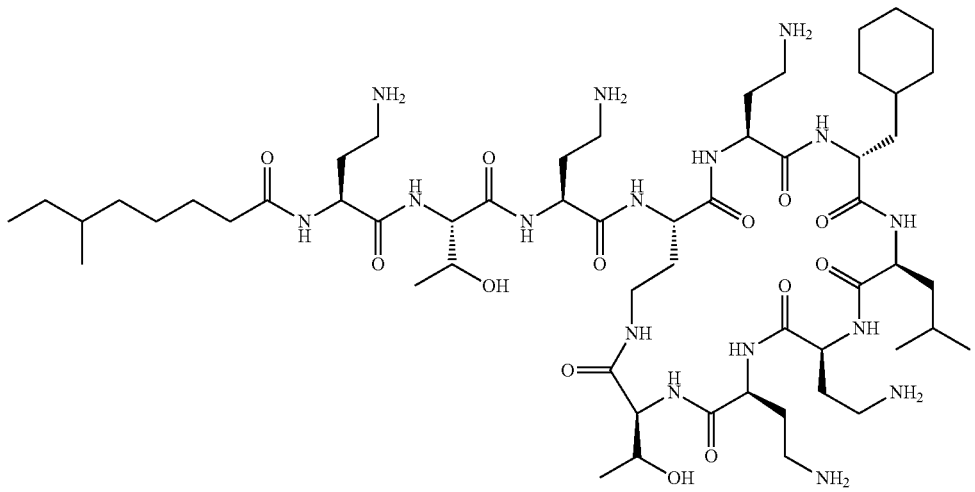

Chemical Formula: $C_{56}H_{104}N_{16}O_{13}$
Exact Mass: 1208.80
Molecular Weight: 1209.55

A suspension of platinum oxide (20 mg, 0.088 mmol) in acetic acid (2 mL) was added to a stirred solution of polymyxin B (200 mg, 0.166 mmol) in acetic acid (20 mL). The reaction was hydrogenated for 24 h at ambient temperature and atmospheric pressure. A further 200 mg Platinum oxide was added portionwise during the course of the reaction. The reaction mixture was filtered through Celite and washed with water (100 mL). The filtrate was evaporated at reduced pressure to leave a beige solid. The solid was dissolved in water (2 mL) and purified by preparative HPLC as described in the general method 1. Product containing fractions were combined and lyophilised to afford the title compound as the TFA salt m/z 1209.8 (MH$^+$), $C_{56}H_{104}N_{16}O_{13}$ exact mass 1208.80.

General Method 5: Catalytic Transfer Hydrogenation with Palladium on Carbon

Exemplified by the synthesis of (Trans-5-(isobutyl-piperidine)-3-carbonyl L-Thr-L-Dap-polymyxin D-[(4-octyl)Phe]-6-heptapeptide.

(Trans-5-(isobutyl -piperidine)-3-carbonyl L-Thr-L-Dap-polymyxin D-[(4-(E)-oct-1-enyl)Phe]-6-heptapeptide Isomer 1 was hydrogenated under the conditions described for Intermediate 7 step 4 to afford the title compound. m/z 1228 [MH$^+$], 614 [M+2H]$^{2+}$. $C_{60}H_{105}N_{15}O_{12}$ requires 1227.81.

Example 24: Polymyxin B[D-(4-cyano)Phe]-6

A suspension of (Boc)$_5$ D-[(4-Bromo)Phe]-6-polymyxin (100 mg, 0.056 mmol), Zinc cyanide (45 mg, 0.383 mmol, 6.8 mol equiv.) and 1,1'-bis(diphenylphosphino)ferrocene (6 mg, 2 mol equiv.) in dry DMF (2 ml) was degassed and then treated with tris(dibenzylideneacetone)dipalladium (0) (5 mg, 1 mol equiv). The tube was sealed and heated to 100° C. for 3 days. The solvent was evaporated and the residue partitioned between water and ethyl acetate. The organic phase was dried over anhydrous magnesium sulfate and evaporated. The residue was chromatographed on silica eluting with 0-10% (1% 0.880 ammonia in methanol) in ethyl acetate, followed by further purification by preparative HPLC eluting with 20-95% acetonitrile in water (plus 1% TFA). Product-containing fractions were combined and evaporated to an oil. This was dissolved in TFA (2 mL) and DCM (8 mL) and stirred at room temperature for 6 h. The solvent was evaporated and the residue lyophilized from water to afford the desired product as a white solid (2.8 mg), m/z 614 [M+2H]$^{2+}$. $C_{57}H_{97}N_{17}O_{13}$ requires 1227.75.

Example 29 L-Dab-L-Thr-L-Dap-polymyxin [D-(4-octyl Phe)]-6 Heptapeptide

Step 1. (BOC)$_3$ D-[(4-Bromo)Phe]-6-Polymyxin heptapeptide (Intermediate 16) was coupled to (S)-2-((S)-2-Benzyloxycarbonylamino-3-tert-butoxy-butyrylamino)-3-tert-butoxycarbonylamino-propionic acid according to the method for Intermediate 7 step 3 to afford CBZ-Tetra-(N-Boc)-L-Thr(O-$^t$Bu)-L-Dap-Polymyxin B [D-(4-Bromo)Phe)]-6 heptapeptide.

Step 2. CBZ-Tetra-(N-Boc)-L-Thr(O-$^t$Bu)-L-Dap-Polymyxin B [D-(4-Bromo)Phe)]-6 heptapeptide was treated with octenyl boronic acid under the suzuki coupling conditions of General method 3, to afford CBZ-Tetra-(N-Boc)-L-Thr(O-$^t$Bu)-L-Dap-Polymyxin B [D-(4-oct-2-enyl)Phe)]-6 heptapeptide.

Step 3. CBZ-Tetra-(N-Boc)-L-Thr(O-$^t$Bu)-L-Dap-Polymyxin B [D-(4-oct-2-enyl)Phe)]-6 heptapeptide was treated with ammonium formate in the presence of 10% Palladium on Carbon, as described for Intermediate 7, step 3 to afford Tetra-(N-Boc)-L-Thr(O-$^t$Bu)-L-Dap-polymyxin B [D-(4-octyl)Phe)]-6 heptapeptide.

Step 4 The product from Step 3 was coupled to (S)-2-((2-(benzyloxy)-2-oxoethyl)amino)-4-((tert-butoxycarbonyl)amino)butanoic acid DCHA salt under the standard coupling conditions of Intermediate 7 step 3, to afford tetra-(N—BOC) L-Dab-L-Thr-L-Dap-polymyxin [D-(4-octyl Phe)]-6 heptapeptide.

Step 5. The product from Step 4 was deprotected as described in the General method 1 step 2, followed by preparative HPLC to affords the title compound, L-Dab-L-Thr-L-Dap-polymyxin [D-(4-octyl Phe)]-6 heptapeptide as a white solid m/z 1161 [MH$^+$], 581[M+2H]$^{2+}$. $C_{54}H_{96}N_{16}O_{12}$ requires 1160.74.

Synthesis of Carboxylic Acids

Carboxylic acids used for the assembly of polymyxin derivatives were secured either via commercial sources, or prepared using methods known to those skilled in the art. Experimental details of the following carboxylic acids serve as representative examples for the synthesis of similar acid intermediates used in the synthesis of the compounds of the present invention.

4-(tert-Butoxycarbonylamino)-2-(4-chlorophenyl) butanoic Acid

Step 1—Ethyl 2-(4-chlorophenyl)-2-oxo-acetate

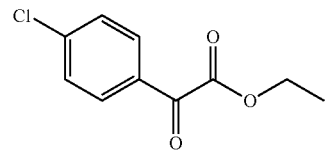

To a solution of diethyl oxalate (1 mL, 7.36 mmol) in tetrahydrofuran (10 mL) at −50° C. was added 4-chlorophenylmagnesium bromide (1M solution in diethyl ether, 7.3 mL, 7.30 mmol). The reaction mixture was allowed to warm to −15° C. and stirred at that temperature for a further 1.5 h. The reaction was quenched by the addition of 1M hydrochloric acid (7 mL) and stirred at room temperature for 2 minutes. The layers were separated and then the aqueous phase was further extracted with diethyl ether (×2). The combined organic phases were dried over magnesium sulphate, filtered and concentrated at reduced pressure to give the crude title compound as a yellow oil (1.63 g, >100%). m/z 235 (MNa$^+$), $C_{10}H_9ClO_3$ exact mass 212.02.

Step 2—Ethyl-2-(4-chlorophenyl)-3-cyano-prop-2-enoate

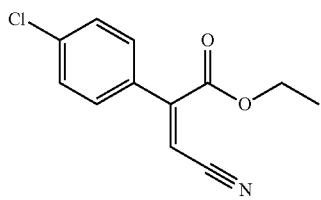 [SMILES: CCOC(=O)/C(=C\C#N)c1ccc(Cl)cc1]

To a solution of crude ethyl 2-(4-chlorophenyl)-2-oxo-acetate (~7.3 mmol) in toluene (30 mL) was added (triphenylphosphoranylidene)acetonitrile (2.20 g, 7.30 mmol). The reaction mixture was stirred at room temperature for 16 hours and then concentrated at reduced pressure. The product was purified by silica gel chromatography eluting with 0-40% ethyl acetate in iso-hexane to give the title compound as a colourless oil (1.38 g, 81%). m/z 258 (MNa$^+$), $C_{12}H_{10}ClNO_2$ exact mass 235.04.

Step 3—Ethyl 4-amino-2-(4-chlorophenyl)butanoate

To a solution of ethyl-2-(4-chlorophenyl)-3-cyano-prop-2-enoate (1.36 g, 5.79 mmol) in methanol (60 mL) was added cobalt chloride (1.51 g, 11.6 mmol). The reaction mixture was cooled to 0° C. and then treated with sodium borohydride (2.2 g, 57.8 mmol) portionwise. After the addition, the reaction was stirred at 0° C. for 1 hour. The mixture was quenched by the addition of 1 M hydrochloric acid and stirred at room temperature for 20 minutes. The pH was adjusted to 11 by the addition of 880 ammonia and then the mixture was filtered through a pad of celite which was washed with dichloromethane. After separation of the layers, the aqueous phase was re-extracted with dichloromethane (×2). The combined organic layers were dried over magnesium sulphate, filtered and concentrated to give the title compound as a pale brown oil (838 mg, 60%). m/z 242 (MH$^+$), $C_{12}H_{16}ClNO_2$ exact mass 241.09.

Step 4—Ethyl 4-(tert-butoxycarbonylamino)-2-(4-chlorophenyl)butanoate

To a solution of ethyl 4-amino-2-(4-chlorophenyl)butanoate (836 mg, 3.47 mmol) in dichloromethane (40 mL) was added di-tert-butyl dicarbonate (1.06 g, 4.86 mmol). The reaction mixture was stirred at room temperature for 16 hours and then concentrated at reduced pressure. The product was purified by silica gel chromatography eluting with 0-40% ethyl acetate in iso-hexane to give the title compound as a colourless oil (784 mg, 66%). m/z 364 (MNa$^+$), $C_{17}H_{24}ClNO_4$ exact mass 341.83.

Step 5—4-(tert-Butoxycarbonylamino)-2-(4-chlorophenyl)butanoic Acid

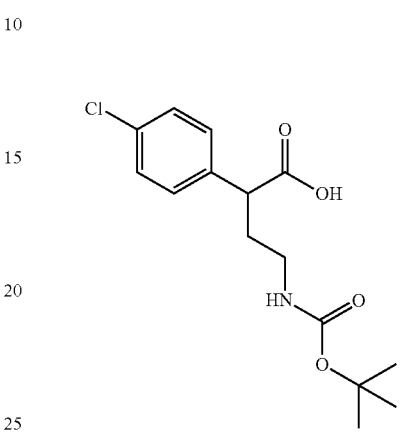

To a solution of ethyl 4-(tert-butoxycarbonylamino)-2-(4-chlorophenyl)butanoate (780 mg, 2.29 mmol) in dioxane (10 mL) and water (10 mL) was added lithium hydroxide monohydrate (300 mg, 7.14 mmol). The reaction mixture was stirred at room temperature for 3 days and then concentrated at reduced pressure. The residue was partitioned between diethyl ether and water and the pH adjusted to 1 by the addition of 1 M hydrochloric acid. After separation of the layers, the aqueous phase was re-extracted with diethyl ether (×2). The combined organic phases were dried over magnesium sulphate, filtered and concentrated. The title compound was isolated as a colourless oil (663 mg, 93%). m/z 312 (M−H)$^-$, $C_{15}H_{20}ClNO_4$ exact mass 313.11.

(S)-2-(benzyloxy)-4-((tert-butoxycarbonyl)amino)butanoic Acid

Step 1—Methyl (S)-2-(benzyloxy)-4-((tert-butoxycarbonyl)amino)butanoate

To a solution of methyl (S)-4-((tert-butoxycarbonyl)amino)-2-hydroxybutanoate (see Dewitt et al. *Org. Biomol. Chem.* 2011, 9, 1846) (233 mg, 1.0 mmol) in dry ethyl acetate (10 mL) was added silver oxide (350 mg, 1.5 mmol) followed by benzyl bromide (0.179 mL, 1.5 mmol). The mixture was stirred in the dark at room temperature overnight, then heated to 50° C. for 8 h. The mixture was cooled, filtered through Kieselguhr, and evaporated. The residue was chromatographed on silica eluting with 0-100% ethyl acetate in hexane to afford the desired product as a colourless oil (67 mg, 20%). m/z 323.6. C17H25NO5 requires 323.17

Step 2—(S)-2-(benzyloxy)-4-((tert-butoxycarbonyl)amino)butanoic Acid

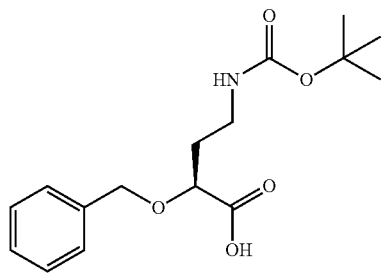 [SMILES: CC(C)(C)OC(=O)NCC[C@H](OCc1ccccc1)C(=O)O]

Methyl (S)-2-(benzyloxy)-4-((tert-butoxycarbonyl)amino)butanoate (67 mg, 0.2 mmol) was dissolved in water (1 mL) and dioxane (2 mL). Lithium hydroxide (15 mg) was added and the mixture stirred at room temperature overnight. The resultant mixture was concentrated under reduced pressure, diluted with water (4 mL) and washed with ethyl acetate. The aqueous phase was adjusted to pH 2 with 1 M HCl and extracted with dichloromethane (3×4 mL). The dichloromethane extracts were combined and evaporated to give the title compounds as a white solid (40 mg, 64%). m/z 309.6 (MH+), 332 (MNa+). $C_{16}H_{23}NO_5$ requires 309.16.

Additional Synthesis Examples (S)-4-Amino-2-(cyclohexylmethoxy)butanoyl L-Thr-L-Dap-polymyxin [D-cyclohexylalanine-6]-heptapeptide (Compound 84)

(S)-4-Amino-2-(benzyloxy)butanoyl L-Thr-L-Dap-polymyxin [D-cyclohexylalanine-6]-heptapeptide trifluoroacetate salt (Example 42) (18 mg) was dissolved in isopropanol (5 mL) and water (1 mL), and treated with 5% rhodium on alumina (10 mg). The mixture was stirred under an atmosphere of hydrogen for 18 h. The catalyst was removed by filtration and the filtrate purified by preparative HPLC using the conditions of General Method 3. Product-containing fractions were combined, evaporated to low volume and lyophilized to a while solid (0.8 mg). m/z 1153 [MH+], 1265 [M+TFA]+. $C_{53}H_{97}N_{15}O_{13}$ requires 1151.74.

Changes to Amino Acid Residues at Positions 6 and/or 7

Example compounds 94 to 99 (as shown in Table 1C below) were prepared by solid phase peptide synthesis, with the cyclisation step carried out off-resin. Suitable methodology is given in WO 2014/188178 (Example 50). An alternative method of solid phase synthesis is given in Velkov et al. and WO 2015/149131.

Structures depict the N-terminal group and side chain on the Polymyxin heptapeptide scaffold (PMBH, shown below). Relative stereochemistry is depicted by heavy or dashed lines. Absolute stereochemistry is depicted by heavy or hashed wedged bonds.

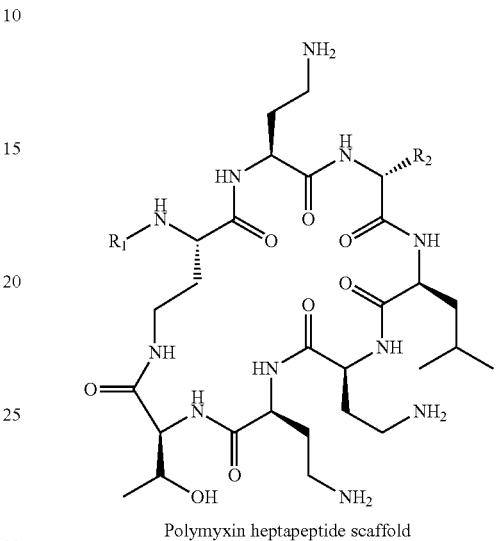

Polymyxin heptapeptide scaffold

The compounds described below have an L-Thr residue at the position corresponding to position 2 in polymyxin. The compounds have either an L-Dap or an L-Dab residue at the position corresponding to position 3 in polymyxin.

The present case is based on GB 1421020.7, the contents of which are hereby incorporated by reference in their entirety. In that case the stereochemistry of the Thr residue at position 2 of some example compounds was incorrectly drawn. This is corrected in the example compounds presented in the present case. In context it is clear that the example compounds, including the compounds of the invention, have an L-Thr residue at position 2 as the compounds are prepared indirectly from polymyxin B, which retains L-Thr residue at position 2, or the compounds are prepared from a polymyxin B heptapeptide which is coupled with a L-Thr-containing group to ultimately yield the appropriate N-terminal-derivatised nonapeptide or decapeptide product.

It is noted also that the correct names for the example compounds were used.

TABLE 1

| Ex | R¹ (N-terminal and side-chain on heptapeptide) | R² | Formula | Mass | Starting material | Name | HPLC RT (min) | m/z |
|---|---|---|---|---|---|---|---|---|
| PMB | | benzyl | | | | | | |
| C1 | | benzyl | C52H89N15O12 | 1115.7 | Int 11 | (trans-5-(isobutyl-piperidine)-3-carbonyl L-Thr-L-Dap-polymyxin B heptapeptide | 5.45 | 1117[MH+] 559[M + 2H]²⁺ |
| C2 | | benzyl | C51H88N16O12 | 1116.7 | Int 11 | (S)-1-isobutyl piperazine-2-carbonyl-L-Thr-L-Dap-polymyxin B heptapeptide | 5.12 | 1118[MH+] 559[M + 2H]²⁺ |
| C3 | | biphenyl-methyl | C62H102N16O13 | 1278.7 | (BOC)₅ polymyxin B[D-(4-bromo Phe]-6] | Polymyxin B[D-(4-phenyl)Phe]-6] | 6.67 | 1279.4[MH⁺] 640.3[M + 2H]²⁺ |

TABLE 1-continued

| Ex | R¹ (N-terminal and side-chain on heptapeptide) | R² | Formula | Mass | Starting material | Name | HPLC RT (min) | m/z |
|---|---|---|---|---|---|---|---|---|
| 1 | | pyridyl-phenyl-CH₂ | C61H101N17O13 | 1279.77 6348 | (BOC)₅ polymyxin [D-(4-bromo Phe]-6 | Polymyxin B[D-(4-(4-pyridyl)Phe]-6] | 5.64 | 1281[MH⁺] 641[M + 2H]²⁺ |
| 2 | | 4-bromophenyl-CH₂ | C56H97BrN16O13 | 1280.66 0275 | Polymyxin B | Polymyxin B[D-(4-bromoPhe)-6] | 6.48 | 1282[MH⁺] 642[M + 2H]²⁺ |
| 3 | | biphenyl-CH₂ | C58H93N15O12 | 1191.71 2698 | Int 16 | (trans-5-(isobutyl)-piperidine)-3-carbonyl L-Thr-L-Dap-polymyxin [D-(4-phenyl)Phe]-6] heptapeptide. Isomer 1 | 6.19 | 1193[MH⁺] 597[M + 2H]²⁺ |

TABLE 1-continued

| Ex | R¹ (N-terminal and side-chain on heptapeptide) | R² | Formula | Mass | Starting material | Name | HPLC RT (min) | m/z |
|---|---|---|---|---|---|---|---|---|
| 4 | | | C58H93 N15O12 | 1191.71 2698 | Int 16 | (trans-5-(isobutyl-piperidine)-3-carbonyl L-Thr-L-Dap-polymyxin [D-(4-phenyl)Phe]-6]heptapeptide. Isomer 2 | 6.40 | 1193[MH⁺] 597[M + 2H]²⁺ |
| 5 | | | C57H92 N16O12 | 1192.71 | Int 16 | (S)-1-isobutyl piperazine-2-carbonyl-L-Thr-L-Dap-polymyxin [D-(4-phenyl)Phe]-6]heptapeptide | 6.14 | 1194[MH⁺] 597[M + 2H]²⁺ |
| 6 | | | C62H10 2N16O1 2 | 1262.79 | Int 16 | (S)-1-octyl piperazine-2-carbonyl-L-Thr-L-Dap-polymyxin [D-(4-phenyl)Phe]-6]heptapeptide | 6.75 | 1265[MH⁺] 632[M + 2H]²⁺ |

TABLE 1-continued

| Ex | R[1] (N-terminal and side-chain on heptapeptide) | R[2] | Formula | Mass | Starting material | Name | HPLC RT (min) | m/z |
|---|---|---|---|---|---|---|---|---|
| 7 | 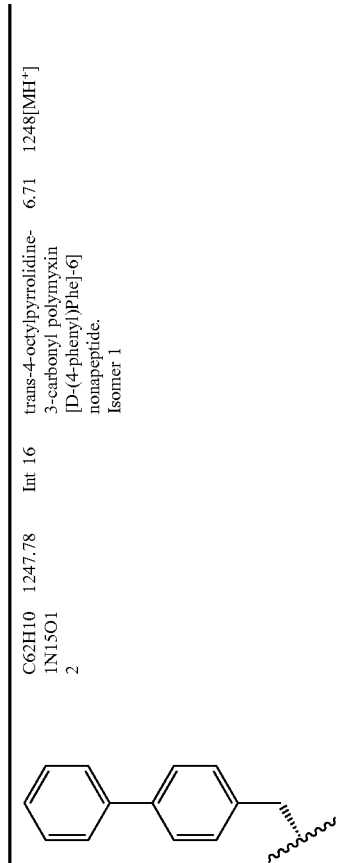 | 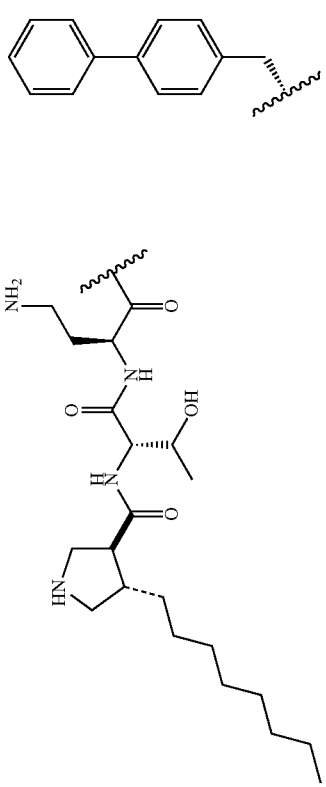 | C62H101N15O12 | 1247.78 | Int 16 | trans-4-octylpyrrolidine-3-carbonyl polymyxin [D-(4-phenyl)Phe-6] nonapeptide. Isomer 1 | 6.71 | 1248[MH+] |
| 8 | | | C62H101N15O12 | 1247.78 | Int 16 | trans-4-octylpyrrolidine-3-carbonyl polymyxin [D-(4-phenyl)Phe-6] nonapeptide. Isomer 2 | 7.04 | 1248[MH+] 625[M + 2H]$^{2+}$ |
| 9 | | 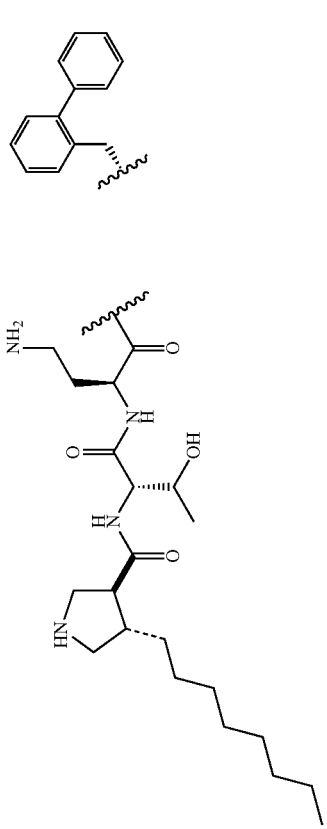 | C62H101N15O12 | 1247.78 | Int 17 | trans-4-octylpyrrolidine-3-carbonyl polymyxin [D-(2-phenyl)Phe-6] nonapeptide. Isomer 1 | 6.70 | 1249[MH+] 625[M + 2H]$^{2+}$ |

TABLE 1-continued

| Ex | R[1] (N-terminal and side-chain on heptapeptide) | R[2] | Formula | Mass | Starting material | Name | HPLC RT (min) | m/z |
|---|---|---|---|---|---|---|---|---|
| 10 | | | C62H101 N15O12 | 1247.78 | Int 17 | trans-4-octylpyrrolidine-3-carbonyl polymyxin [D-(2-phenyl)Phe]-6] nonapeptide. Isomer 2 | 7.08 | 1249[MH$^+$] 625[M + 2H]$^{2+}$ |
| 11 | | | C52H88 BrN15O 12 | 1193.59 | Int 16 | (trans-5-(isobutyl-piperidine)-3-carbonyl L-Thr-L-Dap-polymyxin [D-(4-bromo Phe)]-6] hept apeptide Isomer 1 | 5.91 | 1195/1197 [MH$^+$] 598[M + 2H]$^{2+}$ |
| 12 | | | C52H88 BrN15O 12 | 1193.59 | Int 16 | (trans-5-(isobutyl-piperidine)-3-carbonyl L-Thr-L-Dap-polymyxin [D-(4-bromo Phe)]-6] heptapeptide Isomer 2 | 6.12 | 1195/1197 [MH$^+$] 598[M + 2H]$^{2+}$ |

TABLE 1-continued

| Ex | R¹ (N-terminal and side-chain on heptapeptide) | R² | Formula | Mass | Starting material | Name | HPLC RT (min) | m/z |
|---|---|---|---|---|---|---|---|---|
| 13 | | 4-Br-benzyl | C49H84BrN15O12 | 1153.56 | Int 16 | 2-aminomethyl-4-methyl pentanoyl polymyxin L-Thr-L-Dap-polymyxin [D-(4-bromo Phe)]-6]heptapeptide. Isomer 1 | 5.79 | 1155[MH⁺] |
| 14 | | 4-Br-benzyl | C49H84BrN15O12 | 1153.56 | Int 16 | 2-aminomethyl-4-methyl pentanoyl polymyxin L-Thr-L-Dap-polymyxin [D-(4-bromo Phe)]-6]heptapeptide. Isomer 2 | 5.96 | 1155[MH⁺] |
| 15 | | 4-phenylbenzyl | C55H89N15O12 | 1151.68 | Int 16 | 2-aminomethyl-4-mehtly pentanoyl polymyxin L-Thr-L-Dap-polymyxin [D-(4-phenyl Phe)]-6]heptapeptide. Isomer 1 | 6.21 | 1153[MH⁺] |

TABLE 1-continued

| Ex | R¹ (N-terminal and side-chain on heptapeptide) | R² | Formula | Mass | Starting material | Name | HPLC RT (min) | m/z |
|---|---|---|---|---|---|---|---|---|
| 16 | | biphenylmethyl | C55H89N15O12 | 1151.68 | Int 16 | 2-aminomethyl-4-methyl pentanoyl polymyxin L-Thr-L-Dap-polymyxin [D-(4-phenyl Phe)]-6]heptapeptide. Isomer 2 | 6.36 | 1153[MH⁺] |
| 17 | | (E)-oct-1-enyl-phenylmethyl | C60H103N15O12 | 1225.79 | Int 16 | (trans-5-(isobutyl-piperidine)-3-carbonyl L-Thr-L-Dap-polymyxin [D-(4-(E)-oct-1-enyl) Phe]-6]heptapeptide Isomer 1 | 7.69 | 1226[MH⁺] 614[M + 2H]²⁺ |
| 18 | | (E)-oct-1-enyl-phenylmethyl | C60H103N15O12 | 1225.79 | Int 16 | (trans-5-(isobutyl-piperidine)-3-carbonyl L-Thr-L-Dap-polymyxin [D-(4-(E)-oct-1-enyl) Phe]-6]heptapeptide Isomer 2 | 7.84 | 1226[MH⁺] 614[M + 2H]²⁺ |

TABLE 1-continued

| Ex | R¹ (N-terminal and side-chain on heptapeptide) | R² | Formula | Mass | Starting material | Name | HPLC RT (min) | m/z |
|---|---|---|---|---|---|---|---|---|
| 19 | | CF₃-biphenyl-CH₂- | C56H88F2N15O12 | 1219.67 | Int 16 | 2-Aminomethyl-4-methyl pentanoyl polymyxin L-Thr-L-Dap-polymyxin [D-{4-(4-trifluoromethyl) phenyl} Phe]-6]heptapeptide. Isomer 1 | 6.84 | 1221[MH⁺] |
| 20 | | CF₃-biphenyl-CH₂- | C56H88F3N15O12 | 1219.67 | Int 16 | 2-Aminomethyl-4-methyl pentanoyl polymyxin L-Thr-L-Dap-polymyxin [D-{4-(4-trifluoromethyl) phenyl} Phe]-6]heptapeptide. Isomer 1 | 6.95 | 1221[MH⁺] |
| 21 | | cyclohexyl-CH₂- | C50H93N15O12 | 1095.71 | 2-aminomethyl pentanoyl polymyxin B nonapeptide | 2-Aminomethyl-4-methyl pentanoyl polymyxin D-[cyclohexyl alanine]-6] nonapeptide. | 5.84 | 1096.8[MH⁺] |

TABLE 1-continued

| Ex | R¹ (N-terminal and side-chain on heptapeptide) | R² | Formula | Mass | Starting material | Name | HPLC RT (min) | m/z |
|---|---|---|---|---|---|---|---|---|
| 22 | | cyclohexylmethyl | C56H104N16O13 | 1208.80 | Polymyxin B | Polymyxin [D-cyclohexyl alanine]-6 | 6.54 | 1209.8[MH⁺] |
| 23 | | 4-octylbenzyl | C60H105N15O12 | 1227.81 | Example 18 | (Trans-5-(isobutyl-piperidine)-3-carbonyl L-Thr-L-Dap-polymyxin [D-(4-octyl Phe)]-6 heptapeptide | 7.99 | 1228[MH⁺] 614[M + 2H]²⁺ |
| 24 | | 4-cyanobenzyl | C57H97N17O13 | 1227.75 | (Boc)₅ [D-(4-Bromo)Phe-6]-Polymyxin | Polymyxin B[D-(4-cyanoPhe]-6 | 6.19 | 1229[MH⁺] 614[M + 2H]²⁺ |

TABLE 1-continued

| Ex | R¹ (N-terminal and side-chain on heptapeptide) | R² | Formula | Mass | Starting material | Name | HPLC RT (min) | m/z |
|---|---|---|---|---|---|---|---|---|
| 25 | (structure) | (4-isobutylbenzyl) | C56H97N15O12 | 1171.74 | Int 16 | {trans-5-(isobutyl-piperidine)-3-carbonyl L-Thr-L-Dap-polymyxin [D-(4-isobutyl Phe)]-6}heptapeptide isomer 2 | 6.76 | 1173[MH⁺] 587[M + 2H]²⁺ |
| 26 | (structure) | (biphenyl-4-ylmethyl) | C61H101N15O12 C61H102N15O12 | 1235.78 | Int 16 | 2-(2-Aminoethyl)undecanoyl L-Thr-L-Dap-polymyxin [D-{4-(4-trifluoromethyl)phenyl}Phe]-6 heptapeptide. Isomer 2 | 7.38 | 1237[MH⁺] 619[M + 2H]²⁺ |

TABLE 1A

Additional Synthesis Examples

| Ex | R¹ (N-terminal and side-chain on heptapeptide) | R² | Formula | Mass | Starting material | Name | HPLC RT (min) | m/z |
|---|---|---|---|---|---|---|---|---|
| C4 | | benzyl | C51H89 N15O12 | 1103.68 | Int 7 | 2-(2-Aminoethyl) hexanoyl polymyxin B nonapeptide | 5.31 | 1104.7 [MH⁺] |
| C5 | | benzyl | C53H93 N15O12 | 1131.71 | Int 7 | 2-(2-Aminoethyl) octanoyl polymyxin B nonapeptide | 5.91 | 1132.7 [MH⁺] 567 [M + 2H]²⁺ |
| C6 | | benzyl | C52H91 N15O12 | 1117.70 | Int 11 | 2-(2-Aminoethyl) octanoyl L-Thr-L-Dap-polymyxin heptapeptide | 5.97 | 1161.2 [MH⁺] |

TABLE 1A-continued

Additional Synthesis Examples

| Ex | R¹ (N-terminal and side-chain on heptapeptide) | R² | Formula | Mass | Starting material | Name | HPLC RT (min) | m/z |
|---|---|---|---|---|---|---|---|---|
| 27 | | | C55H95 N15O12 | 1157.73 | Int 16 | 2-(Aminomethyl)-4-methylpentanoyl L-Thr-L-Dap-polymyxin [D-(4-cyclohexyl Phe)]-6 heptapeptide | 6.85 | 1159 [MH⁺] 580 [M + 2H]²⁺ |
| 28 | | | C51H93 N15O12 | 1107.71 | Int 19 | 3-Amino-2-cyclohexyl)propanoyl L-Thr-L-Dap-polymyxin [D-cyclohexylalanine]-6 heptapeptide | 6.05 | 1108.8 [MH⁺] |
| 29 | | | C54H96 N16O12 | 1160.74 | Int 16 | L-Dab-L-Thr-L-Dap-polymyxin [D-(4-octyl Phe)]-6 heptapeptide | 7.50 | 1161 [MH⁺] 581 [M + 2H]²⁺ |

TABLE 1A-continued

Additional Synthesis Examples

| Ex | R¹ (N-terminal and side-chain on heptapeptide) | R² | Formula | Mass | Starting material | Name | HPLC RT (min) | m/z |
|---|---|---|---|---|---|---|---|---|
| 30 | | biphenylmethyl | C61H100N16O12 | 1248.77 | Int 16 | (S)-1-Octylpiperazine-2-carbonyl L-Thr-L-Dap-polymyxin [D-(4-phenyl Phe)-6 heptapeptide. | 6.73 | 1249.8 [MH⁺] |
| 31 | | cyclohexylmethyl | C52H95N15O12 | 1121.73 | Int 19 | 3-amino-2-(cyclohexylmethyl) propanoyl L-Thr-L-Dap-polymyxin [D-cyclohexylalanine]-6 heptapeptide | 6.08 | 1122.7 [MH⁺] |
| 32 | | cyclohexylmethyl | C51H93N15O12 | 1107.71 | Int 19 | 3-amino-3-cyclohexylpropanoyl L-Thr-L-Dap-polymyxin [D-cyclohexylalanine]-6 heptapeptide. Isomer 1 | 5.84 | 1108.8 [MH⁺] |
| 33 | | cyclohexylmethyl | C51H93N15O12 | 1107.71 | Int 19 | 3-amino-3-cyclohexylpropanoyl L-Thr-L-Dap-polymyxin [D-cyclohexylalanine]-6 heptapeptide. Isomer 2 | 5.93 | 1108.7 [MH⁺] |

TABLE 1A-continued

Additional Synthesis Examples

| Ex | R¹ (N-terminal and side-chain on heptapeptide) | R² | Formula | Mass | Starting material | Name | HPLC RT (min) | m/z |
|---|---|---|---|---|---|---|---|---|
| 34 | | | C52H89 N15O12 | 1115.68 | Int 19 | 3-amino-2-benzylpropanoyl L-Thr-L-Dap-polymyxin [D-cyclohexylalanine]-6 heptapeptide. Isomer 2 | 5.95 | 1119 [MH⁺] 559 [M + 2H]²⁺ |
| 35 | | | C53H91 N15O12 | 1129.70 | Int 19 | 4-amino-2-benzylbutanoyl L-Thr-L-Dap-polymyxin [D-cyclohexylalanine]-6 heptapeptide. Isomer 2 | 5.98 | 1131 [MH⁺] 566 [M + 2H]²⁺ |
| 36 | | | C54H93 N15O12 | 1143.71 | Int 20 | 4-amino-2-benzylbutanoyl polymyxin [D-cyclohexylalanine]-6 nonapeptide. isomer 2 | 5.97 | 1144 [MH⁺] 573 [M + 2H]²⁺ |
| 37 | | | C55H100 N16O14 | 1208.76 | Int 20 | 2-cyclohexyl-2-hydroxyacetyl polymyxin [D-cyclohexylalanine]-6 nonapeptide | 5.75 | 1209.6 [MH+] 606 [M + 2H]²⁺ |

TABLE 1A-continued

Additional Synthesis Examples

| Ex | R¹ (N-terminal and side-chain on heptapeptide) | R² | Formula | Mass | Starting material | Name | HPLC RT (min) | m/z |
|---|---|---|---|---|---|---|---|---|
| 38 | | cyclohexylmethyl | C52H89 N15O12 | 1115.68 | Int 19 | 4-amino-2-phenylbutanoyl L-Thr-L-Dap-polymyxin [D-cyclohexylalanine]-6 heptapeptide. isomer 2 | 5.72 | 1116.7 [MH⁺] |
| 39 | | cyclohexylmethyl | C52H89 N15O12 | 1115.68 | Int 19 | 4-amino-3-phenylbutanoyl L-Thr-L-Dap-polymyxin [D-cyclohexylalanine]-6 heptapeptide. | 5.70 | 1116.7 [MH⁺] |
| 40 | | cyclohexylmethyl | C51H95 N15O12 | 1109.73 | Int 20 | 2-(2-aminoethyl) hexanoyl [D-cyclohexylalanine]-6 nonapeptide. | 5.76 | 1111 [MH⁺] 556 [M + 2H]²⁺ |
| 41 | | cyclohexylmethyl | C50H93 N15O12 | 1095.71 | Int 19 | 2-(2-aminoethyl) hexanoyl L-Thr-L-Dap-polymyxin [D-cyclohexylalanine]-6 heptapeptide. Isomer 2 | 5.84 | 1097 [MH⁺] 549 [M + 2H]²⁺ |

TABLE 1A-continued

Additional Synthesis Examples

| Ex | R¹ (N-terminal and side-chain on heptapeptide) | R² | Formula | Mass | Starting material | Name | HPLC RT (min) | m/z |
|---|---|---|---|---|---|---|---|---|
| 42 | | cyclohexylmethyl | C52H95N15O12 | 1121.73 | Int 19 | 4-amino-3-cyclohexylbutanoyl L-Thr-L-Dap-polymyxin [D-cyclohexylalanine]-6 heptapeptide. Isomer 1 | 5.88 | 1122.7 [MH⁺] |
| 43 | | cyclohexylmethyl | C52H95N15O12 | 1121.73 | Int 19 | 4-amino-3-cyclohexylbutanoyl L-Thr-L-Dap-polymyxin [D-cyclohexylalanine]-6 heptapeptide. isomer 2 | 5.95 | 1122.7 [MH⁺] |
| 44 | | cyclohexylmethyl | C52H88FN15O12 | 1133.67 | Int 19 | 4-amino-2-(4-fluorophenyl)butanoyl L-Thr-L-Dap-polymyxin [D-cyclohexylalanine]-6 heptapeptide. Isomer 2 | 5.75 | 1135 [MH⁺] 568 [M + 2H]²⁺ |
| 45 | | cyclohexylmethyl | C53H90FN15O12 | 1147.69 | Int 19 | 4-amino-2-(3-fluorobenzyl)butanoyl L-Thr-L-Dap-polymyxin [D-cyclohexylalanine]-6 heptapeptide. isomer 2 | 5.90 | 1149 [MH⁺] 575 [M + 2H]²⁺ |

TABLE 1A-continued

Additional Synthesis Examples

| Ex | R¹ (N-terminal and side-chain on heptapeptide) | R² | Formula | Mass | Starting material | Name | HPLC RT (min) | m/z |
|---|---|---|---|---|---|---|---|---|
| 46 | | cyclohexylmethyl | C50H93 N15O13 | 1111.71 | Int 19 | (S)-4-amino-2-butoxybutanoyl L-Thr-L-Dap-polymyxin [D-cyclohexylalanine]-6 heptapeptide. | 5.64 | 1113 [MH⁺] 557 [M + 2H]²⁺ |
| 47 | | cyclohexylmethyl | C51H95 N15O12 | 1109.73 | Int 19 | 2-(2-aminoethyl)-4-methylhexanoyl L-Thr-L-Dap-polymyxin [D-cyclohexylalanine]-6 heptapeptide. Isomer 2 | 5.91 | 1111 [MH⁺] 556 [M + 2H]²⁺ |
| 48 | | cyclohexylmethyl | C53H91 N15O13 | 1145.69 | Int 19 | (S)-4-amino-2-(benzyloxy)butanoyl L-Thr-L-Dap-polymyxin [D-cyclohexylalanine]-6 heptapeptide. | 5.72 | 1146.7 [MH⁺] 1259 [M + TFA] |
| 49 | | cyclohexylmethyl | C52H98 N16O12 | 1138.76 | Int 19 | (S)-4-amino-2-(hexylamino)butanoyl L-Thr-L-Dap-polymyxin [D-cyclohexylalanine]-6 heptapeptide. | 5.89 | 1139.6 [MH⁺] |

TABLE 1A-continued

Additional Synthesis Examples

| Ex | R¹ (N-terminal and side-chain on heptapeptide) | R² | Formula | Mass | Starting material | Name | HPLC RT (min) | m/z |
|---|---|---|---|---|---|---|---|---|
| 50 | 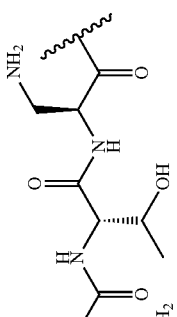 | 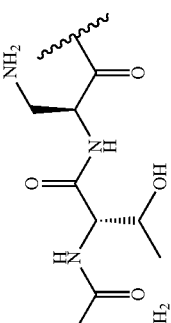 | C52H88 ClN15O12 | 1149.64 | Int 19 | 4-amino-3-(4-chlorophenyl) butanoyl L-Thr-L-Dap-polymyxin [D-cyclohexylalanine]-6 heptapeptide. Isomer 1 | 5.61 | 1150.5 [MH⁺] |
| 51 | 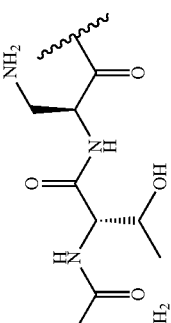 | | C52H88 ClN15O12 | 1149.64 | Int 19 | 4-amino-3-(4-chlorophenyl) butanoyl L-Thr-L-Dap-polymyxin [D-cyclohexylalanine]-6 heptapeptide. Isomer 2 | 5.66 | 1150.4 [MH⁺] |
| 52 | 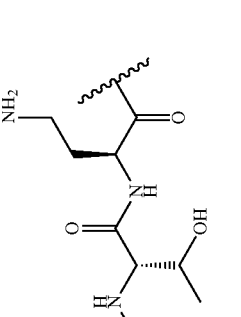 | | C52H96 N16O12 | 1136.74 | Int 20 | (S)-1-isobutylpiperazine-2-carbonyl polymyxin [D-cyclohexylalanine]-6 nonapeptide | 5.50 | 1137 [MH⁺] 570 [M + 2H]²⁺ |
| 53 | 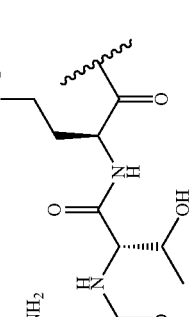 | | C53H91 N15O12 | 1129.70 | Int 20 | 3-amino-2-benzylpropanoyl polymyxin [D-cyclohexylalanine]-6 nonapeptide. Isomer 2 | 5.87 | 1131 [MH⁺] 566 [M + 2H]²⁺ |

TABLE 1A-continued

Additional Synthesis Examples

| Ex | R¹ (N-terminal and side-chain on heptapeptide) | R² | Formula | Mass | Starting material | Name | HPLC RT (min) | m/z |
|---|---|---|---|---|---|---|---|---|
| 54 | | cyclohexylmethyl | C53H90 FN15O12 | 1147.69 | Int 20 | 4-amino-2-(4-fluorophenyl) butanoyl polymyxin [D-cyclohexylalanine]-6 nonapeptide isomer 2 | 5.84 | 1149 [MH⁺] 575 [M + 2H]²⁺ |
| 55 | | cyclohexylmethyl | C53H90 ClN15O12 | 1163.66 | Int 20 | 4-amino-2-(3-chlorophenyl) butanoyl polymyxin [D-cyclohexylalanine]-6 nonapeptide. isomer 2 | 5.95 | 1164 [MH⁺] |
| 56 | | cyclohexylmethyl | C53H91 N15O12 | 1129.70 | Int 20 | 4-amino-3-phenylbutanoyl polymyxin [D-cyclohexylalanine]-6 nonapeptide isomer 1 | 5.57 | 1130.5 [MH⁺] |
| 57 | | cyclohexylmethyl | C53H91 N15O12 | 1129.70 | Int 20 | 4-amino-3-phenylbutanoyl polymyxin [D-cyclohexylalanine]-6 nonapeptide isomer 2 | 5.60 | 1130.5 [MH⁺] |

TABLE 1A-continued

Additional Synthesis Examples

| Ex | R¹ (N-terminal and side-chain on heptapeptide) | R² | Formula | Mass | Starting material | Name | HPLC RT (min) | m/z |
|---|---|---|---|---|---|---|---|---|
| 58 | | cyclohexylmethyl | C53H91 N15O12 | 1129.70 | Int 19 | 4-amino-3-benzylbutanoyl L-Thr-L-Dap-polymyxin [D-cyclohexylalanine]-6 heptapeptide. Isomer 1 | 5.83 | 1131 [MH⁺] 566 [M + 2H]²⁺ |
| 59 | | cyclohexylmethyl | C53H91 N15O12 | 1129.70 | Int 19 | 4-amino-3-benzylbutanoyl L-Thr-L-Dap-polymyxin [D-cyclohexylalanine]-6 heptapeptide. Isomer 2 | 5.90 | 1131 [MH⁺] 566 [M + 2H]²⁺ |
| 60 | | cyclohexylmethyl | C52H89 N15O12 | 1115.68 | Int 19 | 4-amino-4-phenylbutanoyl L-Thr-L-Dap-polymyxin [D-cyclohexylalanine]-6 heptapeptide. Isomer 1 | 5.67 | 1118 [MH⁺] 559 [M + 2H]²⁺ |
| 61 | | cyclohexylmethyl | C52H89 N15O12 | 1115.68 | Int 19 | 4-amino-4-phenylbutanoyl L-Thr-L-Dap-polymyxin [D-cyclohexylalanine]-6 heptapeptide. Isomer 2 | 5.69 | 1117 [MH⁺] 559 [M + 2H]²⁺ |

TABLE 1A-continued

Additional Synthesis Examples

| Ex | R¹ (N-terminal and side-chain on heptapeptide) | R² | Formula | Mass | Starting material | Name | HPLC RT (min) | m/z |
|---|---|---|---|---|---|---|---|---|
| 62 | | cyclohexylmethyl | C53H90 FN15O12 | 1147.69 | Int 20 | 3-amino-2-(2-fluorobenzyl) propanoyl | 5.85 | 1150 [MH⁺] 575 [M + 2H]²⁺ |
| 63 | | cyclohexylmethyl | C52H95 N15O12 | 1121.73 | Int 19 | 4-amino-4-cyclohexylbutanoyl L-Thr-L-Dap-polymyxin [D-cyclohexylalanine]-6 heptapeptide | 5.81 | 1123 [MH⁺] 562 [M + 2H]²⁺ |
| 64 | | cyclohexylmethyl | C53H91 N15O12 | 1129.70 | Int 20 | 4-amino-2-phenylbutanoyl polymyxin [D-cyclohexylalanine]-6 nonapeptide isomer 2 | 5.72 | 1130.5 [MH⁺] |
| 65 | | cyclohexylmethyl | C53H90 FN15O12 | 1147.69 | Int 19 | 4-amino-2-(2-fluorobenzyl)butanoyl L-Thr-L-Dap-polymyxin [D-cyclohexylalanine]-6 heptapeptide. Isomer 2 | 5.90 | 1149 [MH⁺] |

TABLE 1A-continued

Additional Synthesis Examples

| Ex | R¹ (N-terminal and side-chain on heptapeptide) | R² | Formula | Mass | Starting material | Name | HPLC RT (min) | m/z |
|---|---|---|---|---|---|---|---|---|
| 66 | | cyclohexylmethyl | C54H93 N15O12 | 1143.71 | Int 20 | 4-amino-3-benzylbutanoyl polymyxin [D-cyclohexylalanine]-6 nonapeptide isomer 1 | 5.71 | 1146 [MH⁺] 573 [M + 2H]²⁺ |
| 67 | | cyclohexylmethyl | C54H93 N15O12 | 1143.71 | Int 20 | 4-amino-3-benzylbutanoyl polymyxin [D-cyclohexylalanine]-6 nonapeptide isomer 2 | 5.79 | 1145 [MH⁺] 573 [M + 2H]²⁺ |
| 68 | | cyclohexylmethyl | C51H89 N15O12S | 1135.65 | Int 19 | 4-amino-2-(thiophen-3-ylmethyl)butanoyl L-Thr-L-Dap-polymyxin [D-cyclohexylalanine]-6 heptapeptide. | 5.77 | 1138 [MH⁺] 570 [M + 2H]²⁺ |
| 69 | | cyclohexylmethyl | C53H97 N15O12 | 1135.74 | Int 20 | 4-amino-2-cyclohexylbutanoyl polymyxin [D-cyclohexylalanine]-6 nonapeptide isomer 2 | 7.86 | 1136.6 [MH⁺] |

TABLE 1A-continued

Additional Synthesis Examples

| Ex | R[1] (N-terminal and side-chain on heptapeptide) | R[2] | Formula | Mass | Starting material | Name | HPLC RT (min) | m/z |
|---|---|---|---|---|---|---|---|---|
| 70 | | | C51H89 N15O12S | 1135.65 | Int 20 | 4-amino-2-(thiophen-2-yl)butanoyl polymyxin [D-cyclohexylalanine]-6 nonapeptide isomer 2 | 5.71 | 1137 [MH+] 569 [M + 2H]2+ |
| 71 | | | C54H93 N15O13 | 1159.71 | Int 19 | (S)-4-amino-2-((4-methylbenzyl)oxy)butanoyl-polymyxin L-Thr-L-Dap-polymyxin [D-cyclohexylalanine]-6 heptapeptide. | 5.95 | 1160.6 [MH+] 1273 [M + TFA]+ |
| 72 | | | C54H99 N15O12 | 1149.76 | Int 20 | 4-amino-3-(cyclohexylmethyl)butanoyl polymyxin [D-cyclohexylalanine]-6 nonapeptide | 6.27 | 1150.5 [MH+] |
| 73 | | | C53H97 N15O12 | 1135.74 | Int 20 | (trans-5-(isobutyl-piperidine)-3-carbonyl polymyxin [D-cyclohexylalanine]-6 nonapeptide | 6.15 | 1136.6 [MH+] |

TABLE 1A-continued

Additional Synthesis Examples

| Ex | R¹ (N-terminal and side-chain on heptapeptide) | R² | Formula | Mass | Starting material | Name | HPLC RT (min) | m/z |
|---|---|---|---|---|---|---|---|---|
| 74 | | cyclohexylmethyl | C53H90ClN15O13 | 1179.65 | Int 19 | (S)-4-amino-2-((4-chlorobenzyl)oxy)butanoyl L-Thr-L-Dap-polymyxin [D-cyclohexylalanine]-6 heptapeptide. | 6.16 | 1180.5 [MH⁺] 1293.5 [M + TFA]⁺ |
| 75 | | cyclohexylmethyl | C52H95N15O12 | 1121.73 | Int 19 | 4-amino-2-(cyclopentylmethyl)butanoyl L-Thr-L-Dap-polymyxin [D-cyclohexylalanine]-6 heptapeptide. | 6.15 | 1123 [MH⁺] 562 [M + 2H]²⁺ |
| 76 | | cyclohexylmethyl | C52H88ClN15O12 | 1149.64 | Int 19 | 4-amino-2-(2-chlorophenyl)butanoyl L-Thr-L-Dap-polymyxin [D-cyclohexylalanine]-6 heptapeptide. | 6.01 | 1151 [MH⁺] |
| 77 | | cyclohexylmethyl | C53H90ClN15O12 | 1163.66 | Int 20 | 4-amino-2-(2-chlorophenyl)butanoyl polymyxin [D-cyclohexylalanine]-6 nonapeptide | 5.97 | 1166 [MH⁺] 583 [M + 2H]²⁺ |

TABLE 1A-continued

Additional Synthesis Examples

| Ex | R¹ (N-terminal and side-chain on heptapeptide) | R² | Formula | Mass | Starting material | Name | HPLC RT (min) | m/z |
|---|---|---|---|---|---|---|---|---|
| 78 | | | C53H91 N15O13 | 1145.69 | Int 19 | (S)-3-amino-2-((4-methylbenzyl)oxy)propanoyl L-Thr-L-Dap-polymyxin [D-cyclohexylalanine]-6 heptapeptide | 6.09 | 1146.7 [MH⁺] |
| 79 | | | C52H88 ClN15O12 | 1149.64 | Int 19 | 4-Amino-2-(3-chlorophenyl)butanoyl L-Thr-L-Dap-polymyxin [D-cyclohexylalanine]-6 heptapeptide. | 5.89 | 1151 [MH⁺] 576 [M + 2H]²⁺ |

TABLE 1B

Further Additional Synthesis Examples

| Ex | R¹ (N-terminal and side-chain on heptapeptide) | R² | Formula | Mass | Starting material | Name | HPLC RT (min) | m/z |
|---|---|---|---|---|---|---|---|---|
| 80 | | cyclohexylmethyl | C51H95 N15O12 | 1109.73 | Int 19 | 2-(2-aminoethyl)-5-methylhexanoyl L-Thr-L-Dap-polymyxin [D-cyclohexylalanine-6]heptapeptide. isomer 2 | 5.93 | 1111 [MH⁺] |
| 81 | | cyclohexylmethyl | C52H88 ClN15O13 | 1165.64 | Int 19 | (S)-3-amino-2-((4-chlorobenzyl)oxy)propanoyl L-Thr-L-Dap-polymyxin [D-cyclohexylalanine-6]heptapeptide | 5.97 | 1167 [MH⁺] |
| 82 | | cyclohexylmethyl | C53H90 ClN15O13 | 1179.65 | Int 19 | 4-amino-2-((3-chlorobenzyl)oxy)butanoyl L-Thr-L-Dap-polymyxin [D-cyclohexylalanine-6]heptapeptide. Isomer 1 | 5.93 | 1180 [MH⁺] |
| 83 | | cyclohexylmethyl | C53H97 N15O12 | 1135.74 | Int 20 | 4-amino-2-(cyclopentylmethyl)butanoyl polymyxin [D-cyclohexylalanine-6]nonapeptide | 6.10 | 1137 [MH⁺] |
| 84 | | cyclohexylmethyl | C53H97 N15O13 | 1151.74 | Example 48 | (S)-4-amino-2-(cyclohexyl-methoxy)butanoyl L-Thr-L-Dap-polymyxin [D-cyclohexylalanine-6]heptapeptide. | 6.12 | 1153 [MH⁺], 1265 [M + TFA]⁺ |
| 85 | | cyclohexylmethyl | C52H95 N15O12 | 1121.73 | Int 19 | 4-amino-2-cyclohexylbutanoyl L-Thr-L-Dap-polymyxin [D-cyclohexylalanine-6]heptapeptide. | 6.09 | 1123 [MH⁺] |
| 86 | | cyclohexylmethyl | C53H97 N15O12 | 1135.74 | Example 56 | 4-amino-3-cyclohexylbutanoyl polymyxin [D-cyclohexylalanine-6]nonapeptide. Isomer 1 | 5.95 | 1137 [MH⁺] |
| 87 | | cyclohexylmethyl | C53H97 N15O12 | 1135.74 | Example 57 | 4-amino-3-cyclohexylbutanoyl polymyxin [D-cyclohexylalanine-6]nonapeptide. Isomer 2 | 6.04 | 1137 [MH⁺] |

TABLE 1B-continued

Further Additional Synthesis Examples

| Ex | R¹ (N-terminal and side-chain on heptapeptide) | R² | Formula | Mass | Starting material | Name | HPLC RT (min) | m/z |
|---|---|---|---|---|---|---|---|---|
| 88 | (structure) | (cyclohexylmethyl) | C56H97 N15O13 | 1187.74 | Int 19 | (S)-4-amino-2-((4-isopropylbenzyl)oxy)butanoyl L-Thr-L-Dap-polymyxin [D-cyclohexylalanine-6]heptapeptide | 6.44 | 1189 [MH⁺] |
| 89 | (structure) | (cyclohexylmethyl) | C52H97 N15O12 | 1123.74 | Int 20 | 2-(2-aminoethyl)-5-methylhexanoyl polymyxin [D-cyclohexylalanine-6]nonapeptide. Isomer 2 | 5.21 | 1125 [MH⁺] |
| 90 | (structure) | (cyclohexylmethyl) | C55H95 N15O13 | 1173.72 | Int 19 | (S)-4-amino-2-((3,5-dimethylbenzyl)oxy)butanoyl L-Thr-L-Dap-polymyxin [D-cyclohexylalanine-6]heptapeptide | 5.63 | 1175 [MH⁺] |
| 91 | (structure) | (cyclohexylmethyl) | C54H99 N15O12 | 1149.76 | Example 66 | 4-amino-3-(cyclohexylmethyl)butanoyl polymyxin [D-cyclohexylalanine-6]nonapeptide. Isomer 1 | 6.05 | 1151 [MH⁺] |
| 92 | (structure) | (cyclohexylmethyl) | C53H99 N15O12 | 1137.76 | Int 20 | 2-(2-aminoethyl)-4-ethylhexanoyl polymyxin [D-cyclohexylalanine]-6 nonapeptide. Isomer 2 | 5.79 | 1139 [MH⁺] |
| 93 | (structure) | (cyclohexylmethyl) | C53H97 N15O12 | 1135.74 | Tri-(N-Boc) Polymyxin B heptapeptide | 4-amino-2-cyclohexylbutanoyl polymyxin L-alloThr-L-Dap-[D-cyclohexylalanine-6]-heptapeptide. | | |

Additional compounds with modifications at position 6 and/or 7, in general structure A, are shown in Table 1C:

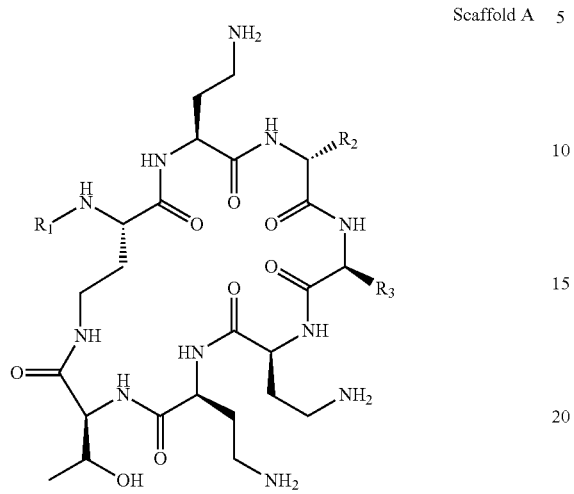

Scaffold A

TABLE 1C

Further Additional Synthesis Examples

| Ex | R¹ (N-terminal and side-chain on heptapeptide) | R² | R³ | Formula | Mass | Name |
|---|---|---|---|---|---|---|
| 94 | | phenyl | n-butyl | C52H89N15O12 | 1115.7 | 4-amino-2-cyclohexylbutanoyl L-Thr-L-Dap-polymyxin[norleu-7] heptapeptide. |
| 95 | | phenyl | benzyl | C55H87N15O12 | 1149.7 | 4-amino-2-cyclohexylbutanoyl L-Thr-L-Dap-polymyxin[Phe-7] heptapeptide |
| 96 | | phenyl | cyclohexyl | C54H91N15O12 | 1141.7 | 4-amino-2-cyclohexylbutanoyl L-Thr-L-Dap-polymyxin[L-cyclohexylglycine-7] heptapeptide |
| 97 | | isobutyl | cyclohexylmethyl | C53H97N15O12 | 1135.7 | 4-amino-2-cyclohexylbutanoyl polymyxin E [L-cyclohexylalanine-7] nonapeptide |

TABLE 1C-continued

Further Additional Synthesis Examples

| Ex | R¹ (N-terminal and side-chain on heptapeptide) | R² | R³ | Formula | Mass | Name |
|---|---|---|---|---|---|---|
| 98 | [structure] | [cyclohexyl] | [isobutyl] | C52H95N15O12 | 1121.7 | 4-amino-2-cyclohexylbutanoyl polymyxin[D-cyclohexylglycine-6] nonapeptide |
| 99 | [structure] | [cyclohexylmethyl] | [n-butyl] | C52H95N15O12 | 1121.7 | 4-amino-2-cyclohexylbutanoyl L-Thr-L-Dab-polymyxin [D-cyclohexylalanine-6], [norVal-7] heptapeptide |

Biological Activity

To evaluate the potency and spectrum of the compounds, susceptibility testing was performed against up to nine strains of each of the Gram negative pathogens, *Escherichia coli, Pseudomonas aeruginosa, Klebsiella pneumoniae* and *Acinetobacter baumannii*.

Comparator compounds C1 to C3 were also tested along with Polymyxin B.

Biological data is presented for examples and comparator compounds.

The values in Table 2 are MIC (µg/mL) against strains of *E. coli, K. pneumoniae, P. aeruginosa* and *A. baumanii*, including strains which show elevated MICs to Polymyxin.

The data shows that the introduction of a halogen atom to D-phenylalanine at position 6 enhances activity against polymyxin resistant strains (see Example 2 compared with PMB).

The introduction of a lipophilic substituent to the phenyl group of the D-phenylalanine at position 6 significantly improves of activity against resistant strains (see Example 4 and C1, and Example 5 and C2).

The modification of the N terminal group further improves the activity of the compounds against resistant strains (see Example 4 and Example 5 compared to C3).

The authors have demonstrated a significant difference in activity between diastereomers in some examples where a compounds has been prepared in two diastereomeric forms in the N-terminal group.

Additional compounds were prepared and the additional biological data is presented in Table 2A. The additional compounds were compared against PMB and comparator compounds C4-C7. Comparator compounds C4-C6 are shown in Table 1A. Comparator compound C7 corresponds to octanoyl-Dab-Thr-Dab-Cy[Dab-Dab-D-Phe-L-OctGly-Dab-Dab-Thr] reported as FADDI-002 by Velkov et al. (*ACS Chemical Biology*, 2014, 9, 1172).

The values in Table 2A are MIC (µg/mL).

Further the inventors have found that in order to provide a polymyxin derivative with a desirable combination of properties (activity against polymyxin-susceptible strains, activity against strains with reduced susceptibility to polymyxins i.e. MIC≤4 µg/mL, cytotoxicity, pharmacokinetics, tissue distribution) it may be helpful to modify both the polymyxin N-terminal group and the amino acid residues at position 6 and/or position 7.

For a given N-terminal group, increasing the lipophilicity of the side-chains of the amino acid residues at position 6 and/or position 7 improves the activity of a compound against strains with reduced susceptibility to polymyxins (MIC≤4 µg/mL; so-called 'polymyxin-resistant strains') as has been discussed above.

The substituents to the core of the molecule and at the N-terminus should not be considered in isolation and the present inventors have found that the combination of these groups both based on their specific geometries as well as the overall lipophilicity of the molecule is very important for the optimum biological properties.

The lipophilicity of a compound can be expressed as the log P where P is the octanol:water partition coefficient. Methods of estimation of this parameter are well known, and one such method of estimation uses the calculated value A log P. The A Log P is a calculation of the Ghose/Crippen group-contribution estimate for Log P, where P is the relative solubility of a compound in octanol versus water (Ghose, A. K., Viswanadhan, V. N., and Wendoloski, "J. J., Prediction of Hydrophobic (Lipophilic) Properties of Small Organic Molecules Using Fragment Methods: An Analysis of A log P and C Log P Methods." J. Phys. Chem. A, 1998, 102, 3762-3772).

Velkov et al. have shown that providing highly lipophilic moieties as the side-chains of the amino acid residues at position 6 and/or position 7 in polymyxin decapeptides (with either the natural polymyxin acyl chain or a suitable replacement acyl group at the N-terminus of a decapeptide) improves activity against resistant strains (see Velkov et al. ACS Chem Biol 9, 1172; 2014).

The present inventors have found that the activity of such compounds can be further improved using the N-terminal groups described herein. For example, compound 26 shows further improved activity against polymyxin-resistant strains compared with C7, which is compound FADDI-02 reported by Velkov et al. The biological activity of compound 26 compared with C7 is reported in Table 2C. The values in Table 2C are MIC (µg/mL).

Thus derivatised polymyxin compounds can be provided with an optimum activity against polymyxin-resistant strains where the combination of N-terminal moieties and amino acid residues at position 6 and position 7 is chosen to give an overall A log P value greater (i.e. less negative) than −4.0, ideally greater than −3.5, such as between −3.0 and −2.0.

It can be seen that compounds such as 26 and C7 are less active against polymyxin-susceptible strains than compounds in a more negative A Log P range. The present inventors have found that compounds having a A Log P values lying in the range −5.0 to −6.3, such as within the range −5.5 and −6.3, provided they have N-terminal groups with optimum geometry, can have excellent activity against both polymyxin-susceptible and resistant strains.

Compounds with A Log P in this region with appropriate N-terminal moieties and amino acid moieties at position 6 and positon 7 can also have reduced cytotoxicity compared with polymyxin B.

If certain favourable moieties are present at the N terminal of the polymyxin scaffold then the A Log P value may not fall into the optimum range. Modulating lipophilicity by changing the side chains of amino acids 6 and/or 7 may bring such compounds into the optimum range.

For example, Comparator compound C4 (A Log P 6.5) with a short alkyl side chain has only moderate activity. This can be improved by increasing the lipophilicity either at the N-terminus with C5 (A Log P 5.5), or by increasing the lipophilicity of the side chain of amino acid 6 by reduction to a cyclohexyl (see compound 40; A Log P 5.8). In some instances increasing lipophilicity in the core (at the amino acid positions 6 and/or 7) rather than the N-terminal moiety can lead to improved biological properties e.g. compound 41 has significantly lower cytotoxicity compared with C6.

TABLE 2

| | E. coli | | | | | K. pneumoniae | | | | | | | P. aeruginosa | | | A. baumanii | | |
|---|---|---|---|---|---|---|---|---|---|---|---|---|---|---|---|---|---|---|
| Ex. | 058 | 059 | 060 | 061 | ATCC 25922 | 062 | 063 | 064 | 065 | 066 | 067 | ATCC 4352 | 068 | 070 | ATCC 27853 | 053 | 056 | ATCC BAA-747 |
| PMB | 4 | 4 | 4 | 16 | 0.25 | 128 | 32 | 8 | 4 | 8 | 128 | 0.25 | 8 | 32 | 0.5 | 128 | 32 | 0.25 |
| C1 | 1 | 2 | 1 | 2 | 0.03 | 32 | 8 | 2 | 2 | 1 | 64 | 0.03 | 2 | 4 | 0.25 | 16 | 1 | 0.06 |
| C2 | 8 | 16 | 8 | 32 | 0.25 | ND | 128 | 32 | 16 | 32 | >256 | 0.125 | 32 | ND | 0.5 | >256 | 256 | 0.25 |
| C3 | 2 | 1 | 4 | 8 | 0.5 | 32 | 8 | 4 | 0.5 | 4 | 32 | 0.5 | 2 | 4 | 1 | 16 | 16 | 1 |
| 1 | ND | ND | 8 | 32 | 1 | >64 | >64 | 32 | ND | 32 | >32 | 1 | 32 | >32 | 1 | >32 | >32 | 1 |
| 2 | 2 | 1 | 2 | 4 | 2 | 8 | 16 | 2 | 0.5 | 4 | 16 | 1 | 2 | 4 | 1 | 16 | 4 | 2 |
| 3 | 8 | 8 | 16 | 32 | 0.5 | >64 | >64 | 32 | 32 | ND | >64 | 0.5 | 4 | 4 | 1 | 64 | 4 | 2 |
| 4 | 0.5 | 0.5 | 0.5 | 2 | 0.5 | ND | 4 | 2 | 1 | 1 | 8 | 0.5 | 1 | 2 | 1 | 2 | 0.5 | 0.5 |
| 5 | 1 | 1 | 2 | 8 | 0.06 | ND | 16 | 4 | 0.5 | 8 | 32 | 0.25 | 4 | 8 | 0.5 | 32 | 4 | 0.125 |
| 6 | 1 | 0.5 | 1 | 2 | 1 | 4 | 4 | 2 | 1 | 0.5 | 4 | 1 | 2 | 2 | ND | 8 | 4 | 1 |
| 7 | 2 | 1 | 4 | 8 | 1 | 16 | 32 | 8 | 1 | 4 | 32 | 1 | 2 | 2 | ND | 8 | 4 | 1 |
| 8 | 2 | 1 | 2 | 4 | 1 | 4 | ND | 1 | 1 | 0.5 | 8 | 1 | 2 | 2 | 1 | 4 | 2 | 1 |
| 9 | 2 | 2 | 4 | 8 | 1 | 64 | >64 | 64 | 8 | 32 | >64 | 0.5 | 2 | 2 | 1 | 64 | 32 | 1 |
| 10 | 1 | 1 | 2 | 2 | 2 | 2 | 8 | 2 | 1 | 4 | 4 | 1 | 2 | 2 | 2 | 4 | 4 | 1 |
| 11 | 16 | 32 | 16 | 64 | 1 | >64 | >64 | >64 | 64 | >64 | >64 | 1 | 8 | 16 | 1 | >64 | 32 | 2 |
| 12 | 0.25 | 1 | 1 | 1 | 0.125 | 8 | 4 | 1 | 0.5 | 1 | 8 | 0.125 | 1 | 1 | 0.25 | 8 | ND | 0.125 |
| 13 | 32 | 32 | 32 | >64 | 1 | >64 | >64 | >64 | >64 | >64 | >64 | 0.5 | 32 | 64 | 0.5 | >64 | >64 | >8 |
| 14 | 4 | 8 | 8 | 16 | 0.25 | 8 | 64 | 8 | 8 | 8 | >64 | 0.25 | 8 | 16 | 0.5 | 32 | 16 | 0.125 |
| 15 | 32 | 16 | 32 | 64 | 1 | >64 | >64 | >64 | 64 | 64 | >64 | 0.5 | 16 | 32 | 1 | >64 | >64 | 8 |
| 16 | 4 | 1 | 5 | 16 | 0.25 | 4 | 16 | 2 | 1 | 4 | 32 | 0.5 | 4 | 8 | 0.5 | 16 | 4 | 0.25 |
| 17 | 2 | 2 | 2 | 2 | 2 | 4 | 16 | 8 | 4 | ND | 32 | 2 | 4 | 4 | 2 | 2 | 2 | 2 |
| 18 | 2 | 1 | 2 | 2 | 2 | 2 | 4 | 4 | 2 | 2 | 4 | 2 | 4 | 4 | 2 | 2 | 2 | 2 |
| 19 | 16 | ND | ND | ND | 1 | ND | ND | ND | 16 | ND | ND | 1 | ND | ND | 2 | ND | ND | 1 |
| 20 | 4 | ND | ND | ND | 1 | ND | ND | ND | 1 | ND | ND | 0.5 | ND | ND | 1 | ND | ND | 0.5 |
| 21 | 8 | 16 | 8 | 32 | 0.25 | 16 | 64 | 8 | ND | 16 | >64 | 0.25 | 32 | 32 | 0.5 | >64 | 64 | 0.5 |
| 22 | 2 | 2 | 4 | 8 | 0.5 | 16 | 32 | 4 | 1 | 4 | 64 | 0.5 | 4 | 4 | 1 | 64 | 32 | 0.5 |
| 23 | 2 | 2 | 2 | 2 | 2 | 4 | 8 | 4 | 2 | 2 | 4 | 1 | 4 | 4 | 2 | 2 | 1 | 2 |

TABLE 2A

Additional Microbial Activity

| | E. coli | | | | K. pneumoniae | | | | P. aeruginosa | | | | A. baumanii | | |
|---|---|---|---|---|---|---|---|---|---|---|---|---|---|---|---|
| Ex. | 058 | 061 | ATCC 25922 | NCTC 9001 | 063 | 065 | ATCC 4352 | ATCC 13882 | CCUG 59347 | 068 | 070 | ATCC 27853 | NCTC 13424 | 053 | 056 | ATCC BAA-747 |
| PMB | 4 | 16 | 0.25 | 0.125 | 32 | 4 | 0.25 | 0.25 | 0.5 | 8 | 32 | 0.5 | 0.25 | >64 | 32 | 0.25 |
| C4 | >64 | ND | 1.0 | ND | ND | >64 | 0.25 | 1 | 2 | ND | ND | 1 | 0.5 | ND | ND | 1 |
| C5 | 2 | 16 | 0.06 | 0.03 | 8 | 1 | 0.06 | 0.125 | 0.5 | 8 | 32 | 0.125 | 0.25 | >64 | 16 | 0.125 |
| C6 | 1 | 8 | 0.125 | 0.06 | 8 | 0.25 | 0.06 | 0.125 | 0.125 | 2 | 8 | 0.125 | 0.03 | 32 | 32 | 0.06 |
| C7 | 2 | ND | 1 | ND | ND | 2 | ND | 1 | 2 | ND | ND | 0.5 | 1 | ND | ND | 1 |
| 24 | 4 | 16 | 0.125 | ND | 64 | 8 | 0.125 | ND | 0.5 | 32 | >64 | 0.25 | 0.25 | >64 | >64 | 0.25 |
| 25 | 1 | 0.5 | 0.5 | ND | 2 | 1 | 0.25 | ND | 2 | 1 | 1 | 1 | 0.5 | ND | ND | 0.5 |
| 26 | 2 | 4 | 1 | 1 | 4 | 1 | 1 | 2 | 2 | 4 | 4 | 2 | 1 | 4 | 2 | 2 |
| 27 | 2 | 8 | 0.5 | 0.5 | 8 | 0.5 | 0.25 | ND | 1 | 4 | 2 | 0.5 | 0.25 | 8 | 4 | 0.5 |
| 28 | 1 | 8 | 0.25 | 0.125 | 8 | 1 | 0.125 | ND | 0.5 | 4 | 4 | 0.25 | 0.125 | 16 | 4 | 0.06 |
| 29 | 32 | ND | 2 | ND | ND | >64 | ND | ND | 8 | ND | ND | 4 | 4 | ND | ND | 4 |
| 30 | 1 | 2 | 1 | ND | 4 | 1 | 1 | 1 | 2 | 2 | 2 | 1 | 2 | 4 | 2 | 1 |
| 31 | 2 | 16 | 0.5 | ND | 16 | 1 | ND | 0.5 | 1 | 2 | 2 | 0.5 | 0.5 | 32 | 16 | 0.25 |

TABLE 2A-continued

Additional Microbial Activity

| | E. coli | | | | K. pneumoniae | | | | P. aeruginosa | | | | A. baumanii | | | |
|---|---|---|---|---|---|---|---|---|---|---|---|---|---|---|---|---|
| Ex. | 058 | 061 | ATCC 25922 | NCTC 9001 | 063 | 065 | ATCC 4352 | ATCC 13882 | CCUG 59347 | 068 | 070 | ATCC 27853 | NCTC 13424 | 053 | 056 | ATCC BAA-747 |
| 32 | 2 | 16 | 0.25 | 0.125 | 16 | ND | 0.06 | 0.25 | 0.5 | 4 | 4 | 0.5 | 0.06 | ND | 64 | 0.25 |
| 33 | 2 | 16 | 0.25 | 0.125 | 64 | 2 | 0.03 | 0.5 | 0.5 | 8 | 8 | 0.25 | 0.125 | 64 | 32 | 0.25 |
| 34 | 2 | 16 | 0.25 | 0.125 | 32 | 4 | 0.125 | 0.125 | 0.25 | 4 | 4 | 0.25 | 0.06 | 32 | 16 | 0.125 |
| 35 | 4 | 16 | 0.25 | 0.06 | 16 | 0.5 | 0.125 | 0.06 | 0.25 | 1 | 2 | 0.25 | 0.25 | >64 | 64 | 0.5 |
| 36 | 8 | ND | 0.125 | ND | ND | 2 | ND | 0.125 | 0.5 | ND | ND | 0.5 | 2 | ND | ND | 1 |
| 37 | 8 | ND | 0.06 | 0.06 | ND | 16 | ND | 0.25 | 0.5 | ND | ND | 0.5 | 0.5 | ND | ND | 0.125 |
| 38 | 2 | 16 | 0.06 | 0.06 | 32 | 1 | ND | 0.125 | 0.25 | 4 | 4 | 0.25 | 0.03 | 32 | 8 | 0.06 |
| 39 | 4 | 32 | 0.125 | 0.06 | 64 | 4 | ND | 0.125 | 0.5 | 4 | 4 | 0.5 | 0.03 | 32 | 64 | 0.06 |
| 40 | 8 | 16 | 0.125 | 0.03 | 16 | 2 | ND | 0.25 | 0.5 | 4 | 8 | 0.5 | 0.125 | >64 | 64 | 0.06 |
| 41 | 4 | 8 | 0.125 | 0.06 | 16 | 1.5 | ND | 0.125 | 0.5 | 4 | 4 | 0.5 | 0.06 | >32 | 32 | 0.06 |
| 42 | 4 | 8 | 0.5 | 0.06 | 32 | 2 | ND | 0.25 | 0.5 | 2 | 4 | 0.5 | 0.125 | >64 | 32 | 0.125 |
| 43 | 1 | 8 | 0.25 | 0.06 | 16 | 0.5 | ND | 0.25 | 0.25 | 2 | 2 | 0.25 | 0.25 | 64 | 32 | 0.125 |
| 44 | 2 | 8 | 0.25 | 0.03 | 16 | 0.5 | 0.125 | 0.25 | 0.5 | 2 | 1 | 0.25 | 0.06 | ND | 8 | 0.06 |
| 45 | 4 | 16 | 0.25 | 0.06 | 16 | 1 | ND | 0.25 | 0.25 | 1 | 1 | 0.125 | 0.25 | 64 | 64 | 0.25 |
| 46 | 8 | ND | 0.125 | ND | >64 | 2 | ND | 0.25 | 0.5 | 16 | 32 | 0.5 | 0.125 | >64 | >64 | 0.125 |
| 47 | 4 | ND | 0.25 | 0.125 | ND | 0.5 | ND | 0.5 | 0.5 | ND | ND | 0.5 | 0.25 | ND | ND | 0.125 |
| 48 | 4 | 32 | 0.125 | ND | 64 | 5 | ND | 0.125 | 0.25 | 8 | 16 | 0.25 | 0.25 | >64 | 32 | 0.125 |
| 49 | 2 | 16 | 0.5 | 0.125 | 32 | 2 | ND | 0.5 | 0.25 | 2 | 2 | 0.25 | 0.25 | 64 | 64 | 0.5 |
| 50 | 2 | 16 | 0.5 | ND | ND | 1 | ND | 0.25 | 0.5 | 1 | 2 | 0.25 | 0.25 | 32 | 16 | 0.125 |
| 51 | 2 | ND | 0.5 | ND | ND | 0.25 | ND | 0.5 | 0.5 | ND | ND | 0.5 | 0.25 | ND | ND | 0.5 |
| 52 | 8 | 16 | 0.25 | ND | 64 | 8 | ND | 0.25 | 1 | 16 | 16 | 0.5 | 0.25 | >64 | >64 | 0.25 |
| 53 | 4 | 32 | 0.25 | 0.125 | 64 | 4 | ND | 0.25 | 0.5 | 8 | 8 | 0.25 | 0.5 | 64 | 64 | 0.5 |
| 54 | 4 | 16 | 0.125 | 0.06 | 32 | 1 | ND | 0.25 | 0.25 | 4 | 4 | 0.25 | 0.25 | 32 | 8 | 0.125 |
| 55 | 2 | 16 | 0.25 | 0.06 | 16 | 1 | ND | 0.25 | 0.5 | 4 | 4 | 0.125 | 0.25 | 8 | 4 | 0.125 |
| 56 | 16 | ND | 0.25 | ND | ND | 16 | ND | 0.25 | 0.5 | ND | ND | 0.25 | 0.125 | ND | ND | 0.125 |
| 57 | 16 | ND | 0.25 | ND | ND | 8 | ND | 0.25 | 0.5 | ND | ND | 0.25 | 1 | ND | ND | 1 |
| 58 | 4 | 16 | 0.25 | 0.125 | 64 | 4 | ND | 0.25 | 0.25 | 2 | 8 | 0.25 | 0.125 | 64 | 64 | 0.03 |
| 59 | 2 | ND | 0.125 | 0.06 | 32 | 2 | 0.125 | 0.25 | 0.25 | 4 | 8 | 0.25 | 0.06 | 32 | 16 | 0.03 |
| 60 | 16 | ND | 0.5 | ND | ND | ND | ND | 0.5 | 1 | ND | ND | ND | 1 | ND | ND | 0.5 |
| 61 | 8 | ND | 0.25 | ND | ND | 32 | ND | 0.25 | 0.5 | ND | ND | 0.25 | 0.25 | ND | ND | 0.25 |
| 62 | 4 | 32 | 0.125 | ND | 64 | 8 | ND | 0.125 | 0.5 | 8 | 16 | 0.5 | 0.5 | >64 | >64 | 0.5 |
| 63 | 4 | 16 | 0.25 | ND | >64 | 4 | ND | 0.125 | 0.5 | 8 | 8 | 0.25 | 0.125 | 64 | 32 | 0.125 |
| 64 | 8 | 32 | 0.125 | ND | 64 | 4 | ND | 0.25 | 0.25 | 8 | 16 | 0.25 | 0.25 | 32 | 32 | 0.125 |
| 65 | 4 | 16 | 0.25 | ND | 16 | 2 | ND | 0.25 | 0.5 | 2 | 2 | 0.5 | 1 | >64 | >64 | 0.25 |
| 66 | 8 | 32 | 0.125 | ND | 64 | 4 | ND | 0.125 | 0.5 | 8 | 32 | 0.25 | 0.06 | >64 | 64 | 0.125 |
| 67 | 4 | 16 | 0.125 | 0.06 | 32 | 1 | ND | 0.25 | 0.25 | 8 | 16 | 0.25 | 0.25 | 64 | 16 | 0.25 |
| 68 | 2 | 16 | 0.125 | ND | 16 | 1 | ND | 0.25 | 0.5 | 1 | 1 | 0.25 | 0.25 | >64 | 64 | 0.25 |
| 69 | 4 | 16 | 0.06 | 0.03 | 16 | 0.5 | 0.25 | 0.25 | 0.5 | 4 | 8 | 0.25 | 0.06 | >64 | 64 | 0.25 |
| 70 | 8 | 32 | 0.125 | ND | 64 | 8 | ND | 0.125 | 0.5 | 8 | 32 | 0.25 | 0.25 | 32 | 16 | 0.25 |
| 71 | 4 | 16 | 0.125 | 0.125 | 64 | 4 | 0.25 | 0.25 | 0.25 | 8 | 16 | 0.25 | 0.125 | 64 | 32 | 0.125 |
| 72 | 2 | 8 | 0.25 | 0.25 | 8 | 0.5 | ND | 0.25 | 0.5 | 4 | 8 | 0.25 | 0.125 | 64 | 16 | 0.25 |
| 73 | 1 | 2 | 0.125 | 0.125 | 8 | 2 | ND | 0.25 | 0.5 | 1 | 1 | 0.5 | 0.125 | 64 | 16 | 0.25 |
| 74 | 2 | 16 | 0.125 | ND | 16 | 2 | ND | 0.25 | 0.25 | 4 | 4 | 0.25 | 0.125 | 32 | 32 | 0.125 |
| 75 | 2 | 16 | 0.125 | ND | 16 | 1 | ND | 0.125 | 0.25 | 2 | 2 | 0.25 | 0.125 | >64 | 64 | 0.125 |
| 76 | 8 | ND | 0.125 | ND | ND | ND | ND | 0.25 | 0.5 | ND | ND | 0.5 | 0.5 | ND | ND | 0.5 |
| 77 | 8 | ND | 0.25 | ND | ND | 8 | ND | 0.5 | 0.5 | ND | ND | 0.5 | 0.5 | ND | ND | 1 |
| 78 | 4 | ND | 0.25 | ND | ND | ND | ND | 0.25 | 0.25 | ND | ND | 0.25 | 0.06 | ND | ND | 0.25 |
| 79 | 2 | ND | 0.5 | ND | ND | 2 | ND | 0.5 | 0.5 | ND | ND | 0.5 | 0.25 | ND | ND | 0.25 |

TABLE 2A-CONT.

Further Additional Microbial Activity

| | E. coli | | | | K. pneumoniae | | | | P. aeruginosa | | | | A. baumanii | | | |
|---|---|---|---|---|---|---|---|---|---|---|---|---|---|---|---|---|
| Ex. | 058 | 061 | ATCC 25922 | NCTC 9001 | 063 | 065 | ATCC 4352 | ATCC 13882 | CCUG 59347 | 068 | 070 | ATCC 27853 | NCTC 13424 | 053 | 056 | ATCC BAA-747 |
| 80 | 2 | 8 | 0.125 | 0.03 | 8 | 2 | 0.06 | 0.25 | 0.5 | 2 | 2 | 0.25 | 0.125 | 64 | 32 | 0.125 |
| 81 | 1 | 16 | 0.125 | 0.03 | 16 | 4 | 0.25 | 0.125 | 0.25 | 2 | 2 | 0.125 | 0.125 | 32 | 8 | 0.125 |
| 82 | 2 | 8 | 0.06 | 0.015 | 32 | 2 | ND | 0.125 | 0.125 | 4 | 8 | 0.125 | 0.03 | 64 | 16 | 0.125 |
| 83 | 4 | 16 | 0.5 | 0.06 | 16 | 1 | ND | 0.25 | 0.25 | 2 | 8 | 0.25 | 0.06 | >64 | 64 | 0.125 |
| 84 | 8 | 8 | 0.125 | ND | 32 | 4 | ND | 0.25 | 0.5 | ND | 8 | 0.25 | 0.25 | >32 | 32 | 0.25 |
| 85 | 4 | 16 | 0.125 | 0.06 | 8 | 0.5 | ND | 0.5 | 0.5 | 2 | 4 | 0.5 | 0.125 | 64 | 64 | 0.125 |
| 86 | 8 | 32 | 0.125 | 0.06 | >64 | 8 | ND | 0.5 | 0.5 | ND | 8 | 0.25 | 0.125 | >64 | 64 | 0.125 |
| 87 | 4 | 16 | 0.125 | 0.125 | 16 | 0.5 | ND | 0.25 | 0.5 | 2 | 8 | 0.25 | 0.125 | 64 | 64 | 0.25 |
| 88 | 2 | 16 | 0.25 | 0.25 | 64 | 0.5 | ND | 0.25 | 0.5 | 4 | 4 | 0.25 | 0.125 | 64 | 32 | 0.25 |

TABLE 2A-CONT.-continued

Further Additional Microbial Activity

| Ex. | E. coli 058 | E. coli 061 | E. coli ATCC 25922 | E. coli NCTC 9001 | K. pneumoniae 063 | K. pneumoniae 065 | K. pneumoniae ATCC 4352 | K. pneumoniae ATCC 13882 | P. aeruginosa CCUG 59347 | P. aeruginosa 068 | P. aeruginosa 070 | P. aeruginosa ATCC 27853 | P. aeruginosa NCTC 13424 | A. baumanii 053 | A. baumanii 056 | A. baumanii ATCC BAA-747 |
|---|---|---|---|---|---|---|---|---|---|---|---|---|---|---|---|---|
| 89 | 16 | ND | 0.125 | ND | ND | 32 | ND | 0.25 | 1 | ND | ND | 0.5 | 0.25 | ND | ND | 0.5 |
| 90 | 2 | 16 | 0.125 | 0.125 | 64 | 4 | ND | 0.25 | 0.25 | 4 | 16 | 0.125 | 0.06 | >64 | 32 | 0.125 |
| 91 | 4 | ND | 0.125 | ND | ND | 4 | ND | 0.25 | 0.5 | ND | ND | 0.25 | 0.125 | ND | ND | 0.25 |
| 92 | 4 | ND | 0.06 | ND | ND | 8 | ND | 0.25 | 1 | ND | ND | 0.25 | 0.125 | ND | ND | 0.125 |

The lipophilicity of the test compounds was estimated using the calculated value A log P, as described above. The A log P values are given in Table 2B.

HK-2 cell $IC_{50}$ values were determined as described herein, and are reported in Table 2B. Values are reported relative to Polymyxin B.

TABLE 2B

AlogP and $IC_{50}$ values

| Example | AlogP | HK-2 $IC_{50}$ (µg/mL) |
|---|---|---|
| PMB | −6.3 | 12 |
| C1 | −6.2 | 161 |
| C2 | −7.2 | 316 |
| C3 | −4.7 | 3 |
| C4 | −6.5 | ND |
| C5 | −5.5 | 29 |
| C6 | −5.6 | 51 |
| C7 | −4.5 | ND |
| 1 | −5.9 | 7 |
| 2 | −5.5 | ND |
| 3 | −4.7 | 34 |
| 4 | −4.7 | 32 |
| 5 | −5.7 | 36 |
| 6 | −3.7 | 3 |
| 7 | −3.1 | ND |
| 8 | −3.1 | 3 |
| 9 | −3.1 | ND |
| 10 | −3.1 | 4 |
| 11 | −5.5 | ND |
| 12 | −5.5 | 54 |
| 13 | −6.3 | ND |
| 14 | −6.3 | 76 |
| 15 | −5.5 | ND |
| 16 | −5.5 | 32 |
| 17 | −3.0 | ND |
| 18 | −3.0 | ND |
| 19 | −4.6 | ND |
| 20 | −4.6 | 10 |
| 21 | −6.3 | 83 |
| 22 | −5.6 | 17 |
| 23 | −2.6 | ND |
| 24 | −6.4 | ND |
| 25 | −4.6 | 20 |
| 26 | −2.7 | 2 |
| 27 | −4.9 | 18 |
| 28 | −5.8 | 86 |
| 29 | −5.9 | ND |
| 30 | −3.7 | 4 |
| 31 | −5.4 | ND |
| 32 | −5.8 | 73 |
| 33 | −5.8 | 75 |
| 34 | −6.0 | 99 |
| 35 | −5.7 | 152 |
| 36 | −5.7 | ND |
| 37 | −7.1 | ND |
| 38 | −6.2 | 255 |
| 39 | −6.3 | 337 |
| 40 | −5.8 | ND |
| 41 | −5.8 | 206 |
| 42 | −5.7 | ND |
| 43 | −5.7 | ND |
| 44 | −6.0 | ND |
| 45 | −5.5 | ND |
| 46 | −6.8 | ND |
| 47 | −5.6 | ND |
| 48 | −6.6 | ND |
| 49 | −6.2 | ND |
| 50 | −5.7 | ND |
| 51 | −5.7 | ND |
| 52 | −6.5 | ND |
| 53 | −6.0 | ND |
| 54 | −5.9 | ND |
| 55 | −5.5 | ND |
| 56 | −6.3 | ND |
| 57 | −6.3 | ND |
| 58 | −5.9 | ND |
| 59 | −5.9 | ND |
| 60 | −6.1 | ND |
| 61 | −6.1 | ND |
| 62 | −5.8 | ND |
| 63 | −5.5 | ND |
| 64 | −6.1 | ND |
| 65 | −5.5 | ND |
| 66 | −5.8 | ND |
| 67 | −5.8 | 60 |
| 68 | −6.1 | ND |
| 69 | −5.4 | ND |
| 70 | −6.2 | ND |
| 71 | −6.1 | ND |
| 72 | −5.1 | ND |
| 73 | −5.5 | ND |
| 74 | −5.9 | 52 |
| 75 | −5.5 | ND |
| 76 | −5.5 | ND |
| 77 | −5.5 | ND |
| 78 | −6.2 | ND |
| 79 | −5.5 | ND |

| Example | AlogP |
|---|---|
| 80 | −5.6 |
| 81 | −6.0 |
| 82 | −5.9 |
| 83 | −5.4 |
| 84 | −6.0 |
| 85 | −5.5 |
| 86 | −5.6 |
| 87 | −5.6 |
| 88 | −5.4 |
| 89 | −5.5 |
| 90 | −5.6 |
| 91 | −5.1 |
| 92 | −5.1 |

The in vitro activity of compounds 26 and C7 (FADDI-02) against resistant bacterial strains was compared. The resistant strains included including *Escherichia coli*,

*Pseudomonas aeruginosa, Klebsiella pneumoniae* and *Acinetobacter baumannii* strains. The data is provided in Table 2C, where the strains are identified. The values in Table 2 are MIC (µg/mL).

TABLE 2C

Comparison of in vitro activity between compounds 26, C7 and PMB

| Strain | 26 | C7 (FADDI-02) | PMB |
|---|---|---|---|
| *E. coli* | | | |
| CA059 | 1 | 2 | 4 |
| CA060 | 1 | 2 | 4 |
| CA061 | 2 | 4 | 16 |
| *K. pneumoniae* | | | |
| CA062 | 2 | 16 | 64 |
| CA063 | 2 | 8 | 32 |
| CA064 | 2 | 4 | 8 |
| CA066 | 1 | 2 | 8 |
| CA067 | 2 | 64 | >64 |
| N655 | 2 | 8 | 32 |
| *P. aeruginosa* | | | |
| CA068 | 2 | 4 | 8 |
| CA070 | 2 | 2 | 32 |
| *A. baumannii* | | | |
| CA053 | 2 | 4 | >64 |
| CA056 | 2 | 4 | 32 |

Further Definitions

The compounds of formula (I), and optionally the compounds of formula (II) also, have an N terminal group —X—$R^T$.

The group —$R^T$ may be a group —$R^5$ as described in WO 2013/072695, a group —$R^5$ as described in PCT/GB2014/051547 (WO 2014/188178) or a group —$R^{15}$ as described in GB 1404301.2, and WO 2015/135976.

The examples of GB 1404301.2 and WO 2015/135976 describe the preparation of polymyxin compounds having modified N terminals. For each of the compounds described and tested, the amino acid residues at positions 6 and 7 were not modified, thus an L-phenylalanine residue (polymyxin B) or an L-leucine residue (colistin) is present at position 6 and an L-leucine residue is present at position 7.

These examples show that modification to the N terminal group may be made without limiting biological activity. Further, those examples show that changes to the N terminal group may improve biological activity with respect to Polymyxin B. The modification of the N terminal group may also be associated with a reduction in toxicity, especially a reduction in nephrotoxicity.

The worked examples in the present show that these N terminal group may be used within compounds that are variant at position 6 and/or 7 without loss in biological activity. Indeed, in some instances the changes at the 6 and/or 7 position may provide compounds having improved biological activity.

Additional Preferences

The comments below are preferences for the terminal group —$R^T$ taking into account the terminal groups described in PCT/GB2014/051547 (now published as WO 2014/188178) and GB 1404301.2, and additionally or alternatively WO 2015/135976.

-Q-

In one embodiment, -Q- is a covalent bond.

In one embodiment, -Q- is —CH($R^B$)—. In this embodiment, —$R^B$ may be a group -$L^A$-$R^{BB}$, or —$R^B$ together with —$R^{17}$ may form a 5- to 10-membered nitrogen-containing monocyclic or bicyclic heterocycle, as described in further detail below.

Where —$R^{17}$ and —$R^A$ together form a nitrogen-containing heterocycle, the group -Q- is preferably a covalent bond.

In one embodiment, -Q- is —CH($R^B$)—, and forms part of a nitrogen-containing heterocycle. In this embodiment, —$R^B$ may be hydrogen.

Nitrogen-Containing Heterocycle

The groups —$R^{17}$ and —$R^A$ may, together with the carbon atoms to which they are attached, form a nitrogen-containing heterocycle. Similarly, —$R^{17}$ and —$R^B$ may, together with the carbon atoms to which they are attached, form a nitrogen-containing heterocycle. The nitrogen in the nitrogen-containing heterocycle refers to the nitrogen atom in —N($R^{16}$)—.

The nitrogen-containing heterocycle may be a monocyclic or bicyclic nitrogen-containing heterocycle. A bicyclic nitrogen-containing heterocycle has two fused rings.

The nitrogen-containing heterocycle contains a total of 5 to 10 ring atoms. Where the nitrogen-containing heterocycle is monocyclic it may have 5 to 7 ring atoms, for example 5 to 6, such as 6, ring atoms. Where the nitrogen-containing heterocycle is bicyclic it may have 8 to 10 ring atoms, such as 9 to 10, such as 10, ring atoms. Each ring in the bicyclic heterocycle may have 5 to 7 ring atoms, for example 5 or 6, such as 6, ring atoms.

Where the nitrogen-containing heterocycle is bicyclic, one ring may be aromatic or partially unsaturated. The ring that is formed together with the carbon atoms α and β to the group —X— (the first ring) is not aromatic. It is the second ring, which is the ring fused to the first, that may be aromatic. The first ring is saturated, except for the carbon ring atoms that are shared with the second ring (bridge atoms), which may be may be part of the aromatic ring system of the second ring, for example.

Where the nitrogen-containing heterocycle is monocyclic, each carbon ring atom in —$R^{17}$ and —$R^A$ or each carbon ring atom in —$R^{17}$ and —$R^B$ is optionally mono- or di-substituted with —$R^C$.

Where the nitrogen-containing heterocycle is bicyclic, each carbon ring atom in —$R^{17}$ and —$R^A$ or each carbon ring atom in —$R^{17}$ and —$R^B$ is optionally mono- or di-substituted with —$R^D$, as appropriate. A carbon ring atom may be unsubstituted or mono-substituted with —$R^D$ if that carbon ring atom is part of an aromatic ring system, or is part of an unsaturated bond.

The group —$R^D$ includes the group —$R^C$. In one embodiment, where the nitrogen-containing heterocycle is bicyclic, each carbon ring atom in the second ring is optionally mono- or di-substituted with —$R^C$ and each carbon ring atom in the first ring in is optionally mono- or di-substituted with —$R^C$.

In one embodiment, the nitrogen-containing heterocycle is a monocyclic nitrogen-containing heterocycle.

In one embodiment, the nitrogen-containing heterocycle is a bicyclic nitrogen-containing heterocycle.

In one embodiment, one carbon ring atom in the nitrogen-containing heterocycle is mono- or di-substituted, such as mono-substituted, with —$R^C$ or substituted with -$L^B$-$R^{BB}$, where present, for example mono-substituted with —$R^C$. In one embodiment, one carbon ring atom in —$R^{17}$ and —$R^A$ or —$R^{17}$ and —$R^B$ is mono- or di-substituted, such as mono-substituted, with —$R^C$, for example -$L^A$-$R^{CC}$. In these embodiments, the remaining carbon atoms in the nitrogen-containing heterocycle are unsubstituted. This embodiment is preferred when the nitrogen-containing heterocycle is monocyclic.

Where the nitrogen-containing heterocycle is bicyclic, each carbon ring atom in the nitrogen-containing heterocycle may be unsubstituted. Alternatively, where the nitrogen heterocycle is bicyclic one carbon ring atom in the nitrogen-containing heterocycle may be mono- or di-substituted, such as mono-substituted, with —$R^C$ or -$L^B$-$R^{BB}$, such as with —$R^C$. For example, where the nitrogen heterocycle is bicyclic one carbon ring atom in —$R^{17}$ and —$R^A$ or —$R^{17}$ and —$R^B$ is mono- or di- substituted, such as mono-substituted, with —$R^C$, for example -$L^A$-$R^{CC}$. In these embodiments, the remaining carbon atoms in the nitrogen-containing heterocycle are unsubstituted.

The nitrogen-containing heterocycle may contain further hetero ring atoms independently selected from nitrogen, oxygen and sulfur. Where the nitrogen-containing heterocycle is a monocyclic, the heterocycle optionally contains one further nitrogen, oxygen or sulfur ring atom. Where the nitrogen-containing heterocycle is a bicyclic nitrogen-containing heterocycle, the heterocycle optionally contains one, two or three further heteroatoms, where each heteroatom is independently selected from the group consisting of nitrogen, oxygen and sulfur. In a bicyclic system, the further heteroatoms atoms may be provided in the first or second rings, such as the first ring.

In one embodiment, where a further heteroatom is provided, that heteroatom is nitrogen.

In one embodiment, one further heteroatom is provided, such as one further nitrogen heteroatom.

In one embodiment, the nitrogen-containing heterocycle does not contain a further heteroatom.

Where two heteroatoms are provided in a ring, they are not separated by an unsubstituted methylene group (—$CH_2$—) or a mono-substituted methylene group (e.g. —CH($R^C$)—), and optionally they are not separated by a di-substituted methylene group (e.g. —C($R^C$)$_2$—).

Where reference is made to a further nitrogen ring atom, the ring atom may be provided as a group —NH—, and the nitrogen atom may be optionally substituted with —$R^N$ or —$R^{NA}$, as appropriate. A further nitrogen ring atom may be unsubstituted if it is part of an aromatic ring system, or is part of an unsaturated bond.

Where reference is made to a further sulfur ring atom, the sulfur ring atom may be provided as —S—, —S(O)— or —S(O)$_2$—, such as —S—.

Each further nitrogen ring atom is optionally substituted with a group —$R^N$, as appropriate, with the exception of a further nitrogen ring atom that is connected to the carbon that is α to the group —X—, which nitrogen ring atom is optionally substituted with —$R^{NA}$. This is shown schematically below for two exemplary $R^{15}$—X— groups comprising monocyclic heterocycles containing a further nitrogen ring atom:

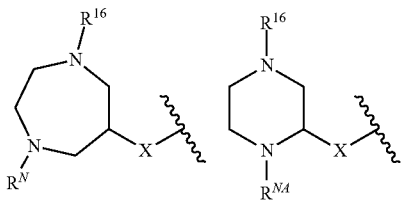

where the ring system on the right has a nitrogen ring atom that is connected to the carbon atom that is α to the group —X—. Such a nitrogen atom is optionally substituted with —$R^{NA}$, and is shown substituted with —$R^{NA}$. The ring system on the left has a nitrogen ring atom that is not connected to the carbon atom that is α to the group —X— (it is attached to a carbon β to the group —X—). Such a nitrogen atom is optionally substituted with —$R^N$, and is shown substituted with —$R^N$. In the exemplary ring structures shown above the carbon ring atoms are shown to be unsubstituted. As described herein, carbon ring atoms that are present in —$R^{17}$ and —$R^A$ are optionally mono- or di-substituted.

It is noted that the definitions for —$R^{NA}$ do not encompass groups that would together with the further nitrogen ring atom form an amide group.

When a second ring is present and that second ring is an aromatic ring containing one or more further nitrogen atoms, a nitrogen atom in the aromatic ring may not be substituted with a group —$R^N$, as appropriate.

Where a further nitrogen ring atom is substituted with —$R^N$ or —$R^{NA}$, as appropriate, each carbon ring atom in the nitrogen-containing heterocycle may be unsubstituted.

Where —$R^{17}$ and —$R^A$ together form a monocyclic nitrogen-containing heterocycle, the heterocycle is substituted with at least one group selected from —$R^C$, and —$R^N$, —$R^{NA}$ and -$L^B$-$R^{BB}$ i.e. at least one of these groups must be present as a ring substituent at the appropriate position. Thus, in this embodiment, where the nitrogen-containing heterocycle is monocyclic and does not contain a further nitrogen atom, at least one carbon ring atom must be substituted with —$R^C$ or -$L^B$-$R^{BB}$, where present. Further, in this embodiment, where the nitrogen-containing heterocycle is monocyclic and contains a further nitrogen atom, and that nitrogen atom is unsubstituted, at least one carbon ring atom must be substituted with —$R^C$ or -$L^B$-$R^{BB}$, where present. If a further nitrogen atom in the monocyclic nitrogen-containing heterocycle is substituted with a group —$R^N$ or —$R^{NA}$, the carbon ring atoms may be unsubstituted or optionally mono- or di-substituted.

Where —$R^{17}$ and —$R^B$ together form a monocyclic nitrogen-containing heterocycle, the heterocycle is substituted with at least one group selected from —$R^C$, and —$R^N$, where present. Alternatively the heterocycle is optionally substituted if —$R^A$ is -$L^A$-$R^{AA}$. In one embodiment, the monocyclic nitrogen-containing heterocycle is unsubstituted when the group —$R^A$ is -$L^A$-$R^{AA}$.

If —$R^A$ is hydrogen, the monocyclic nitrogen-containing heterocycle must be substituted with at least one group selected from —$R^C$, and —$R^N$, where present. Here, if the nitrogen-containing heterocycle is monocyclic and does not contain a further nitrogen atom, at least one carbon ring atom must be substituted with —$R^C$. Further, in this embodiment, where the nitrogen-containing heterocycle is monocyclic and contains a further nitrogen atom, and that nitrogen atom is unsubstituted, at least one carbon ring atom must be substituted with —$R^C$. If a further nitrogen atom in the monocyclic nitrogen-containing heterocycle is substituted with a group —$R^N$, the carbon ring atoms may be unsubstituted or optionally mono- or di-substituted.

Where a nitrogen-containing heterocycle is bicyclic, each further nitrogen ring atom may be unsubstituted. Alternatively, where the nitrogen heterocycle is bicyclic one further nitrogen ring atom may be substituted with a group —$R^N$, except where the further nitrogen ring atom is connected to the carbon that is α to the group —X—, that further nitrogen ring atom is substituted with a group —$R^{NA}$.

In one embodiment, a monocyclic nitrogen-containing heterocycle is mono-substituted with —$R^C$. Thus, one carbon ring atom in the group —$R^{17}$ and —$R^A$ or —$R^{17}$ and —$R^B$ is mono-substituted with —$R^C$.

In one embodiment, a monocyclic nitrogen-containing heterocycle containing a further nitrogen ring atom is mono-substituted with a group —$R^C$, —$R^N$ or —$R^{NA}$, for example mono-substituted with a group —$R^N$ or —$R^{NA}$ or mono-substituted with a group —$R^C$. Thus, one ring atom in the group —$R^{17}$ and —$R^A$ or —$R^{17}$ and —$R^B$ is mono-substituted.

The nitrogen-containing heterocycle may be selected from the group consisting of pyrrolidine, piperidine, piperazine, 1,4-diazepine, indoline, 1,2,3,4-tetrahydroquinoline, 1,2,3,4-tetrahydroisoquinoline, 1,2,3,4-tetrahydroquinoxaline, 1,2,3,4,6,7,8,8a-octahydropyrrolo[1,2-a]pyrazine, 1,2,3,4-tetrahydropyrrolo[1,2-a]pyrazine, 5,6,7,8-tetrahydro-1,6-naphthyridine and 1,2,3,4-tetrahydro-2,6-naphthyridine. In the bicyclic systems the aromatic ring, where present, is provided as the second ring.

The monocyclic nitrogen-containing heterocycles pyrrolidine, piperidine, piperazine, and 1,4-diazepine are substituted as discussed above.

The bicyclic nitrogen-containing heterocycles indoline, 1,2,3,4-tetrahydroquinoline, 1,2,3,4-tetrahydroisoquinoline and 1,2,3,4-tetrahydroquinoxaline may be substituted or unsubstituted, as discussed above.

A nitrogen-containing heterocycle may be selected from the group consisting of pyrrolidine, piperidine, piperazine, and 1,4-diazepine.

In one embodiment, a nitrogen-containing heterocycle is selected from pyrrolidine, piperidine and piperazine.

In one embodiment, a bicyclic nitrogen-containing heterocycle has a first ring selected from pyrrolidine, piperidine and piperazine fused to a second ring, which may be an aromatic ring. Examples of the second ring include cyclohexane, benzene and pyridine ring In one embodiment, the groups —$R^{17}$ and —$R^A$ together form a nitrogen heterocycle when -Q- is a covalent bond. Here, the group —$NR^{16}$— is located on a carbon atom that is β to the group —X—.

In another embodiment, the groups —$R^{17}$ and —$R^A$ together form a nitrogen heterocycle when -Q- is not a covalent bond. Here, the group —$NR^{16}$— is located on a carbon atom that is γ to the group —X—.

In one embodiment, —$R^{17}$ and —$R^A$ are selected from *—$CH(R^{C1})CH(R^{C1})CH(R^{C1})$—, *—$CH(R^{C1})CH(R^{C1})$—, and *—$N(R^{NA})CH(R^{C1})CH(R^{C1})$— where * indicates the point of attachment to the carbon α to the group —X—, —$R^{C1}$ is hydrogen or —$R^C$, and at least one carbon or nitrogen atom is substituted with —$R^C$ or —$R^{NA}$, as appropriate.

Exemplary nitrogen-containing heterocycle structures are given in the —$R^{15}$ section below.

Carbocycle and Heterocycle

In one embodiment, —$R^A$ and —$R^B$ together form a 5- to 10-membered carbocycle or heterocycle. Here, -Q- is not a covalent bond. The carbocycle or heterocycle may be substituted or unsubstituted.

A carbocycle or a heterocycle may be monocyclic or bicyclic. A bicyclic carbocycle or a heterocycle has two fused rings.

The carbocycle or heterocycle contains a total of 5 to 10 ring atoms. Where the carbocycle or heterocycle is monocyclic it may have 5 to 7 ring atoms, for example 5 to 6, such as 6, ring atoms. Where the carbocycle or heterocycle is bicyclic it may have 8 to 10 ring atoms, such as 9 to 10, such as 10, ring atoms. Each ring in the bicyclic system may have 5 to 7 ring atoms, for example 5 or 6, such as 6, ring atoms.

Where the carbocycle or heterocycle is bicyclic, one ring may be aromatic or partially unsaturated. The ring that is formed together with the carbon atoms α and β to the group —X— (the first ring) is not aromatic. It is the second ring, which is the ring fused to the first, that may be aromatic. The first ring is saturated, except for the carbon ring atoms that are shared with the second ring (bridge atoms), which may be may be part of the aromatic ring system of the second ring.

A bicyclic heterocycle is a heterocycle having a heteroatom, such as N, S, or O in either the first or second ring.

In one embodiment, a heteroatom is present in the first ring. In one embodiment, a heteroatom is present in the second ring.

The heterocycle includes one or more heteroatoms independently selected from N, S, and O. In one embodiment heterocycle includes one or two, such as one heteroatom.

In one embodiment, the heteroatom is nitrogen.

In one embodiment, one heteroatom present, such as one nitrogen heteroatom.

Where the carbocycle or a heterocycle is monocyclic, each carbon ring atom in —$R^A$ and —$R^B$ is optionally mono- or di-substituted with —$R^C$.

Where the carbocycle or a heterocycle is bicyclic, each carbon ring atom in —$R^A$ and —$R^B$ is optionally mono- or di-substituted with —$R^D$, which includes —$R^C$.

Where reference is made to a nitrogen ring atom, the ring atom may be provided as a group —NH—, and the nitrogen atom may be optionally substituted with —$R^N$ or —$R^{NA}$, as appropriate. A further nitrogen ring atom may be unsubstituted if it is part of an aromatic ring system, or is part of an unsaturated bond.

Where reference is made to a sulfur ring atom in the heterocycle, the sulfur ring atom may be provided as —S—, —S(O)— or —S(O)$_2$—, such as —S—.

In one embodiment, one carbon ring atom in the carbocycle or heterocycle is mono- or di-substituted, such as mono-substituted, with —$R^C$ or —$R^D$, where appropriate. In this embodiment, the remaining carbon atoms in the carbocycle or heterocycle may be unsubstituted. This embodiment is preferred when the carbocycle or heterocycle is monocyclic.

In one embodiment, the heterocycle has a nitrogen ring atom and that atom is optionally substituted with —$R^N$, with the exception of a nitrogen ring atom that is connected to the carbon that is α to the group —X—, which nitrogen ring atom is optionally substituted with —$R^{NA}$. In one embodiment, where a nitrogen ring atom is present in the heterocycle, that ring atom may be substituted. In this embodiment, the remaining carbon atoms in the carbocycle or heterocycle may be unsubstituted. This embodiment is preferred when the heterocycle is monocyclic.

It is noted that the definitions for —$R^{NA}$ do not encompass groups that would together with a nitrogen ring atom form an amide group.

When a second ring is present and that second ring is an aromatic ring containing one or more nitrogen atoms, a nitrogen atom in the aromatic ring may be substituted with a group —$R^N$, as appropriate.

In one embodiment, a monocyclic carbocycle is selected from cyclohexane and cyclopentane, which may be substituted as discussed above.

In one embodiment, a monocyclic heterocycle is selected from pyrrolidine, tetrahydrofuran, tetrahydrothiophene, piperidine, piperazine, 1,4-dioxane, morpholine, thiomorpholine and 1,4-diazepine, which may be substituted as discussed above.

In one embodiment, a monocyclic carbocycle is selected from indane and tetralin.

In one embodiment, a bicyclic heterocycle is selected from indoline, 1,2,3,4-tetrahydroquinoline, 1,2,3,4-tetrahydroisoquinoline, 1,2,3,4-tetrahydroquinoxaline, chromane, and dihydrobenzofuran, which may be substituted as discussed above.

—$R^{15}$

The group —$R^{15}$ together with —X— may be regarded as an N terminal substituent group in the compounds of formula (III). —$R^{15}$ contains an amino group which may be a group —$NR^{16}R^{17}$, or a group —$NR^{16}$— where the nitrogen is present as a ring atom in a nitrogen-containing heterocycle.

In the compounds of the invention, the nitrogen group —$NR^{16}R^{17}$ must be bonded to one methylene group (i.e. a group —$CH_2$—). Thus, —$R^{15}$ must contain a group —$CH_2NR^{16}R^{17}$.

When the nitrogen group —$NR^{16}$— is provided in a nitrogen-containing heterocycle (i.e. —$R^{17}$ and —$R^A$ form a ring, or —$R^{17}$ and —$R^B$ form a ring), the nitrogen atom must be bonded to one neighboring carbon atom that is part of a methylene group. This is a requirement for the group —$R^{15}$. However, the other neighboring ring carbon atom is not necessarily part of a methylene group (it may be a methylene or methine group). In one embodiment, the nitrogen atom in —$NR^{16}$— is bonded to two ring methylene groups (i.e. both neighboring ring carbon atoms are provided in methylene groups). In one embodiment, the nitrogen atom in —$NR^{16}$— is bonded to a carbon ring atom that is part of a methylene group and a carbon ring atom that is part of a methylene or methine group.

In one embodiment, —$R^{15}$ is selected from the groups listed below. The groups shown below include groups where —$R^{17}$ and —$R^A$ together form a nitrogen-containing heterocycle.

In the embodiments below —$R^{C1}$ is hydrogen or —$R^C$; —$R^{N1}$ is hydrogen or —$R^{NA}$; —$R^{D1}$ is hydrogen or —$R^D$; —$R^A$ is hydrogen or -$L^A$-$R^{AA}$—, —$R^B$ is hydrogen or -$L^B$-$R^{BB}$; and —$R^{16}$ is independently hydrogen or $C_{1-4}$ alkyl; —$R^{17}$ is independently hydrogen or $C_{1-4}$ alkyl; or —$NR^{16}R^{17}$ is a guanidine group. As noted above, where -Q- is a covalent bond —$R^A$ is -$L^A$-$R^{AA}$, and where -Q- is —$CH(R^B)$— one or both of —$R^A$ and —$R^B$ is not hydrogen. Where the nitrogen-containing heterocycle is monocyclic, it should be substituted with at least one group selected from —$R^C$, and -$L^B$-$R^{BB}$, —$R^{NA}$ and —$R^N$.

In one embodiment, —$R^{15}$ is selected from the group consisting of:

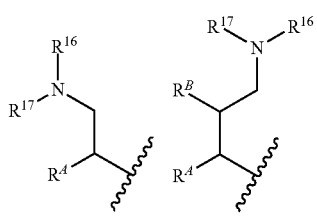

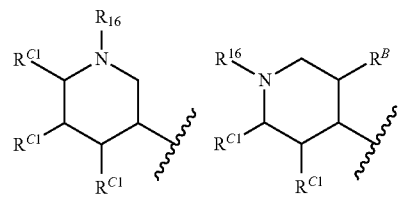

In one embodiment, —$R^{15}$ is selected from the group consisting of:

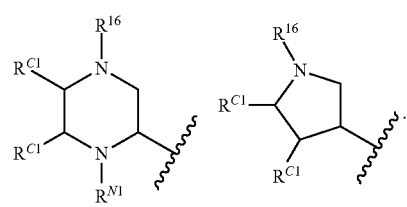

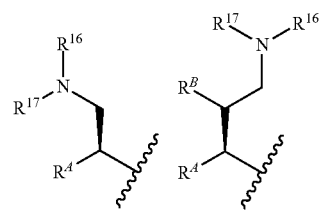

In one embodiment, —$R^{15}$ is selected from the group consisting of:

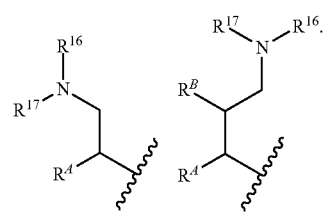

In one embodiment, —R$^{15}$ is selected from the group consisting of:

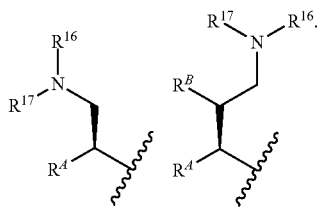

In one embodiment, —R$^{15}$ is selected from the group consisting of:

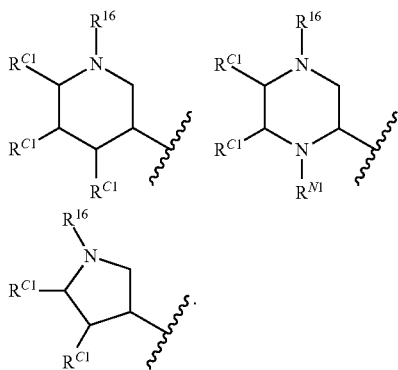

In one embodiment, —R$^{15}$ is selected from the group consisting of:

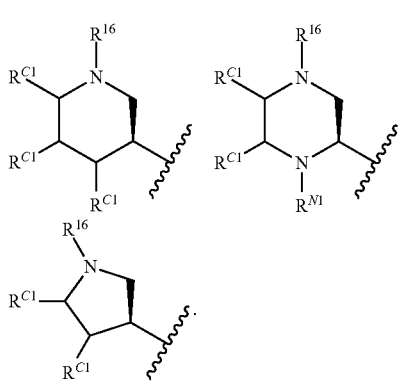

In one embodiment, —R$^{15}$ is selected from the group consisting of:

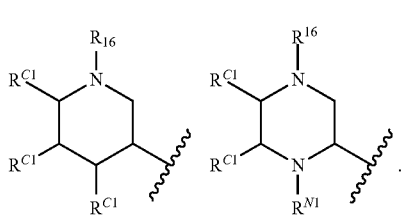

In one embodiment, —R$^{15}$ is selected from the group consisting of:

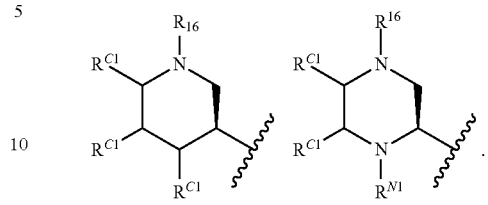

In one embodiment, —R$^{15}$ is selected from the group consisting of:

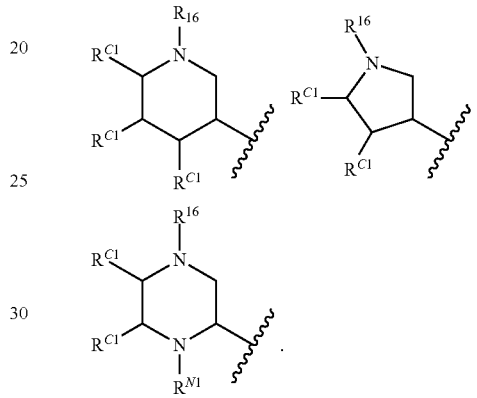

In one embodiment, —R$^{15}$ is selected from the group consisting of:

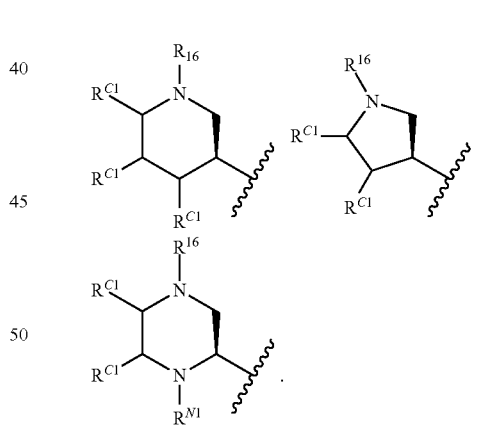

In one embodiment, —R$^{15}$ is selected from the group consisting of:

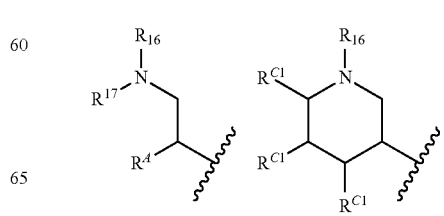

-continued
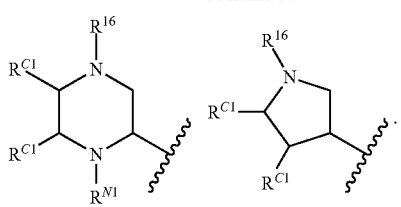
In one embodiment, —$R^{15}$ is selected from the group consisting of:
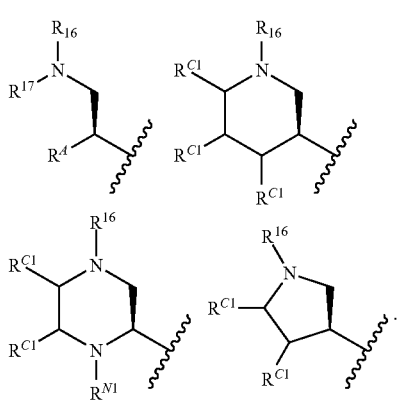
In one embodiment, —$R^{15}$ is:
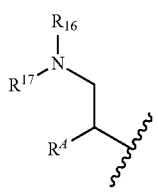
such as
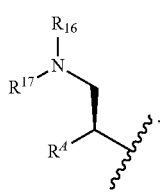
In one embodiment, —$R^{15}$ is:
such as
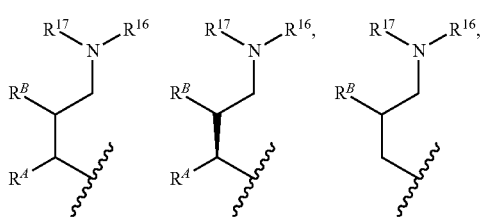
-continued
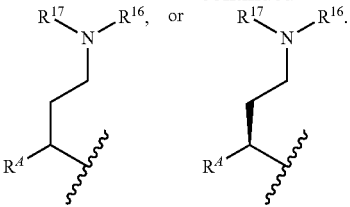
In one embodiment, —$R^{15}$ is:
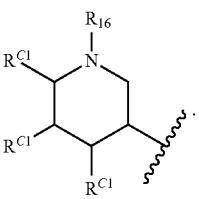
such as,
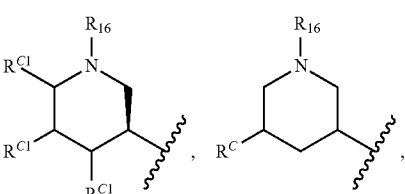
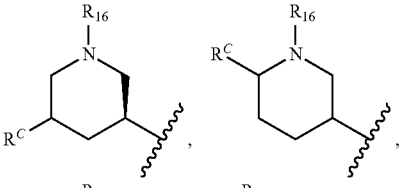
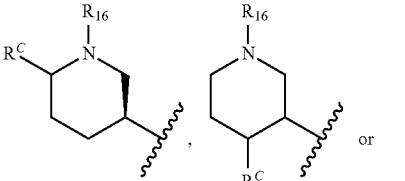
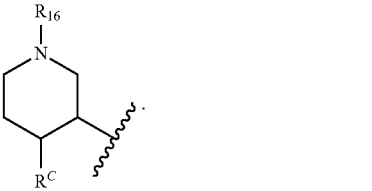
In one embodiment, —$R^{15}$ is:
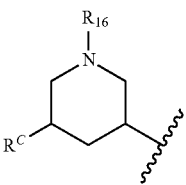

such as

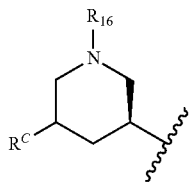

In one embodiment, —R$^{15}$ is:

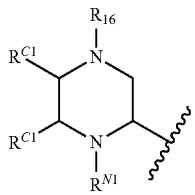

such as

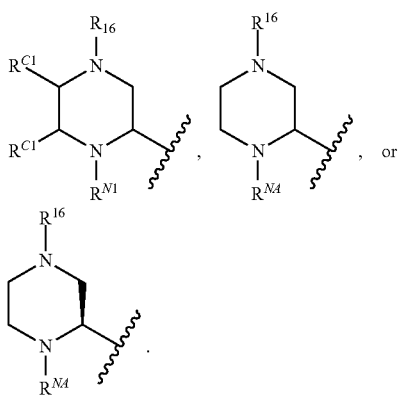

The structures shown above include examples where —R$^{15}$ contains a nitrogen-containing heterocycle. These are compounds where the groups —R$^{17}$ and —R$^A$, together with the carbon atoms to which they are attached, form a nitrogen heterocycle. The nitrogen heterocycles shown above are monocyclic nitrogen heterocycles.

Each carbon ring atom in the group —R$^{17}$ and —R$^A$ may be substituted with —R$^{C1}$. Where —R$^{C1}$ is hydrogen, the carbon ring atom is unsubstituted.

A nitrogen ring atom in the group —R$^{17}$ and —R$^A$, where present, is substituted with —R$^{N1}$.

Where —R$^{N1}$ is hydrogen, the nitrogen ring atom is unsubstituted.

Where the nitrogen-containing heterocycle contains a further nitrogen atom, it is preferred that the further nitrogen atom is substituted with —R$^N$ or —R$^{NA}$, as appropriate. In this embodiment, the ring carbon atoms may be unsubstituted. Where the nitrogen-containing heterocycle does not contain a further nitrogen atom, one of the carbon ring atoms is substituted with —R$^C$ or -L$^B$-R$^{BB}$, and preferably one of the carbon ring atoms group —R$^{17}$ and —R$^A$ is substituted with —R$^C$.

The compounds of the invention also include compounds where —R$^{17}$ and —R$^A$, together with the carbon atoms to which they are attached, form a bicyclic nitrogen heterocycle. In this embodiment, it is not necessary for the carbon or nitrogen ring atoms in —R$^{17}$ and —R$^A$ to be substituted (i.e. each of —R$^C$ and —R$^N$ may be hydrogen).

Additionally or alternatively to the —R$^{15}$ groups shown above, —R$^{15}$ is selected from:

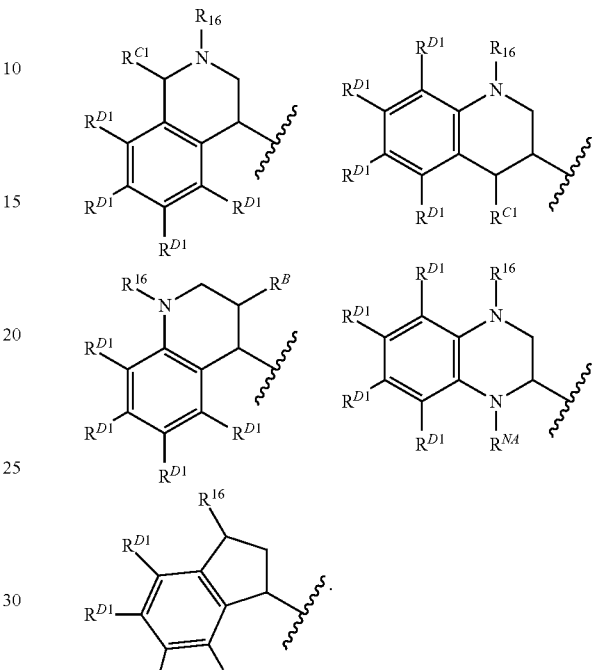

Additionally or alternatively to the —R$^{15}$ groups shown above, —R$^{15}$ is selected from:

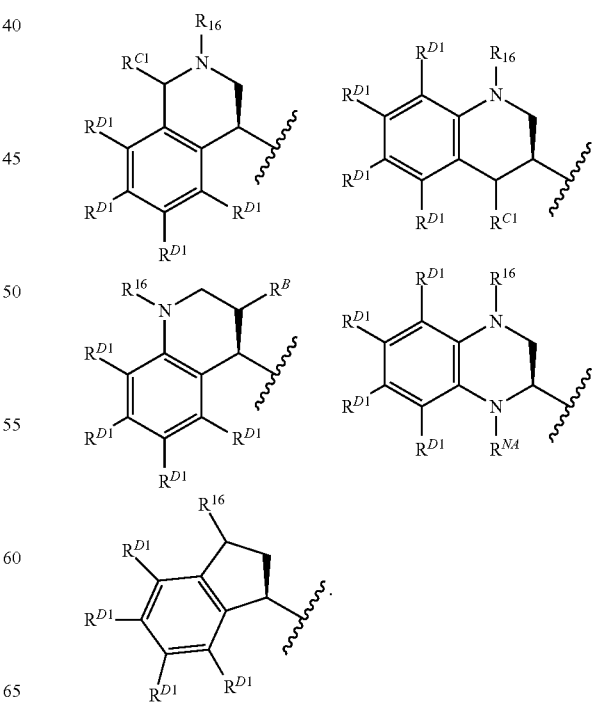

Additionally or alternatively to the —R$^{15}$ groups shown above, in one embodiment —R$^{15}$ is selected from:

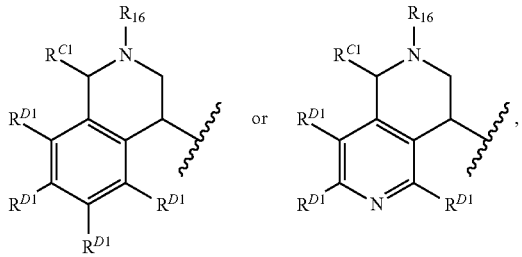

such as

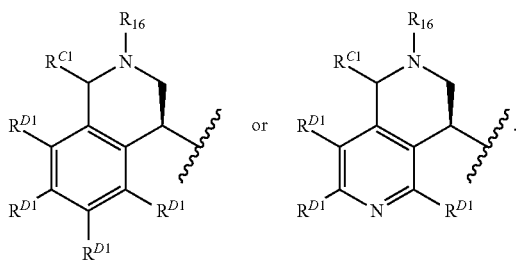

In one embodiment, —R$^A$ and —R$^B$ may together form a carbocycle or a heterocycle. The ring atoms of the carbocycle or heterocycle may be optionally substituted. A carbon ring atom may be optionally mono- or di-substituted with —R$^C$. A nitrogen ring atom, where present, may be optionally substituted with —R$^N$, except that a nitrogen ring atom that is connected to the carbon that is α to the group —X— is optionally substituted with —R$^{NA}$.

In the embodiments below —R$^{C1}$ is hydrogen or —R$^C$; —R$^{N1}$ is hydrogen or —R$^{NA}$; —R$^{D1}$ is hydrogen or —R$^D$; and —R$^{16}$ is independently hydrogen or C$_{1-4}$ alkyl; —R$^{17}$ is independently hydrogen or C$_{1-4}$ alkyl; or —NR$^{16}$R$^{17}$ is a guanidine group. Where the nitrogen-containing carbocycle heterocycle is monocyclic, it is optionally substituted with at least one group selected from —R$^C$, and —R$^{NA}$ and —R$^N$.

Additionally or alternatively to the —R$^{15}$ groups shown above, in one embodiment —R$^{15}$ is selected from:

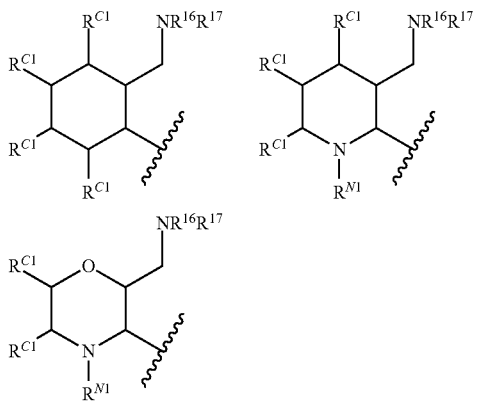

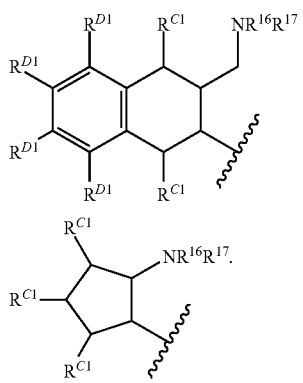

Additionally or alternatively to the —R$^{15}$ groups shown above, in one embodiment —R$^{15}$ is selected from:

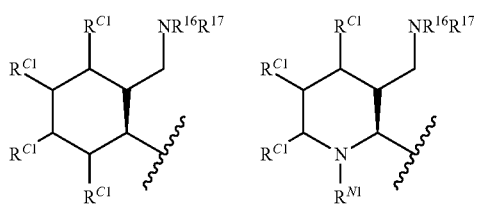

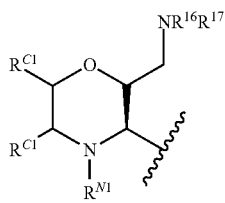

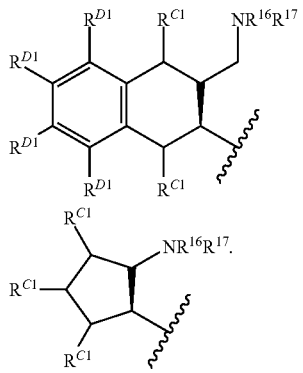

—R$^A$

In one embodiment, —R$^A$ is not hydrogen. In one embodiment, —R$^A$ is -L$^A$-R$^{AA}$. In one embodiment, —R$^A$ is —R$^{AA}$. In these embodiments, —R$^B$, if present, may be hydrogen.

In one embodiment, where —R$^A$ is not hydrogen, for example where —R$^A$ is -L$^A$-R$^{AA}$ or —R$^A$ and —R$^{17}$ together form a nitrogen-containing heterocycle, —R$^{15}$ is an amino-containing group:

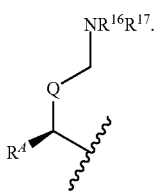

Where —$R^A$ is -$L^A$-$R^{AA}$ it is noted that this group does not encompass a substituent containing the group —C(O)N($R^{11}$)—*, where the asterisk indicates the point of attachment to the carbon that is α to the group —X—. The inventors have found that where the group —C(O)N($R^{11}$)—* is present, biological activity is reduced.

In one embodiment, —$R^A$ and —$R^{17}$ together form a 5- to 10-membered nitrogen-containing monocyclic or bicyclic heterocycle.

In one embodiment, —$R^A$ and —$R^B$ together form a 5- to 10-membered carbocycle or heterocycle. Here, -Q- is not a covalent bond.

In one embodiment, —$R^A$ is not —NHEt or —$NEt_2$, for example where $R^{15}$—X— is an N terminal substituent to Polymyxin B nonapeptide (PMBN).

In one embodiment, —$R^A$ is not —$NHR^{PA}$ or —$N(R^{PA})_2$, where each —$R^{PA}$ is $C_{1-10}$ alkyl, such as $C_{8-10}$ alkyl, such as $C_{1-8}$ alkyl, such as $C_{1-4}$ alkyl, such as $C_{1-2}$ alkyl, for example where $R^{15}$—X— is an N terminal substituent to Polymyxin B nonapeptide (PMBN).

In one embodiment, —$R^A$ is not a group having an oxygen atom attached to the carbon that is α to the group —X—. In one embodiment, —$R^A$ is not a group having a nitrogen atom attached to the carbon that is α to the group —X—. The definitions for the group -$L^A$-$R^{AA}$ may be construed accordingly.

—$R^B$

In one embodiment, —$R^B$, where present, is hydrogen. In one embodiment, -Q- is a covalent bond and —$R^B$ is accordingly absent.

In one embodiment, —$R^B$ is -$L^A$-$R^{BB}$. In one embodiment, —$R^B$ is —$R^{BB}$. In these embodiments, —$R^A$ may be hydrogen.

In one embodiment, —$R^B$ is not $C_{3-10}$ cycloalkyl, for example is not cyclohexyl.

In one embodiment, —$R^B$ and —$R^{17}$ together form a 5- to 10-membered nitrogen-containing monocyclic or bicyclic heterocycle.

In one embodiment, —$R^A$ and —$R^B$ together form a 5- to 10-membered carbocycle or heterocycle. Here, -Q- is not a covalent bond.

Where -Q- is present and is part of a nitrogen-containing heterocycle and —$R^B$ is -$L^A$-$R^{BB}$, the nitrogen-containing heterocycle is optionally substituted. Thus each carbon ring atom in —$R^B$ and —$R^{17}$ is optionally substituted with —$R^C$, and each nitrogen ring atom in —$R^B$ and —$R^{17}$ is optionally substituted with —$R^N$.

In one embodiment one of —$R^A$ and —$R^B$ is hydrogen. The other of —$R^A$ and —$R^B$ is therefore not hydrogen.

It is noted that the group -$L^B$-$R^{BB}$ encompasses a substituent containing the group —C(O)N($R^{11}$)—*, where the asterisk indicates the point of attachment to the carbon that is β to the group —X—.

—$R^C$, —$R^N$ and —$R^{NA}$

The groups —$R^A$ and —$R^{17}$ or —$R^B$ and —$R^{17}$ may together form a 5- to 10-membered nitrogen-containing monocyclic or bicyclic heterocycle, and —$R^A$ and —$R^B$ may together form a 5- to 10-membered monocyclic or bicyclic carbocycle, or together form a 5- to 10-monocyclic or bicyclic heterocycle. The ring atoms that are present in the nitrogen-containing heterocycle and the carbocycle or heterocycle may be substituted or unsubstituted as described herein.

The nitrogen-containing heterocycle includes ring atoms that are part of —$R^A$ and —$R^{17}$ or —$R^B$ and —$R^{17}$. Where —$R^A$ and —$R^{17}$ or —$R^B$ and —$R^{17}$ form a nitrogen-containing monocyclic or bicyclic heterocycle, each carbon ring atom in the group —$R^A$ and —$R^{17}$ or the group —$R^B$ and —$R^{17}$ may be optionally substituted with —$R^C$. These carbon ring atoms may be mono- or di-substituted with —$R^C$. In one embodiment, each carbon ring atom is optionally mono-substituted with —$R^C$.

As described herein a nitrogen-containing monocyclic heterocycle must be substituted. The substituent may be present as a substituent to a ring atom that is part of —$R^A$ and —$R^{17}$ or —$R^B$ and —$R^{17}$. Thus, a group —$R^C$, —$R^N$ or —$R^{NA}$, where appropriate, is present. Alternatively the substituent may be present at the carbon to the group —X— i.e. -$L^B$-$R^{BB}$ is present.

The nitrogen-containing heterocycle may contain further nitrogen ring atoms. Each further nitrogen ring atom may be optionally substituted with —$R^N$, as appropriate. However, where the further nitrogen atom is bonded to the carbon that is α to the group —X—, that ring nitrogen atom is optionally substituted with —$R^{NA}$.

In one embodiment, —$R^A$ and —$R^B$ together form a 5- to 10-membered monocyclic or bicyclic carbocycle or heterocycle. In the monocycle, each ring carbon atom in —$R^A$ and —$R^B$ is optionally mono- or di-substituted with —$R^C$. These carbon ring atoms may be mono- or di-substituted with —$R^C$. In one embodiment, each carbon ring atom is optionally mono- substituted with —$R^C$. In the bicycle, each ring carbon atom in —$R^A$ and —$R^B$ is optionally mono- or di-substituted with —$R^C$. These carbon ring atoms may be mono- or di-substituted with —$R^D$.

A 5- to 10-membered monocyclic or bicyclic heterocycle may contain a nitrogen ring atom. Each nitrogen ring atom may be optionally substituted with —$R^N$, as appropriate. However, where the further nitrogen atom is bonded to the carbon that is α to the group —X—, that ring nitrogen atom is optionally substituted with —$R^{NA}$.

One of the carbon ring atoms that is part of —$R^A$ and —$R^{17}$, —$R^B$ and —$R^{17}$, or —$R^A$ and —$R^B$ may be substituted with oxo (=O). A ring carbon atom that is connected to the nitrogen atom in —N($R^{16}$)— is not substituted with oxo. Where such a carbon ring atom is substituted with oxo it may be joined to a further nitrogen ring atom (where such is present) to from an amide group. It is noted that a further nitrogen atom may be connected to the carbon atom that is α to the group —X—. The inventors understand that where an amide group is present within a nitrogen-containing heterocycle as a substituent to the carbon β to the group —X—, biological activity is not reduced.

In one embodiment, where a ring carbon atom is connected to a further nitrogen ring atom that is connected to the carbon atom that is α to the group —X—, that ring carbon atom is not substituted with oxo.

Similarly, where such a carbon ring atom is substituted with oxo it may be joined to a further oxygen ring atom (where such is present) and an ester group may be formed.

In one embodiment, the nitrogen-containing heterocycle does not include a ring amide, carbamate, urea or ester group.

In one embodiment, a further nitrogen ring atom connected to the carbon that is α to the group —X— is not part of an amide, carbamate or urea group.

In one embodiment, a further oxygen ring atom connected to the carbon that is α to the group —X— is not part of a carbamate or ester group.

Where —$R^{17}$ and —$R^A$ form a monocyclic nitrogen-containing heterocycle, one ring atom (formed together with the carbon atoms α and β to the group —X—) must be substituted. Here the monocyclic nitrogen heterocycle must have a substituent group present on a carbon ring atom or further nitrogen ring atom, where present. Thus at least one group —$R^C$, —$R^N$, —$R^{NA}$ or -$L^B$-$R^{BB}$ must be present as a substituent to the nitrogen-containing heterocycle. In one embodiment, at least one group —$R^C$, —$R^N$ and —$R^{NA}$ must be present as a substituent to the nitrogen-containing heterocycle.

In one embodiment, where —$R^{17}$ and —$R^A$ form a monocyclic nitrogen-containing heterocycle, one or two ring atoms in —$R^{17}$ and —$R^A$ are substituted. The remaining ring atoms in —$R^{17}$ and —$R^A$ are unsubstituted. In one embodiment, one ring atom in —$R^{17}$ and —$R^A$ is substituted.

In one embodiment, where $R^{17}$ and —$R^A$ form a monocyclic nitrogen-containing heterocycle, one carbon ring atom in —$R^{17}$ and —$R^A$ is substituted with —$R^C$, and the remaining ring atom in —$R^{17}$ and —$R^A$ are unsubstituted.

In one embodiment, where $R^{17}$ and —$R^A$ form a monocyclic nitrogen-containing heterocycle, and the heterocycle has a further nitrogen ring atom, the further nitrogen is substituted with —$R^N$ or —$R^{NA}$, as appropriate, and the remaining ring atoms in —$R^{17}$ and —$R^A$ are unsubstituted. In one embodiment, where $R^{17}$ and —$R^A$ form a monocyclic nitrogen-containing heterocycle, and the heterocycle has a further nitrogen ring atom, one carbon ring atom in —$R^{17}$ and —$R^A$ is substituted with —$R^C$, and the remaining ring atoms in —$R^{17}$ and —$R^A$ are unsubstituted.

Where —$R^{17}$ and —$R^B$ form a monocyclic nitrogen heterocycle, the ring atoms in the ring (formed together with the carbon atom β to the group —X—) need not be substituted. If the group —$R^A$ is hydrogen, the monocyclic nitrogen heterocycle must have a substituent group present on a carbon ring atom or further nitrogen ring atom, where present. However, if the group —$R^A$ is not hydrogen, then the carbon ring atoms or further nitrogen ring atom, where present, need not be substituted.

In one embodiment, where —$R^{17}$ and —$R^B$ form a monocyclic nitrogen-containing heterocycle, one or two ring atoms in —$R^{17}$ and —$R^B$ are substituted. The remaining ring atoms in —$R^{17}$ and —$R^B$ are unsubstituted. In one embodiment, one ring atoms in —$R^{17}$ and —$R^B$ is substituted. In these embodiments, —$R^A$ may be hydrogen.

In one embodiment, where $R^{17}$ and —$R^B$ form a monocyclic nitrogen-containing heterocycle, one carbon ring atom in —$R^{17}$ and —$R^B$ is substituted with —$R^C$, and the remaining ring atoms in —$R^{17}$ and —$R^B$ are unsubstituted.

In one embodiment, where $R^{17}$ and —$R^B$ form a monocyclic nitrogen-containing heterocycle, and the heterocycle has a further nitrogen ring atom, the further nitrogen is substituted with —$R^N$, and the remaining ring atoms in —$R^{17}$ and —$R^B$ are unsubstituted.

In one embodiment, where $R^{17}$ and —$R^B$ form a monocyclic nitrogen-containing heterocycle, and the heterocycle has a further nitrogen ring atom, one carbon ring atom in —$R^{17}$ and —$R^B$ is substituted with —$R^C$, and the remaining ring atoms in —$R^{17}$ and —$R^B$ are unsubstituted.

A bicyclic nitrogen-containing heterocycle may be unsubstituted. Here the second fused ring may be regarded as a substituent to the first ring.

In one embodiment, where $R^{17}$ and —$R^A$ form a bicyclic nitrogen-containing heterocycle, one carbon ring atom in —$R^{17}$ and —$R^A$ is substituted with —$R^D$, and the remaining ring atoms in —$R^{17}$ and —$R^A$ are unsubstituted.

In one embodiment, where $R^{17}$ and —$R^A$ form a bicyclic nitrogen-containing heterocycle, and the heterocycle has a further nitrogen ring atom, the further nitrogen is substituted with —$R^N$ or —$R^{NA}$, as appropriate, and the remaining ring atoms in —$R^{17}$ and —$R^A$ are unsubstituted.

In one embodiment, where $R^{17}$ and —$R^A$ form a bicyclic nitrogen-containing heterocycle, and the heterocycle has a further nitrogen ring atom, one carbon ring atom in —$R^{17}$ and —$R^A$ is substituted with —$R^D$, and the remaining ring atoms in —$R^{17}$ and —$R^A$ are unsubstituted.

In one embodiment, a group —$R^D$ is —$R^C$ when it is provided as a substituent on the first ring of a bicyclic nitrogen-containing heterocycle.

—$R^D$

In one embodiment, each —$R^D$ is independently selected from —$R^C$, halo, —OH, and —$NH_2$.

In one embodiment, each —$R^D$ is independently selected from —$R^C$ and halo.

In one embodiment, each —$R^D$ is independently —$R^C$.

In one embodiment, each —$R^D$ is independently -$L^C$-$R^{CC}$.

A bicyclic nitrogen-containing heterocycle contains a first ring and a second ring. The first ring is the nitrogen heterocycle including the carbon atom that is β to the group —X—.

In one embodiment each carbon ring atom in —$R^{17}$ and —$R^A$ that is part of the first ring is optionally mono- or di-substituted with —$R^C$.

The second ring is the ring fused to the first ring. Each carbon ring atom in —$R^{17}$ and —$R^A$ that is part of the second ring is optionally mono- or di-substituted with —$R^D$.

-$L^A$-

The group -$L^A$- may be a covalent bond.

Alternatively -$L^A$- may be a linking group. An asterisk is used to indicate the point of attachment of the group -$L^A$- to —$R^{AA}$. Thus, the remaining attachment point connects to the carbon that is α to the group —X—.

It is noted that -$L^A$- is not a group —N($R^{11}$)C(O)—* where the asterisk is the point of attachment to —$R^{AA}$. The inventors have found that such groups have a poor biological activity, as discussed above.

In one embodiment, the linking group is selected from —$R^L$—*, —O-$L^{AA}$-*, —N($R^{11}$)-$L^{AA}$-*, and —C(O)-$L^{AA}$-*.

In one embodiment, the linking group is selected from —$R^L$—*, —O-$L^{AA}$-*, and —C(O)-$L^{AA}$-*.

In one embodiment, the linking group is selected from —$R^L$—*, —N($R^{11}$)-$L^{AA}$-*, and —C(O)-$L^{AA}$-*.

In one embodiment, the linking group is selected from —$R^L$—* and —C(O)-$L^{AA}$-*.

In one embodiment, the linking group is selected from —$R^L$—*, —O-$L^{AA}$-*, and —N($R^{11}$)-$L^{AA}$-*.

In one embodiment, the linking group is selected from —$R^L$—* and —O-$L^{AA}$-*.

In one embodiment, the linking group is —$R^L$—*.

-$L^B$-

The group -$L^B$- may be a covalent bond.

Alternatively -$L^B$- may be a linking group.

An asterisk is used to indicate the point of attachment of the group -$L^B$- to —$R^{BB}$. Thus, the remaining attachment point connects to the carbon that is β to the group —X— (i.e. the carbon atom in —CH($R^B$)—).

In one embodiment, the linking group is selected from $R^L$—*, —O-$L^{AA}$-*, —OC(O)-$L^{AA}$-*, —N($R^{11}$)-$L^{AA}$-*, —C(O)-$L^{AA}$-*, and —C(O)O-$L^{AA}$-*.

In one embodiment, the linking group is selected from —$R^L$—*, —O-$L^{AA}$-*, —N($R^{11}$)-$L^{AA}$-*, —C(O)-$L^{AA}$-*, —C(O)O-$L^{AA}$-*, and —C(O)N($R^{11}$)-$L^{AA}$-*.

In one embodiment, the linking group is selected from —$R^L$—*, —O-$L^{AA}$-*, —N($R^{11}$)-$L^{AA}$-*, —C(O)-$L^{AA}$-*, and —C(O)O-$L^{AA}$-*.

In one embodiment, the linking group is selected from —$R^L$—*, —O-$L^{AA}$-*, and —N($R^{11}$)-$L^{AA}$-*.

In one embodiment, the linking group is —$R^L$—*.

Additionally or alternatively, the linking group is selected from —N($R^{11}$)S(O)-$L^{AA}$-* and —N($R^{11}$)S(O)$_2$-$L^{AA}$-*.

In one embodiment, the linking group is —N($R^{11}$)S(O)$_2$-$L^{AA}$-*.

In one embodiment, the linking group is —N($R^{11}$)S(O)$_2$—*.

Additionally or alternatively, the linking group is selected from —S(O)N($R^{11}$)-$L^{AA}$-*, and —S(O)$_2$N($R^{11}$)-$L^{AA}$-*.

In one embodiment, the linking group is —S(O)N($R^{11}$)-$L^{AA}$-*.

In one embodiment, the linking group is —S(O)$_2$N($R^{11}$)-$L^{AA}$-*.

-$L^C$-

The group -$L^C$- may be a covalent bond.

Alternatively -$L^C$- may be a linking group.

An asterisk is used to indicate the point of attachment of the group -$L^C$- to —$R^{CC}$. Thus, the remaining attachment point connects to the carbon ring atom.

In one embodiment, the linking group is selected from $R^L$—*, —O-$L^{AA}$-*, —OC(O)-$L^{AA}$-*, —N($R^{11}$)-$L^{AA}$-*, —C(O)-$L^{AA}$-*, and —C(O)O-$L^{AA}$-*.

In one embodiment, the linking group is selected from —$R^L$—*, —O-$L^{AA}$-*, —N($R^{11}$)-$L^{AA}$-*, —C(O)-$L^{AA}$-*, —C(O)O-$L^{AA}$-*, and —C(O)N($R^{11}$)-$L^{AA}$-*.

In one embodiment, the linking group is selected from —$R^L$—*, —O-$L^{AA}$-*, —N($R^{11}$)-$L^{AA}$-*, —C(O)-$L^{AA}$-*, and —C(O)O-$L^{AA}$-*.

In one embodiment, the linking group is selected from —$R^L$—*, —O-$L^{AA}$-*, and —N($R^{11}$)-$L^{AA}$-*.

In one embodiment, the linking group is —$R^L$—*.

Additionally or alternatively, the linking group is selected from —N($R^{11}$)S(O)-$L^{AA}$-* and —N($R^{11}$)S(O)$_2$-$L^{AA}$-*.

In one embodiment, the linking group is —N($R^{11}$)S(O)$_2$-$L^{AA}$-*.

In one embodiment, the linking group is —N($R^{11}$)S(O)$_2$—*.

Additionally or alternatively, the linking group is selected from —S(O)N($R^{11}$)-$L^{AA}$-*, and —S(O)$_2$N($R^{11}$)-$L^{AA}$-*.

In one embodiment, the linking group is —S(O)N($R^{11}$)-$L^{AA}$-*.

In one embodiment, the linking group is —S(O)$_2$N($R^{11}$)-$L^{AA}$-*.

-$L^{AA}$-

In one embodiment, a group -$L^{AA}$- is independently a covalent bond.

In one embodiment, a group -$L^{AA}$- is independently —$R^L$.

-$L^N$-

In one embodiment, a group -$L^N$- is independently a covalent bond.

In one embodiment, a group -$L^N$- is a linking group.

An asterisk is used to indicate the point of attachment of the group -$L^N$- to —$R^{NN}$. Thus, the remaining attachment point connects to the nitrogen ring atom.

The linking group may be independently selected from —S(O)-$L^{AA}$-*, —S(O)$_2$-$L^{AA}$-*, —C(O)-$L^{AA}$-* and —C(O)N($R^{11}$)-$L^{AA}$-*. Thus, the linking groups may together with the nitrogen atom to which they are attached, form sulfinamide, sulfonamide, amide and urea functionality respectively.

In one embodiment, the linking group is independently selected from —S(O)$_2$-$L^{AA}$-*, —C(O)-$L^{AA}$-* and —C(O)N($R^{11}$)-$L^{AA}$-*.

In one embodiment, linking is independently selected from —S(O)$_2$-$L^{AA}$-* and —C(O)N($R^{11}$)-$L^{AA}$-*.

It is noted that the group -$L^N$- is present only as a substituent to a further ring nitrogen atom that is not connected to the carbon that is α to the group —X—. Where a further ring nitrogen atom is connected to the carbon that is α to the group —X—, it is optionally substituted with —$R^L$—$R^{NN}$. The group —$R^L$—$R^{NN}$ does not allow for sulfinamide, sulfonamide, amide and urea groups connected to the carbon that is α to the group —X—. The presence of sulfinamide, sulfonamide, amide and urea functionality is believed to be tolerated at other ring positions.

—$R^L$—

In one embodiment, each —$R^L$— is independently selected from $C_{1-12}$ alkylene, $C_{2-12}$ heteroalkylene, $C_{3-10}$ cycloalkylene and $C_{5-10}$ heterocyclylene.

However, where -$L^{AA}$- is connected to a group $C_{1-12}$ alkyl, —$R^L$— is not $C_{1-12}$ alkylene. In a further embodiment, where -$L^{AA}$- is connected to a group $C_{1-12}$ alkyl, —$R^L$— is not $C_{1-12}$ alkylene and it is not $C_{2-12}$ heteroalkylene.

Where —$R^L$— is a heteroalkylene it may be connected to —$R^{AA}$, —$R^{BB}$, —$R^{CC}$, or —$R^{NN}$ via a heteroatom of the heteroalkylene group, such as N, O or S, where present, or a carbon atom of the heteroalkylene group. The other point of connection is made via a carbon atom of the heteroalkylene group, for example where the heteroalkylene is attached to a carbon atom or a heteroatom, such as N, O or S. The other point of connection may be made via a heteroatom of the heteroalkylene group, for example where the heteroalkylene is attached to a carbon atom. However, it is preferred that the other point of connection is made via a carbon atom of the heteroalkylene group, particularly where —$R^L$— is present in a group -$L^{AA}$-.

Where —$R^L$— is a heterocyclylene it may be connected to —$R^{AA}$, —$R^{BB}$, —$R^{CC}$, or —$R^{NN}$ via a ring nitrogen heteroatom of the heterocyclylene group, where present, or a carbon ring atom of the heterocyclylene group. The other point of connection is made via a ring carbon atom of the heterocyclylene group, for example where the heterocyclylene is attached to a carbon atom or a heteroatom, such as N, O or S. The other point of connection may be made via a ring nitrogen heteroatom of the heterocyclylene group, for example where the heterocyclylene is attached to a carbon atom.

In one embodiment, a group —$R^L$— is independently selected from $C_{1-12}$ alkylene, and $C_{2-12}$ heteroalkylene.

In one embodiment, a group —$R^L$— is independently selected from $C_{1-12}$ alkylene and $C_{3-10}$ cycloalkylene.

In one embodiment, a group —$R^L$— is independently $C_{1-12}$ alkylene.

The group —$R^L$— may be substituted with one or more groups —$R^S$. Thus, each $C_{1-12}$ alkylene, $C_{2-12}$ heteroalkylene, $C_{3-10}$ cycloalkylene and $C_{5-10}$ heterocyclylene is optionally substituted with one or more groups —$R^S$. The specified groups may be unsubstituted or mono-substituted. The group —$R^S$ may be present as a substituent to a carbon atom. A carbon atom may be optionally mono- or di-substituted with —$R^S$.

Where a nitrogen atom is present in a group, such as in a heterocyclylene group or a heteroalkylene group, that nitrogen atom may be optionally substituted with a group —$R^{12}$.

In one embodiment, a group —$R^L$— is unsubstituted.

In one embodiment, a $C_{1-12}$ alkylene group is selected from $C_{1-6}$ alkylene, $C_{1-4}$ alkylene, $C_{2-6}$ alkylene, and $C_{2-4}$ alkylene.

In one embodiment, an alkylene group is linear.

In one embodiment, a $C_{1-12}$ alkylene group is selected from —$CH_2$—, —$CH_2CH_2$—, and —$CH(CH_3)$—.

In one embodiment, a $C_{1-12}$ alkylene group is —$CH_2$—, for example when it is connected to a cycloalkyl, heterocyclyl, or aryl group.

In one embodiment, a $C_{2-12}$ heteroalkylene group is selected from $C_{2-6}$ heteroalkylene, and $C_{2-4}$ heteroalkylene.

In one embodiment, a $C_{2-12}$ heteroalkylene group is selected from —$CH_2O$—*, —$CH_2CH_2O$—*, —$CH_2NH$—*, —$CH_2CH_2NH$—*, —$CH_2N(R^{12})$—*, and —$CH_2CH_2N(R^{12})$—*, where the asterisk indicates the point of attachment to —$R^{AA}$, —$R^{BB}$, —$R^{CC}$, or —$R^{NN}$. Thus, a heteroatom in the heteroalkylene group may be connected to —$R^{AA}$, —$R^{BB}$, —$R^{CC}$, or —$R^{NN}$. The other point of connection may be made via a carbon atom of the heteroalkylene group.

Where an S atom is present in the heteroalkylene group, it may be in the form S, S(O) or $S(O)_2$.

In one embodiment, the $C_{3-10}$ cycloalkylene is selected from cyclopropylene, cyclopentylene and cyclohexylene. In one embodiment, the $C_{3-10}$ cycloalkylene is cyclohexylene.

In one embodiment, the $C_{5-10}$ heterocyclylene is $C_{5-6}$ heterocyclylene.

In one embodiment, the $C_{5-10}$ heterocyclylene is selected from piperidinene, piperazinene, morpholinene and thiomorpholinene. The heterocyclylene may be connected to —$R^{AA}$, —$R^{BB}$, —$R^{CC}$, or —$R^{NN}$ via a ring carbon or ring nitrogen atom. The other point of connection may be made via a carbon atom of the heterocyclylene group.

A nitrogen atom, where present, is optionally substituted with —$R^{12}$.

Where an S atom is present in the heterocyclylene group, it may be in the form S, S(O) or $S(O)_2$.

—$R^{AA}$, —$R^{BB}$, —$R^{CC}$, and —$R^{NN}$

Each of —$R^{AA}$, —$R^{BB}$, —$R^{CC}$, and —$R^{NN}$, where present, is independently selected from $C_{1-12}$ alkyl, $C_{3-10}$ cycloalkyl, $C_{4-10}$ heterocyclyl, and $C_{5-12}$ aryl.

In one embodiment, a $C_{1-12}$ alkyl group is selected from $C_{1-6}$ alkyl, $C_{1-7}$ alkyl, $C_{1-4}$ alkyl, $C_{2-6}$ alkyl, $C_{2-4}$ alkyl, $C_{3-10}$ alkyl, $C_{3-7}$ alkyl, $C_{4-10}$ alkyl and $C_{6-10}$ alkyl.

In one embodiment, an alkyl group is linear.

In one embodiment, an alkyl group is branched.

In one embodiment, the $C_{1-12}$ alkyl group does not include $C_8$ alkyl.

In one embodiment, a $C_{3-10}$ cycloalkyl group is $C_{3-6}$ cycloalkyl or $C_{5-6}$ cycloalkyl.

In one embodiment, a $C_{3-10}$ cycloalkyl group is cyclohexyl.

In one embodiment, a $C_{4-10}$ heterocyclyl group is selected from $C_{5-10}$ heterocyclyl, $C_{6-10}$ heterocyclyl, $C_{5-7}$ heterocyclyl and $C_{5-6}$ heterocyclyl.

In one embodiment, a $C_{4-10}$ heterocyclyl group is selected from tetrahydrofuranyl, pyrrolidinyl, tetrahydropyranyl, morpholinyl, thiomorpholinyl, piperidinyl and piperazinyl.

In one embodiment, a $C_{4-10}$ heterocyclyl group is selected from tetrahydropyranyl, morpholinyl, piperidinyl and piperazinyl.

Where an S atom is present in a heterocyclyl group, it may be in the form S, S(O) or $S(O)_2$.

A nitrogen atom, where present, is optionally substituted with —$R^{12}$.

A heterocyclyl group may be connected via a ring nitrogen heteroatom atom or a ring carbon atom. Where the heterocyclyl group is a substituent to a nitrogen atom (e.g. present in the group —$R^L$—), the heterocyclyl group is connected to that nitrogen atom via a ring carbon atom.

An aryl group, particularly a heteroaryl group such as indole, may be connected via a ring nitrogen heteroatom atom or a ring carbon atom. Where the heteroaryl group is a substituent to a nitrogen atom, the heteroaryl group is connected to that nitrogen atom via a ring carbon atom. Typically, the aryl group is connected via a ring carbon atom.

In one embodiment, the $C_{5-12}$ aryl is selected from $C_{6-12}$ carboaryl and $C_{5-12}$ heteroaryl.

In one embodiment, the $C_{5-12}$ aryl is selected from phenyl, pyridyl, and naphthyl, optionally together with 1,3-benzodioxolyl and pyridonyl.

In one embodiment, the $C_{6-12}$ carboaryl is selected from phenyl, naphthyl, chromanyl, iso-chromanyl and 1,3-benzodioxolyl. The chromanyl, iso-chromanyl and 1,3-benzodioxolyl groups are connected via an aromatic ring carbon atom. Further discussion about the meaning of the term carboaryl is provided below with reference to the group -G.

In one embodiment, the $C_{5-12}$ carboaryl is selected from phenyl and naphthyl, In one embodiment, the $C_{5-12}$ heteroaryl is selected from $C_{5-10}$ heteroaryl and $C_{5-6}$ heteroaryl.

In one embodiment, the $C_{5-12}$ heteroaryl is selected from the group consisting of independently furanyl, thienyl, pyrrolyl, imidazolyl, pyrazolyl, oxazolyl, isoxazolyl, thiazolyl, isothiazolyl, pyridyl, pyrimidinyl, pyrazinyl, pyridazinyl, quinolinyl, isoquinolinyl, indolyl and pyridonyl.

Further discussion about the meaning of the term heteroaryl is provided below with reference to the group -G.

Each $C_{1-12}$ alkyl, $C_{3-10}$ cycloalkyl, $C_{4-10}$ heterocyclyl, and $C_{5-12}$ aryl group is optionally substituted with —$R^S$ at carbon and —$R^{12}$ at nitrogen, where present. Each group may have one, two, three or more groups —$R^S$. In one embodiment, a heterocyclyl group or a heteroaryl group may have one, two, three or more groups —$R^{12}$.

In one embodiment, a group is mono-substituted.

In one embodiment, a group is unsubstituted.

The group —$R^S$ is present as a substituent to a carbon atom. A carbon atom may be optionally mono- or di-substituted with —$R^S$.

Where a nitrogen atom is provided, such as in a heterocyclyl group or a heteroaryl group, that nitrogen may be optionally substituted with a group —$R^{12}$.

In one embodiment, —$R^{AA}$ is independently selected from $C_{1-12}$ alkyl and $C_{5-12}$ aryl.

In one embodiment, —$R^{AA}$ is independently $C_{1-12}$ alkyl. In one embodiment, —$R^{AA}$ is independently $C_{2-12}$ alkyl, such as $C_{3-12}$ alkyl.

In one embodiment, —$R^{AA}$ is independently $C_{5-12}$ aryl.

In one embodiment, —$R^{BB}$ is independently selected from $C_{1-12}$ alkyl, $C_{4-10}$ heterocyclyl, and $C_{5-12}$ aryl, for example when -$L^B$- is a covalent bond, or for example when —$R^A$ is hydrogen.

In one embodiment, —$R^{BB}$ is independently selected from $C_{1-12}$ alkyl, $C_{3-10}$ cycloalkyl, $C_{4-10}$ heterocyclyl, and $C_{5-12}$ aryl, for example when —$R^B$ is a substituent to a heterocycle ring carbon atom.

In one embodiment, —$R^{BB}$ is independently selected from $C_{1-12}$ alkyl and $C_{5-12}$ aryl.

In one embodiment, —$R^{BB}$ is independently $C_{1-12}$ alkyl. In one embodiment, —$R^{BB}$ is independently $C_{2-12}$ alkyl, such as $C_{3-12}$ alkyl.

In one embodiment, —$R^{BB}$ is independently $C_{5-12}$ aryl.

In one embodiment, a group —$R^{NN}$ is independently selected from $C_{1-12}$ alkyl and $C_{5-12}$ aryl.

In one embodiment, —$R^{NN}$ is independently $C_{1-12}$ alkyl. In one embodiment, —$R^{NN}$ is independently $C_{2-12}$ alkyl, such as $C_{3-12}$ alkyl.

In one embodiment, —$R^{NN}$ is independently $C_{5-12}$ aryl.

—$R^S$

The group —$R^S$ is an optional substituent to each $C_{1-12}$ alkyl, $C_{3-10}$ cycloalkyl, $C_{4-10}$ heterocyclyl, $C_{5-12}$ aryl, $C_{1-12}$ alkylene, $C_{2-12}$ heteroalkylene, $C_{3-10}$ cycloalkylene and $C_{5-10}$ heterocyclylene group. Where a group is optionally substituted, it may be optionally substituted with one or more groups —$R^S$. A group may be optionally mono-substituted with —$R^S$.

The group —$R^S$ is an optional substituent to a carbon atom. A carbon atom may be mono-, di- or tri-substituted.

In one embodiment, each —$R^S$, where present, is independently selected from —OH, —$OR^{12}$, halo, —$R^{12}$, —$NHR^{12}$, —$NR^{12}R^{13}$, —$C(O)R^{12}$, —COOH and —$COOR^{12}$.

In one embodiment, each —$R^S$, where present, is independently selected from —$OR^{12}$, halo, —$R^{12}$, —$NHR^{12}$, —$NR^{12}R^{13}$, —$C(O)R^{12}$, —COOH and —$COOR^{12}$.

In one embodiment, each —$R^S$, where present, is independently selected from —$OR^{12}$, halo, and —$R^{12}$.

Where —$R^S$ is a substituent to an alkyl group, —$R^S$ is not —$R^{12}$.

Where —$R^S$ is halo it may be selected from fluoro, chloro, bromo and iodo, such as chloro and bromo, such as chloro.

In one embodiment, where a carbon atom is di-substituted with —$R^S$, these groups may together with the carbon to which they are attached form a $C_{3-6}$ carbocycle or a $C_{5-6}$ heterocycle, where the carbocycle and the heterocycle are optionally substituted with one or more groups —$R^{12}$. Where an S atom is present in the heterocycle group, it may be in the form S, S(O) or $S(O)_2$.

In one embodiment, a $C_{3-6}$ carbocycle is cyclopentane or cyclohexane, such as cyclohexane.

In one embodiment, a $C_{5-6}$ heterocycle is selected from piperidine, piperazine, morpholine, thiomorpholine, tetrahydrofuran and tetrahydropyran.

—$R^{12}$ and —$R^{13}$

Each —$R^{12}$ and —$R^{13}$ is independently $C_{1-6}$ alkyl, $C_{1-6}$ haloalkyl, phenyl or benzyl.

Where —$R^{12}$ and —$R^{13}$ are both attached to N, they may together with the N atom form a 5- or 6-membered heterocycle, such as pyrrolidine, piperazine, piperidine, thiomorpholine or morpholine. The heterocyclic ring is optionally substituted with $C_{1-6}$ alkyl, $C_{1-6}$ haloalkyl, phenyl or benzyl.

In one embodiment, a —$R^{12}$ or —$R^{13}$ group is independently $C_{1-6}$ alkyl, phenyl or benzyl.

In one embodiment, a —$R^{12}$ or —$R^{13}$ group is independently $C_{1-6}$ alkyl.

In one embodiment, the $C_{1-6}$ alkyl is selected from methyl and ethyl.

In one embodiment, the $C_{1-6}$ haloalkyl is —$CF_3$.

—$R^{11}$

In one embodiment, a group —$R^{11}$ is independently selected from hydrogen, methyl and ethyl.

In one embodiment, —$R^{11}$ is independently hydrogen.

Embodiments Relating to Compounds (I) and (II) from WO 2014/188178

The compounds of the present case may use a group —$R^5$ from compounds (I) and (II) of WO 2014/188178 as a group —$R^T$.

—X— and —$R^5$

The compounds of formula (I) do not encompass the deacylated versions of Polymyxin B (Deacylpolymyxin B-DAPB), D, E (Deacylcolistin-DAC) or M, or Circulin A. The compounds of formula (I) do not encompass the nonapeptide versions of Polymyxin B (PMBN), D, E or M, or Circulin A.

In one embodiment, —X— and —$R^5$ together are not an α-amino acid residue, for example when -A- is a covalent bond. An α-amino acid residue is a group where —X— is —C(O)— and —$R^5$ has a group —$NR^6R^7$ (such as —$NH_2$) as a substituent to the carbon atom that is α to the group —X—.

In one embodiment, —X— and —$R^5$ together are not Thr, Ser, α,γ-diaminobutyric acid (Dab) or α,β-diaminopropionic acid (Dap) residues.

In one embodiment, for example where the core of the compound of formula (I) is Polymyxin B, X and $R^5$ together are not Lys, Arg, Dap, Ser, Phe, Trp, Leu or Ala residues.

In one embodiment, —X— and —$R^5$ together are not Lys, Arg, Dap, Ser, Phe, Trp, Leu, Ala α,γ-diaminobutyric acid (Dab) or α,β-diaminopropionic acid (Dap) residues.

In one embodiment, —X— and —$R^5$ together are not Ala, Ser, Thr, Val, Leu, Ile, Pro, Phe, Tyr, Trp, His, Lys or Arg residues.

In one embodiment, —X— and —$R^5$ together are not Ala, Ser, Thr, Val, Leu, Ile, Pro, Phe, Tyr, Trp, His, Lys, Arg, α,γ-diaminobutyric acid (Dab) or α,β-diaminopropionic acid (Dap) residues.

In one embodiment, —X— and —$R^5$ together are not an α-amino acid, for example a D or L α-amino acid, for example a L α-amino acid.

In one embodiment, —$R^5$ is not diaminophenyl, for example, 3,5-diaminophenyl when —X— is —C(O)—.

—$R^5$

In one embodiment, —$R^5$ is G-$L^2$-$L^1$-.

—$R^5$ may be G-$L^1$-, for example where -$L^2$- is a covalent bond.

—$R^5$ may be G-$L^2$-, for example where -$L^1$- is a covalent bond.

—$R^5$ may be -G, for example where -$L^1$- and -$L^2$- are covalent bonds.

In one embodiment, —$R^5$ is D-$L^1$-.

—$R^5$ may be -D, for example where -$L^1$- is a covalent bond.

In one embodiment, —$R^5$ has one, two or three hydroxyl and/or —$NR^6R^7$ groups. These groups may be provided on any group within —$R^5$, including -G, -D, -$L^1$- and -$L^2$-. In one embodiment, these groups are provided as substituents to -G, -D, and -$L^1$-.

It is noted that the hydroxyl and —$NR^6R^7$ groups are optionally substituents to the group D-$L^1$-.

Where the hydroxyl and —$NR^6R^7$ substituents are discussed below, they may be referred to as substituents to —$R^5$.

In one embodiment, the one, two or three hydroxyl and/or —$NR^6R^7$ groups are optional substituents to —$R^5$. This may be the case where -$L^1$- is a nitrogen-containing $C_{2-12}$ heteroalkylene, and/or -$L^2$- is a nitrogen-containing $C_{4-10}$ heterocyclylene, and/or -D is a nitrogen-containing $C_{4-10}$ heterocyclyl.

In one embodiment, —$R^5$ has at least 5, at least 6, at least 7 or at least 8 carbon atoms present.

In one embodiment, —$R^5$ has 1, 2, or 3 nitrogen atoms present. In one embodiment, the nitrogen atom is a basic nitrogen atom. The nitrogen atom may be present as NH.

In one embodiment, —$R^5$ has 1, 2, or 3 oxygen atoms present.

In one embodiment, —$R^5$ is not aminocyclohexyl, for example when -A- is a covalent bond, —X— is —C(O)— and —$R^1$, —$R^2$ and —$R^3$ are amino acid residues of polymyxin B.

Okimura et al. describe Polymyxin B nonapeptide compounds having aminocyclohexyl groups at the N terminal. These compounds are not described for use in combination with an active agent, In one embodiment, —$R^5$ is not an aminocyclohexyl group selected from the groups consisting of cis-2-aminocylcohexyl, trans-2-aminocylcohexyl, cis-3-aminocyclohexyl, cis-4-aminocylcohexyl, and trans-4-aminocylcohexyl. Additionally or alternatively, —$R^5$ is not trans-3-aminocylcohexyl.

Linker: -$L^2$-$L^1$- and -$L^1$-

Within the groups G-$L^2$-$L^1$- and D-$L^1$-, -$L^2$-$L^1$- and -$L^1$- may be regarded as linkers connecting the group —X— to -G or -D. The linker may be absent, for example where -$L^1$- and -$L^2$- are covalent bonds.

-$L^2$-$L^1$- in G-$L^2$-$L^1$-

In one embodiment, -$L^1$- and -$L^2$- are both covalent bonds. Thus, the group -G is connected directly to —X—. Here, the hydroxyl or amino groups (such as one, two or three hydroxyl and/or —$NR^6R^7$ groups) must be present on -G.

Where -$L^1$- is a nitrogen-containing $C_{2-12}$ heteroalkylene and/or -$L^2$- is a nitrogen-containing $C_{4-10}$ heterocyclylene, it is not necessary for G-$L^2$-$L^1$- to be substituted with one, two or three hydroxyl and/or —$NR^6R^7$ groups.

-$L^1$- in D-$L^1$-

In one embodiment, -$L^1$- is a covalent bond. Thus, the group -D is connected directly to —X—.

Where the group D-$L^1$- is substituted with a hydroxyl group or an amino group (such as one, two or three hydroxyl and/or —$NR^6R^7$ groups), the groups must be present on -D.

Where -$L^1$- is a nitrogen-containing $C_{2-12}$ heteroalkylene and/or -D is a nitrogen-containing $C_{4-10}$ heterocyclyl it is not necessary for D-$L^1$- to be substituted with one, two or three hydroxyl and/or —$NR^6R^7$ groups.

-$L^1$-

In one embodiment, -$L^1$- is a covalent bond or a $C_{1-12}$ alkylene group.

In one embodiment, -$L^1$- is a covalent bond.

In one embodiment, -$L^1$- is a $C_{1-12}$ alkylene group or a $C_{2-12}$ heteroalkylene group.

In one embodiment, -$L^1$- is a $C_{1-12}$ alkylene group.

In one embodiment, -$L^1$- is $C_{1-12}$ alkylene, for example $C_{1-6}$, $C_{1-4}$ or $C_{1-2}$ alkylene.

In one embodiment, -$L^1$- is —$CH_2$— or —$CH_2CH_2$—.

In one embodiment, -$L^1$- is $C_{2-12}$ alkylene, for example $C_{2-6}$ or $C_{2-4}$ alkylene.

In one embodiment, -$L^1$- is $C_{3-12}$ alkylene, for example $C_{3-6}$, $C_{4-12}$, $C_{5-12}$ or $C_{6-12}$ alkylene.

The alkylene group is a saturated, aliphatic alkylene group.

The alkylene group may be a linear or a branched alkylene group. In one embodiment, the alkylene group is linear.

Where -$L^1$- is an alkylene group and $R^5$ is substituted with one, two or three hydroxyl and/or —$NR^6R^7$ groups, one or more of the substituents may be substituents to the alkylene group.

In one embodiment, the alkylene group has one, two or three substituents.

In one embodiment, the alkylene group has one or two substituents, such as one substituent.

In one embodiment, the number of substituents on the alkylene group is no greater than the number of carbon atoms in the alkylene group. Thus, where -$L^1$- is a $C_2$ alkylene group it may be substituted with no more than two substituents.

Additional substituents, where present, may be located on -G or -D, where appropriate.

In one embodiment, the alkylene group is unsubstituted.

In one embodiment, -$L^1$- is $C_{2-12}$ heteroalkylene. A heteroalkylene group is an alkylene group where one or more, such as two or three, or more, of the carbon atoms is replaced with a heteroatom selected from N, O and S. The superscript e.g. 4 in $C_4$ refers to the total number of carbon atoms and heteroatoms. The heteroatom of the heteroalkylene group is understood not to be a pendant amino, hydroxyl or thiol group.

In one embodiment, the heteroalkylene group contains one or two heteroatoms, for example one or two nitrogen atoms, such as one or two —NH—.

In one embodiment, heteroalkylene group is a nitrogen-containing heteroalkylene group.

The heteroatom may be provided as an interruption of the alkylene chain e.g. —$CH_2$—NH—$CH_2$—.

The heteroatom may be provided as a terminal group for connection to —X—, -$L^2$-, -G or -D, for example —$CH_2$—$CH_2$—NH— or —NH—$CH_2$—$CH_2$—. In these embodiments, the heteroatom is bonded to a carbon atom in —X—, -$L^2$-, -G or -D.

In one embodiment, the heteroatom of the heteroalkylene group is not covalently bonded to the group —X—.

In one embodiment, the heteroatom of the heteroalkylene group is not covalently bonded to the group -$L^2$-, -G or -D, where present. In an alternative embodiment, a heteroatom of the heteroalkylene group, such as —NH—, is covalently bonded to the group -$L^2$-, -G or -D, where present.

In one embodiment, -$L^1$- is $C_{2-12}$ heteroalkylene, for example $C_{2-6}$, $C_{2-4}$, $C_{3-6}$, $C_{3-12}$, $C_{4-6}$ or $C_{4-12}$ heteroalkylene.

The heteroalkylene group is a saturated, aliphatic heteroalkylene group.

The heteroalkylene group may be a linear or a branched heteroalkylene group. In one embodiment, the heteroalkylene group is linear.

In one embodiment, -$L^1$- is —NH—$CH_2CH_2$—NH—$CH_2$—.

In one embodiment, -$L^1$- is —$CH_2$—NH—$CH_2CH_2$—.

In one embodiment, the heteroalkylene group is unsubstituted.

In one embodiment, the heteroalkylene group is substituted, for example with one or two hydroxyl and/or —$NR^6R^7$ groups, such as one hydroxyl or —$NR^6R^7$ group. The substituents are provided on the carbon atoms within the heteroalkylene group In one embodiment, the number of substituents on the heteroalkylene group is no greater than the number of carbon atoms in the heteroalkylene group.

Where the heteroalkylene group is substituted, the substituents are preferably not provided on a carbon atom that is covalently bonded to a heteroatom of the heteroalkylene group.

Where the heteroalkylene group is substituted, the substituents may be provided on a carbon atom that is not bonded to a heteroatom.

-L²-

In one embodiment, -L²- is a covalent bond.

In one embodiment, -L²- is a $C_{4-10}$ heterocyclylene group, for example when -L¹- is a $C_{1-12}$ alkylene group.

In one embodiment, -L²- is a $C_{4-7}$ heterocyclylene group, for example a $C_{5-7}$ or $C_{5-6}$ heterocyclylene group.

In one embodiment, the $C_{4-10}$ heterocyclylene contains one or two heteroatoms selected from N, S and O. Where a S atom is present, it may be in the form S, S(O) or $S(O)_2$. Where an N atom is present it may be in the form NH or NR, where —R is $C_{1-4}$ alkyl, such as methyl or ethyl.

In one embodiment, the heterocyclylene group is a nitrogen-containing heterocyclylene.

The heterocyclylene group may contain one or two nitrogen atoms. Each nitrogen atom may be optionally substituted with $C_{1-4}$ alkyl, where appropriate. In one embodiment the heterocyclylene group contains only nitrogen heteroatoms.

In one embodiment, the heterocyclylene group is unsubstituted. Thus, the hydroxyl and/or —$NR^6R^7$ groups are provided elsewhere, as required, for example on -L¹-, where present, or on -G or -D.

In one embodiment, the heterocyclylene is connected to -L¹- or —X— via a carbon atom or nitrogen atom, where present, of the heterocyclylene ring.

In one embodiment, the heterocyclylene is connected to -G via a carbon atom or nitrogen atom, where present, of heterocyclylene ring.

In one embodiment, -L²- is selected from piperidinylene, piperazinylene and pyrroldinylene.

In one embodiment, -L²- is selected from piperidinyl-1,4-ene, piperazinyl-1,4-ene and pyrroldinyl-1,3-ene.

Location of Hydroxyl and —$NR^6R^7$ Substituents

In one embodiment, a group —$R^5$, such as G-L²-L¹- or D-L¹-, may be substituted with one, two or three hydroxyl groups.

In one embodiment, —$R^5$ is substituted with one hydroxyl group.

In one embodiment, a group —$R^5$ may be substituted with one, two or three groups —$NR^6R^7$.

In one embodiment, —$R^5$ is substituted with one —$NR^6R^7$ group.

In one embodiment, —$R^5$ is substituted with two or three groups —$NR^6R^7$.

In one embodiment, a group —$R^5$ may be substituted with one or two groups —$NR^6R^7$, and one, two or three hydroxyl groups.

In one embodiment, —$R^5$ is substituted with one —$NR^6R^7$ group and one hydroxyl group.

In one embodiment, a hydroxyl group, such as one, two or three hydroxyl groups, are substituents to -G.

In one embodiment, a hydroxyl group, such as one, two or three hydroxyl groups, are substituents to -D.

In one embodiment, a hydroxyl group, such as one, two or three hydroxyl groups, are substituents to -L¹-, where appropriate, for example where -L¹- is alkylene or heteroalkylene.

In one embodiment, a hydroxyl group, such as one, two or three hydroxyl groups, are substituents to -L²-, where appropriate, for example where -L²- is heterocyclylene.

In one embodiment, a —$NR^6R^7$ group, such as one, two or three —$NR^6R^7$ groups, are substituents to -G.

In one embodiment, a —$NR^6R^7$ group, such as one, two or three —$NR^6R^7$ groups, are substituents to -D.

In one embodiment, a —$NR^6R^7$ group, such as one, two or three —$NR^6R^7$ groups, are substituents to -L¹-, where appropriate, for example where -L¹- is alkylene or heteroalkylene.

In one embodiment, a —$NR^6R^7$ group, such as one, two or three —$NR^6R^7$ groups, are substituents to -L²-, where appropriate, for example where -L²- is heterocyclylene.

In one embodiment, G-L²-L¹- is optionally substituted with (i), (ii) and (iii), for instance where L¹- is a nitrogen-containing $C_{2-12}$ heteroalkylene and/or -L²- is a nitrogen-containing $C_{4-10}$ heterocyclylene. In one embodiment, the proviso does not apply, therefore that (i), (ii) and (iii) are not optional substituents.

In one embodiment, G-L²-L¹- is substituted with:
(i) one or two hydroxyl groups, or
(ii) one or two groups —$NR^6R^7$, or
(iii) one group —$NR^6R^7$ and one hydroxyl groups,
with the proviso that (i), (ii) and (iii) are optional substituents when -L¹- is a nitrogen-containing $C_{2-12}$ heteroalkylene and/or -L²- is a nitrogen-containing $C_{4-10}$ heterocyclylene.

For the avoidance of doubt, where a group —$R^5$ is said to be substituted with one hydroxyl group (—OH), no further hydroxyl groups are present within —$R^5$. Likewise, where a group —$R^5$ is said to be substituted with one group —$NR^6R^7$, no further groups —$NR^6R^7$ are present within —$R^5$. Similarly, where —$R^5$ has two or three hydroxyl or —$NR^6R^7$ groups, the total number of hydroxyl or —$NR^6R^7$ groups is two or three.

As described herein, where a group —$NR^6R^7$ is present, it is preferred that it is not a substituent at a carbon atom a to the group —X—.

As described in further detail below, where a hydroxyl group is present, it is preferred that it is a substituent at a carbon atom a to the group —X—.

In one embodiment, where —$R^5$ has more than one substituent, the substituents are not located on the same carbon atom.

A carboxylic group (—COOH) is not to be construed as a hydroxyl group in the present case.

Where -L¹- has more than two carbon atoms present (e.g. $C_{2-12}$ alkylene or $C_{3-12}$ heteroalkylene) a substituent, where present, may be provided at a carbon atom that is α to the group —X—.

Similarly, where -L¹- and -L²- are both covalent bonds, and -G is $C_{2-12}$ alkyl, the group $C_{2-12}$ alkyl may have a substituent at a carbon atom that is α to the group —X—.

In one embodiment, -L¹- is substituted with a hydroxyl group (for example one, two or three hydroxyl groups) and the hydroxyl group is provided at the carbon atom that is α to the group —X—. Examples of compounds having such a substitution include Example compound 27 in the present case. The present inventors have found that compounds having a hydroxyl group at the α carbon have a particularly improved potentiating activity compared to those compounds where the hydroxyl group is connected, for example, to a carbon atom that is not α the group —X—, for example β or γ to the group —X—, such as Example compound 25.

Similarly, where -L¹- and -L²- are both covalent bonds, and -G is $C_{2-12}$ alkyl, the group $C_{2-12}$ alkyl may have a hydroxyl group provided at a carbon atom that is α to the group —X—.

Where -L¹- has more than two carbon atoms present (e.g. $C_{2-12}$ alkylene or $C_{3-12}$ heteroalkylene) a substituent, where present, may be provided at a carbon atom that is not α to the group X. For example, the substituent may be provided at a carbon atom that is β or γ to the group —X—. In one embodiment, no substituent is provided at the carbon atom α to the group —X—.

Similarly, where -$L^1$- and -$L^2$- are both covalent bonds, and -G is $C_{2-12}$ alkyl, the group $C_{2-12}$ alkyl may have a substituent that is not provided at a carbon atom that is α to the group —X—. For example, the substituent may be provided at a carbon atom that is β or γ to the group —X—.

In one embodiment, -$L^1$- is substituted with an amino group (for example one or two amino groups) and the amino group (i.e. —$NR^6R^7$) is provided at a carbon atom that is not α to the group X. Examples of compounds having such a substitution include Example compound 10 in the present case. The present inventors have found that compounds having an amino group at the α carbon, such as Example compound 40, have particularly reduced potentiating activity compared to those compounds where the amino group is connected, for example, to a carbon atom that is γ or γ to the group —X—.

Similarly, where -$L^1$- and -$L^2$- are both covalent bonds, and -G is $C_{2-12}$ alkyl, the group $C_{2-12}$ alkyl may have an amino group provided at a carbon atom that is not α to the group —X—, for example β or γ to the group —X—.

In one embodiment, an amino or hydroxyl substituent is provided at a terminal carbon of the group -$L^1$- (e.g. $C_{2-12}$ alkylene or $C_{2-12}$ heteroalkylene) or the terminal carbon of the —$C_{2-12}$ alkyl, where present.

In one embodiment, the group -$L^1$- in D-$L^1$- is a covalent bond. Thus -D, which is a $C_{4-10}$ heterocyclyl, is connected directly to the group —X—.

In one embodiment, the group -$L^2$- is a $C_{4-10}$ heterocyclyl. Where -$L^1$- is a covalent bond, -$L^2$- is connected directly to the group —X—.

The connection of either these heterocyclyl groups to —X— is discussed below.

In one embodiment, an atom that is α to the group —X— may be a ring carbon atom of the heterocyclyl group. A ring heteroatom of the heterocyclyl group may be covalently bonded to the ring carbon atom that is α to the group —X— i.e. the ring heteroatom is β to the group —X—. In one embodiment, a ring heteroatom β to the group X is O or S, such as O. In one embodiment the ring heteroatom β to the group —X— is not N.

In one embodiment, a ring heteroatom γ to the group X is O, S or N.

In one embodiment, where -$L^1$- and -$L^2$- are both covalent bonds, and -G is a $C_{5-12}$ heteroaryl, the heteroaryl may be connected to the group —X— via a ring carbon atom, which is α to the group —X—). In one embodiment, a ring heteroatom, such as N, is not connected to the carbon atom which is α to the group —X—. Alternatively, a ring heteroatom, such as O or S, is connected to the carbon atom which is α to the group —X—.

In one embodiment, the group G-$L^2$-$L^1$- has one, two or three hydroxyl group and/or —$NR^6R^7$ substituents. These substituents may be provided on one or more of the groups -G-, -$L^2$- or -$L^1$-, where appropriate. In one embodiment, the substituents are provided on -G- and/or -$L^1$-. Where -$L^1$- is $C_{2-12}$ heteroalkylene, the one, two or three hydroxyl group and/or —$NR^6R^7$ substituents are optional.

The group D-$L^1$- optionally has one, two or three hydroxyl group and/or —$NR^6R^7$ substituents.

Where the substituents are present they may be provided on -D or -$L^1$-, where appropriate.

In one embodiment, —$R^5$ is G-$L^2$-$L^1$-, where -G is $C_{5-12}$ aryl.

In one embodiment, —$R^5$ is G-$L^2$-$L^1$-, where -G is $C_{3-10}$ cycloalkyl or —$C_{2-12}$ alkyl, or —$R^5$ is D-$L^1$-, where D is $C_{4-10}$ heterocyclyl.

In one embodiment, G-$L^2$-$L^1$- is substituted with (i) one, two or three hydroxyl groups, (ii) one, two or three groups —$NR^6R^7$, or (iii) one or two groups —$NR^6R^7$, and one, two or three hydroxyl groups. Where an aryl group is present in G-$L^2$-$L^1$- it is independently optionally substituted one or more substituents selected from —$C_{1-4}$ alkyl, halo, —CN, —$NO_2$, —$CF_3$, —$NR^{10}C(O)R^{10}$, —$CON(R^{10})_2$, —$COOR^9$, —$OCOR^{10}$, —$NR^{10}COOR^{10}$, —$OCON(R^{10})_2$, —$OCF_3$, —$NR^{10}CON(R^{10})_2$, —$OR^9$, —$SR^9$, —$NR^{10}SO_2R^{10}$, —$SO_2N(R^{10})_2$ and —$SO_2R^{10}$ where each —$R^9$ is independently —$C_{1-4}$ alkyl and each —$R^{10}$ is independently —H or —$C_{1-4}$ alkyl.

In one embodiment, D-$L^1$- is optionally substituted with (i) one, two or three hydroxyl groups, (ii) one, two or three groups —$NR^6R^7$, or (iii) one, two or three groups —$NR^6R^7$, and one, two or three hydroxyl groups.

In one embodiment, D-$L^1$- is substituted with (i) one, two or three hydroxyl groups, (ii) one, two or three groups —$NR^6R^7$, or (iii) one, two or three groups —$NR^6R^7$, and one, two or three hydroxyl groups.

The groups $C_{3-10}$ cycloalkyl $C_{2-12}$ alkyl and $C_{4-10}$ heterocyclyl may be substituted with hydroxyl and/or —$NR^6R^7$ groups. Where the cycloalkyl or heterocyclyl groups include a fused aromatic ring, that aromatic ring may be optionally substituted with the optional substituents described herein. The optional further substituents do not include hydroxyl and/or —$NR^6R^7$ groups.

The group $C_{5-12}$ aryl is substituted with hydroxyl and/or —$NR^6R^7$ groups and the $C_{5-12}$ aryl group is optionally further substituted. The optional further substituents do not include hydroxyl and/or —$NR^6R^7$ groups.

It is not essential for the $C_{3-10}$ cycloalkyl, $C_{2-12}$ alkyl, $C_{5-12}$ aryl and $C_{4-10}$ heterocyclyl groups of -G and -D to be substituted with hydroxyl and/or —$NR^6R^7$ groups. In one embodiment, the hydroxyl and/or —$NR^6R^7$ groups may be provided on the linker elements of —$R^5$ e.g. -$L^1$- and/or -$L^2$-, where present.

Where —$R^5$ contains a heterocyclyl or heteroalkylene group, for example as part of -$L^1$-, -$L^2$- or -D, such as nitrogen-containing heterocyclyl or heteroalkylene groups, the hydroxyl and/or —$NR^6R^7$ groups may be optional.

In one embodiment, G-$L^2$-$L^1$- is substituted with:
(i) one, two or three hydroxyl groups, or
(ii) one, two or three groups —$NR^6R^7$, or
(iii) one or two groups —$NR^6R^7$, and one, two or three hydroxyl groups,
with the proviso that (i), (ii) and (iii) are optional substituents when -$L^1$- is a nitrogen-containing $C_{2-12}$ heteroalkylene and/or -$L^2$- is a nitrogen-containing $C_{4-10}$ heterocyclyl.

In one embodiment, G-$L^2$-$L^1$- is substituted with:
(i) one, two or three hydroxyl groups, or
(ii) one, two or three groups —$NR^6R^7$, or
(iii) one or two groups —$NR^6R^7$, and one, two or three hydroxyl groups.

-D

The N terminal substituent of the polymyxin compound may include a $C_{4-10}$ heterocyclyl group ("heterocyclyl group"). Thus, in one embodiment, —$R^5$ includes the group -D, which is a $C_{4-10}$ heterocyclyl.

In one embodiment, -D is a nitrogen-containing heterocyclyl group. In such embodiments the hydroxyl and —$NR^6R^7$ groups are optional.

Where a heterocyclyl group does not contain a nitrogen atom, either or both of -D and -$L^1$-must be substituted with one, two or three hydroxyl and/or —$NR^6R^7$ groups or -$L^1$- must be a nitrogen-containing $C_{2-12}$ heteroalkylene.

In one embodiment, $C_{4-10}$ heterocyclyl is $C_{4-6}$ or $C_{5-6}$ heterocyclyl, such as $C_5$ heterocyclyl or $C_6$ heterocyclyl.

In one embodiment, the $C_{4-10}$ heterocyclyl contains one or two heteroatoms selected from N, S and O. Where a S atom is present, it may be in the form S, S(O) or S(O)$_2$. Where an N atom is present it may be in the form NH or NR, where R is $C_{1-4}$ alkyl, such as methyl or ethyl.

In one embodiment, the heterocyclyl group is a nitrogen-containing heterocyclyl group.

In one embodiment, the $C_{4-10}$ heterocyclyl is piperidinyl, piperazinyl, morpholinyl, dioxanyl, thiomorpholinyl (including oxidised thiomorpholinyl), or pyrroldinyl.

In one embodiment, the $C_{4-10}$ heterocyclyl is piperidinyl, piperazinyl, thiomorpholinyl (including oxidised thiomorpholinyl), pyrroldinyl or morpholinyl.

In one embodiment, the $C_{4-10}$ heterocyclyl is piperidinyl, piperazinyl or pyrroldinyl.

Where a heterocyclyl is present it is connected to -$L^1$- or —X— via a ring carbon atom or a ring N atom, where present. In one embodiment, the heterocyclyl is connected via a ring carbon atom. In another embodiment, the heterocyclyl is connected via a ring nitrogen atom, where present.

Where a heterocyclyl is substituted with one, two or three hydroxyl and/or —$NR^6R^7$ groups, these groups are substituents to the heterocyclyl ring carbon atoms.

In one embodiment, a hydroxyl or —$NR^6R^7$ group, where present, is a substituent to a ring carbon atom that is β to a ring heteroatom.

In one embodiment, the heterocyclyl, if substituted, has a maximum of one or two substituents, which may be the same or different.

In one embodiment, the total number of carbon atoms in the heterocyclyl group, together with the total number of carbon atoms present in —$R^6$ and —$R^7$ (where present) is at least 5, at least 6, at least 7 or at least 8.

For the avoidance of doubt, the index "$C_{x-y}$" in terms such as "$C_{4-7}$ heterocyclyl", and the like, refers to the number of ring atoms, which may be carbon atoms or heteroatoms (e.g., N, O, S). For example, piperidinyl is an example of a $C_6$heterocycyl group.

The term "heterocyclyl" in reference to the group -D refers to a group (1) which has one or more heteroatoms (e.g., N, O, S) forming part of a ring system, wherein the ring system comprises one ring or two or more fused rings, wherein at least one ring of the ring system is a non-aromatic ring, and (2) which is attached to the rest of the molecule by a non-aromatic ring atom (i.e., a ring atom that is part of a non-aromatic ring that is part of the ring system). For example: piperidino and piperidin-4-yl are both examples of a $C_6$heterocycyl group; 2,3-dihydro-1H-indol-1-yl is an example of a $C_9$heterocycyl group; and both decahydro-quinolin-5-yl and 1,2,3,4-tetrahydroquinolin-4-yl are examples of a $C_{10}$heterocyclyl group.

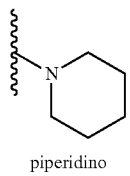
piperidino

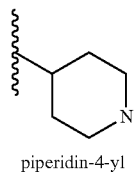
piperidin-4-yl

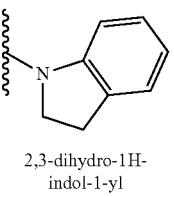
2,3-dihydro-1H-indol-1-yl

-continued

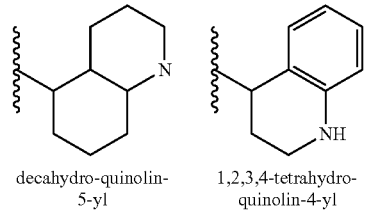

decahydro-quinolin-5-yl 1,2,3,4-tetrahydro-quinolin-4-yl

The optional substituents are those described as optional substituents for the $C_{5-12}$ aryl group.

In one embodiment, where a heterocyclyl group contains two or more fused rings, each ring is non-aromatic.

In one embodiment, the heterocyclyl group comprises one ring.

-G

The group -G is selected from $C_{3-10}$ cycloalkyl, $C_{2-12}$ alkyl and $C_{5-12}$ aryl. A description of each of these is given below. The groups discussed below may be used together with any -$L^1$- and -$L^2$-, as appropriate.

$C_{3-10}$ cycloalkyl

The N terminal substituent of the polymyxin compound may include a $C_{3-10}$ cycloalkyl group ("cycloalkyl group"). Thus, -G may be $C_{3-10}$ cycloalkyl.

When -G is $C_{3-10}$ cycloalkyl, -$L^1$- may be a covalent bond, $C_{1-12}$ alkylene or $C_{2-10}$ heteroalkylene, for example a covalent bond or $C_{1-12}$ alkylene.

When -G is $C_{3-10}$ cycloalkyl, -$L^2$- may be a covalent bond or $C_{4-12}$ heterocyclyl, for example a covalent bond.

In one embodiment, $C_{3-10}$ cycloalkyl is a $C_{3-8}$ or $C_{3-6}$ cycloalkyl.

In one embodiment, $C_{3-10}$ cycloalkyl is cyclopentyl or cyclohexyl.

In one embodiment, the cycloalkyl, if substituted, has a maximum of one or two substituents, which may be the same or different.

In one embodiment, the number of substituents on the cycloalkyl group is no greater than the number of carbon atoms in the cycloalkyl group. Thus, where the alkyl group is a $C_6$ alkyl group it may be substituted with no more than six substituents.

In one embodiment, the total number of carbon atoms in the cycloalkyl group, together with the total number of carbon atoms present in —$R^6$ and —$R^7$ (where present) is at least 5, at least 6, at least 7 or at least 8.

In one embodiment, the cycloalkyl is cyclohexyl having a single hydroxyl or —$NR^6R^7$ group, such as a 4-substituted cyclohexyl group. In one embodiment, the cycloalkyl is cyclopentyl having a single hydroxyl or —$NR^6R^7$ group, such as a 2- or 3-substituted cyclopentyl group.

In one embodiment, the cycloalkyl is unsubstituted. In this embodiment, the substituents are located on the linker -$L^2$-$L^1$-, which accordingly cannot be a covalent bond.

In one embodiment, for example where the core of the compound of formula (I) is Polymyxin B, the group G-$L^2$-$L^1$- is not 2-aminocyclohexyl, 3-aminocyclohexyl or 4-aminocyclohexyl.

For the avoidance of doubt, "cycloalkyl" refers to a group (1) which has a ring system comprising one ring or two or more fused rings, wherein one ring of the fused ring system may be an aromatic ring, and (2) which is attached to the rest of the molecule by a non-aromatic ring atom (i.e., a ring atom that is part of a non-aromatic ring that is part of the ring system). For example: cyclohexyl is an example of a $C_6$ cycloalkyl group; and tetralin-2-yl is an example of a $C_{10}$ cycloalkyl group.

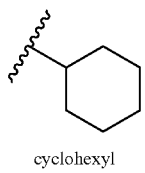 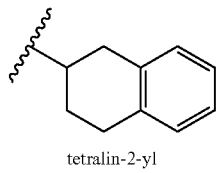

cyclohexyl     tetralin-2-yl

Where an aromatic ring is present, it may be optionally substituted. The optional substituents are those described as optional substituents for the $C_{5-12}$ aryl group.

In one embodiment, where the cycloalkyl comprises two or more fused rings, each ring is non-aromatic.

In one embodiment, the cycloalkyl group comprises one ring.

$C_{2-12}$ Alkyl

The N terminal substituent of the polymyxin compound may be a $C_{2-12}$ alkyl group ("alkyl group"). Thus, -G may be $C_{2-12}$ alkyl.

When -G is $C_{2-12}$ alkyl, $-L^1-$ may be a covalent bond or $C_{2-10}$ heteroalkylene, such as a covalent bond.

When -G is $C_{2-12}$ alkyl, $-L^2-$ may be a covalent bond or $C_{4-12}$ heterocyclyl, for example a covalent bond.

In one embodiment, where -G is $C_{2-12}$ alkyl, both $-L^2-$ and $-L^1-$ are covalent bonds. Thus, -G is connected directly to —X—.

In one embodiment, $C_{2-12}$ alkyl is $C_{3-12}$ alkyl, for example $C_{4-12}$ or $C_{6-12}$ alkyl.

In one embodiment, $C_{2-12}$ alkyl is $C_{2-6}$ alkyl, for example $C_{2-4}$ alkyl.

The alkyl group is a saturated, aliphatic alkyl group. The alkyl group may be a linear or a branched alkyl group.

In one embodiment, the alkyl group is branched and the branch is not at the carbon atom that is α to the group $-L^2-$, $-L^1-$, or —X—.

In one embodiment, the number of substituents on the alkyl group is no greater than the number of carbon atoms in the alkyl group. Thus, where the alkyl group is a $C_2$ alkyl group it may be substituted with no more than two substituents.

In one embodiment, the total number of carbon atoms in the alkyl group, together with the total number of carbon atoms present in $—R^6$ and $—R^7$ (where present) is at least 5, at least 6, at least 7 or at least 8.

In one embodiment, the alkyl group has a substituent at the terminal carbon. Terminal carbon refers to a carbon atom that would be a —CH$_3$ if it bore no substituents. In a branched alkyl group this carbon may be the carbon atom that is at the terminal of the longest linear portion of the alkyl group.

In one embodiment, the alkyl group has a substituent that is located at a carbon atom that is β or γ the terminal carbon atom.

As noted above, in one embodiment, a $—NR^6R^7$ group, where present as a substituent to the alkyl group, is a substituent to a carbon atom that is not α to the group $-L^2-$, $-L^1-$, or —X—.

As noted above, in one embodiment, a hydroxyl group, where present as a substituent to the alkyl group, is a substituent to the carbon atom a to the group $-L^2-$, $-L^1-$, or —X—.

In one embodiment, the alkyl group has no substituent at the carbon atom a to the group $-L^2-$, $-L^1-$, or —X—.

In one embodiment, the alkyl, if substituted, has a maximum of one or two substituents, which may be the same or different.

In alternative aspects of the present invention, the N terminal substituent of the polymyxin compound is a $C_{1-12}$ alkyl group. In one embodiment, $—R^5$ is $C_{1-12}$ alkyl group, such as $C_1$ alkyl. Where $—R^5$ is $C_1$ alkyl, one substituent is present, such as one $—NR^6R^7$ group.

$C_{5-12}$ Aryl

The N terminal substituent of the polymyxin compound may include or be a $C_{5-12}$ aryl group ("a group"). Thus, -G may be $C_{5-12}$ aryl.

When -G is $C_{5-12}$ aryl, $-L^1-$ may be a covalent bond, $C_{1-12}$ alkylene or $C_{2-10}$ heteroalkylene, for example a covalent bond or $C_{1-12}$ alkylene.

When -G is $C_{5-12}$ aryl, $-L^2-$ may be a covalent bond or $C_{4-12}$ heterocyclyl, for example a covalent bond.

The aryl group is optionally substituted, with these substituents being in addition to any hydroxyl or $—NR^6R^7$ groups.

In one embodiment, $C_{5-12}$ aryl is $C_{5-7}$ aryl

In one embodiment, $C_{5-12}$ aryl is $C_{6-10}$ carboaryl or $C_{5-12}$ heteroaryl.

In one embodiment, $C_{5-12}$ aryl is $C_{6-10}$ carboaryl.

In one embodiment, $C_{6-10}$ carboaryl is phenyl or napthyl.

In one embodiment, $C_{6-10}$ carboaryl is phenyl.

In one embodiment, $C_{5-12}$ aryl is $C_{5-12}$ heteroaryl, for example $C_{5-10}$, $C_{5-6}$, $C_5$ or $C_6$ heteroaryl.

The heteroaryl may contain one or two nitrogen atoms and additionally or alternatively, where the heteroaryl is a $C_5$ heteroaryl, it may contain an oxygen or sulfur atom In one embodiment, $C_{5-12}$ heteroaryl is independently furanyl, thienyl, pyrrolyl, imidazolyl, pyrazolyl, oxazolyl, isoxazolyl, thiazolyl, isothiazolyl, pyridyl, pyrimidinyl, pyrazinyl, pyridazinyl, quinolinyl, isoquinolinyl or indole. Additionally or alternatively, the $C_{5-12}$ heteroaryl is independently pyridone.

Where a heteroaryl is present in group -G it is connected to $-L^1-$, $-L^2-$ or —X— via a ring carbon atom or a ring N atom, where present. In one embodiment, the heteroaryl is connected via a ring carbon atom. In another embodiment, the heteroaryl is connected via a ring nitrogen atom, where present.

In one embodiment, $C_{5-12}$ aryl is phenyl or pyridine.

For the avoidance of doubt, "heteroaryl" refers to a group (1) which has one or more heteroatoms (e.g., N, O, S) forming part of a ring system, wherein the ring system comprises one ring or two or more fused rings, wherein at least one ring of the ring system is an aromatic ring, and (2) which is attached to the rest of the molecule by an aromatic ring atom (i.e., a ring atom that is part of an aromatic ring that is part of the ring system). For example: pyridyl is an example of a $C_6$ heteroaryl group; isoquinolyl is an example of a $C_{10}$ heteroaryl group; and 1,2,3,4-tetrahydro-isoquinoline-7-yl is an example of a $C_{10}$ heteroaryl group.

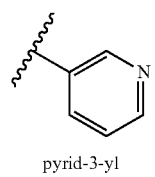 

pyrid-3-yl     isoquinolin-7-yl

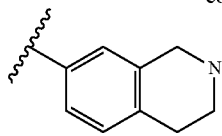

1,2,3,4-tetrahydro-isoquinolin-7-yl

Where a non-aromatic ring is provided, it has no optional substituents (though it may be provided with one or more hydroxyl or —NR$^6$R$^7$ groups).

In one embodiment, where a heteroaryl comprises two or more fused rings, each ring is an aromatic ring.

In one embodiment, the heteroaryl group comprises one aromatic ring.

A heteroaryl group may also include a pyridonyl group, which may be regarded as a structure corresponding to a pyridinyl group having a 2- or 4- hydroxyl substituent.

Similarly, "carboaryl" refers to a group (1) which has a ring system comprising one ring or two or more fused rings, wherein at least one ring of the ring system is an aromatic ring, and (2) which is attached to the rest of the molecule by an aromatic ring atom (i.e., a ring atom that is part of an aromatic ring that is part of the ring system). For example: phenyl is an example of a C$_6$ carboaryl group; and tetralin-6-yl is an example of a C$_{10}$ carboaryl group.

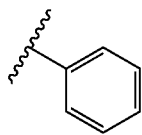 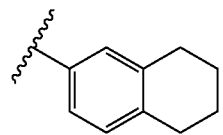

phenyl    tetralin-6-yl

In one embodiment, where a carboaryl comprises two or more fused rings, each ring is an aromatic ring.

Where a non-aromatic ring is present, that ring may be a carbocycle (such as shown above for tetralin), or the ring may be a heterocycle, as shown below for the group dihydrobenzo[b][1,4]dioxin-6-yl.

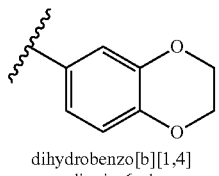

dihydrobenzo[b][1,4]dioxin-6-yl

In one embodiment, C$_{6-12}$ aryl is not diaminophenyl, such as 3,5-diaminophenyl, for example when —X— is —C(O)— and when -L$^1$- and -L$^2$- and are both covalent bonds.

In one embodiment, C$_{5-12}$ aryl is not trihydroxyphenyl, such as 3,4,5-trihydroxyphenyl, for example when —X— is —C(O)—.

It is noted that Sandow et al. describe Polymyxin octapeptides having a modified N terminal. The N terminal group contains a phenyl group that is optionally substituted by 1, 2 or 3 identical or different groups selected from hydroxyl, alkoxy, amino, carboxyl, alkylamino and halogen.

The phenyl group may be linked to the N terminal via an alkylene pacer and/or an imino oxime group. Alternatively, the N terminal group contains a 2-aminothiazol-4-yl group.

The worked examples in Sandow et al. are limited to octapeptides having a 2-aminothiazol-4-yl group, a benzyl group or a 3,4,5-trihydroxyphenyl group. There are no examples where a nonapeptide or decapeptide are used, and there are no examples where the N terminal group contains amino functionality.

It is noted that WO 2012/168820 describes Polymyxin decapeptides having a modified N terminal. The publication suggests that the N terminal group could include aryl, aralkyl, heteroaryl and heteroaralkyl functionality, amongst other options. Aryl and heteroaryl groups may be linked to another aryl or heteroaryl group, amongst other options. The linker may be a bond, —(CH$_2$)$_n$—, —(CH$_2$)$_n$—O—(CH$_2$)$_p$—, —(CH$_2$)$_n$—S—(CH$_2$)$_p$—, or —(CH$_2$)$_n$—NR$^3$—(CH$_2$)$_p$—, where n is 0, 1, 2 or 3; and p is 0, 1, 2 or 3; and R$^3$ is H or CH$_3$.

The worked examples in WO 2012/168820 are limited to compounds where one aryl or heteroaryl group is linked directly to another aryl or heteroaryl group. There are no examples where a linker is present.

Aryl Group Substituents

The group —R$^5$ may include an aryl group, for example where -G is C$_{5-12}$ aryl or C$_{3-10}$ cycloalkyl contains a fused aromatic ring, or where -D is C$_{4-10}$ heterocyclyl containing a fused aromatic ring.

Each aryl group is optionally substituted with one or more substituents.

Where the aryl group is optionally substituted, there may be one, two or three optional substituents.

Where a heteroaryl group is substituted, the substituents may be provided on a ring carbon atom, for example an aromatic ring carbon atom.

Each optional substituent is selected from the list consisting of —C$_{1-4}$ alkyl, halo, —CN, —NO$_2$, —CF$_3$, —NR$^{10}$C(O)R$^{10}$, —CON(R$^{10}$)$_2$, —COORS, —OCOR$^{10}$, —NR$^{10}$COOR$^{10}$, —OCON(R$^{10}$)$_2$, —OCF$_3$, —NR$^{10}$CON(R$^{10}$)$_2$, —OR$^9$, —SR$^9$, —NR$^{10}$SO$_2$R$^{10}$, —SO$_2$N(R$^{10}$)$_2$ and —SO$_2$R$^{10}$ where each —R$^9$ is independently —C$_{1-4}$ alkyl and each —R$^{10}$ is independently —H or —C$_{1-4}$ alkyl In one embodiment, each optional substituent is independently selected from —C$_{1-4}$ alkyl, halo, —NR$^{10}$C(O)R$^{10}$, —CON(R$^{10}$)$_2$, —COOR$^9$, —OCOR$^{10}$, —NR$^{10}$COOR$^{10}$, —OCON(R$^{10}$)$_2$, —OCF$_3$, —NR$^{10}$CON(R$^{10}$)$_2$, —OR$^9$, and —SR$^9$, where each —R$^9$ is independently —C$_{1-4}$ alkyl and each —R$^{10}$ is independently —H or —C$_{1-4}$ alkyl.

In one embodiment, each optional substituent is independently selected from —C$_{1-4}$ alkyl and halo.

In one embodiment, a halo group is —F, —Cl or —Br.

In one embodiment, where a nitrogen atom is provided in an aromatic ring, it may be optionally substituted with —R$^9$ or —R$^{10}$, where appropriate.

The optional substituents may include a C$_{1-4}$ alkyl group, e.g. —R$^9$ or —R$^{10}$, either alone or as part of a larger substituent group. It is noted that each C$_{1-4}$ alkyl group present may be substituted with the one, two or three hydroxyl and/or —NR$^6$R$^7$ groups.

In one embodiment, —R$^9$ or —R$^{10}$ are not substituted with a hydroxyl or —NR$^6$R$^7$ group.

—R$^6$ and —R$^7$

In one embodiment, each —R$^6$ and —R$^7$, where present, is H.

In one embodiment, —R$^6$ is H and —R$^7$ is alkyl, such as methyl or ethyl, such as methyl.

In one embodiment, —R⁶ is methyl or ethyl, such as methyl.

Where -G is an aryl or cycloalkyl group, —R⁶ and —R⁷ may together with the nitrogen atom form a heterocycle, for example $C_{4-10}$ heterocyclyl.

In one embodiment, the $C_{4-10}$ heterocyclyl contains one or two heteroatoms selected from N, S and O. Where a S atom is present, it may be in the form S, S(O) or S(O)₂. Where an N atom is present it me be in the form NH or NR, where R is $C_{1-4}$ alkyl, such as methyl or ethyl.

In one embodiment, the $C_{4-10}$ heterocyclyl is piperidinyl, piperazinyl, morpholinyl, dioxanyl, thiomorpholinyl (including oxidised thiomorpholinyl), or pyrroldinyl.

In one embodiment, the $C_{4-10}$ heterocyclyl is piperidinyl, piperazinyl, thiomorpholinyl (including oxidised thiomorpholinyl), pyrroldinyl or morpholinyl.

In one embodiment, the $C_{4-10}$ heterocyclyl is piperidinyl, piperazinyl or pyrroldinyl.

In one embodiment, one group —NR⁷R⁸, where present, is a guanidine group, such as —NHC(NH)NH₂.

—R⁹

In one embodiment, —R⁹ is methyl or ethyl.
In one embodiment, —R⁹ is methyl.
—R¹⁰
In one embodiment, —R¹⁰ is —H.
In one embodiment, —R¹⁰ is methyl or ethyl.
In one embodiment, —R¹⁰ is methyl.

REFERENCES

All documents mentioned in this specification are incorporated herein by reference in their entirety.

de Visser et al, *J. Peptide Res*, 61, 2003, 298-306
Dewitt et al. *Org. Biomol. Chem.* 2011, 9, 1846
GB 1421020.7
GCC 2012/22819
Ghose et al. *J. Phys. Chem. A*, 1998, 102, 3762-3772
Handbook of Pharmaceutical Excipients, 5th edition, 2005
Katsuma et al. Chem. Pharm. Bull. 2009; 57, 332-336
Petrosillo et al. Clin. Microbiol. Infect. 2008; 14, 816-827
Quale et al. *Microb. Drug Resist.* 2012; 18, 132-136
Remington's Pharmaceutical Sciences, 18th edition, Mack Publishing Company, Easton, Pa., 1990
Sato et al. Chem. Pharm. Bull. 2011; 59, 597-602
Telkov et al. *ACS Chemical Biology* 2014, 9, 1172
TW 101142961
U.S. Pat. No. 8,415,307
Vaara et al, *Antimicrob. Agents and Chemotherapy*, 52, 2008. 3229-3236
Vaara et al. Microbiol. Rev. 1992; 56, 395-411
Velkov et al. *ACS Chemical Biology*, 2014, 9, 1172
WO 1988/00950
WO 2008/017734
WO 2010/075416
WO 2012/168820
WO 2013/072695
WO 2014/188178
WO 2015/135976
Yamada et al, *J. Peptide Res.* 64, 2004, 43-50
Yousef et al., Antimicrob. Agents Chemother. 2011, 55, 4044-4049

The invention claimed is:

1. A compound of formula (I):

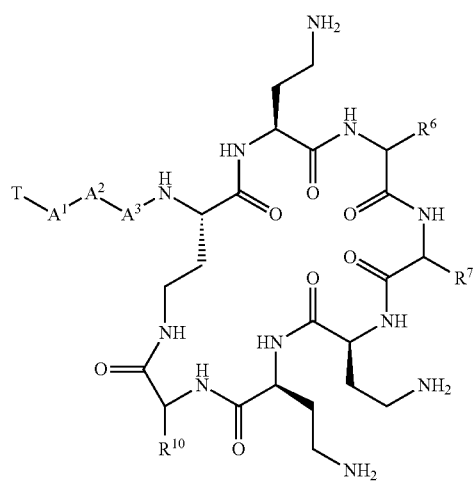

wherein:
-T is $R^T$-X-;
-A1- is absent
-A2- is an amino acid residue selected from threonine and serine;
-A3- is an amino acid residue represented by:

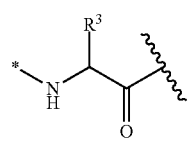

where the asterisk is the point of attachment to -A2-, and —R3 is $C_{1-6}$ alkyl, having one amino or one hydroxyl substituent;
—X— is —C(O)—, —NHC(O), —OC(O)—, —CH₂— or —SO₂—;
—$R^T$ is an amino-containing group:

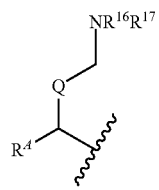

where:
—$R^A$ is hydrogen;
-Q- is —CH($R^B$)—;
—$R^B$ is -$L^B$-$R^{BB}$;
—R¹⁶ is independently hydrogen or $C_{1-4}$ alkyl;
—R¹⁷ is independently hydrogen or $C_{1-4}$ alkyl;
or —NR16R17 is a guanidine group;
or, —R17 and —$R^B$ together form a 5-to 10-membered nitrogen-containing monocyclic or bicyclic heterocycle;
where —R¹⁷ and —$R^B$ together form a monocyclic nitrogen-containing heterocycle, each ring carbon atom in the monocyclic nitrogen-containing heterocycle formed by —$R^{17}$ and —$R^B$ is optionally mono- or di-substituted with —$R^C$, and the monocyclic heterocycle is substituted with at least one group selected from —$R^C$ and —$R^N$, and the monocyclic nitrogen-containing heterocycle optionally contains one further nitrogen, oxygen or sulfur ring atom, and where a further nitrogen ring atom is present it is optionally substituted with -$R^N$, with the exception of a further nitrogen ring atom that is connected to the carbon that is α to the group —X—, which nitrogen ring atom is optionally substituted with —$R^{NA}$;

where —$R^{17}$ and —$R^B$ together form a bicyclic nitrogen-containing heterocycle, each ring carbon atom in the bicyclic nitrogen-containing heterocycle formed by —$R^{17}$ and —$R^B$ is optionally mono-or di-substituted with —$R^D$;

and the bicyclic nitrogen-containing heterocycle optionally contains one, two or three further heteroatoms, where each heteroatom is independently selected from the group consisting of nitrogen, oxygen and sulfur, and where further nitrogen ring atoms are present, each further nitrogen ring atom is optionally substituted with —$R^N$, with the exception of a nitrogen ring atom that is connected to the carbon that is α to the group —X—, which nitrogen ring atom is optionally substituted with —$R^{NA}$;

and where —$R^{17}$ and —$R^B$ together form a 5-to 10-membered nitrogen-containing monocyclic or bicyclic heterocycle, and a carbon ring atom in the 5-to 10-membered nitrogen-containing monocyclic or bicyclic heterocycle formed by —R17 and -$R^B$ is optionally substituted with oxo (=O);

each —$R^C$ is independently -LC-RCC;

each —$R^D$ is independently selected from —$R^C$, halogen, —$NO_2$, —OH, and —$NH^2$;

each —RN is independently -$L^N$-$R^{NN}$;

each —RNA is independently -$R^L$-$R^{NN}$ or -$R^{NN}$;

—$R^{BB}$, and each —$R^{CC}$ and —$R^{NN}$ where present, is independently selected from $C_{1-12}$ alkyl, $C_{3-10}$ cycloalkyl, $C_{4-10}$ heterocyclyl, and $C_{5-12}$ aryl;

each -$L^B$-and -$L^C$- is independently a covalent bond or a linking group selected from —$R^L$-*, —O-$L^{AA}$-*, —OC(O)-$L^{AA}$-*, —N($R^{11}$)-$L^{AA}$-*, —N($R^{11}$) C(O)-$L^{AA}$-*, —C(O)-$L^{AA}$-*, —C(O)O-$L^{AA}$-*, and —C(O)N($R^{11}$)-$L^{AA}$-*, and optionally further selected from —N ($R^{11}$) S(O)-$L^{AA}$-*, —N($R^{11}$)S(O)$_2$-$L^{AA}$-*, —S(O)N($R^{11}$)-$L^{AA}$-*, and —S(O)$_2$N($R^{11}$)-$L^{AA}$-* where the asterisk indicates the point of attachment of the group -$L^B$- to —$R^{BB}$ or the group -$L^C$- to —$R^{CC}$;

each -$L^N$- is independently a covalent bond or a group selected from —S(O)-$L^{AA}$-*, —S(O)$_2$-$L^{AA}$-*, —C(O)-$L^{AA}$-* and —C(O)N($R^{11}$)-$L^{AA}$*, where the asterisk indicates the point of attachment of the group -$L^N$-to —$R^{NN}$;

and each-LAA- is independently a covalent bond or-RL-;

and each-RL-is independently selected from $C_{1-12}$ alkylene, $C_{2-12}$ heteroalkylene, $C_{3-10}$cycloalkylene and $C_{5-10}$heterocyclylene, and where -$L^{AA}$-is connected to a group $C_{1-12}$alkyl,-RL-is not $C_{1-12}$alkylene;

and each $C_{1-12}$alkyl, $C_{3-10}$cycloalkyl, $C_{4-10}$heterocyclyl, $C_{5-12}$aryl, $C_{1-12}$alkylene, $C_{2-12}$heteroalkylene, $C_{3-10}$cycloalkylene and $C_{5-10}$heterocyclylene group is optionally substituted with —$R^S$ and —$R^{12}$, where —$R^S$ is an optional substituent to carbon and —$R^{12}$ is an optional substituent to nitrogen;

each —$R^S$ is independently selected from —OH, —$OR^{12}$, —$OC(O)R^{12}$, halogen, —$R^{12}$, —$NHR^{12}$, —$NR^{12}R^{13}$, —$NHC(O)R^{12}$, —$N(R^{12})C(O)R^{12}$, —SH, —$SR^{12}$, —C(O) $R^{12}$, —COOH, —C (O)$OR^{12}$, —$C(O)NH_2$, —$C(O)NHR^{12}$ and —$C(O)NR^{12}R^{13}$; except that —$R^{12}$ is not a substituent to a C1-12 alkyl group; or where a carbon atom is di-substituted with-RS, these groups may together with the carbon to which they are attached form a $C_{3-6}$ carbocycle or a $C_{5-6}$ heterocycle, where the carbocycle and the heterocycle are optionally substituted with one or more groups -$R^{12}$;

each —$R^{12}$ is independently $C_{1-6}$ alkyl, $C_{1-6}$ haloalkyl, phenyl or benzyl;

each —$R^{13}$ is independently $C^{1-6}$ alkyl, $C_{1-6}$ haloalkyl, phenyl or benzyl;

or —$R^{12}$ and -$R^{13}$, where attached to N, may together form a 5-or 6-membered heterocyclic ring, which is optionally substituted with $C_{1-6}$ alkyl, $C_{1-6}$ haloalkyl, phenyl or benzyl;

each —R11 is independently hydrogen or $C_1$-4 alkyl;

—$R^6$ together with the carbonyl group and nitrogen alpha to the carbon to which it is attached is an amino acid residue;

—$R^7$ together with the carbonyl group and nitrogen alpha to the carbon to which it is attached is an amino acid residue;

and —$R^6$ together with the carbonyl group and nitrogen alpha to the carbon to which it is attached is not a phenylalanine, leucine or valine residue and/or —$R^7$ together with the carbonyl group and nitrogen alpha to the carbon to which it is attached is not a leucine, isoleucine, phenylalanine, threonine, valine or norvaline residue;

—$R^{10}$ together with the carbonyl group and nitrogen alpha to the carbon to which it is attached, is a threonine or leucine residue;

or a salt, protected form, and/or prodrug form thereof.

2. The compound of claim 1, or a salt thereof, wherein —$R^6$ together with the carbonyl group and nitrogen alpha to the carbon to which it is attached is not a phenylalanine, leucine or valine residue.

3. The compound of claim 2, or a salt thereof, wherein —$R^7$ together with the carbonyl group and nitrogen alpha to the carbon to which it is attached is a leucine, isoleucine, phenylalanine, threonine, valine or norvaline residue.

4. The compound of claim 1, or a salt thereof, wherein —$R^6$ is $C_{1-12}$ alkyl, $C_{0-12}$ alkyl ($C_{3-10}$ cycloalkyl), $C_{0-12}$alkyl ($C_{3-10}$ heterocyclyl) or $C_{0-12}$alkyl ($C_{5-10}$ aryl), where the $C_{1-12}$ alkyl, $C_{3-10}$cycloalkyl group, $C_{3-10}$heterocyclyl group, and the $C_{5-10}$aryl group are optionally substituted.

5. The compound of claim 4, or a salt thereof, wherein —$R^6$ is $C_{0-12}$ alkyl($C_{3-10}$ cycloalkyl), where the $C_{3-10}$ cycloalkyl group is optionally substituted.

6. The compound of claim 5, or a salt thereof, wherein the $C_{3-10}$cycloalkyl group is unsubstituted.

7. The compound of claim 5, or a salt thereof, wherein $C_{0-12}$ alkyl ($C_{3-10}$ cycloalkyl) is $C_1$alkyl ($C_{3-10}$ cycloalkyl).

8. The compound according to claim 4, or a salt thereof, wherein —$R^6$ is unsubstituted $C_{1-12}$ alkyl.

9. The compound of claim 8, or a salt thereof, wherein —X—is —C(O)—.

10. The compound of claim 4, or a salt thereof, wherein
(i) —$R^6$ is optionally substituted $C_{1-12}$alkyl;
(ii) —$R^6$ is $C_{0-12}$alkyl ($C_{5-10}$ aryl), where the $C_{5-10}$aryl group is optionally substituted; or
(iii) —$R^6$ is $C_{0-12}$alkyl ($C_{3-10}$ cycloalkyl), where the $C_{3-10}$cycloalkyl group is optionally substituted.

11. The compound of claim 5, or a salt thereof, wherein $C_{0-12}$ alkyl ($C_{5-10}$ aryl) is $C_1$alkyl ($C_{5-10}$ aryl).

12. The compound according to claim 1, or a salt thereof, wherein:
   (i) —$A^2$— is L-threonine or L-serine; and/or
   (ii) —$R^3$ together with the carbonyl group and nitrogen alpha to the carbon to which it is attached, is α, γ-diaminobutyric acid (Dab) or α, β-diaminopropionic acid (Dap); and/or
   (iii) —$R^{10}$ together with the carbonyl group and nitrogen alpha to the carbon to which it is attached is a threonine residue; and/or
   (iv) —X—is —C(O)—.

13. The compound of claim 12, or a salt thereof, wherein
   (i) —$A^2$—is L-threonine; and
   (ii) —$R^3$ together with the carbonyl group and nitrogen alpha to the carbon to which it is attached, is α, β-diaminopropionic acid (Dap).

14. The compound of claim 1, or a salt thereof, wherein at least one of the following conditions is met:
   (i) —$A^2$— is L-threonine or L-serine;
   (ii) —$R^{10}$ together with the carbonyl group and nitrogen alpha to the carbon to which it is attached is a threonine residue; or
   (iii) —X—is —C(O)-.

15. The compound according to claim 1, or a salt thereof, wherein -$R^3$ together with the carbonyl group and nitrogen alpha to the carbon to which it is attached, is α, γ-diaminobutyric acid (Dab) or α,β-diaminopropionic acid (Dap).

16. The compound of claim 1, or a salt thereof, wherein -$R^7$ is $C_{1-12}$ alkyl.

17. The compound of claim 1, or a salt thereof, wherein —$R^6$ together with the carbonyl group and nitrogen alpha to the carbon to which it is attached is a leucine residue.

18. The compound of claim 1, or a salt thereof, wherein —$R^7$ together with the carbonyl group and nitrogen alpha to the carbon to which it is attached is a 2-aminobutyric acid (Abu) residue.

19. The compound of claim 1, or a salt thereof, wherein —$A^2$—is L-threonine.

20. The compound of claim 1, or a salt thereof, wherein —$R^3$ together with the carbonyl group and nitrogen alpha to the carbon to which it is attached, is α, β-diaminopropionic acid (Dap).

21. A pharmaceutical composition comprising a compound or salt thereof according to claim 1.

22. A compound of the formula

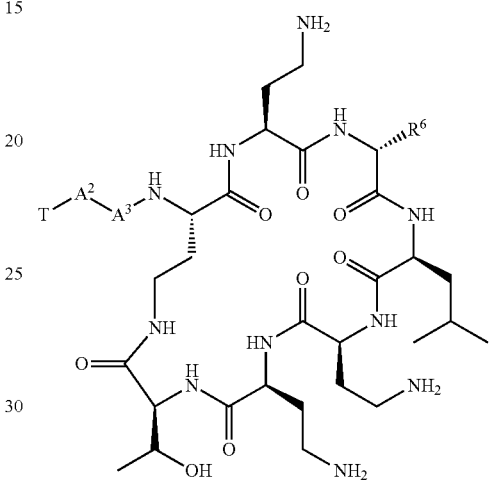

selected from the group consisting of compounds and the salts thereof in which T—$A^2$—$A^3$—and—$R^6$ are:

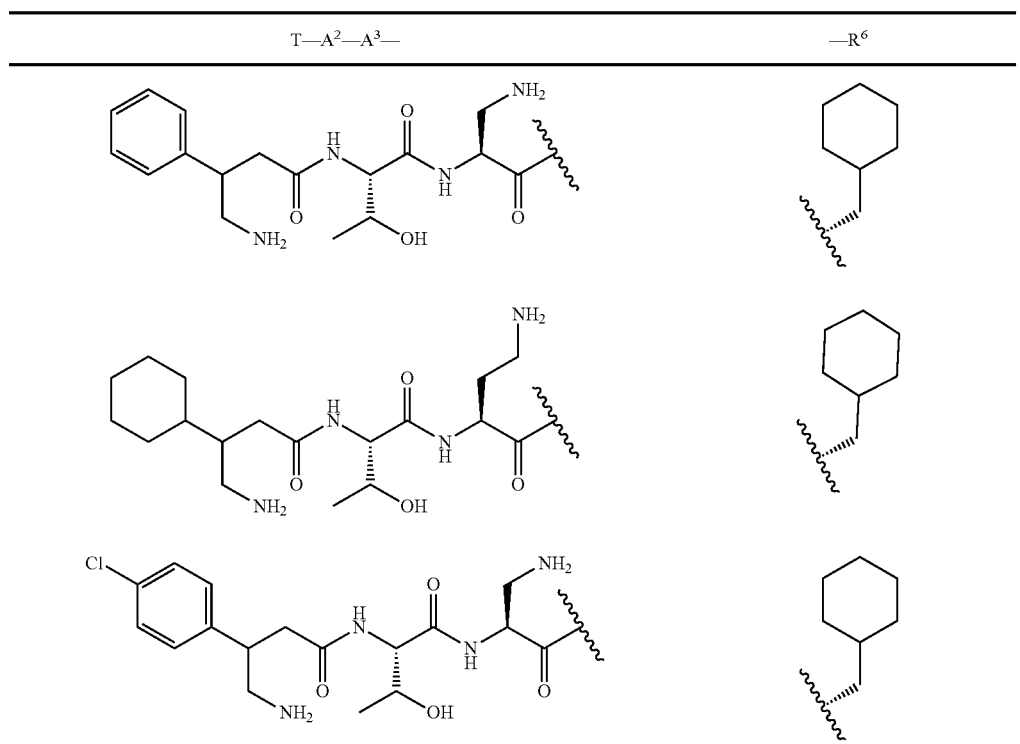

-continued
| T—A²—A³— | —R⁶ |
|---|---|
| 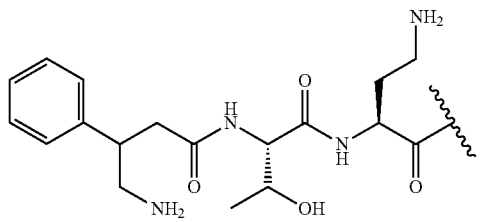 [SMILES: *C(=O)[C@H](CCN)NC(=O)[C@@H](NC(=O)CC(CN)c1ccccc1)C(C)O] | 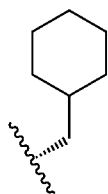 |
| 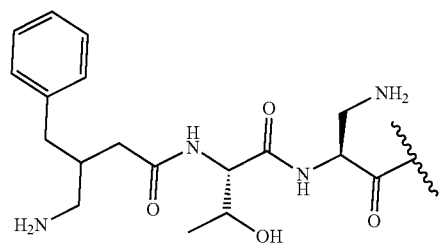 [SMILES: *C(=O)[C@H](CN)NC(=O)[C@@H](NC(=O)CC(CN)Cc1ccccc1)C(C)O] | 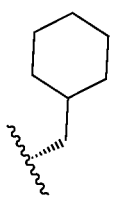 |
| 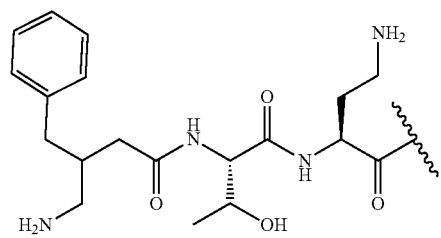 | 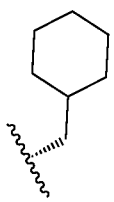 |
| 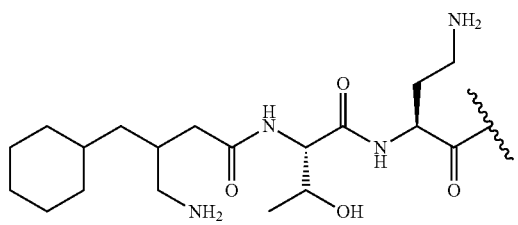 [SMILES: *C(=O)[C@H](CCN)NC(=O)[C@@H](NC(=O)CC(CN)CC1CCCCC1)C(C)O] | 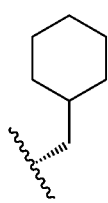 |
| 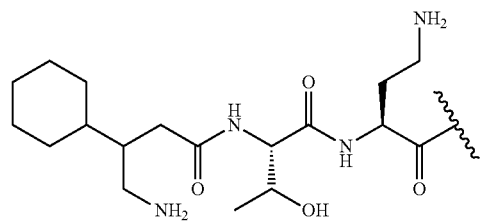 | 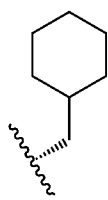 |
| 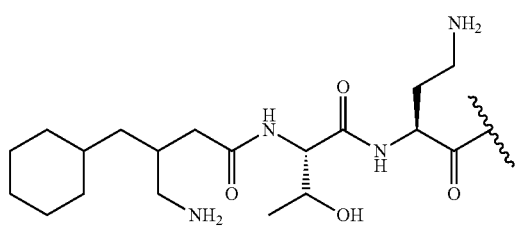 [SMILES: *C(=O)[C@H](CCN)NC(=O)[C@@H](NC(=O)CC(CN)CC1CCCCC1)C(C)O] | 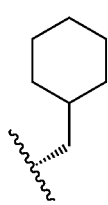 |

23. A compound of formula (I):

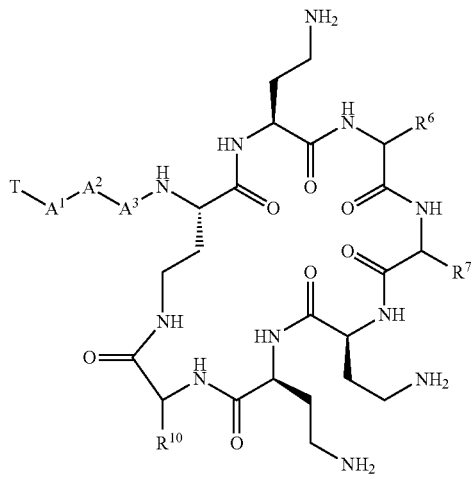

wherein:
-T is $R^T$—X—;
-$A^1$- is absent
-$A^2$- is an amino acid residue selected from threonine and serine;
- A3- is an amino acid residue represented by:

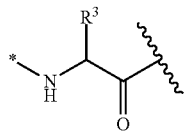

where the asterisk is the point of attachment to -$A^2$-, and —$R^3$ is $C_{1-6}$ alkyl, having one amino or one hydroxyl substituent;
—X— is —C(O)—, —NHC(O)—, —OC(O)—, —$CH_2$— or —$SO_2$—;
—RT is an amino-containing group:

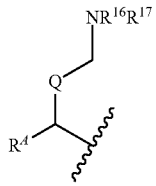

where:
—RA is hydrogen or -$L^A$-$R^{AA}$;
-Q- is —CH($R^B$)—; $R^B$ is -$L^B R^{BB}$, -$L^B$- is a covalent bond, and —$R^{BB}$ is $C_{3-12}$ alkyl;
—$R^{16}$ is independently hydrogen or $C_{1-4}$ alkyl;
—$R^{17}$ is independently hydrogen or $C_{1-4}$ alkyl;
or —$NR^{16}R^{17}$ is a guanidine group;
or —$R^{17}$ and —$R^A$ together form a 5- to 10-membered nitrogen-containing monocyclic or bicyclic heterocycle;
or —$R^{17}$ and —$R^B$ together form a 5- to 10-membered nitrogen-containing monocyclic or bicyclic heterocycle;

where —$R^{17}$ and —$R^A$ together form a monocyclic nitrogen-containing heterocycle, each ring carbon atom in the monocyclic nitrogen-containing heterocycle formed by —$R^{17}$ and —RA is optionally mono-or di-substituted with —$R^C$, and the monocyclic heterocycle is substituted with at least one group selected from —$R^C$, —$R^N$, —$R^{NA}$ and -$L^B$-$R^{BB}$, where —$R^{17}$ and —$R^B$ together form a monocyclic nitrogen-containing heterocycle, each ring carbon atom in the monocyclic nitrogen-containing heterocycle formed by —$R^{17}$ and —$R^B$ is optionally mono- or di-substituted with —$R^C$, and the monocyclic heterocycle is substituted with at least one group selected from —$R^C$, and —$R^N$, or the monocyclic heterocycle is optionally substituted when —$R^A$ is -$L^A$—$R^{AA}$, and the monocyclic nitrogen-containing heterocycle optionally contains one further nitrogen, oxygen or sulfur ring atom, and where a further nitrogen ring atom is present it is optionally substituted with -$R^N$, with the exception of a further nitrogen ring atom that is connected to the carbon that is a to the group —X—, which nitrogen ring atom is optionally substituted with —$R^{NA}$;

where —$R^{17}$ and —RA or —$R^{17}$ and —$R^B$ together form a bicyclic nitrogen-containing heterocycle, each ring carbon atom in the bicyclic nitrogen-containing heterocycle formed by —$R^{17}$ and —RA or —$R^{17}$ and —RB is optionally mono-or di-substituted with —$R^D$;

and the bicyclic nitrogen-containing heterocycle optionally contains one, two or three further heteroatoms, where each heteroatom is independently selected from the group consisting of nitrogen, oxygen and sulfur, and where further nitrogen ring atoms are present, each further nitrogen ring atom is optionally substituted with —$R^N$, with the exception of a nitrogen ring atom that is connected to the carbon that is a to the group —X—, which nitrogen ring atom is optionally substituted with —$R^{NA}$;

and where $R^{17}$ and —$R^A$ or —$R^{17}$ and —$R^B$ together form a 5-to 10-membered nitrogen-containing monocyclic or bicyclic heterocycle, and a carbon ring atom in —$R^{17}$ and —$R^A$ or —$R^{17}$ and —$R^B$ 5- to 10-membered nitrogen-containing monocyclic or bicyclic heterocycle is optionally substituted with oxo (=O);

each —$R^C$ is independently -$L^C R^{CC}$;
each —$R^D$ is independently selected from —$R^C$, halogen, —$NO_2$, —OH, and —$NH_2$;
each —$R^N$ is independently -$L^N$-$R^{NN}$;
each —$R^{NA}$ is independently —$R^L R^{NN}$ or —$R^{NN}$;
—$R^{AA}$, —$R^{CC}$ and —$R^{NN}$, where present, is independently selected from $C_{1-12}$ alkyl, $C_{3-10}$ cycloalkyl, $C_{4-10}$ heterocyclyl, and $C_{5-12}$ aryl;

each -$L^A$- is independently a covalent bond or a linking group selected from $R^L$-*, O-$L^{AA}$-*, —OC(O)-$L^{AA}$-*, and —C(O)-$L^{AA}$-*, where the asterisk indicates the point of attachment of the group -$L^A$- to —$R^{AA}$;

each -$L^B$- and -$L^C$-is independently a covalent bond or a linking group selected from —$R^L$- *, —O-$L^{AA}$-*, —OC(O)-$L^{AA}$-*, —N($R^{11}$)—$L^{AA}$-*, —N($R^{11}$) C(O)-$L^{AA}$-*, —C(O)-$L^{AA}$-*, —C(O)O-$L^{AA}$-*, and —C(O)N($R^{11}$)-$L^{AA}$-*, and optionally further selected from —N($R^{11}$) S(O)-$L^{AA}$-*, —N($R^{11}$)S(O)$_2$-$L^{AA}$-*, —S(O)N($R^{11}$)-$L^{AA}$-*, and —S(O)$_2$N($R^{11}$)-$L^{AA}$-* where the asterisk indicates the point of attachment of the group -$L^B$- to —$R^{BB}$ or the group -$L^C$- to -$R^{CC}$;

each -L$^N$- is independently a covalent bond or a group selected from —S(O)-L$^{AA}$-*, —S(O)$_2$-L$^{AA}$-*, —C(O)-L$^{AA}$-* and —C(O)N(R$^{11}$)-L$^{AA}$*, where the asterisk indicates the point of attachment of the group -L$^N$- to —R$^{NN}$;

and each -L$^{AA}$- is independently a covalent bond or —R$^L$-;

and each —R$^L$- is independently selected from C$_{1-12}$ alkylene, C$_{2-12}$ heteroalkylene, C$_{3-10}$ cycloalkylene and C$_{5-10}$ heterocyclylene, and where -L$^{AA}$- is connected to a group C$_{1-12}$ alkyl, —R$^L$- is not C$_{1-12}$ alkylene;

and each C$_{1-12}$ alkyl, C$_{3-10}$ cycloalkyl, C$_{4-10}$ heterocyclyl, C$_{5-12}$ aryl, C$_{1-12}$ alkylene, C$_{2-12}$ heteroalkylene, C$_{3-10}$ cycloalkylene and C$_{5-10}$ heterocyclylene group is optionally substituted with —R$^S$ and —R$^{12}$, where —R$^S$ is an optional substituent to carbon and —R$^{12}$ is an optional substituent to nitrogen;

each —R$^S$ is independently selected from —OH, —OR$^{12}$, —OC(O)R$^{12}$, halogen, —R$^{12}$, —NHR$^{12}$, —NR$^{12}$R$^{13}$, —NHC(O)R$^{12}$, —N(R$^{12}$)C(O)R$^{12}$, —SH, —SR$^{12}$, —C(O)R$^{12}$, —C(O)OH, —C(O)OR$^{12}$, —C(O)NH$_2$, —C(O)NHR$^{12}$ and C(O)NR$^{12}$R$^{13}$; except that —R$^{12}$ is not a substituent to a C$_{1-12}$ alkyl group; or where a carbon atom is di-substituted with —R$^S$, these groups may together with the carbon to which they are attached form a C$_{3-6}$ carbocycle or a C$_{5-6}$ heterocycle, where the carbocycle and the heterocycle are optionally substituted with one or more groups —R$^{12}$;

each —R$^{12}$ is independently C$_{1-6}$ alkyl, C$_{1-6}$ haloalkyl, phenyl or benzyl;

each —R$^{13}$ is independently C$_{1-6}$ alkyl, C$_{1-6}$ haloalkyl, phenyl or benzyl;

or —R$^{12}$ and -R$^{13}$, where attached to N, may together form a 5-or 6-membered heterocyclic ring, which is optionally substituted with C$_{1-6}$ alkyl, C$_{1-6}$ haloalkyl, phenyl or benzyl;

each —R$^{11}$ is independently hydrogen or C$_{1-4}$ alkyl;

—R$^6$ together with the carbonyl group and nitrogen alpha to the carbon to which it is attached is an amino acid residue;

—R$^7$ together with the carbonyl group and nitrogen alpha to the carbon to which it is attached is an amino acid residue;

and —R$^6$ together with the carbonyl group and nitrogen alpha to the carbon to which it is attached is not a phenylalanine, leucine or valine residue and/or —R7 together with the carbonyl group and nitrogen alpha to the carbon to which it is attached is not a leucine, isoleucine, phenylalanine, threonine, valine or norvaline residue;

R$^{10}$ together with the carbonyl group and nitrogen alpha to the carbon to which it is attached, is a threonine or leucine residue;

or a salt, protected form, and/or prodrug form thereof.

24. A method of treating a Gram negative bacterial infection in a patient, comprising administering the compound or salt thereof according to claim 1 to a patient in need thereof.

25. The method according to claim 24, wherein the bacterial infection is an *Acinetobacteria baumanii, Acinetobacteria calcoaceticus, Bdellovibrio, Citrobacteria, Enterobacter aerogenes, Enterobacter agglomerans, Enterobacter cloacae, Escherichia coli, Hemophilus influenzae, Helicobacteria pylori, Klebsiella pneumoniae, Klebsiella oxytoca, Legionella pneumophila, Klebsiella, Moraxella catarrhalis, Morganella morganii, Neisseria gonorrhoeae, Neisseria meningitidis, Proteus mirabilis, Proteus vulgaris, Providencia stuartii, Pseudomonas aeruginosa, Salmonella enterica, Shigella, Stenotrophomonas, Wolbachia,* or *Yersinia pseudotuberculosis* bacterial infection.

26. The method according to claim 24, wherein the Gram-negative bacterial infection is selected from the group consisting of *Escherichia* spp., *Klebsiella* spp., *Enterobacter* spp., *Salmonella* spp., *Shigella* spp., *Citrobacter* spp., *Morganella morganii, Yersinia pseudotuberculosis* and other *Enterobacteriaceae, Pseudomonas* spp., *Acinetobacter* spp., *Moraxella, Helicobacter, Stenotrophomonas, Bdellovibrio,* acetic acid bacteria, *Legionella* and alpha-proteobacteria.

* * * * *